(12) United States Patent
Hergenrother et al.

(10) Patent No.: US 10,081,592 B2
(45) Date of Patent: Sep. 25, 2018

(54) COMPLEX AND STRUCTURALLY DIVERSE COMPOUNDS

(71) Applicants:THE BOARD OF TRUSTEES OF THE UNIVERSITY OF ILLINOIS, Urbana, IL (US); Paul J. Hergenrother, Champaign, IL (US); Robert W. Huigens, III, Gainesville, FL (US); Karen C. Morrison, Champaign, IL (US); Robert W. Hicklin, II, Urbana, IL (US); Timothy A. Flood, Jr., Champaign, IL (US)

(72) Inventors: Paul J. Hergenrother, Champaign, IL (US); Robert W. Huigens, III, Gainesville, FL (US); Karen C. Morrison, Champaign, IL (US); Robert W. Hicklin, II, Urbana, IL (US); Timothy A. Flood, Jr., Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 402 days.

(21) Appl. No.: 14/387,028

(22) PCT Filed: Mar. 25, 2013

(86) PCT No.: PCT/US2013/033746
§ 371 (c)(1),
(2) Date: Sep. 22, 2014

(87) PCT Pub. No.: WO2013/142873
PCT Pub. Date: Sep. 26, 2013

(65) Prior Publication Data
US 2015/0274638 A1    Oct. 1, 2015

Related U.S. Application Data

(60) Provisional application No. 61/614,842, filed on Mar. 23, 2012.

(51) Int. Cl.
*C07D 401/14* (2006.01)
*C07C 69/757* (2006.01)
(Continued)

(52) U.S. Cl.
CPC ............ *C07C 69/757* (2013.01); *C07B 37/06* (2013.01); *C07B 37/08* (2013.01); *C07C 59/205* (2013.01); *C07C 62/32* (2013.01); *C07C 62/38* (2013.01); *C07D 223/14* (2013.01); *C07D 303/10* (2013.01); *C07D 307/93* (2013.01); *C07D 311/94* (2013.01); *C07D 313/06* (2013.01); *C07D 313/08* (2013.01); *C07D 401/04* (2013.01); *C07D 401/14* (2013.01); *C07D 405/06* (2013.01); *C07D 405/12* (2013.01); *C07D 413/06* (2013.01);
(Continued)

(58) Field of Classification Search
CPC ..... C07C 69/757; C07C 62/32; C07C 59/205; C07C 62/38; C07C 2101/16; C07C 2102/44; C07C 2103/86; C07C 493/08; C07C 223/14; C07J 73/005; C07J 75/005; C07J 21/008; C07J 73/008; C07J 71/001; C07J 69/00; C07J 71/0031; C07B 37/08; C07B 37/06; C07D 405/06; C07D 405/12; C07D 413/06; C07D 313/08; C07D 307/93; C07D 471/04; C07D 401/04; C07D 471/08; C07D 519/00; C07D 313/06; C07D 311/94; C07D 493/08; C07D 223/14; C07D 401/14; C07D 513/04
See application file for complete search history.

(56) References Cited

U.S. PATENT DOCUMENTS

| 3,929,795 A | 12/1975 | Gutzwiller et al. |
| 2003/0212098 A1 | 11/2003 | Somberg et al. |

(Continued)

FOREIGN PATENT DOCUMENTS

| CN | 1560044 A | 1/2005 |
| EP | 2407475 A2 | 1/2012 |

(Continued)

OTHER PUBLICATIONS

Nielsen, J., "Combinatorial synthesis of natural products." Current opinion in chemical biology 6.3 (2002): 297-305.*

(Continued)

*Primary Examiner* — Noble E Jarrell
(74) *Attorney, Agent, or Firm* — Haukaas Fortius PLLC; Michael H. Haukaas

(57) ABSTRACT

The invention a novel, general, and facile strategy for the creation of small molecules with high structural and stereochemical complexity. Aspects of the methods include ring system distortion reactions that are systematically applied to rapidly convert readily available natural products to structurally complex compounds with diverse molecular architectures. Through evaluation of chemical properties including fraction of $sp^3$ carbons, ClogP, and the number of stereogenic centers, these compounds are shown to be significantly more complex and diverse than those in standard screening collections. This approach is demonstrated with natural products (gibberellic acid, adrenosterone, and quinine) from three different structural classes, and methods are described for the application of this strategy to any suitable natural product.

12 Claims, 19 Drawing Sheets

(51) Int. Cl.

| | |
|---|---|
| *C07D 311/94* | (2006.01) |
| *C07D 313/06* | (2006.01) |
| *C07D 223/14* | (2006.01) |
| *C07D 401/04* | (2006.01) |
| *C07D 471/04* | (2006.01) |
| *C07D 471/08* | (2006.01) |
| *C07D 493/08* | (2006.01) |
| *C07D 513/04* | (2006.01) |
| *C07D 519/00* | (2006.01) |
| *C07D 303/10* | (2006.01) |
| *C07C 59/205* | (2006.01) |
| *C07C 62/32* | (2006.01) |
| *C07C 62/38* | (2006.01) |
| *C07B 37/06* | (2006.01) |
| *C07B 37/08* | (2006.01) |
| *C07D 307/93* | (2006.01) |
| *C07D 313/08* | (2006.01) |
| *C07D 405/06* | (2006.01) |
| *C07D 405/12* | (2006.01) |
| *C07D 413/06* | (2006.01) |
| *C07J 21/00* | (2006.01) |
| *C07J 69/00* | (2006.01) |
| *C07J 71/00* | (2006.01) |
| *C07J 73/00* | (2006.01) |
| *C07J 75/00* | (2006.01) |

(52) U.S. Cl.
CPC ......... *C07D 471/04* (2013.01); *C07D 471/08* (2013.01); *C07D 493/08* (2013.01); *C07D 513/04* (2013.01); *C07D 519/00* (2013.01); *C07J 21/008* (2013.01); *C07J 69/00* (2013.01); *C07J 71/001* (2013.01); *C07J 73/005* (2013.01); *C07J 73/008* (2013.01); *C07J 75/005* (2013.01); *C07C 2601/16* (2017.05); *C07C 2602/44* (2017.05); *C07C 2603/86* (2017.05)

(56) References Cited

U.S. PATENT DOCUMENTS

2009/0221436 A1   9/2009  Slanetz
2012/0270881 A1   10/2012  Obrecht et al.

FOREIGN PATENT DOCUMENTS

| GB | 964987 A | 7/1964 |
| WO | 2008042240 A2 | 4/2008 |
| WO | 2009120795 A1 | 10/2009 |
| WO | WO 2010062372 A2 * | 6/2010 ........... A61K 31/191 |

OTHER PUBLICATIONS

Tan, D. S., "Current progress in natural product-like libraries for discovery screening." Combinatorial chemistry & high throughput screening 7.7 (2004): 631-643.*

Joseph. Chemogenomics in Drug Discovery: A Medicinal CHemistry Perspective, 2004, Chapter 15, pp. 405-432.*

Newman. Macrocycles in Drug Discovery, 2014, chapter 1, pp. 1-36.*

Avent, A.G. et al., "The Stereoschemistry and Hydrolysis of Gibberellin 16, 17-Episodes. X-Ray Molecular Structures of ent-17-Acetoxy-1a, 10a-epoxy-2B, 3a, 13, 16B-tetra-hydroxy-20-norgibberella-7, 19-dioic Acid 19,2-Lactone 7-Methyl Ester and of ent-17-Chloro-1a, 10a-epoxy-2B, 3a, 13, 16B-tetrahydroxy-20-norgibberella-7, 19-dioic Acid 19, 2-Lactone 7-Methyl Ester", J. Chem. Soc. Perkin Trans. 1, 1989, pp. 627-632.

Castellaro, S.J. et al., "Preparation and Occurrence of Gibberellins A75 and A76 and 3-Epi-A72", J. Chem. Soc. Perkin Trans. 1, 1990, pp. 145-152.

Huigens III, R.W., "A ring-distortion strategy to construct stereochemically complex and structurally diverse compounds from natural products", Nature Chemistry, vol. 5, Mar. 2013, published online Jan. 20, 2013, pp. 195-202.

International Search Report and Written Opinion for PCT/US2013/033746 dated Oct. 31, 2013, 12 pp.

Seto, H. et al., "Improved Procedures for Direct Conversions of Natural 3B-Hydroxy-Gibberellins to 3a-Hydroxy- and 3-OXO-Gibberellins", Heterocycles, vol. 48, No. 11, 1998, pp. 2245-2251.

* cited by examiner

Daunorubicin

Paclitaxel

Actinomycin D

Trabectedin

Morphine

Mitomycin C

COMPLEX AND STRUCTURALLY DIVERSE COMPOUNDS

RELATED APPLICATIONS

This application claims priority under 35 U.S.C. § 119(e) to U.S. Provisional Patent Application No. 61/614,842, filed Mar. 23, 2012, which is incorporated herein by reference.

GOVERNMENT SUPPORT

This invention was made with government support under contract number N00014-09-1-0249 awarded by the Office of Naval Research. The government has certain rights in the invention.

BACKGROUND OF THE INVENTION

Historically, natural products or their close analogues have been considered end points in the drug discovery process. To date, this thinking has been quite fruitful. For example, 47% of anticancer drugs and 60% of antibacterial drugs are natural products or very close derivatives. The features that make natural products different from most synthetic compounds (e.g., high Fsp3, low ClogP, presence of stereogenic centers) give these compounds a propensity to bind to their macromolecular target with high affinity and specificity, while retaining the solubility and cell permeability needed for a therapeutic agent. Thus, drug candidates with natural product-like properties may have higher likelihoods of becoming clinical drugs than less structurally complex synthetic compounds. Accordingly, there is a pressing need in the art for new methods to create compounds that are structurally complex and diverse, and for new methods to systematically diversify the structural complexity of natural products.

High-throughput screening is the dominant method to identify lead compounds in drug discovery. As such, the makeup of screening libraries will largely dictate the biological targets that can be modulated and the therapeutics that can be developed. Most compound screening collections consist principally of planar molecules with little structural or stereochemical complexity. While such relatively simple structures are effective in certain settings (e.g., kinase inhibition), they do not offer the arrangement of chemical functionality necessary for modulation of many drug targets. Furthermore, certain chemical properties, such as molecular complexity and multiple stereogenic centers are extremely difficult to build in when producing large collections of compounds for high-throughput screening.

Thus, what is needed in the art is a novel strategy for the creation of small molecules with high structural and stereochemical complexity. Also needed are compounds that are significantly more complex and diverse than those in standard screening collections. New methods to rapidly convert readily available natural products to structurally complex compounds with diverse molecular architectures would provide stereochemically complex molecules that could provide much needed lead compounds for drug discovery.

SUMMARY

The invention provides a novel, general, and facile strategy for the creation of small molecules with high structural and stereochemical complexity. Aspects of the methods include ring system distortion reactions that are systematically applied to rapidly convert readily available natural products to structurally complex compounds with diverse molecular architectures. Through evaluation of chemical properties including fraction of $sp^3$ carbons, ClogP, and the number of stereogenic centers, these compounds are shown to be significantly more complex and diverse than those in standard screening collections. This approach is demonstrated with natural products (gibberellic acid, adrenosterone, and quinine) from three different structural classes, and methods are described for the application of this strategy to any suitably complex natural product.

In the search for new biologically active molecules, diversity-oriented synthetic strategies seek to break through the limitation of traditional library synthesis by sampling new chemical space. Many natural products can be regarded as intriguing starting points for diversity-oriented synthesis, where stereochemically rich core structures may be reorganized into chemotypes that are distinctly different from the parent structure. Ideally, to be suited to library applications, such transformations should be general and involve few steps. With this objective in mind, the stereochemically rich tetracarbocyclic natural product gibberellic acid has been successfully remodeled in several ways using an approach based on a diversity of reactions, including various combinations of ring distortion reactions, oxidations, esterifications, alkylations, and halogenations, among others. The method was further applied to adrenosterone and quinine. Screening the diverse array of products provided highly active compounds provided multiple novel drug candidates.

The invention thus provides a method for preparing a high-throughput screening library comprising:

a) carrying out a ring expansion reaction, a ring fusion reaction, a ring rearrangement reaction, a ring cleavage reaction, or a combination thereof, on a natural product or a derivative thereof, wherein the natural product has high structural and stereochemical complexity;

b) carrying out an oxidation reaction, a reduction reaction, an esterification, an amidation, an addition reaction, a substitution reaction, an elimination reaction, an aromatization reaction, a functional group transformation, or a protection reaction; optionally followed by carrying out an additional ring expansion reaction, a ring fusion reaction, a ring rearrangement reaction, or a ring cleavage reaction; and c) repeating steps a) and b) multiple times using different selections of reactions to provide a series of products for a high-throughput screening library. For example, steps a) and b) can be carried out 2, 3, 4, 5, 10, 20, 50 or more times to provide a diverse library of compounds.

The products can comprise at least one ring distortion compared to the natural product, often two or three ring distortions. The products can comprise, for example, at least three oxygen atoms, or at least two oxygen atoms and three nitrogen atoms, often four or more oxygen atoms, other heteroatoms including sulfur and or phosphorus, or a combination of any of the forgoing. The products can comprise at least 2 stereogenic centers, at least 3 stereogenic centers, at least 4 stereogenic centers, at least 5 stereogenic centers, at least 6 stereogenic centers, or at least 7 stereogenic centers. The molecular weights of the products can be at least about 200 Daltons, at least about 250 Daltons, at least about 300 Daltons, at least about 350 Daltons, at least about 375 Daltons, at least about 400 Daltons, or at least about 450 Daltons. The molecular weights of the products can be less than about 1,200 Daltons, less than about 1,000 Daltons, less than about 900 Daltons, less than about 800 Daltons, less than about 750 Daltons, less than about 700 Daltons, less than about 650 Daltons, less than about 600 Daltons, less than about 550 Daltons, less than about 500 Daltons, less than about 450 Daltons, or less than about 400 Daltons.

In some embodiments, the method can further comprising a one or more additional ring expansion reactions, ring fusion reactions, ring rearrangement reactions, ring cleavage reactions, oxidation reactions, reduction reactions, esterifications, amidations, addition reactions, substitution reactions, elimination reactions, aromatization reactions, functional group transformations, protection reactions, or deprotection reactions.

Accordingly, the invention also provides a method of diversifying the structural complexity of a natural product by carrying out the reaction sequences described above, wherein at least one ring distortion reaction is carried out on the natural product. When the method is repeated several or more times, the invention thus provides a method for preparing a high-throughput screening library.

The invention also provides methods for increasing the diversity of molecules in a library by including compounds having high structural and stereochemical complexity prepared by the methods described herein in the library, to increase the likelihood of active compounds in the library. For example, the methods described herein can be used to provide compound libraries where at least 50%, at least 60%, at least 75%, at least 90%, or at least 95% of the compounds have at least 1, 2, 3, 4, 5, 6, 7, or 8 stereogenic centers. In some embodiments, the median number of stereogenic centers can be 4 or 5. The methods can provide the compounds in one to about six chemical transformations, with an average of 3-4 chemical transformations per compound. The ring structures of the products of the methods can be different than the core ring structure of the natural product or derivative thereof. One or more, or all compounds in the library, can have such ring distortions. In various embodiments, the compounds of the library can have Tanimoto coefficients each of less than about 0.4, or less than about 0.35.

In one embodiment, the natural product is gibberellic acid, adrenosterone, or quinine. In another embodiment, the natural product is gibberellic acid or a derivative of gibberellic acid having Formula X-G:

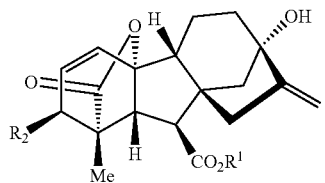

(X-G)

wherein
R$^1$ is H or Me; and
R$^2$ is OH or OMe.

In one embodiment, steps a) and b) of the method described above includes a ring cleavage reaction and an esterification, and step c) includes one or more of:
  i) a ring cleavage reaction, an esterification, and ring cleavage reaction or a ring fusion reaction;
  ii) a ring rearrangement reaction, an amidation, and a ring rearrangement reaction;
  iii) a ring cleavage reaction, an esterification, and a ring expansion reaction;
  iv) a ring cleavage reaction with concomitant a decarboxylation and aromatization, an esterification, and a ring rearrangement; and
  v) a ring cleavage reaction with concomitant a decarboxylation and aromatization, a ring rearrangement, and a ring expansion reaction.

In another embodiment, the natural product is adrenosterone or a derivative of adrenosterone having Formula X-A:

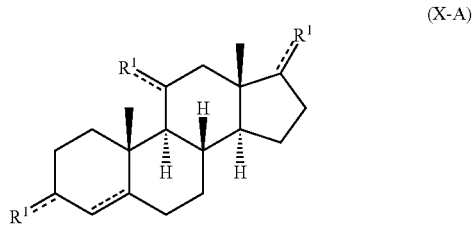

(X-A)

wherein
each R$^1$ is independently O, H or OH; and
each dotted line independently represents an optionally present double bond. The methods of steps a) and b) can include a ring cleavage reaction and a functional group transformation, and step c) can include one or more of:
  i) a ring cleavage reaction, a ring expansion reaction, a functional group transformation, a reduction, and a protection reaction;
  ii) a ring cleavage reaction, an esterification, and a ring expansion reaction;
  iii) a ring cleavage reaction, a ring fusion reaction, and a ring cleavage reaction; and
  iv) a ring fusion reaction, an alkyl addition reaction, and an epoxidation.

In yet another embodiment, the natural product is quinine or a derivative of quinine having Formula X-Q:

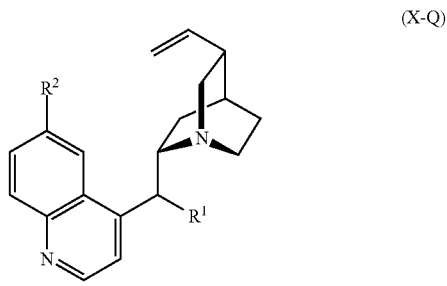

(X-Q)

wherein R$^1$ and R$^2$ are each independently H, OH, or alkoxy. The method steps a) and b) can include a ring cleavage reaction, a protection reaction, and ring fusion reaction or a conjugation reaction, and step c) can include one or more of:
  i) a ring cleavage reaction, a protection reaction, and ring fusion reaction;
  ii) a ring cleavage reaction, an esterification, and a functional group transformation;
  iii) a ring cleavage reaction, and a functional group transformation;
  iv) a ring formation reaction, an alkyl addition reaction.

The methods can also include analyzing the products of the methods, for example, for inhibitory activity against bacteria, inflammation, or cancer cells. The invention also provides a compound prepared by any of the methods described herein. The compound can be, for example, any formula or specific compound described or illustrated herein. The compound can be used to provide a pharmaceutical composition that includes the compound in combination with a pharmaceutically acceptable diluent, excipient, or carrier.

The invention also provides a method of cleaving a cyclopentanone ring comprising contacting a compound of Formula (X):

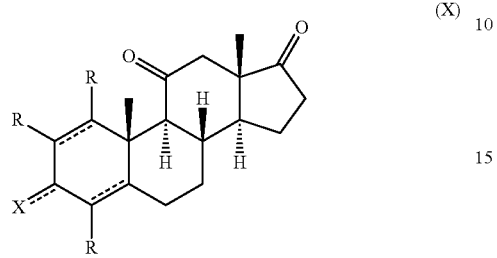
(X)

wherein X is O, OH, or R; each R is independently H, OH, halo, alkyl, or aryl; and each dotted line independently represents the presence of an optional double bond; with a strong mineral acid, such as sulfuric acid, and sodium azide or a hydrazoic acid precursor, thereby cleaving the cyclopentanone ring of Formula (X) to provide a product comprising Formula (XI):

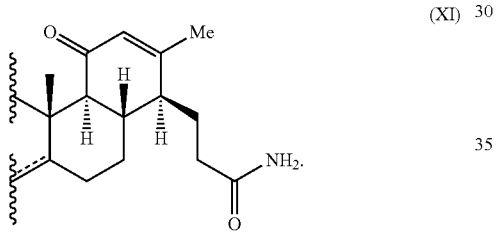
(XI)

In one embodiment, the compound of Formula (X) is adrenosterone. In another embodiment, the compound of Formula (XI) is A6A or A7A:

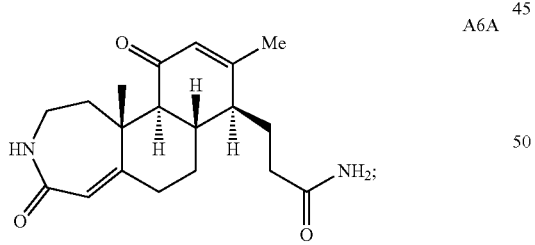
A6A

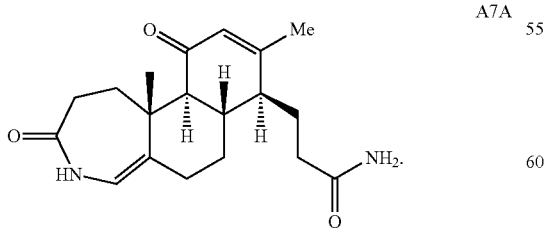
A7A

In further embodiments, the method includes allowing the primary amides to dehydrate to provide compound A6, A7, or a combination thereof:

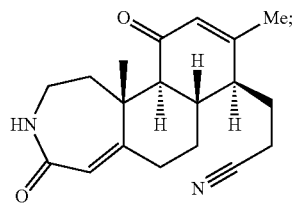
A6

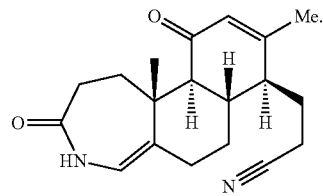
A7

In some embodiments, the cyclopentanone ring can be substituted, for example, with a substituent as described herein, thereby providing substituted products of compound XI.

The invention further provides a method to cleave a quinuclidine ring structure comprising contacting a compound containing a quinuclidine ring system with a thionochloroformate to effect ring cleavage of the quinuclidine at N1-C2 to provide a ring opened product comprising a 1-chloroethyl-piperidine moiety. The quinuclidine can include a 3-vinyl quinuclidine substituent and a carbon at the quinuclidine 8-position having a hydroxyl group, wherein the reaction provides a cyclized thiocarbamate moiety. In one specific embodiment, the compound containing a quinuclidine ring system is quinine and the method provides the compound Q1:

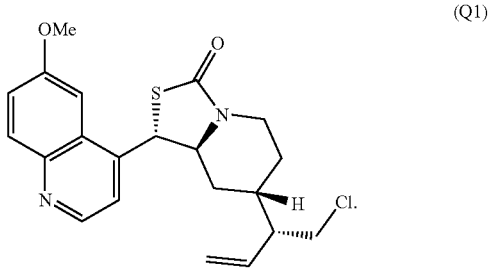 [SMILES: C=C[C@@H](CCl)[C@H]1CCN2C(=O)S[C@@H](c3ccnc4ccc(OC)cc34)[C@@H]2C1]
(Q1)

In another embodiment, the invention provides a compound of formula GAX:

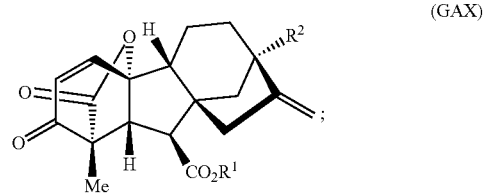
(GAX)

wherein $R^1$ is alkyl, alkylaryl, or aryl; and $R^2$ is H, OH, halo, alkoxy, or OP wherein P is an oxygen protecting group. In a specific embodiment, the compound is GA-4:

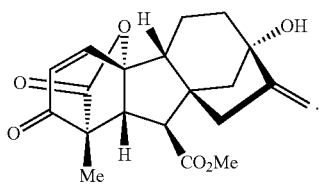

(GA-4)

In yet another embodiment, the invention provides a compound of formula GAZ:

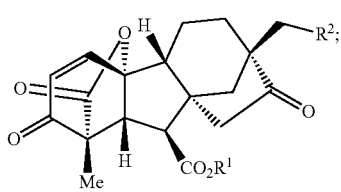

(GAZ)

wherein $R^1$ is alkyl, alkylaryl, or aryl; and $R^2$ is H, OH, halo, alkoxy, or OP wherein P is an oxygen protecting group. In another specific embodiment, the compound is GA-81:

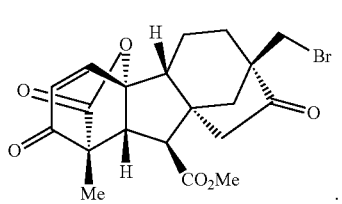

(GA-81)

The invention further provides a method of killing a cancer cell comprising contacting the cancer cell with an effective amount of a compound described herein to thereby kill the cancer cell. In some embodiments, the cancer cell is a lymphoma cell, a cervical cancer cell, a lung cancer cell, a breast cancer cell, a melanoma cell, or another type of cancer cell recited or referenced herein. Active compounds described herein, or prepared by the methods described herein, can therefore be used to treat cancer in a patient in need thereof.

The invention thus provides novel compounds of the formulas described herein, intermediates for the synthesis of compounds described herein, as well as methods of preparing compounds of the formulas described herein The invention also provides compounds that are useful as intermediates for the synthesis of other useful compounds. The invention provides for the use of the compounds described herein for the manufacture of medicaments useful for the treatment of bacterial infections or cancer in a mammal, such as a human. The invention thus provides for the use of the compositions described herein for use in medical therapy. The medical therapy can be treating inflammation, treating a bacterial infection, or treating cancer, for example, breast cancer, lung cancer, pancreatic cancer, prostate cancer, or colon cancer. The invention also provides for the use of a compound or composition as described herein for the manufacture of a medicament to treat a disease or adverse condition in a mammal. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3. Tanimoto similarity coefficients for compounds from FIG. 1 relative to the three natural products and to each other, where 1.0 represents perfect similarity.

DETAILED DESCRIPTION

Figure 1A:
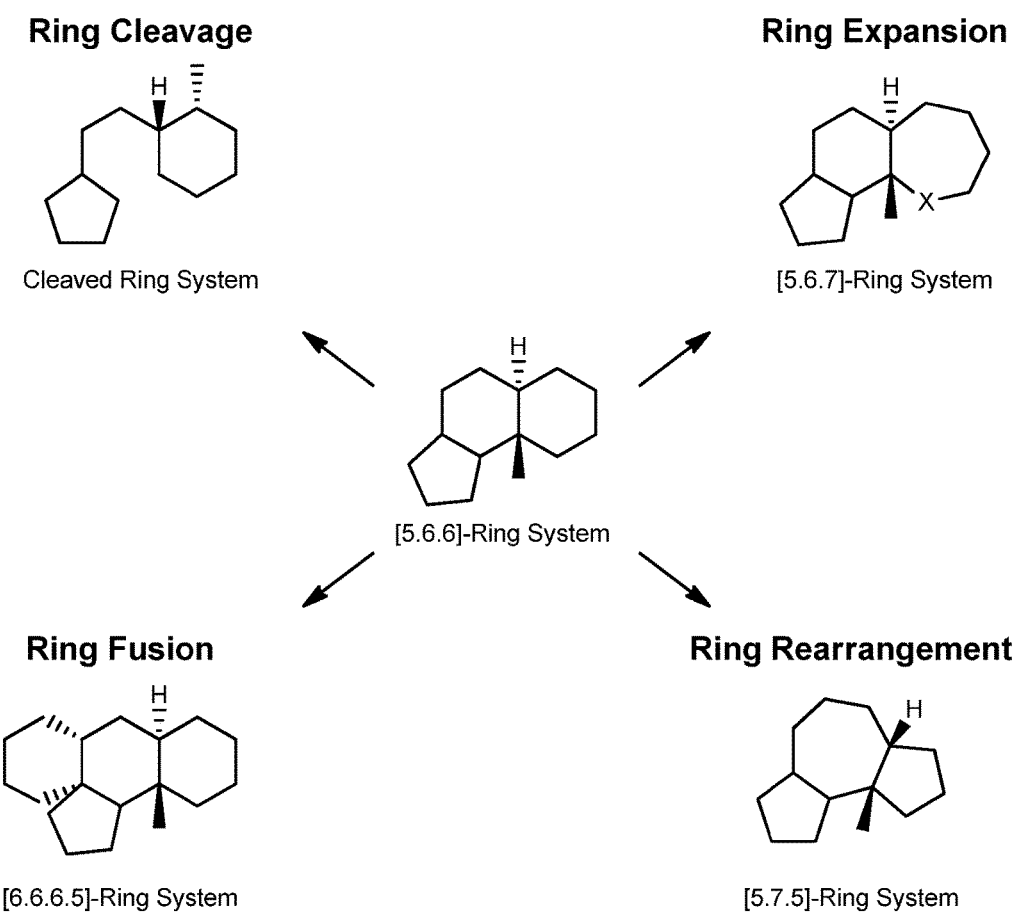
FIG. 1. A) Examples of structural diversity available from a [5.6.6] ring system. Complex and diverse structures produced from B) gibberellic acid, C) adrenosterone, and D) quinine.

The approach described herein uses natural products not as the end point, but as the starting point of methods for providing complex and structurally diverse compounds, starting with compounds inherently biased for biological success and systematically transforming them into diverse compounds of similar complexity. Certain chemical properties, such as molecular complexity and multiple stereogenic centers are extremely difficult to build in when producing large collections of compounds for high-throughput screening. The systematic application of ring distortion reactions on appropriate natural product starting materials offers a convenient approach to rapidly generate large numbers of complex and diverse small molecules. Natural products and their derivative compounds possess a high degree of molecular complexity, as shown by examination of Fsp3 and their number of stereogenic centers, and are structurally diverse, as indicated by Tanimoto similarity analysis. Depending on the exact application, specific structural features (e.g., MW, ClogP, H-bond donors/acceptors, and the like) can be programmed in by careful selection of diversification reactions and building blocks. This method to construct complex and diverse small molecules can rapidly provide compounds with properties suitable for a wide variety of biological and medicinal applications.

Collections of small molecules are routinely used in high-throughput screens to find new drug leads. In fact, from 1999 to 2008, 45 of the 50 first-in-class small molecule new molecular entity FDA approvals originated from a screen. The content of compound screening collections can have a significant impact on the types of drugs that come to market and the efficiency by which next-generation therapeutics are developed.

Many high-throughput screening (HTS) success stories involve biological targets that can be modulated by low molecular weight, relatively planar organic compounds with high $sp^2$ character and low, if any, stereochemical complexity. For example, kinases are outstanding drug targets whose enzymatic activity is typically inhibited at the adenosine triphosphate (ATP) binding site by organic compounds with no stereogenic centers and high aromatic content. However, tremendous challenges in lead identification still exist for more complex biological targets. For example, disruptors of protein-protein interactions and inhibitors of transcription factors are rarely small planar compounds with little stereochemical complexity. Thus, HTS campaigns versus these targets using compounds present in standard screening collections will fail. In addition, compounds active in certain therapeutic areas (e.g., antibacterials) tend to be larger and more complex than the average screening compound. For the reasons described above and many others, there exists a pressing need for the creation of compounds that are structurally complex and diverse.

Creative strategies to rapidly generate collections of complex molecules are therefore needed in the art. One approach is diversity-oriented synthesis (DOS), where simple starting materials are coupled to make diverse structures that are more natural product-like in terms of size, percentage of $sp^3$ carbons, and number of stereogenic centers (see e.g., Schreiber, *Science* 287, 1964-1969 (2000); Cui et al., *Proc. Natl. Acad. Sci. USA* 108, 6763-6768 (2011)). Other methods include the synthesis of natural product-inspired scaffolds that can be efficiently and differentially decorated, skeletal diversifications, and the synthesis of chiral and conformationally constrained oligomers (see, e.g., Pelish et al., *J. Am. Chem. Soc.* 123, 6740-6741 (2001); Goess et al., *J. Am. Chem. Soc.* 128, 5391-5403 (2006); Kumar et al., *Org. Lett.* 7, 2535-2538 (2005); Balthaser et al., *Nature Chem.* 3, 969-973 (2011)). A novel approach for the rapid creation of complex and diverse compounds is disclosed herein.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantifies of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl(iso-propyl), 1-butyl, 2-methyl-1-propyl (isobutyl), 2-butyl(sec-butyl), 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent (e.g., linking two groups together), and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, irifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano, as well as the moieties illustrated in the schemes and Figures of this disclosure, and combinations thereof. Additionally, suitable substituent groups can be, e.g., —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, —NC (=O)R, —C(=O)R, —C(=O)NRR, —S(=O)$_2$O$^-$, —S(=O)$_2$OH, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with one or more of the substituents above.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

When used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

As used herein, "natural product" refers to a chemical compound or substance that is produce and/or modified by a living organism, the living organism can be eukaryotic or prokaryotic. A natural product can be a compound produced by an organism and secreted to the environment upon which another organism modifies that compound to form yet another natural product.

As used herein, "non-natural product" refers to a chemical compound or substance that is not produce by a living organism, but rather is produced synthetically, such as a derivative of a natural product.

As used herein, "small molecule" refers to an organic compound having a molecular weight of greater than about 150 Daltons and less than 1,500 Daltons. Small molecules of the invention, in various embodiments, can have molecular weights of about 250 to about 1,200 Daltons, about 275 to about 1,000 Daltons, about 300 to about 900 Daltons, about 300 to about 750 Daltons, about 310 to about 600 Daltons, about 325 to about 500 Daltons, about 500 to about 1200 Daltons, about 250 to about 475 Daltons, about 400 to about 600 Daltons, or about 325 to about 500 Daltons.

As used herein, a compound with "high structural complexity" refers to a compound that has at least two ring structures and at least one type of heteroatom (e.g., O, N, S, P, or a halogen). In some embodiments, a compound having high structural complexity has at least 3, at least 4, or at least 5 rings. In certain embodiments, a compound having high structural complexity has at least two different types of heteroatoms, or at least three different types of heteroatoms. In various embodiments, a compound having high structural complexity has at least two, at least three, at least four, at least five, at least six heteroatoms. In some embodiments, at least two of the rings are fused, spiro-fused, or bicyclic. In various embodiments, at least two of the rings are at least five-membered rings, or at least one of the ring is an at least a five-membered ring and at least one of the rings is an at least six-membered ring. In some embodiments, a compound having high structural complexity has at least one, at least two, or at least three non-aromatic rings.

As used herein, a compound with "high stereochemical complexity" refers to a compound that has at least two stereogenic centers. In some embodiments, a compound with high stereochemical complexity has at least two stereogenic centers wherein the at least two stereogenic centers are atoms of ring structures of the compound. In other embodiments, the compound with high stereochemical complexity can have three, four, five, six, seven, eight, nine, ten or more stereogenic centers, and any number of the stereogenic centers can be atoms of ring structures of the compound. In certain embodiments, each stereogenic center is at an atom of a ring structure of the compound.

The term "Fsp3" refers to the number of sp$^3$-hybridized carbon atoms in a compound divided by the sum of the sp$^3$- and sp$^2$-hybridized carbon atoms. A higher Fsp3 value correlates with a lower melting point and enhanced aqueous solubility.

As used herein, a "ring distortion" refers to a ring cleavage, a ring expansion, a ring fusion, a ring rearrangement, or a combination thereof.

As used herein, a "derivative of a natural product" is a compound that has the same core ring structure as the natural product but has been altered by an addition reaction, elimination reaction, by transforming one functional group to new functional group (e.g., an oxidation or reduction reaction), and/or has an additional protecting group.

ClogP is used as an approximate measure of lipophilicity. See http://www.biobyte.com/. Compounds with higher ClogP values tend to have non-ideal solubility, promiscuity and off-target toxicity.

Compounds and Methods of the Invention

A novel approach for the rapid creation of complex and diverse compounds is disclosed herein. In this process structurally complex natural product compounds are converted, in an average of three chemical steps, to markedly different core scaffolds that are distinct from each other and from the natural product starting compound. Using chemoselective reactions, the core ring structures of readily available natural product compounds can be systematically altered via ring system distortion reactions, i.e., ring expansions, ring cleavage, ring rearrangements, ring fusion, ring substitution, or combinations thereof (FIG. 1A). Importantly, this method stands in contrast to traditional optimization campaigns whose goals are to enhance the inherent biological activity of a natural product compound (e.g., erythromycin to azithromycin, or penicillin to amoxicillin).

Figure 1B:
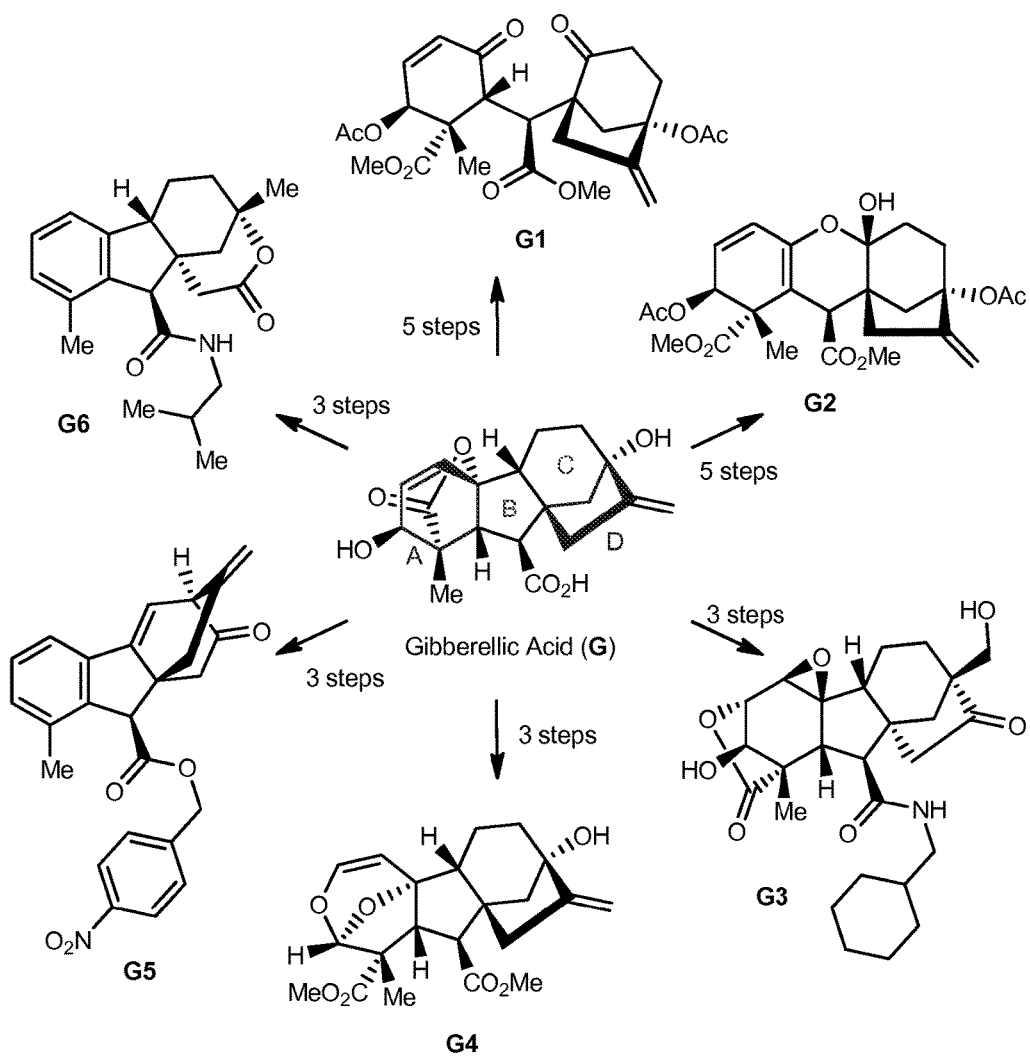
Figure 1C:
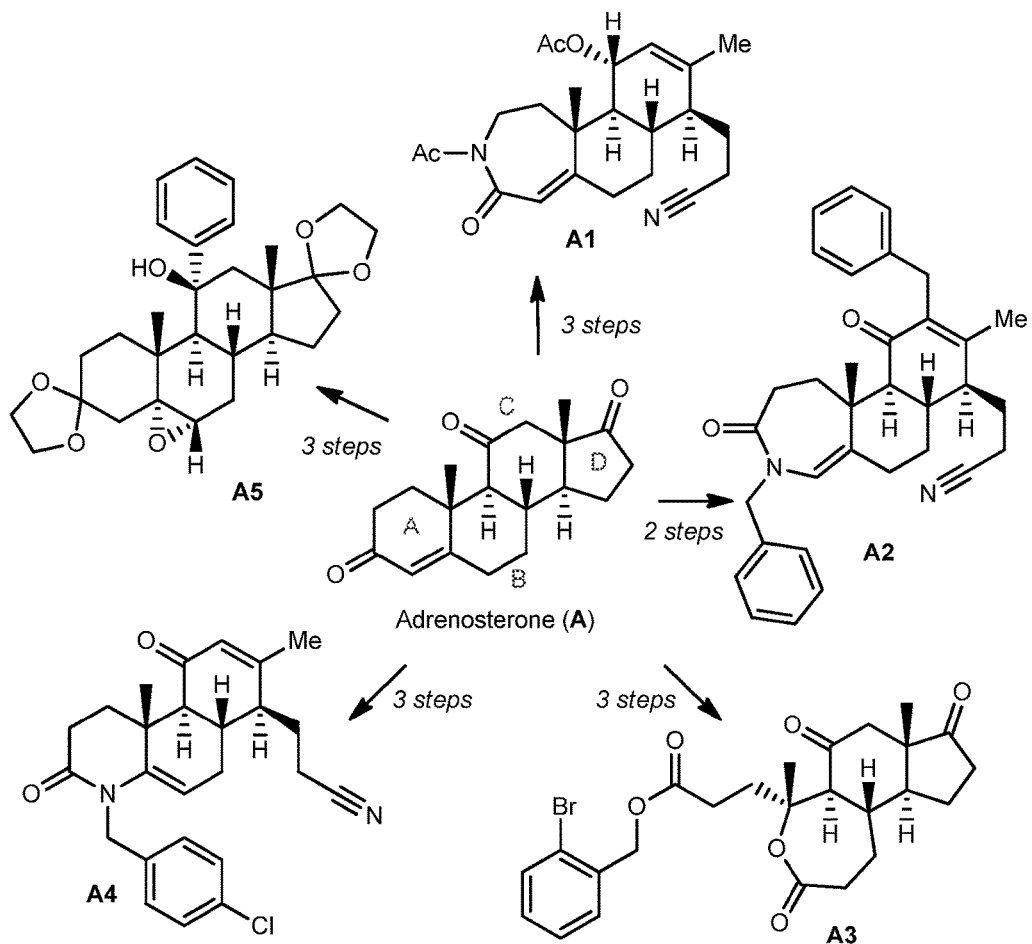
Figure 1D:
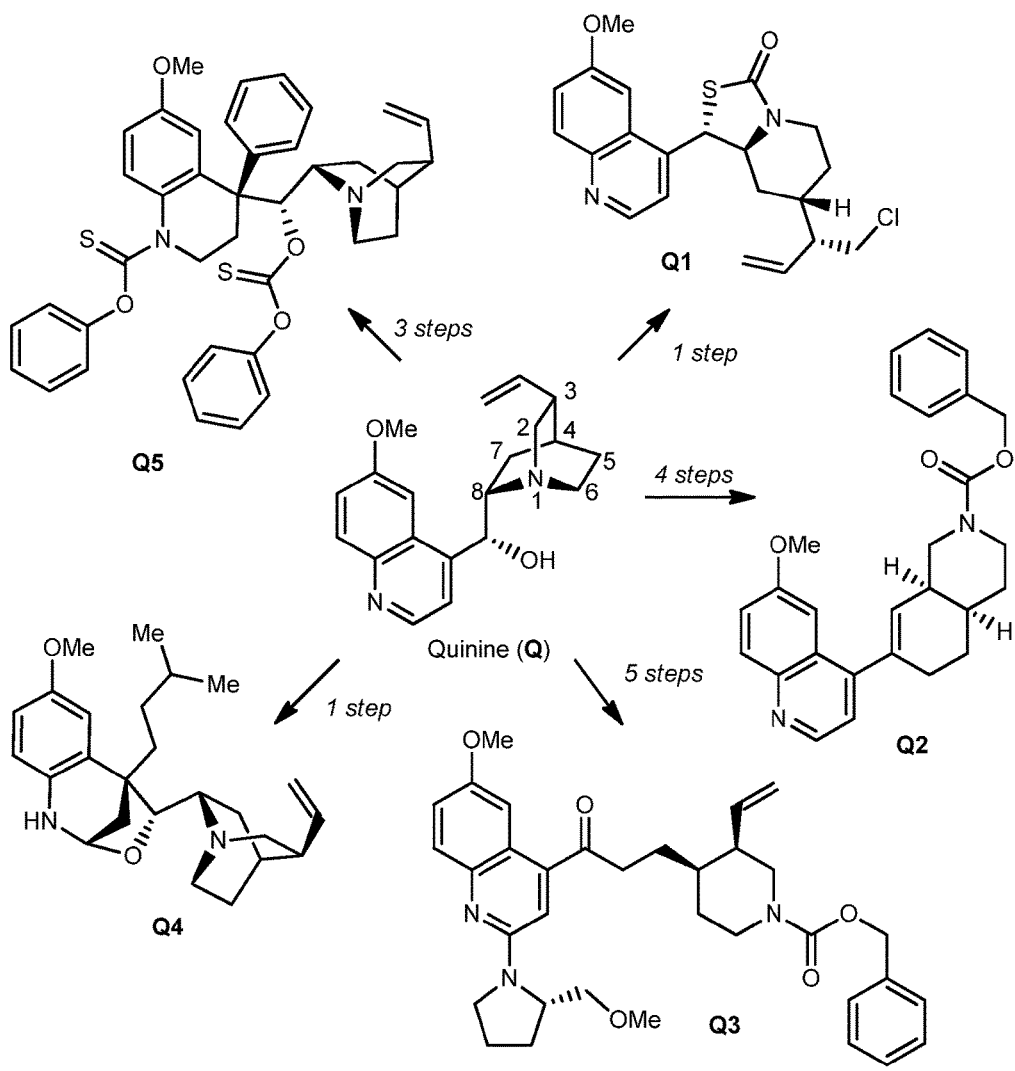

To demonstrate this scaffold diversification approach, three commercially available ($2-20 per gram) natural product compounds were selected from different structural classes: gibberellic acid (diterpene), adrenosterone (steroid), and quinine (alkaloid) (FIG. 1B-D). However, numerous other readily available natural and non-natural product compounds can likewise be converted into diverse and complex derivatives using this strategy. Compounds other than natural product compounds, i.e., non-natural product compounds or semi-synthetic compounds, can be used as starting materials if those compounds possess sufficiently appropriate chemical specificities (functional groups, number of ring structures, number of chiral centers, $Fsp^3$, ClogP, etc.) as the natural compounds.

Gibberellic Acid.

Gibberellic acid (G, FIG. 1B) is a plant hormone isolated from *Gibberella fujikuroi* and produced industrially on the ton scale. Gibberellic acid contains a tetracyclic diterpene core with a fused lactone, two allylic alcohols, an exocyclic olefin, and a carboxylic acid, enabling selective and independent functionalization of each ring of the core structure via a variety of ring system distortion reactions. These structural features have been utilized in concert with known degradation reactions of G (see, e.g., Avent et al., *Magn Reson Chem* 27, 237-240 (1989); Mulholland et al., *J. Chem. Soc.*, 2693-2701 (1958)) in the construction of complex and diverse scaffolds in 3-5 steps from gibberellic acid (FIG. 1B, G1-G6).

Hydrazine-promoted elimination of the lactone on G (Grove et al., *J. Chem. Soc.*, 3007-3022 (1960)), followed by methylation and acetylation, affords triene G7 (Scheme 1A). Treatment with meta-chloroperoxybenzoic acid (mCPBA) yields an intermediate epoxide with complete selectivity for the tetrasubstituted olefin, which, when subjected to oxidative cleavage conditions using pyridinium chlorochromate (PCC), produces diketone G1. Following exposure of G1 to silica or acid, the A-ring ketone tautomerizes and collapses onto the C-ring ketone to form ketal G2; this can be achieved directly from the epoxide precursor using PCC and an acidic workup.

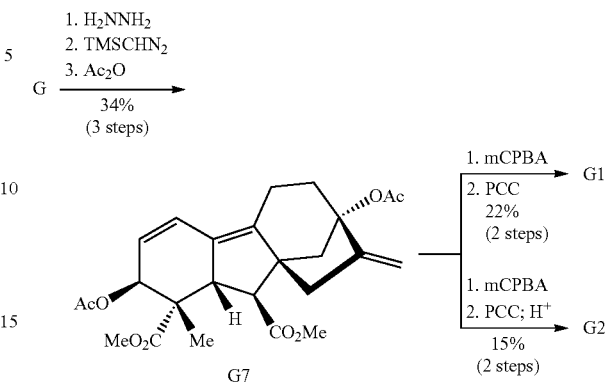

Exposure of gibberellic acid to basic conditions leads to lactone rearrangement and the generation of alkene G8 (Scheme 1B) (Henderson et al., *Nature* 193, 1055-1056 (1962)). Amidation of G8, followed by treatment with trifluoroperacetic acid provides G3 via epoxidation of both alkenes and Wagner-Meerwein rearrangement to afford the primary alcohol.

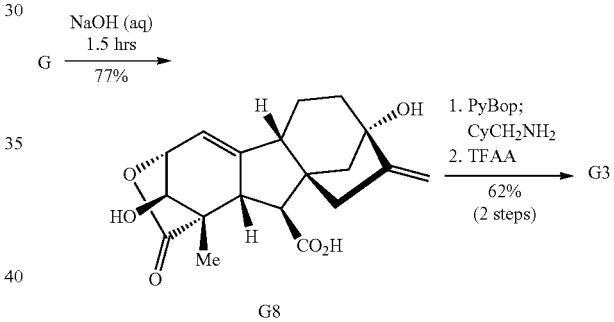

Prolonged exposure to base led to the cleavage of the lactone ring to provide diol G9 (Scheme 1C). Methylation of the carboxylic acids, followed by oxidative cleavage of the diol with sodium periodate and intramolecular [4+2] cycloaddition provides acetal G4.

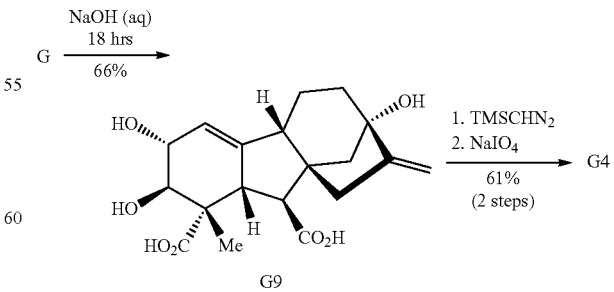

Treatment of gibberellic acid with dilute hydrochloric acid results in the elimination of the lactone and decarboxylation to aromatize the A-ring (Cross et al., *J. Chem. Soc.*, 4670-4676 (1954)), enabling the isolation of allo-gibberic acid (G10, Scheme 1D). Esterification followed by oxidative rearrangement with 2,3-dichloro-5,6-dicyanobenzoquinone (DDQ) gives [2.2.2]-bicycle G5.

Scheme 1D. Route to G5.

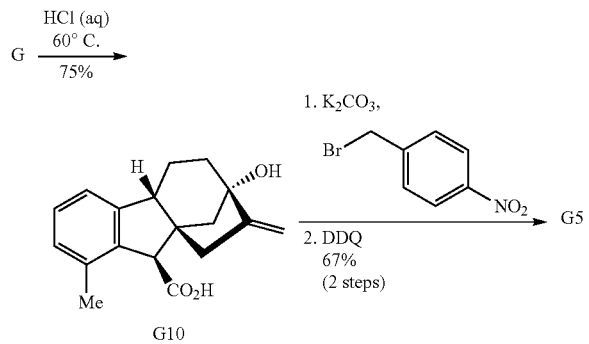

Exposure of gibberellic acid to refluxing hydrochloric acid resulted in aromatization and a Wagner-Meerwein rearrangement; to form gibberic acid (G11, Scheme 1E). Amidation through an intermediate acyl chloride followed by Baeyer-Villiger oxidation produces lactone G6.

Scheme 1E. Route to G6.

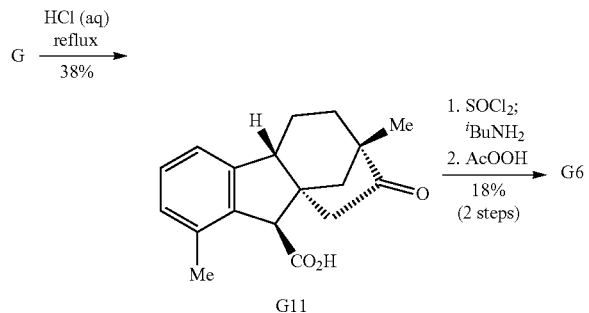

Adrenosterone.

Adrenosterone (A, FIG. 1C) is a steroid hormone that is produced in the adrenal cortex of mammals. Adrenosterone's structurally complex steroidal framework contains five contiguous stereogenic centers; in addition, each of the four individual carbocyclic rings of adrenosterone is functionalized with an enone or ketone. Though embedded in the A-ring, the enone is also connected to the B-ring as an exocyclic double bond, while the C- and D-rings are each functionalized with a ketone. These key functional groups provide synthetic handles that can be strategically manipulated to synthesize novel, diverse, and complex chemical scaffolds (FIG. 1C, A1-A5).

During the synthetic investigations of adrenosterone a novel, substrate-dependent Schmidt reaction was discovered that effected both ring expansion and ring cleavage in a single synthetic transformation. Subjecting adrenosterone to Schmidt conditions for one hour gives two constitutional isomers (A6 and A7 in Scheme 2A) resulting from a tandem D-ring cleavage and A-ring expansion. Final dehydration of the subsequent primary amide in concentrated sulfuric acid results in the observed cyano groups in A6 and A7 (Scheme 2A).

Scheme 2A. Route to A1 and A2.

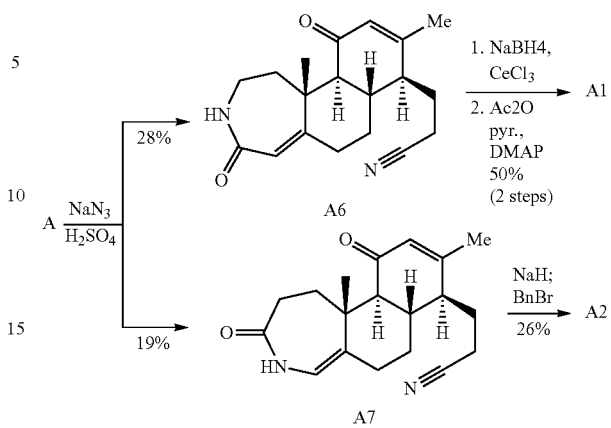

Enamide A6 and lactam A7 were each elaborated to novel complex molecular scaffolds. Lactam A6 was subjected to Luche conditions to reduce the C-ring enone followed by treatment with acetic anhydride in pyridine with catalytic 4-dimethylaminopyridine (DMAP) to afford bis-acylated structure A1 (Scheme 2A). Enamide A7 was treated with sodium hydride followed by benzyl bromide, resulting in bis-benzylated enone A2.

Oxidative cleavage of various steroidal A-ring enones is known using NaIO$_4$ and catalytic KMnO$_4$ (Boruah et al., Steroids 73, 637-641 (2008)). The oxidative cleavage of adrenosterone's A-ring was successfully carried out to give acid A8 (Scheme 2B), which upon treatment with 2-bromobenzyl alcohol and dicyclohexylcarbodiimide (DCC) provides the corresponding ester. Finally, a selective ring expansion at the B-ring ketone was carried out using a Baeyer-Villiger reaction with peracetic acid to give lactone A3.

Scheme 2B. Route to A3 and A4.

Acid A8 was also condensed with 4-chlorobenzylamine upon heating in ethanol in a sealed tube to provide the corresponding A-ring substituted enamide. The A-ring substituted enamide was then subjected to a final Schmidt ring cleavage reaction of the D-ring using the previously described Schmidt protocol to yield structure A4 (Scheme 2B).

Adrenosterone underwent a double ring fusion (at the A- and D-rings) reaction upon treatment with ethylene glycol and catalytic para-toluenesulfonic acid (p-TsOH). The resulting ketone intermediate was then reacted with phenyllithium to give A9 (Scheme 2C) (see Stephan et al., *Tetrahedron* 62, 3052-3055 (2006)). Final treatment of A9 with mCPBA resulted in epoxide ring fusion at the B-ring to yield A5.

Scheme 2C. Route to A5.

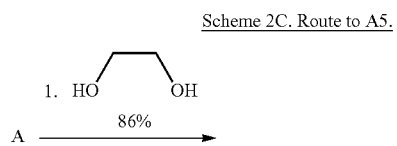

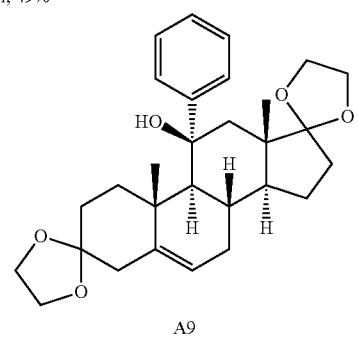

Quinine.

Quinine (Q, FIG. 1D), an alkaloid isolated from the bark of the genus Cinchona, is used commercially as an antimalarial therapeutic and food additive. Unlike some natural products employed herein, quinine is composed of two discrete ring systems; however, the stereochemical complexity and diverse functionality (tertiary aliphatic amine, secondary alcohol, vinyl olefin, aryl ether, quinoline) of quinine make it amenable to selective ring system distortion to create diverse molecular scaffolds (FIG. 1D, Q1-Q5).

In the course of these investigations an unprecedented tandem ring cleavage/ring fusion of Q effected by treatment with thionochloroformate was discovered. Ring cleavage of the quinuclidine by the mild amine dealkylating reagent O-phenyl thionochloroformate (Millan et al., *Aust. J. Chem.* 52, 841-850 (1999)) was found to occur regioselectively at N1-C2. In addition to the expected ring cleavage and chloride addition, this reaction also leads to diastereoselective rearrangement of the free alcohol and thionocarbamate to form (S)-thiocarbamate Q1 (Scheme 3A) as a single isomer, as confirmed by X-ray crystallography.

Scheme 3A. Route to Q1.

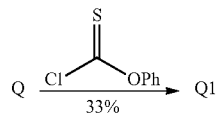

In contrast to the regioselectivity observed with O-phenyl thionochloroformate, acid-catalyzed Hoffman-type elimination of quinine (Smith and Williams, *Angew. Chem. Int. Ed.*

*Engl.* 47, 1736-1740 (2008)) occurred exclusively at N1-C8 and addition of benzyl chloroformate to the crude degradation product resulted in ketone Q6 (Scheme 3B) which was elaborated to form two unique structures (Q2-Q3). Petasis methylenation of ketone Q6 followed by 1,2-ring fusion via ring-closing metathesis using second generation Grubbs catalyst formed [4.4.0]-bicycle Q2. Quinoline N-oxidation of Q6 using mCPBA, chlorination with oxalyl chloride, and nucleophilic displacement of the chloride by (S)-2-(methoxymethyl)pyrrolidine provides amine Q3.

Scheme 3B. Route to Q2 and Q3.

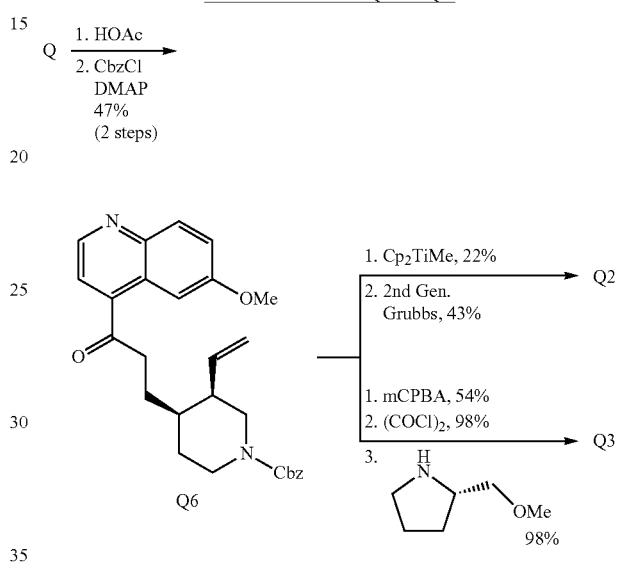

Ring system distortions of the quinoline ring were accomplished through the addition of Grignard reagents (Hintermann et al., *Angew. Chem. Int. Ed.* 46, 5164-5167 (2007)). Exposure of quinine to isoamylmagnesium bromide in toluene resulted in nucleophilic addition to the quinoline ring followed by hemiaminal ether formation to provide Q4 as a single diastereomer (Scheme 3C).

Scheme 3C. Route to Q4.

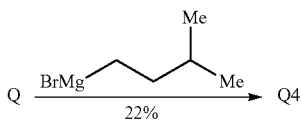

Alternatively, reduction of the hemiaminal ether formed through the addition of phenylmagnesium chloride to quinine with sodium cyanoborohydride provided tetrahydroquinoline Q7 (Scheme 3D). Treatment of Q7 with O-phenyl thionochloroformate resulted in bis-acylation to form Q5 as the major product with no observed chlorine incorporation.

Scheme 3D. Route to Q5.

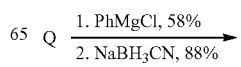

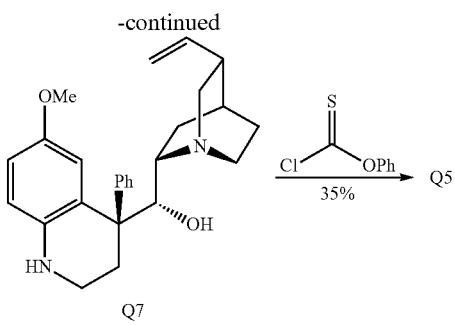

In certain embodiments, each step in any given reaction scheme and/or protocol can be carried out any number of times in order to achieve a desired structural endpoint of the derivative compound. The order of steps in any given sequence can be altered to provide additional variations. The steps can be repeated sequentially or following other steps depending on the chemical nature of the starting compound and that of the desired derivative.

Compound Analysis.

Figure 4:
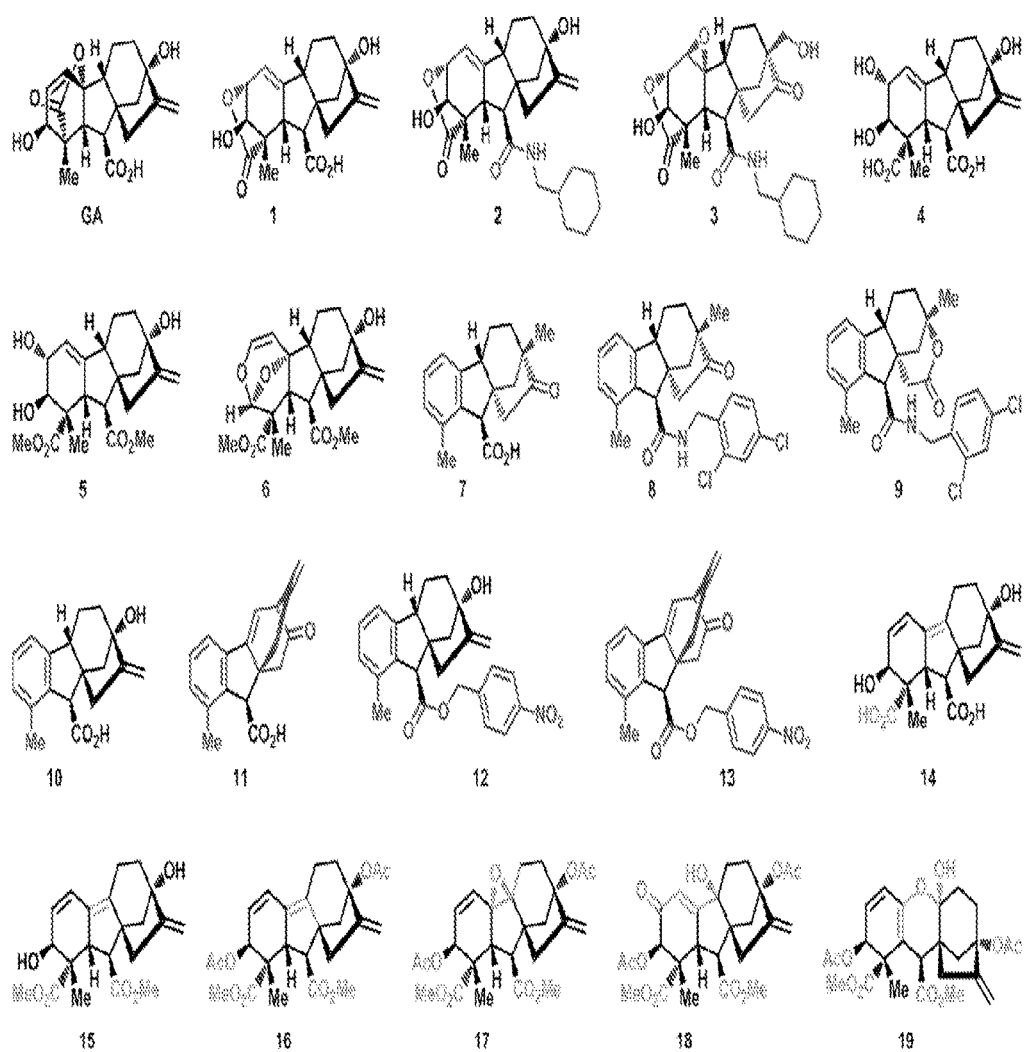
FIG. 4. Summary of a variety of specific compounds prepared.
Figure 5A:
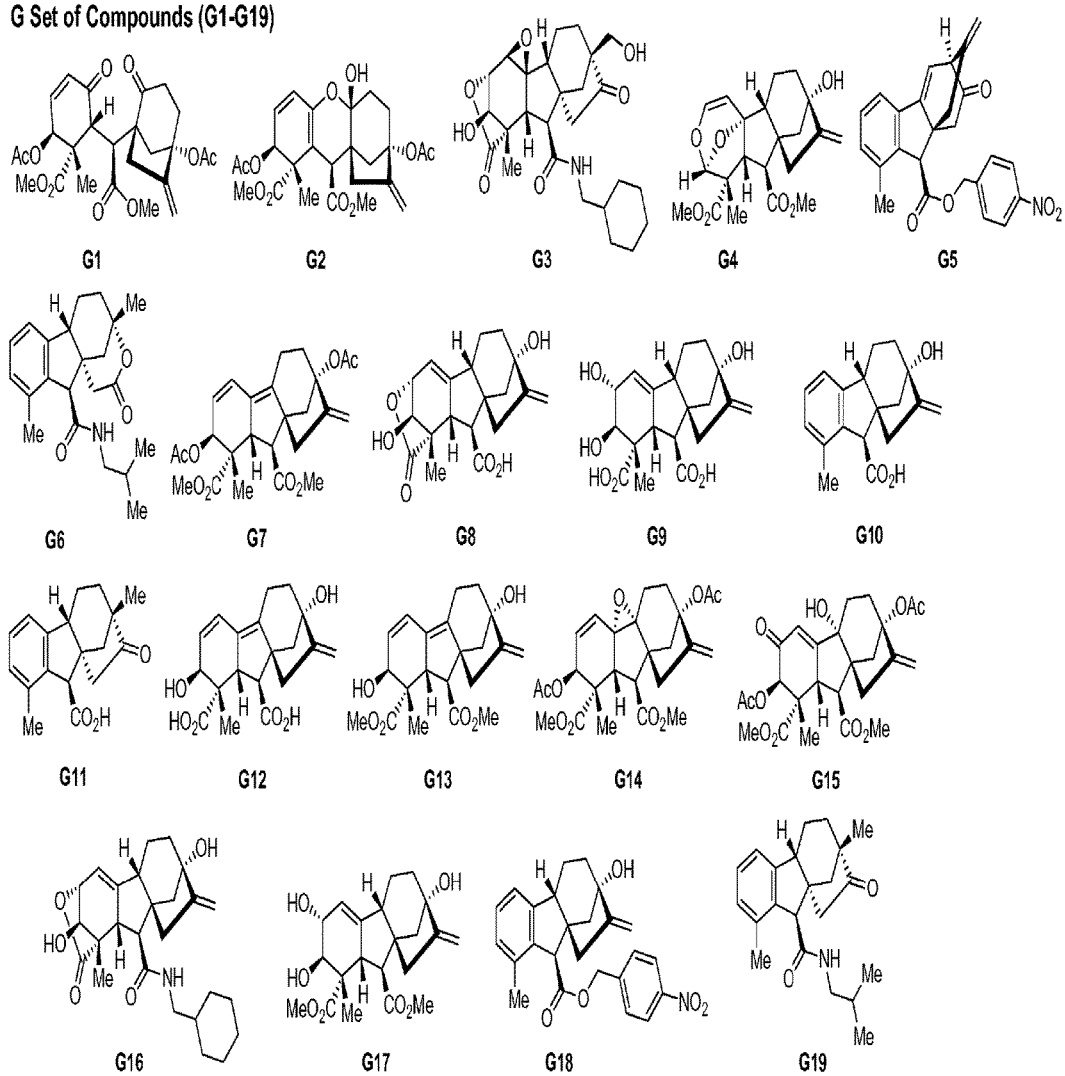
FIG. 5. Chemical structures of 49 compounds produced through the complexity-to-diversity method. A) G Set of Compounds (G1-G19); B) A Set of Compounds (A1-A18); C) Q Set of Compounds (Q1-Q12).
Figure 5B:
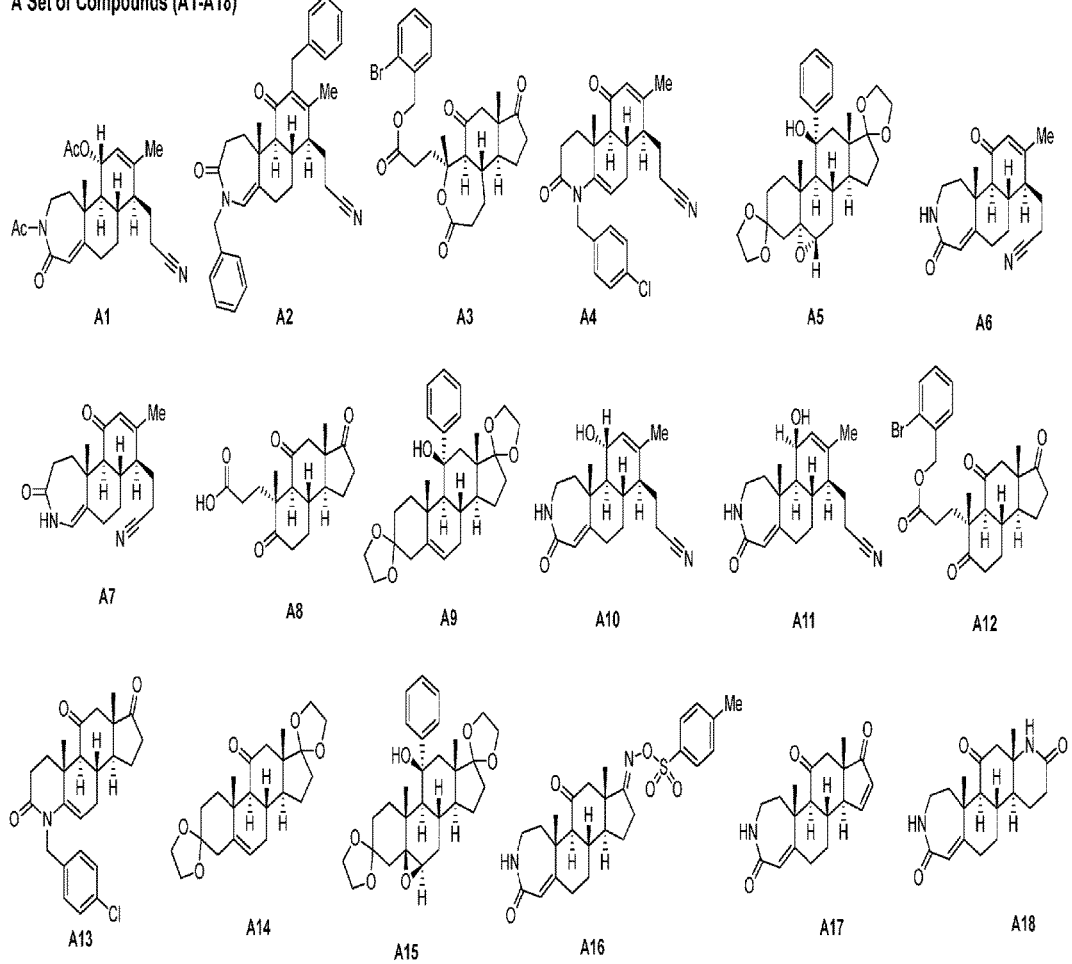
Figure 5C:
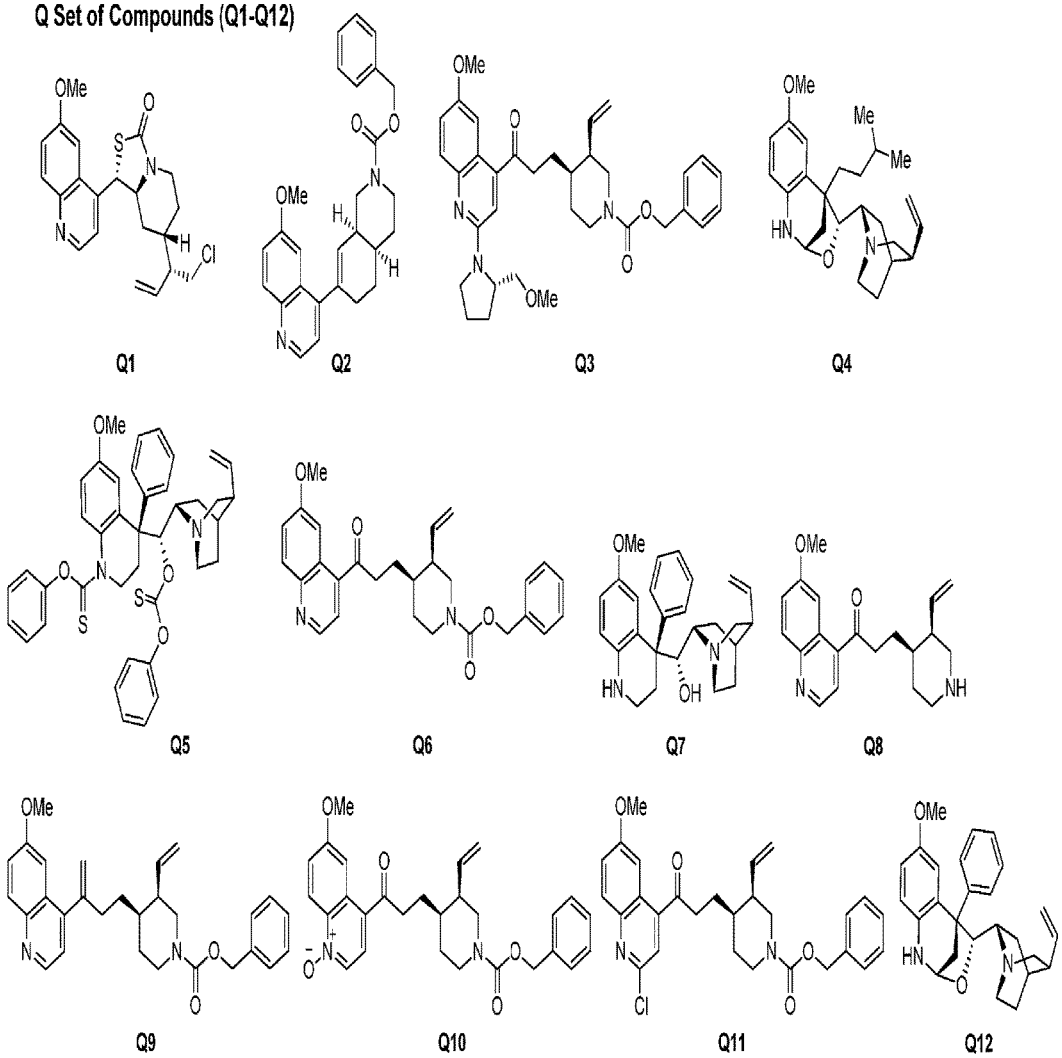

In contrast to many standard small molecule library constructions in which simple starting materials are built up into more complex products, an important consequence of starting with natural product compounds is that all intermediates are structurally complex and worthy of inclusion in the final library in their own right. For example, in the synthesis of the compounds depicted in FIGS. 1B, 1C, and 1D, there are 19, 18, and 12 complex structures produced, respectively (exemplary structures are shown in FIGS. 4 and 5). Thus, detailed in FIG. 1 is the synthesis of 49 structurally and stereochemically complex small molecules from three readily available natural products. Most of these compounds are created in good yield, and importantly, the compounds can be prepared on a multigram scale, which allows for full structural characterization (see Examples 1-7) and multiple biological screens. In addition, each of these compounds possesses sites for diversification, allowing for the facile and rapid creation of dozens of additional complex and diverse compounds.

Advances in chemoinformatics enable the evaluation of massive chemical and biological data sets, which allows for an approximated determination of the structural features of small molecules that correlate with biological activity. It is apparent that many compounds in screening collections have non-trivial liabilities, including non-specific reactivity and a propensity to aggregate, leading to false positives and complicating the development of a hit into a drug. When specific disease areas are examined, the problem is more acute. For example, analysis of compounds that kill Gram-negative bacterial pathogens shows an average ClogP of −0.1, a realm occupied by vanishingly few compounds in commercial screening collections (O'Shea and Moser, *J. Med. Chem.* 51, 2871-2878 (2008)).

To quantify the structural complexity and diversity of the novel compounds created through this paradigm, structural features known to track with biological activity were analyzed. A recent study examined eight structural parameters (molecular weight, ClogP, polar surface area, rotatable bonds, hydrogen bond donors/acceptors, complexity, and fraction $sp^3$ carbons (Fsp3)) of compounds synthesized by medicinal chemists over the last 50 years, and then compared them to marketed drugs (Walters et al., *J. Med. Chem.* 54, 6405-6416 (2011)). An important conclusion from the analysis is that medicinal chemists are creating compounds with lower-than-ideal Fsp3, and with ClogP values that are higher than ideal. The Fsp3 and ClogP of several compounds described herein were calculated and compared to compounds in large screening collections. For this analysis a 150,000-member compound collection was used from the ChemBridge MicroFormat Library, which is a standard commercial screening collection and one used by others in comparison analyses.

Fsp3 is the number of $sp^3$-hybridized carbon atoms in a compound divided by the total number of carbons (Yan and Gasteiger, *QSAR Comb. Sci.* 22, 821-829 (2003)). The benefits of higher Fsp3 include lower melting points and enhanced aqueous solubility. Analyses of these properties have revealed that lead or "discovery" compounds have lower Fsp3 than actual drugs (0.36 vs. 0.47). The analysis of medicinal compounds synthesized over the last 50 years has shown that average Fsp3 is declining, a result attributed in part to the increasing ease of $sp^2$-$sp^2$ coupling reactions.

ClogP is often used as a rough measure of lipophilicity; among other things, compounds with higher ClogP values tend to have non-ideal solubility, promiscuity, and off-target toxicity. Analysis has shown that the average ClogP for all medicinal compounds synthesized since 1985 has gone up significantly, and is higher than the average for marketed drugs. Indeed, a survey of 18 pharmaceutical companies from 2000-2010 shows the majority are still synthesizing compounds with a mean ClogP over 4.

Figure 2:
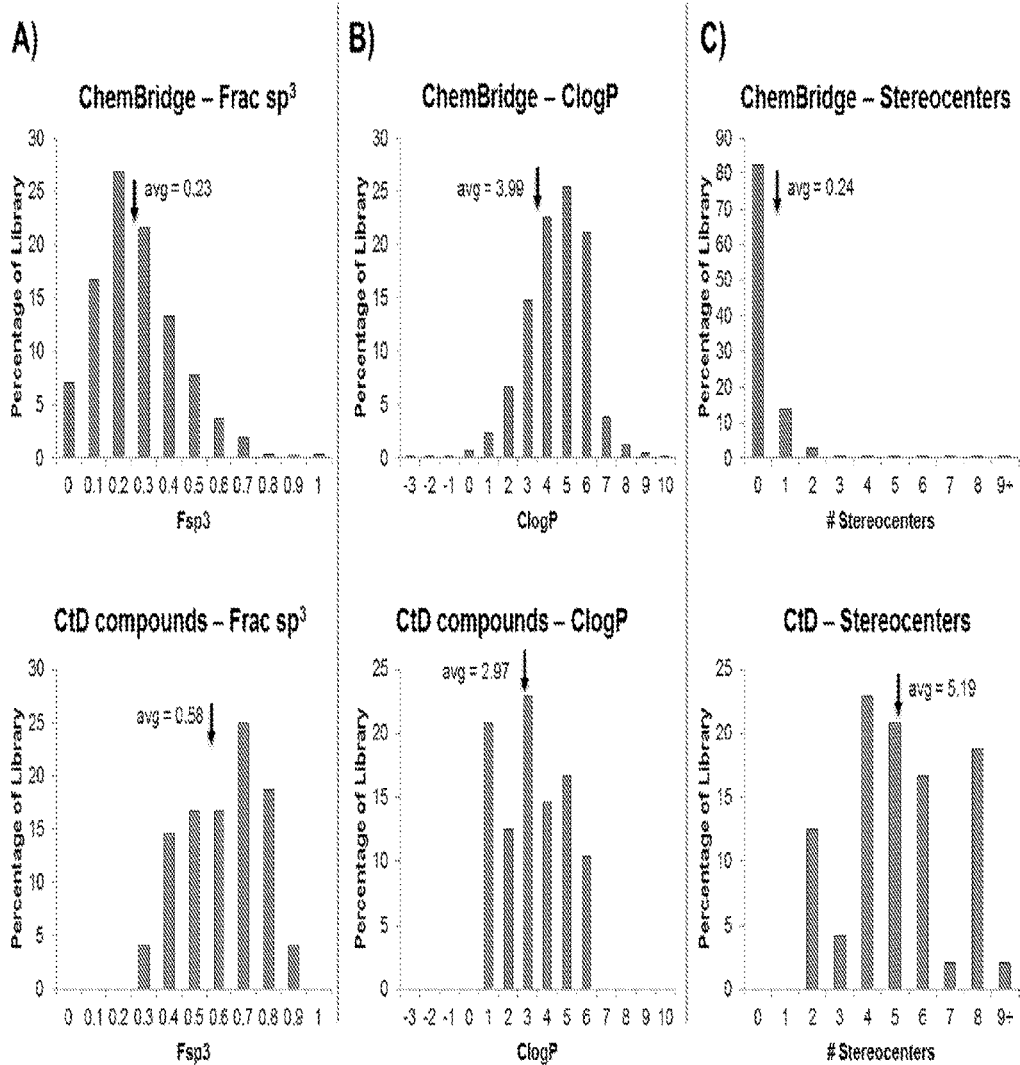
FIG. 2. Compounds created through the complexity-to-diversity (CtD) method have markedly different properties from those in commercial screening collections. For this analysis, a 150,000 compound collection from ChemBridge Corporation was utilized and compared to the 45 compounds described herein for A) Fraction of $sp^3$-hybridized carbons (Fsp3), B) Calculated logP (ClogP), and C) number of stereogenic centers per compound.

As shown by the histograms in FIG. 2A, the compounds illustrated in FIG. 5 have an average Fsp3 of 0.58, a number considerably higher than those in the commercial collection (avg=0.23). In a similar vein, the average ClogP for the compounds illustrated in FIG. 5 is a factor of 10 lower than those in the commercial screening set (2.97 vs. 3.99; FIG. 2B).

The presence of stereogenic centers in a compound can also be used as a surrogate for molecular complexity. Compounds with stereogenic centers may interact more specifically with their chiral receptors, and compounds with low or no stereogenic centers are more prone to attrition during the various stages of drug discovery. Commercial screening collections are dominated by achiral compounds; for example, of the 150,000 compound ChemBridge collection 82% have no stereogenic centers, while 14% have a single stereocenter, leaving 4% of these compounds with multiple stereogenic centers (FIG. 2C). Accordingly, the synthesis of complex and diverse compounds using natural products as input materials offers a tremendous advantage in this regard. Of the 45 compounds illustrated in FIG. 5, all have two or more stereogenic centers, with the average number being 5.2 (FIG. 2C).

While visual inspection of the structures in FIG. 1 readily reveals considerable structural diversity, a similarity metric has been applied to allow for more quantitative comparisons. For this, Tanimoto coefficients were generated in Discovery Studio® Visualizer software (Accelrys Software Inc.) using ECFP_6 molecular fingerprints, for example, as described by Huigens et al., *Nature Chemistry* (2013) 5, 195-202, and its supplementary information.

Figure 3:
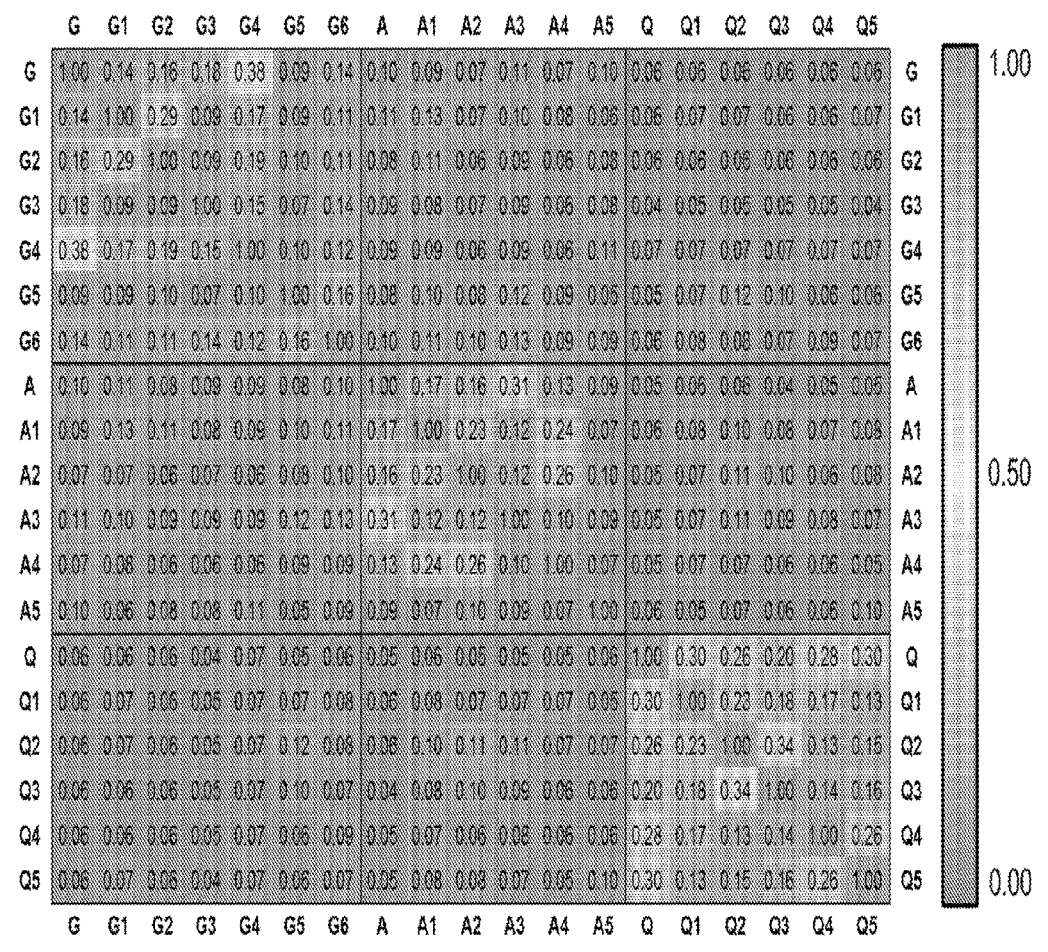
Figure 6:
FIG. 6. Tanimoto similarity coefficients for compounds with peripheral transformations of the three natural products, as compared to Tanimoto coefficients for the G, A, and Q sets.
Figure 7A:
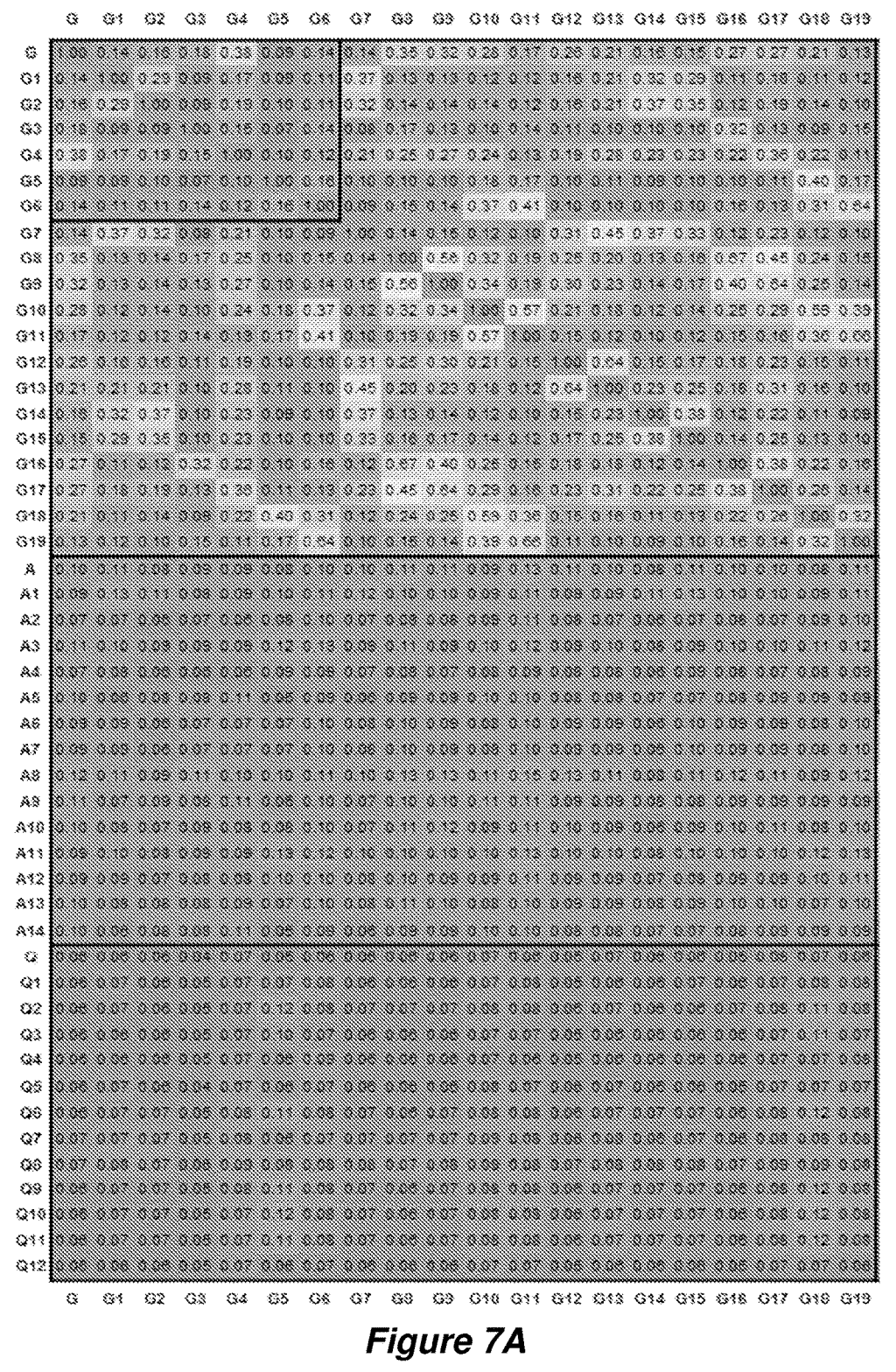
Figure 7B:
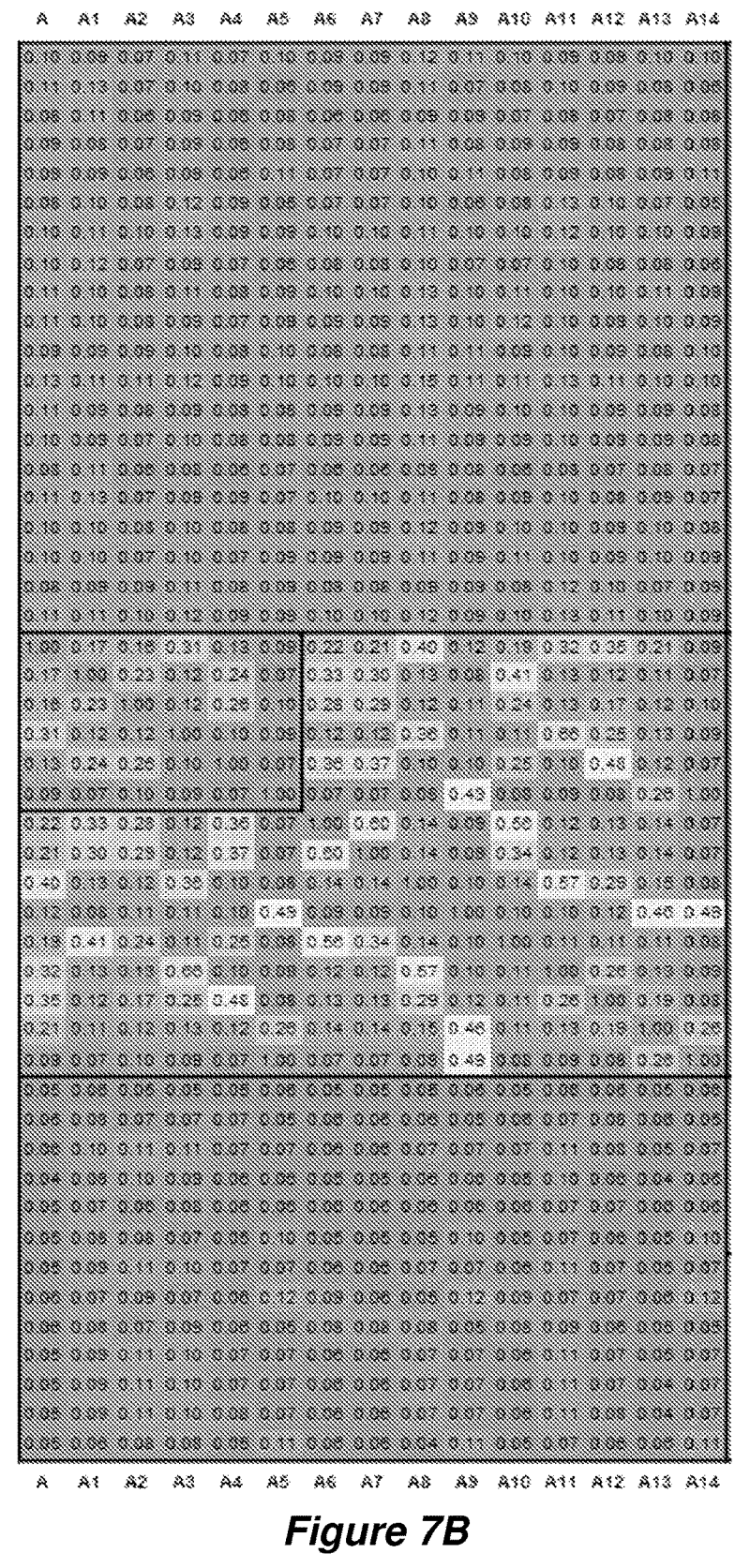
Figure 7C:
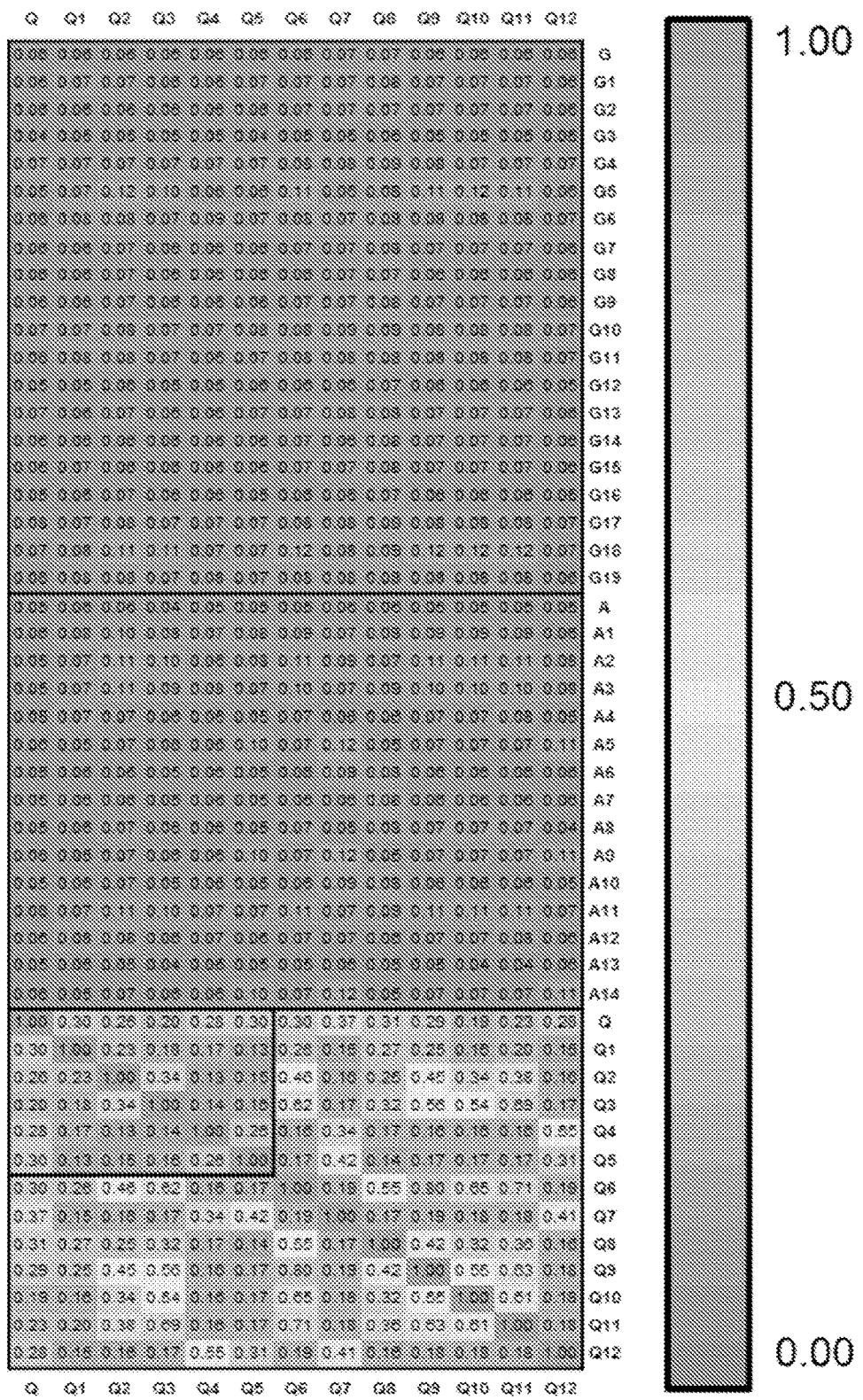
FIG. 7. Full Tanimoto similarity matrix for all synthesized compounds (A) left panel of the matrix; B) middle panel of the matrix; C) right panel of the matrix). Each compound was used as the reference input for every other compound and Tanimoto coefficient was calculated in Discovery Studio (Accelrys Software Inc.) based on ECFP_6 molecular fingerprints. Target compounds shown in FIG. 1 (i.e. G1-G6, A1-A5, Q1-Q5) are indicated by additional frames. Note that diastereomeric compounds A5 and A14 appear identical by this connectivity-based analysis.

Each structure in FIG. 1 was used as the reference input for every other compound in the set, and a similarity score was obtained for each pair on a scale from 0 to 1, with 1 representing perfect similarity. As shown by the data in FIG. 3, the compounds depicted in FIG. 1 are very different both from one another and from the parent natural products. The G, A, and Q compound sets are expected to be quite different from one another; however, even within the sets the compounds show low Tanimoto coefficients (average for G set=0.15, average for A set=0.15, average for Q set=0.22), indicating considerable structural diversity. For calibration purposes, this analysis was also performed on structures representing simple modifications to the parent compounds. As expected, these minor structural changes afford higher similarity scores (average of 0.7, see FIG. 6), consistent with work of others using Tanimoto coefficients (Huggins et al., *ACS Chem. Biol.* 6, 208-217 (2011)). For the similarity matrix of the full 49 compound set, see FIG. 7.

Various Methods of the Invention.

To demonstrate that traditional derivatization strategies can be applied even to these highly complex compounds that contain an array of chemical moieties, small libraries were synthesized based on 12 of 49 specific compounds prepared. As shown in Schemes 1.1, 1.2, 13, 1.4, 2.1, 2.2, 3.1, 3.2, 3.3, and 3.4 (Examples 1-3 below), small collections of imides, N-benzylated amides, aryl amides, amides, lactones, secondary and tertiary alcohols, epoxides, triazoles, ureas and sulfonamides were created readily from these 12 small molecules, and in this manner an additional 119 highly complex compounds were synthesized.

Figure 8:
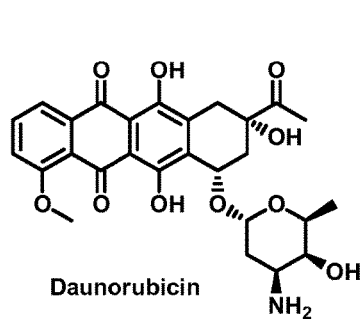
FIG. 8. Representative natural products amenable to modification by a Complexity-to-Diversity approach based on structural complexity and availability, according to various embodiments.
Figure 8:
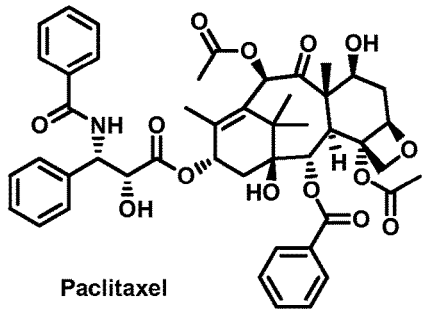
Figure 8:
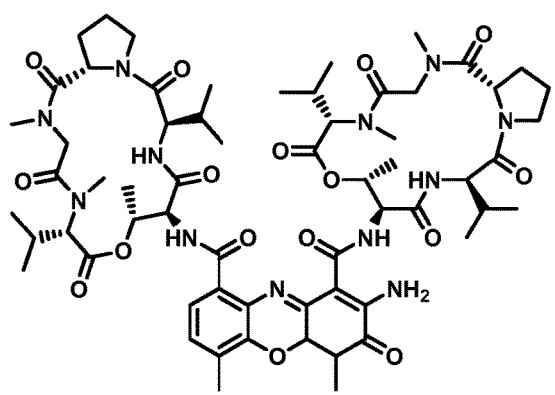
Figure 8:
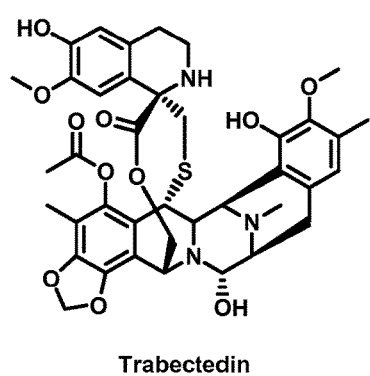
Figure 8:
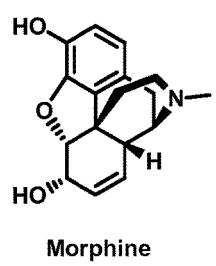
Figure 8:
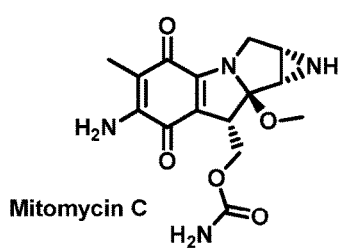
Figure 9:
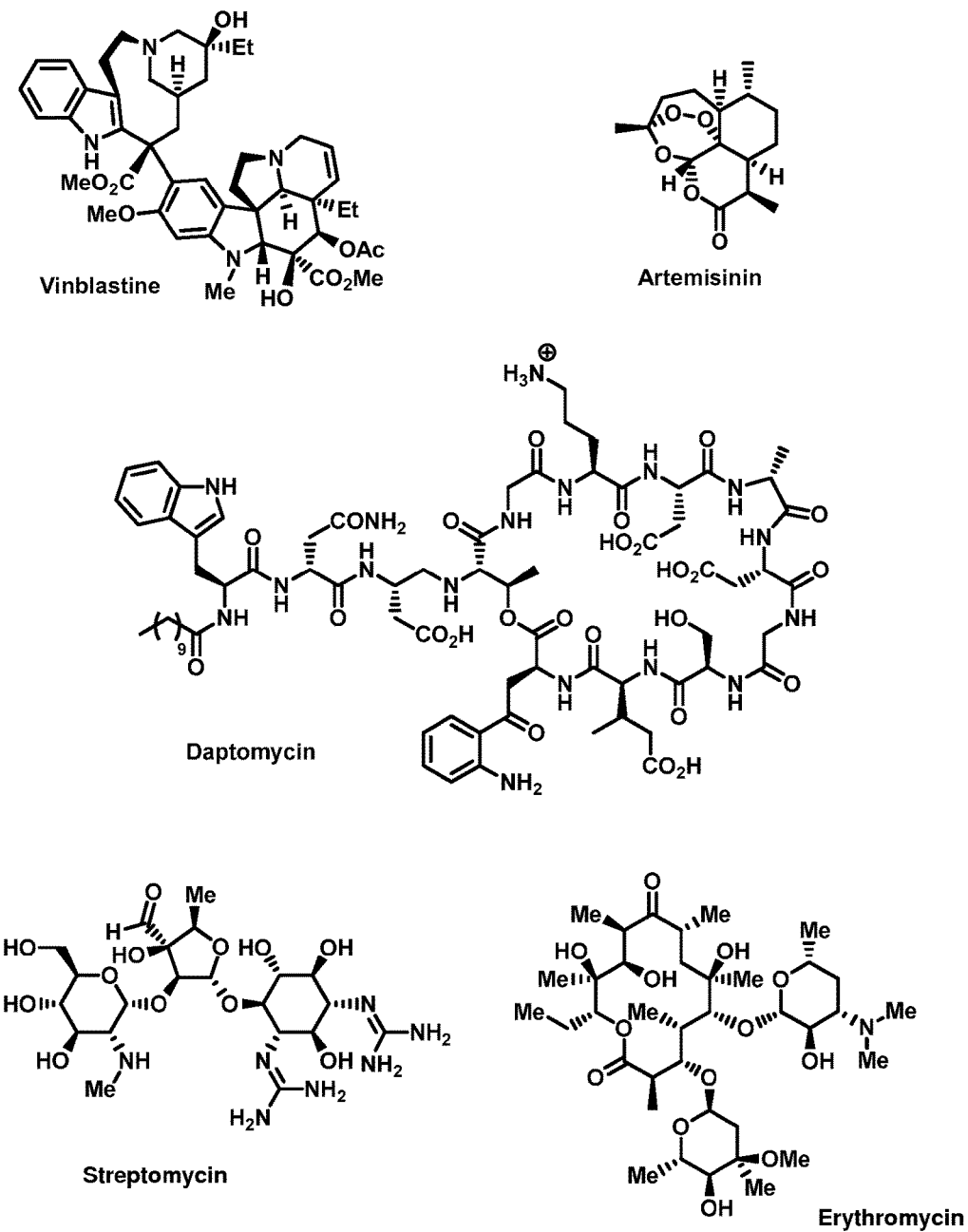
FIG. 9. Representative natural products amenable to modification by a Complexity-to-Diversity approach based on structural complexity and availability, according to various embodiments.
Figure 10:
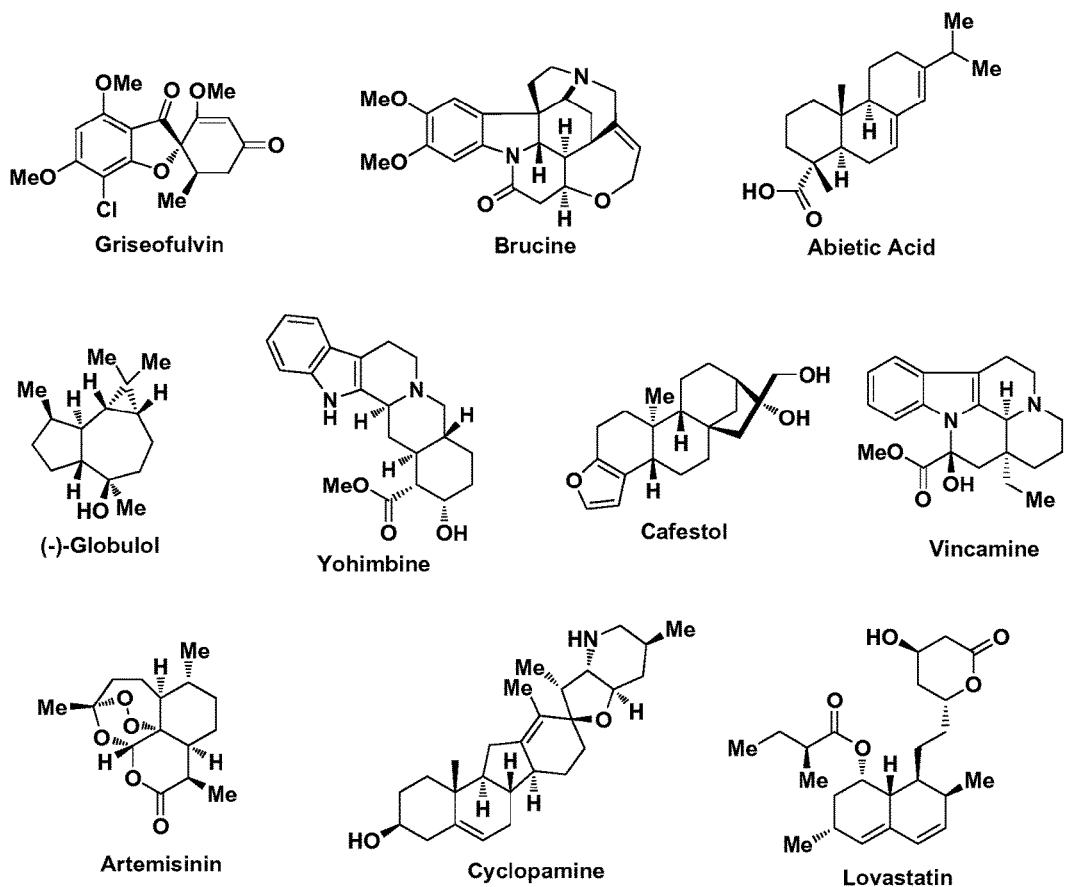
FIG. 10. Representative natural products amenable to modification by a Complexity-to-Diversity approach based on structural complexity and availability, according to various embodiments.

Thus, the complexity-to-diversity (CtD) approach has been demonstrated with three complex natural products. The same methods and strategy can be applied to a multitude of other natural products (including, but not limited to, the compounds illustrated in FIGS. 8-10 and other natural products recited herein). In certain embodiments, compounds amenable to diversification through this method will be available in suitable quantities (either from commercial sources or through isolation) and possess orthogonal functional groups allowing for ring system distortion and diversification through chemoselective reactions. As exemplified with gibberellic acid, adrenosterone, and quinine, certain common ring distortion strategies facilitate the rapid diversification (in ≤5 synthetic steps) of complex natural products. The methods described herein can include, for example, one or more of the following reactions.

1) Ring Cleavage Reactions.

Ring cleavage reactions enable dramatic structural changes in one chemical step and a frequently utilized tactic in the complexity-to-diversity (CtD) approach. A benefit of ring cleavage reactions is that they typically provide new functional groups that can be further diversified. Examples include the base-promoted hydrolysis of the lactone on isogibberellic acid (G9), oxidative cleavage on adrenosterone (A8), and N—C cleavage (e.g., Hoffmann-type elimination) on quinine (Q).

2) Ring Expansion Reactions.

Ring expansion reactions are chemical reactions that increase the number of atoms in a ring of a cyclic compound. Ring expansion reactions can be useful in forming novel ring skeletons or can act as a prelude to ring cleavage reactions. There are several options for chemical reactions that induce ring expansion, with the Baeyer-Villiger and Schmidt reactions being powerful methods to target ketone and enone functionalities for ring expansion. Ring expansion, as a ring system distortion tactic, has been successfully applied in the synthesis of target structures G5, A3, A6, and A7. In certain embodiments, other ring expansion reactions can include, but are not limited to, the Beckmann rearrangement, the Dowd-Beckwith ring expansion reaction, the Tiffeneau-Demjanov rearrangement, the vinylcyclopropane-cyclopentene rearrangement, and the Buchner ring expansion.

3) Ring Fusion Reactions.

Ring fusion reactions can provide further diversification by connecting disparate structural elements in the pre-existing ring system or addition of a new, constrained ring to the ring system. Various modes of ring fusion were used to demonstrate this tactic on each natural product. For example, the ring-closing metathesis product Q2 (1,2-ring fusion), formation of the [4+2] cycloaddition product G3, and formation of bis-ketal A9 (1,1-ring fusion) result from ring fusion reactions. Ring substitution reactions can also be an example of ring fusion. In the example of ring substitution, the composition of the ring changes without altering the ring size, as exemplified by the creation of the A-ring enamide in A4.

4) Ring Rearrangement Reactions.

Ring rearrangement reactions that reorganize the core structure can be dictated by the natural product and can be applicable on a case-by-case basis. This tactic can be illustrated with gibberellic acid in the acid-catalyzed Wagner-Meerwein rearrangement to provide ketone G11, or the DDQ oxidation of G10. These transformations are facilitated by the propensity of the tertiary alcohol in gibberellic acid's C-ring to form a ketone upon carbon migration, altering the molecular topology.

5) Ring Contraction Reactions.

Ring contraction reactions are chemical reactions that decrease the number of atoms in a ring of a cyclic compound. Examples of ring contraction reactions include the Favorskii rearrangement, which results in a new carboxylic acid functional group from a starting cycloalkyl α-halo ketone.

In various embodiments, other reactions can be used in combination with the ring distortion strategies described above. Examples of such reactions can include, but are not limited to, the following reactions and other reactions exemplified herein.

Oxidation Reactions.

Oxidation reactions involve a loss of electrons in a compound of interest, or the gain of oxygen, for example, when a compound combines chemically with one or more oxygen atoms. Examples include oxidations with DDQ or PCC.

Reduction Reactions.

Reduction reactions involve a gain of electrons in a compound of interest, or alternatively, a gain of one or more hydrogen atoms. Reduction reactions include, for example, Luche reductions, Birch reductions, and various reductions with hydrides.

Conjugation Reactions.

Conjugation reactions involve the linking of two molecules together, such as various addition reactions, including alkylation reactions. Conjugation reactions typically involve combining two relatively complex structures and/or structures with differing functional groups. A variety of reactions can be used carry out conjugation reactions. Techniques for conjugating one compound to another are standard transformations and are well known in the art. Such techniques are described by, for example, by Greg T. Hermanson in *Bioconjugate Techniques*, Academic Press, San Diego, Calif. (1996).

Substitution Reactions.

In various embodiments, a substitution reaction is a reaction in which a functional group of a compound is replaced by another functional group. Examples of substitution reactions include but not be limited to those that are nucleophilic, electrophilic, radical, or organometallic in nature.

Elimination Reactions.

An elimination reaction can be a reaction in which two substituents are removed from a compound in either a one or two-step mechanism, typically to form an unsaturated bond.

Protections Deprotection Reactions.

Protection reactions can include, but not limited to, those reactions that introduce a protective or protecting group into a functional group on a compound which thereby modifies the reactivity of that functional group when exposed to certain reagents and/or chemical environments. In certain embodiments, the protective group lowers the reactivity of the target functional group toward certain chemical environments and/or reagents. In various embodiments and by way of example, an alcohol (R—OH) can be protected by reacting it with acetyl halide to form an ester. The alcohol can thereafter be recovered by reaction with acid or base. This recovery of the original functional group can be referred to as a deprotection or a deprotection reaction.

Variations of these reactions and additional reactions include hydrolysis reactions, aromatisation reactions, decarboxylation reactions, acylation or acetylation reactions, lactone formation, lactam formation, aminal formation, acetal formation, epoxidation reactions, and functional group transformation reactions, such as an amidation, which is a functional group transformation that results in the formation of an amide.

General Synthetic Methods

The invention relates to methods of making chemically diverse compounds. Individual synthetic transformations used in the methods can be those known in the art and the compounds can be prepared using any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure*, 5$^{th}$ Ed. By M. B. Smith and J. March (John Wiley & Sons, New York, 2001); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., as necessary for the reaction of interest, solvents will be aprotic or protic depending on the conditions required, and reaction times can be about 1 minute to about 10 days. Work-up typically consists of quenching any unreacted reagents followed by partition between a water organic layer system (extraction) and separation of the layer containing the product of interest.

Oxidation and reduction reactions are typically carried out at temperatures near room temperature (about 23° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and can be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group or heteroatom. The particular removable blocking group employed is not always critical and preferred removable hydroxyl blocking groups include conventional groups such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of various schemes and formulas herein can be protecting groups, as described herein.

Suitable protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Additional Embodiments

The invention also provides a method of preparing a compound, wherein the compound is a natural product, such as gibberellic acid, adrenosterone, or quinine, or a derivative thereof. The method can include at least one of following steps performed one or more times in any order: carrying out a ring expansion reaction on the natural product; carrying out a ring fusion reaction on the natural product; carrying out a ring rearrangement reaction on the natural product; carrying out a ring cleavage reaction on the natural product; carrying out an oxidation reaction on the natural product; carrying out a conjugation reaction on the natural product; carrying out a reduction reaction on the natural product; carrying out a substitution reaction on the natural product; carrying out a elimination reaction on the natural product; removing a portion of the structure on the natural product; protecting one or more functional groups on the natural product; or deprotecting one or more functional groups on the natural product starting compound. In any event, the method includes at least one ring distortion reaction.

In some embodiments, the disclosure provides a method for constructing a library of compounds for high-throughput screening. The method can include selecting a natural product wherein the molecular weight of the natural product starting compound is about 200 to about 1000; modifying the starting compound to form a plurality of modified compounds, wherein each compound includes at least one ring distortion compared to the natural product (or derivative thereof); analyzing the plurality of resulting compounds (products); and optionally selecting at least one of the plurality of modified compounds as a potential drug lead based on the analysis.

In other embodiments, the disclosure provides a compound prepared by a method described herein wherein the compound is a derivative of a natural product, for example, gibberellic acid, adrenosterone, or quinine, or another natural product recited or illustrated herein, wherein at least one ring of the natural product has been distorted to provide the ring structure of the resulting compound. The method can also be carried out on derivatives of a natural product, for example, a natural product recited or illustrated herein. The invention further provides novel compounds as described herein, for example, for inclusion and evaluation in biological screens, including high-throughput screens.

In one specific embodiment, the invention provides the compound GA-4:

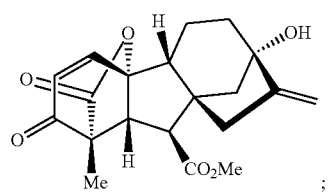

(GA-4)

and/or a derivative, salt, or solvate thereof. In another specific embodiment, the invention provides the compound GA-81:

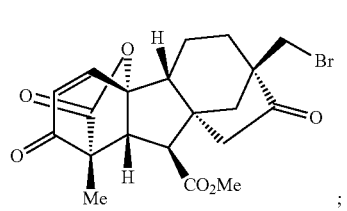

(GA-81)

and/or a derivative, or solvate thereof.

In further embodiments, the invention provides a pharmaceutical composition comprising a pharmaceutically acceptable carrier, and at least one compounds prepared by a method described herein. In some embodiments, the compound can be a ring distortion product of gibberellic acid, adrenosterone, or quinine, or a derivative thereof. The invention further provides methods of treating cancer, inflammation, or a bacterial infection in a patient in need of such treatment, the method comprising administering an effective amount of a pharmaceutically composition as described herein. Further embodiments, forms, features, aspects, benefits, objects, and advantages of the disclosure shall become apparent from the detailed description and figures provided herewith.

Various Embodiments of the Disclosure

In various embodiments, the invention provides a compound prepared by a synthetic method wherein the compound comprises a ring distortion compared to the starting material compound. In certain embodiments, the starting material compound is a natural product or a non-natural product. Natural products, for example and by way of example only, can include but are not limited to hormones, secondary metabolites, primary metabolites, pigments or constituent compounds. In certain embodiments, pigments can include but are not limited to porphyrins, carotenoids, betalains and anthocyanins. Example porphyrins can include but are not limited to chlorophylls. Primary metabolites can include compounds that are directly involved in normal growth, development, and reproduction of an organism. These compounds can include amino acids, nucleotides, vitamins, or antioxidants.

Other natural products that can be used in the methods described herein include, but are not limited to abeitic acid, abrisentan, ampicillin, amrubicin, anidulafungin, apomorphine, artemotil, aztreonam, biapenem, bivalirudin, bleomycin, brucine, cafestol, caryophyllene oxide, capsaicin, caspofungin, cefditoren, codinaeopsin, colchicine, daptomycin, dimethyltryptamine, doripenem, dronabinol, ephedrine, ergotamine, erlotinib, ertapenem, erythromycin, everolimus, exenatide, fumagillin, galantamine, griseofulvin, isosorbide, ixabepilone, lisdexamfetamine, lapatinib, macrolides, maraviroc, mescaline, methylnaltrexoneonicafungin, miglustat, mycophenolate, nitisinone, orlistat, paclitaxel, pazopanib, phenethylamine, pimecrolimus, quinine, retapamulin, rimonanbant, rivaroxaban, romidepsin, rosuvastatin, sorafenib, spiruchostatins, streptomycin, telavancin, telithromycin, temsirolimus, tigecycline, tipranavir, tiotropium, trabectedin, vincamine, yohimbine, ziconotide, and zotarolimus.

Furthermore, in certain embodiment's, natural products for the method can be selected using a number of structural and stereochemical properties as initial criteria. The structural and stereochemical properties can include, for example and by way of example only, molecular weight, the number of stereogenic centers, carbon content, atomic ratios such as CN content, functional group content, aromatic content, the number of rings, Fsp3, ClogP, Tanimoto coefficients, planarity non-planarity, and the like. In certain embodiments natural products may be selected when those compounds may have molecular weights of, for example, about 200 to about 1000, or about 250 to about 900, or about 350 to about 750, or about 400 to about 500. In various embodiments, selected natural product compounds may have Fsp3 values that are, for example, about 0.3 to about 1, about 0.4 to about 1, about 0.35 to about 1, about 0.4 to about 1, about 0.5 to about 1, about 0.6 to about 1, about 0.7 to about 1, about 0.8 to about 1, or about 0.85 to about 1. Additionally, in certain embodiments, selected natural product compounds may have ClogP values containing ranges of values. For example, the ClogP values can be less than about 4. Further, selected compounds can be non-planar. In various embodiments, these properties can be elements or limitations of the range of products produced by the methods of the invention.

In further embodiments, the invention provides a method for providing compounds having high structural and stereochemical complexity, for example, by performing a series of reactions described herein, including at least one ring distortion reaction. The reactions can include at least one of following reactions performed one or more times in any order: selecting a natural product; carrying out a ring expansion reaction; carrying out a ring fusion reaction; carrying out a ring rearrangement reaction; carrying out a ring cleavage reaction; carrying out an oxidation reaction; carrying out a conjugation reaction; carrying out a reduction reaction; carrying out a substitution reaction; carrying out an elimination reaction; removing a portion of the structure of the compound or intermediate; protecting one or more functional groups on the compound; or deprotecting one or more functional groups on the compound. These reactions can be performed on the starting natural product, or a derivative thereof, and/or on any subsequent compound prepared as a result of carrying out a particular reaction.

Thus, the invention provides methods for constructing a library of compounds for high-throughput screening. The method can include, for example, selecting a starting material compound wherein the molecular weight of the starting material compound is from about 200 to about 1000; modifying the starting compound to form a plurality of modified compounds, wherein the modifications include at least one ring distortion reaction; optionally analyzing the plurality of modified compounds; and optionally selecting at least one of the plurality of modified compounds as a lead compound for further analysis and modification.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mgm$^2$, conveniently 10 to 750 mgm$^2$, most conveniently, 50 to 500 mgm$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the assays as described herein as well as those well known to those of skill in the art.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials and Methods

Chemical reagents were purchased from commercial sources and used without further purification. Quinine and adrenosterone were purchased from Sigma-Aldrich (at ≥98.0% purity for both natural products) and gibberellic acid (90% purity) was purchased from AK Scientific. These three natural products can be purchased for between $2 and $20 per gram. Anhydrous solvents used during these studies were dried after being passed through columns with activated alumina.

All G, A and Q compounds from FIG. 5 have $^1$H NMR, $^{13}$C NMR and HRMS (all spectra shown in separate NMR file). Various 2-D NMR experiments were conducted on these compounds as necessary. All library compounds derived from the G, A and Q compound sets have $^1$H NMR and HRMS (representative spectra shown in separate NMR file).

$^1$H NMR and $^{13}$C NMR experiments were recorded on Varian Unity spectrometers at 400 MHz and 500 MHz and 125 MHz, respectively. Spectra were obtained in the following solvents (reference peaks also included for $^1$H and $^{13}$C NMRs): CDCl$_3$ ($^1$H NMR: 7.26 ppm; $^{13}$C NMR: 77.23 ppm), d$_6$-DMSO ($^1$H NMR: 2.50 ppm; $^{13}$C NMR: 39.52 ppm), d$_6$-acetone ($^1$H NMR: 2.05 ppm; $^{13}$C NMR: 206.26 ppm), d$_6$-benzene ($^1$H NMR: 7.16 ppm; $^{13}$C NMR: 128.06 ppm), CD$_3$OD ($^1$H NMR: 3.31 ppm). NMR experiments were performed at room temperature unless otherwise indicated. Chemical shift values are reported in parts per million (ppm) for all $^1$H NMR and $^{13}$C NMR spectra. $^1$H NMR multiplicities are reported as: s=singlet, d=doublet, t=triplet, q=quartet, m=multiplet, br=broad. All melting points were uncorrected and obtained using a Digimelt MPA 160.

Example 1. Adrenosterone Derived Compounds: Synthesis and Characterization

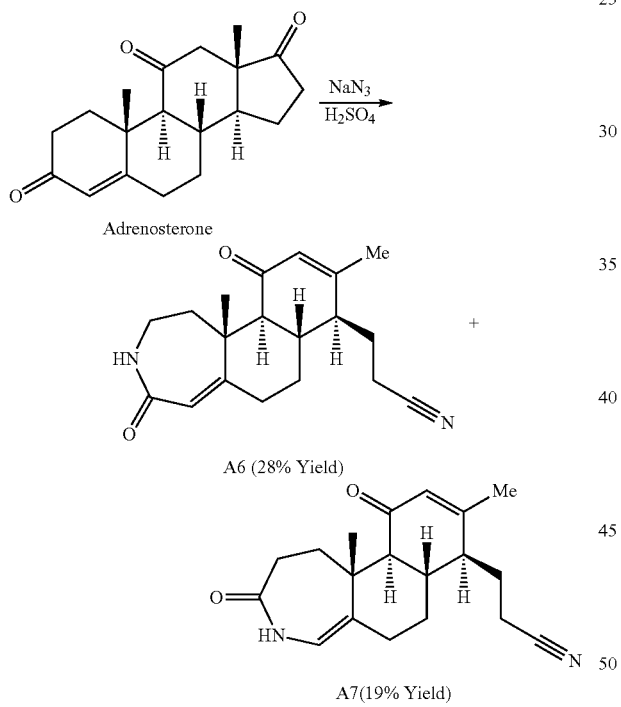

Procedure: Adrenosterone (107.3 mg, 0.357 mmol) was dissolved in concentrated sulfuric acid (1 mL) at room temperature before cooling to 0° C. Sodium azide (70 mg, 1.072 mmol) was then added to the reaction slowly and the resulting reaction mixture was allowed to stir for 1 hour at 0° C. After this time, ice was added to quench the reaction and stirring continued for an additional 3 minutes before being transferred to a separatory funnel and partitioned between brine and dichloromethane. Dichloromethane was used to extract the desired Schmidt products (3×). The organic layers were combined, dried with magnesium sulfate and concentrated under reduced pressure to give a crude white foam. The two products were purified via column chromatography using 100:0 to 95:5 ethyl acetate/methanol to afford 31.7 mg (28% yield) of lactam A6 as a white foam and 21.4 mg of enamide A7 (19% yield) as a white foam.

A6 $^1$H NMR (CDCl$_3$, 500 MHz): δ 6.72 (br m, 1H), 5.88 (s, 1H), 5.76 (s, 1H), 3.30-3.20 (m, 1H), 3.13 (dt, J=14.7, 6.8 Hz, 1H), 2.91 (ddd, J=15.0, 8.3, 2.8 Hz, 1H), 2.51 (td, J=13.7, 4.0 Hz, 1H), 2.33 (d, J=11.5 Hz, 1H), 2.32-2.08 (m, 7H), 2.03 (dq, J=16.0, 5.0 Hz, 1H), 1.93 (dd, J=19.0, 11.5 Hz, 1H), 1.89 (s, 3H), 1.40-1.25 (m, 1H), 1.32 (s, 3H). $^{13}$C NMR (CDCl$_3$, 125 MHz): δ 198.0, 169.8, 158.4, 156.4, 131.1, 120.3, 119.3, 57.9, 46.3, 43.8, 41.2, 37.0, 36.3, 35.2, 33.1, 24.1, 21.5, 21.4, 12.6. HRMS(ESI): m/z calc. for C$_{19}$H$_{25}$N$_2$O$_2$ [M+H]$^+$: 313.1916. found: 313.1917. IR (cm$^{-1}$ NaCl plates, thin film in CDCl$_3$): 3262 (b, m), 2943 (b, m), 2245 (m), 1658 (s), 1607 (m), 1440 (m), 1380 (m). Melting point: 63-65° C.

A7 $^1$H NMR (CDCl$_3$, 500 MHz): δ 7.25-7.16 (br m, 1H), 5.88 (s, 1H), 5.58 (d, J=5.8 Hz, 1H), 2.78 (ddd, J=14.5, 6.5, 3.9 Hz, 1H), 2.47 (m, 2H), 2.36-2.06 (m, 8H), 2.03-1.87 (m, 3H), 1.88 (s, 3H), 1.27 (s, 3H), 1.19 (dq, J=13.5, 4.0 Hz, 1H). $^{13}$C NMR (CDCl$_3$, 125 MHz): δ 198.5, 177.4, 156.2, 131.2, 128.9, 119.4, 115.8, 57.3, 46.3, 41.2, 36.7, 33.5, 32.9, 31.9, 31.7, 24.2, 21.6, 20.6, 12.7. HRMS(ESI): m/z calc. for C$_{19}$H$_{25}$N$_2$O$_2$ [M+H]$^+$: 313.1916. found: 313.1918. IR (cm$^{-1}$ NaCl plates, thin film in CDCl$_3$): 3242 (b, m), 2928 (b, m), 2245 (m), 1660 (s), 1437 (m), 1380 (m). Melting point: 63-65° C.

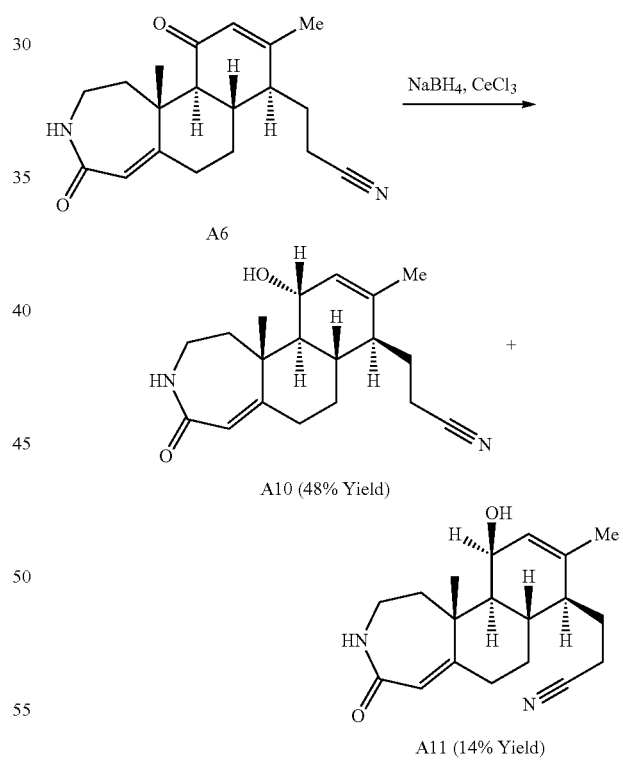

Procedure: Lactam A6 (299 mg, 0.957 mmol) was dissolved in anhydrous methanol (6 mL) at room temperature. Then cerium(III) chloride (428 mg, 1.15 mmol) was added to the reaction vial and dissolved before the solution was cooled to 0° C. After the reaction was cooled, sodium borohydride (354 mg, 9.57 mmol) was added in three portions at the start of the reaction. The reaction was allowed to stir at 0° C. for 2 hours before warming to room temperature on its own accord (ice bath was not removed)

overnight. After 16 hours, a saturated solution of ammonia chloride was added slowly to the reaction vial to quench the reaction. The contents of the reaction mixture were transferred to a separatory funnel where dichloromethane was used to extract the product (3×). The organic layers were combined, dried with magnesium sulfate and concentrated to give a crude white foam. The crude diastereomers were purified via column chromatography using 100:0 to 95:5 dichloromethane/methanol to afford 144 mg (48% yield) of A10 as a white foam and 43 mg (14% yield) of A11 as a white foam.

A10 $^1$H NMR (CDCl$_3$, 500 MHz): δ 7.30 (br m, 1H), 5.68 (s, 1H), 5.44 (m, 1H), 4.08 (d, J=7.0 Hz, 1H), 3.20 (ddd, J=13.6, 7.8, 4.8 Hz, 1H), 3.10 (ddd, J=14.1, 8.9, 5.3 Hz, 1H), 2.76 (br s, 1H), 2.47 (td, J=13.4, 4.3 Hz, 1H), 2.35 (dd, J=15.0, 8.6 Hz, 1H), 2.22-2.05 (m, 5H), 2.04-1.93 (m, 3H), 1.63 (s, 3H), 1.58 (m, 1H), 1.40 (dd, J=11.6, 8.5 Hz, 1H), 1.16 (s, 3H), 1.14 (m, 1H). $^{13}$C NMR (CDCl$_3$, 125 MHz): δ 170.4, 160.6, 134.0, 131.2, 120.1, 119.4, 67.5, 53.9, 45.1, 44.5, 43.3, 37.0, 35.8, 34.4, 33.2, 24.1, 22.4, 20.9, 12.1. HRMS(ESI): m/z calc. for C$_{19}$H$_{27}$N$_2$O$_2$ [M+H]$^+$: 315.2073. found: 315.2072.

A11 $^1$H NMR (CDCl$_3$, 500 MHz): δ 7.08 (s, 1H), 5.81 (dt, J=6.4, 1.6 Hz, 1H), 5.63 (s, 1H), 4.22 (dd, J=6.5, 2.4 Hz, 1H), 3.27 (ddd, J=13.6, 9.0, 4.2 Hz, 1H), 3.15 (dt, J=14.5, 7.1 Hz, 1H), 2.57 (td, J=13.5, 4.5 Hz, 1H), 2.38 (ddd, J=17.2, 10.0, 5.8 Hz, 1H), 2.28-1.82 (m, 9H), 1.63 (s, 3H), 1.33 (s, 3H), 1.26 (dd, J=12.2, 2.5 Hz, 1H), 1.21-1.08 (m, 1H). $^{13}$C NMR (CDCl$_3$, 125 MHz): δ 170.4, 161.0, 137.7, 128.7, 120.6, 118.0, 63.7, 51.3, 46.1, 44.8, 42.2, 36.6, 35.8, 35.1, 29.4, 25.4, 24.3, 21.2, 12.5. HRMS(ESI): m/z calc. for C$_{19}$H$_{27}$N$_2$O$_2$ [M+H]$^+$: 315.2073. found: 315.2073. Melting point: 55-57° C.

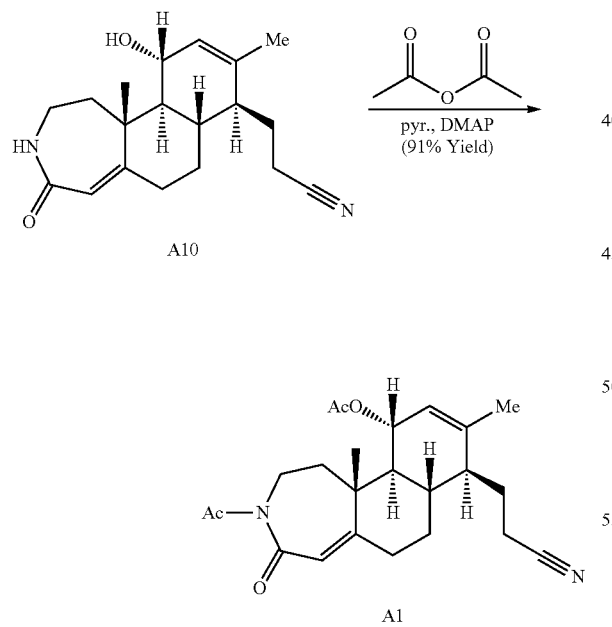

Procedure: Alcohol A10 (41.9 mg, 0.133 mmol) was taken up in anhydrous pyridine (500 μL) and catalytic 4-(dimethylamino)-pyridine (2 mg, 0.016 mmol) was added. After 2 minutes of stirring at room temperature, all solids were completely dissolved. Acetic anhydride (500 μL, 5.29 mmol) was then added to the stirring solution and allowed to run overnight at room temperature. After 25 hours, the reaction was quenched with a saturated solution of sodium bicarbonate and extracted with dichloromethane (3×). The organic layer was then washed with a 5% solution of aqueous hydrochloric acid followed by brine (1× each). The organic layer was then collected, dried with magnesium sulfate and concentrated under reduced pressure. The desired target compound A1 was purified via flash chromatography using 1:1 hexanes/ethyl acetate to yield 48.5 mg (91% yield) as a white foam.

$^1$H NMR (CDCl$_3$, 500 MHz): δ 5.90 (s, 1H), 5.33 (m, 1H), 5.32 (m, 1H), 3.98 (dd, J=15.0, 8.4 Hz, 1H), 3.68 (dd, J=14.9, 8.5 Hz, 1H), 2.53-2.47 (m, 1H), 2.51 (s, 3H), 2.29-2.06 (m, 4H), 2.05 (s, 3H), 2.02 (m, 3H), 1.90 (dd, J=15.4, 8.7 Hz, 1H), 1.77 (dd, J=15.0, 8.0 Hz, 1H), 1.68 (m, 2H), 1.65 (s, 3H), 1.22 (m, 1H), 1.14 (s, 3H). $^{13}$C NMR (CDCl$_3$, 125 MHz): δ 172.6, 170.6, 168.7, 159.8, 136.4, 126.1, 121.1, 119.9, 70.2, 49.7, 44.5, 44.1, 41.1, 36.4, 35.1, 34.2, 32.9, 27.7, 24.1, 21.9, 21.8, 20.8, 12.2. HRMS(ESI): m/z calc. for C$_{23}$H$_{31}$N$_2$O$_4$ [M+H]$^+$: 399.2284. found: 399.2288. Melting point: 57-58 T.

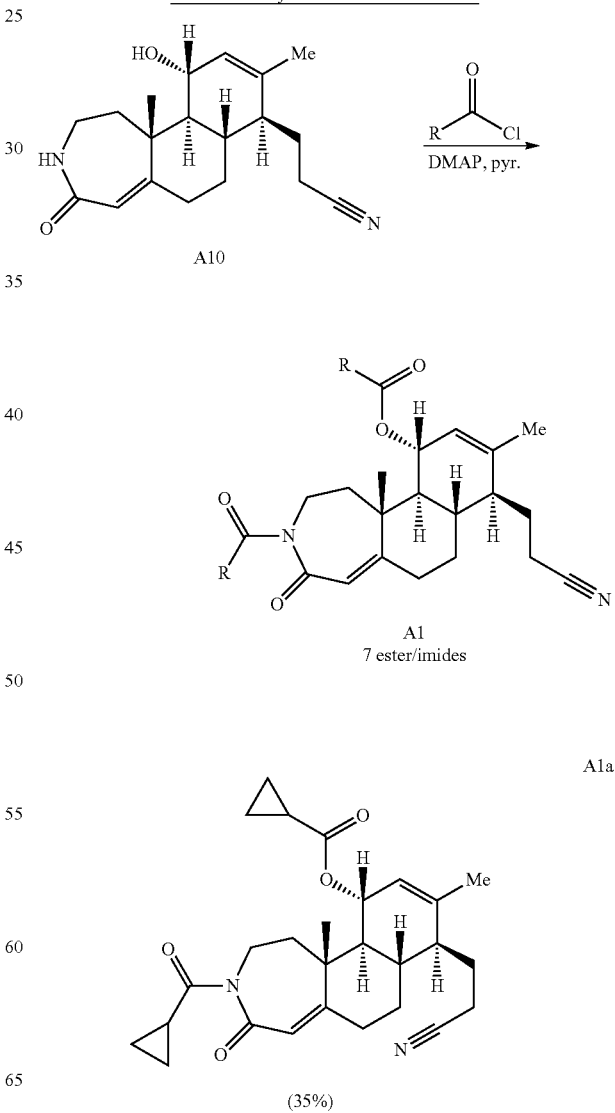

Scheme 1.1. Synthesis of A1 derivatives.

A1b
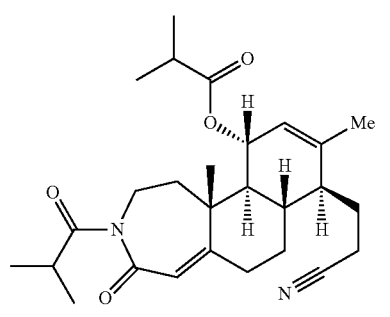
(52%)
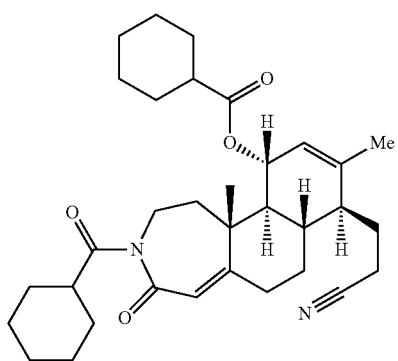
(76%)
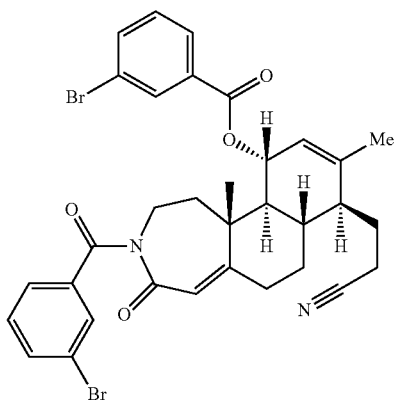
(39%)
A1e
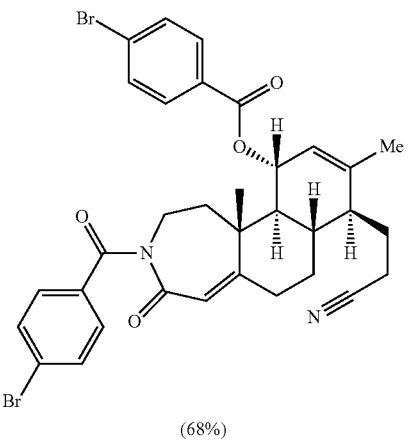
(68%)
A1f
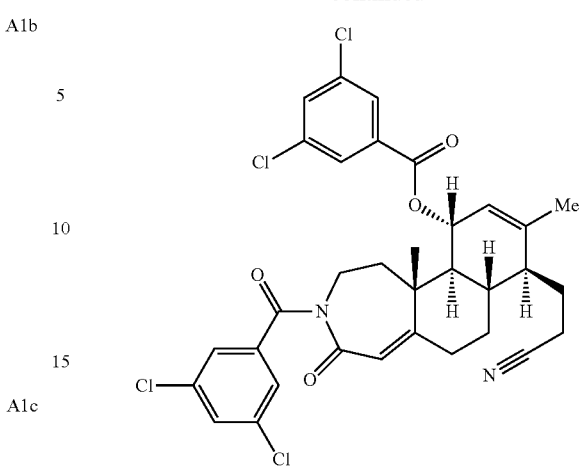
(55%)
A1g
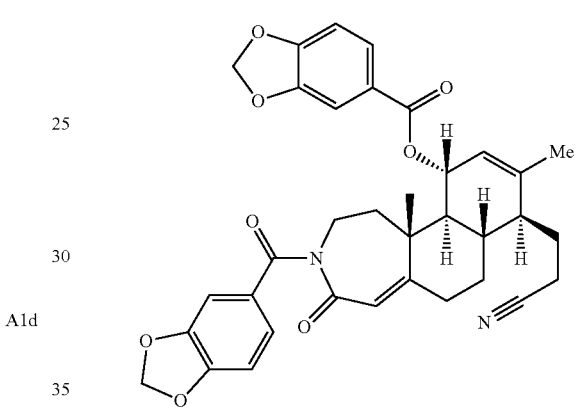
(39%)
Preparation of A2.
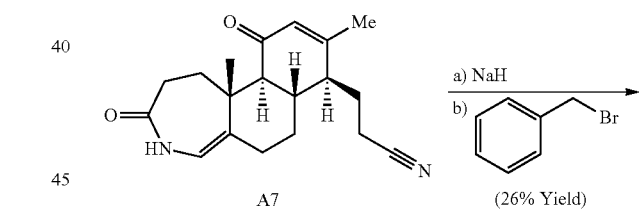
(26% Yield)
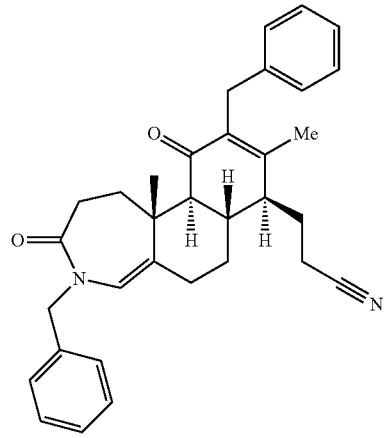
A2
Procedure: Enamide A7 (77.0 mg, 0.246 mmol dissolved in 0.8 mL tetrahydrofuran) was added dropwise to a stirring suspension of sodium hydride (50 mg, 0.986 mmol) in tetrahydrofuran (1.2 mL) at 0° C. The resulting mixture was allowed to stir for 30 minutes before benzyl bromide (59 µL, 0.493 mmol) was added to the reaction. The reaction was allowed to stir at 0° C. for an additional 20 minutes before the ice bath was removed and the reaction stirred at room temperature for 16 hours. Upon completion of the reaction (monitored by TLC) a saturated solution of ammonia chloride was added to quench the reaction and ethyl acetate was used to extract the product. The ethyl acetate layer was then washed with brine (2×), dried with magnesium sulfate and concentrated under reduced pressure. The crude material was purified by column chromatography using 10:1 to 2:1 hexanes/ethyl acetate to afford 27.4 mg enamide A2 (26% yield) as a white foam.

$^1$H NMR (CDCl$_3$, 500 MHz): δ 7.43-7.13 (m, 8H), 7.12-7.02 (m, 2H), 5.61 (s, 1H), 4.71 (d, J=15.0 Hz, 1H), 4.58 (d, J=15.0 Hz, 1H), 3.74 (d, J=14.9 Hz, 1H), 3.56 (d, J=14.9 Hz, 1H), 2.58-2.42 (m, 3H), 2.39-2.22 (m, 2H), 2.21-1.83 (m, 9H), 1.85 (s, 3H), 1.31 (s, 3H), 1.15 (m, 1H). $^{13}$C NMR (CDCl$_3$, 125 MHz): δ 198.6, 174.8, 149.3, 140.0, 139.2, 137.7, 130.9, 128.8 (2), 128.7 (2), 128.2 (2), 127.8 (2), 127.5, 126.3, 121.6, 119.6, 56.3, 51.3, 47.5, 41.2, 35.4, 34.3, 34.0, 32.5, 32.4, 32.2, 25.6, 21.1, 18.5, 12.7. HRMS (ESI): m/z calc. for C$_{33}$H$_{37}$N$_2$O$_2$ [M+H]$^+$: 493.2855. found: 493.2859.

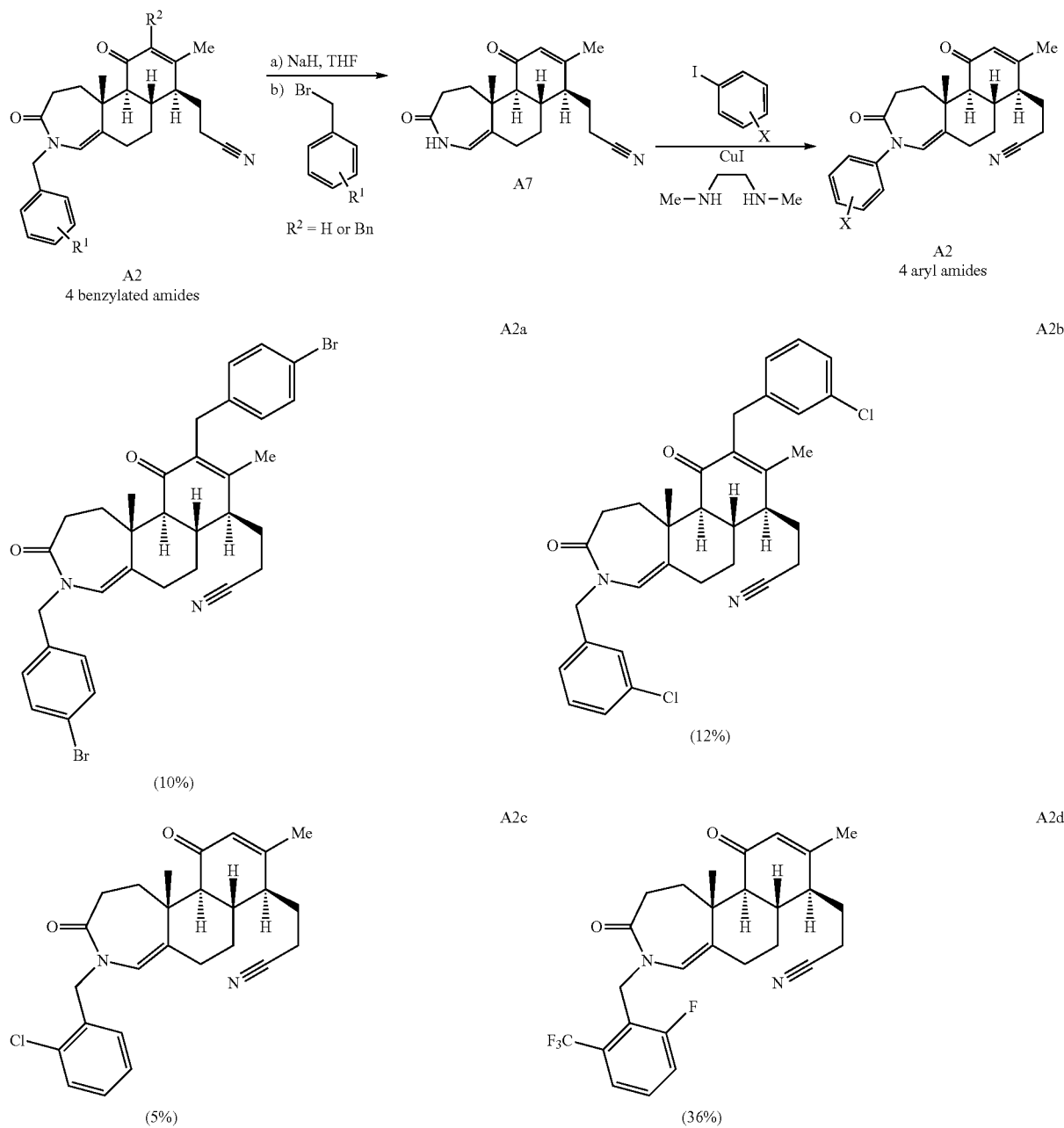

Scheme 1.2. Synthesis of A2 derivatives.

-continued

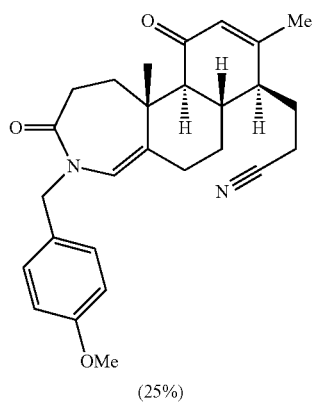

A2e (25%)

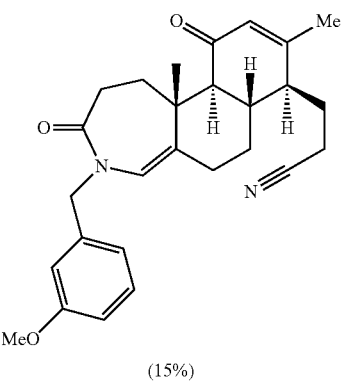

A2f (15%)

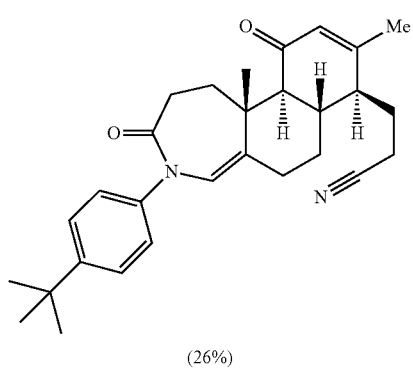

A2g (26%)

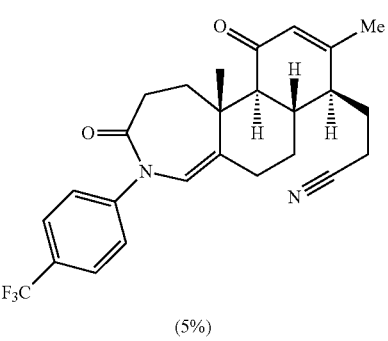

A2h (5%)

Preparation of A8.

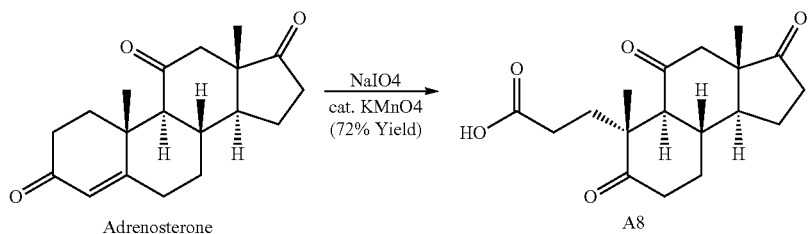

Procedure: Adrenosterone (2.29 g, 7.61 mmol) was dissolved in isopropanol (30 mL) and sodium carbonate (914 mg, 8.62 mmol) was added to the resulting solution. The reaction mixture was heated to reflux. A solution of sodium periodate (9.14 g, 42.7 mmol) and catalytic potassium permanganate (69 mg, 0.44 mmol) in water (25 mL) was preheated at 75° C. and added to the reaction mixture dropwise using a slow addition funnel over a 30 minute period. The slow addition funnel was then removed and a reflux condenser was placed on the reaction flask. The reaction was allowed to stir for an additional 2.5 hours before being cooled to room temperature. The reaction was filtered and the remaining solids were washed with water. The isopropanol was then removed under reduced pressure and the remaining aqueous solution was acidified with concentrated hydrochloric acid to pH 2. This aqueous solution was extracted with dichloromethane (3×). The organic layers were collected, dried using magnesium sulfate and concentrated under reduced pressure to give 1.75 grams (72% yield) of the desired acid A8 as a white foam.

$^1$H NMR (d$_6$-DMSO, 500 MHz): δ 11.91 (s, 1H), 2.65 (td, J=14.4, 6.4 Hz, 1H), 2.56-2.45 (m, 4H), 2.30-1.89 (m, 10H), 1.64 (m, 1H), 1.43 (dq, J=13.5, 4.5 Hz, 1H), 1.20 (s, 3H), 0.75 (s, 3H). $^{13}$C NMR (d$_6$-DMSO, 125 MHz): δ 217.0, 212.1, 208.2, 174.6, 55.9, 49.9, 49.5, 49.1, 47.9, 36.8, 35.7, 34.6, 29.5, 28.9, 28.7, 21.1, 20.1, 14.4. HRMS(ESI): m/z calc. for C$_{18}$H$_{24}$O$_6$Na [M+Na]$^+$: 343.1521. found: 343.1519.

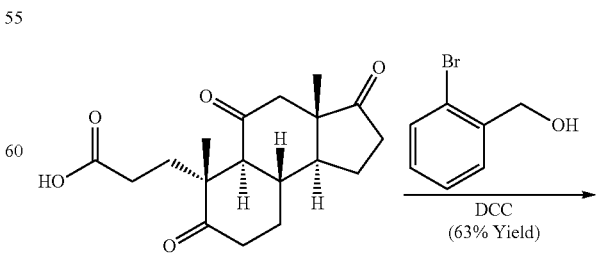

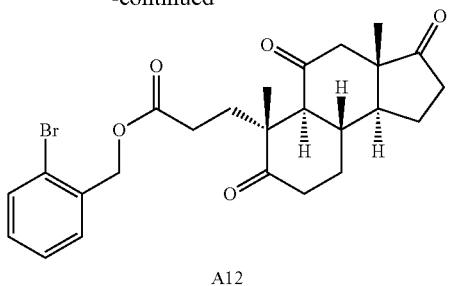

A12

Procedure: Acid A8 (215 mg, 0.672 mmol) was dissolved in anhydrous dichloromethane (7 mL) and cooled to 0° C. before 2-bromobenzyl alcohol (126 mg, 0.672 mmol) was added. N,N'-Dicyclohexylcarbodiimide (125 mg, 0.605 mmol) and 4-dimethylaminopyridine (8 mg, 0.067 mmol) were added to the reaction which was allowed to warm to room temperature and stirred for 21 hours. The reaction contents were then directly passed through a half-inch plug of silica gel eluting with ethyl acetate. The product was further purified by flash chromatography by using 5:1 to 1:1 hexanes/ethyl acetate to give 208.3 mg ester A12 (63% yield) as a white amorphous solid.

$^1$H NMR (CDCl$_3$, 500 MHz): δ 7.55 (dd, J=7.9, 1.2 Hz, 1H), 7.41 (dd, J=7.7, 1.7 Hz, 1H), 7.31 (td, J=7.5, 1.2 Hz, 1H), 7.17 (td, J=7.7, 1.8 Hz, 1H), 5.14 (m, 2H), 2.66-2.53 (m, 2H), 2.48 (d, J=13.2 Hz, 1H), 2.42-2.10 (m, 11H), 1.90 (ddd, J=12.5, 10.5, 5.9 Hz, 1H), 1.71 (tt, J=12.5, 9.2 Hz, 1H), 1.53-1.36 (m, 1H), 1.34 (s, 3H), 0.89 (s, 3H). $^{13}$C NMR (CDCl$_3$, 125 MHz): δ 216.7, 212.0, 207.2, 173.4, 135.6, 133.0, 130.2, 129.9, 127.7, 123.6, 66.0, 57.7, 50.6, 50.1, 50.0, 49.9, 37.2, 36.1, 35.7, 30.3, 29.9, 28.8, 21.8, 20.5, 15.0. HRMS(ESI): m/z calc. for C$_{25}$H$_{30}$O$_6$Br [M+H]$^+$: 489.1277. found: 489.1274.

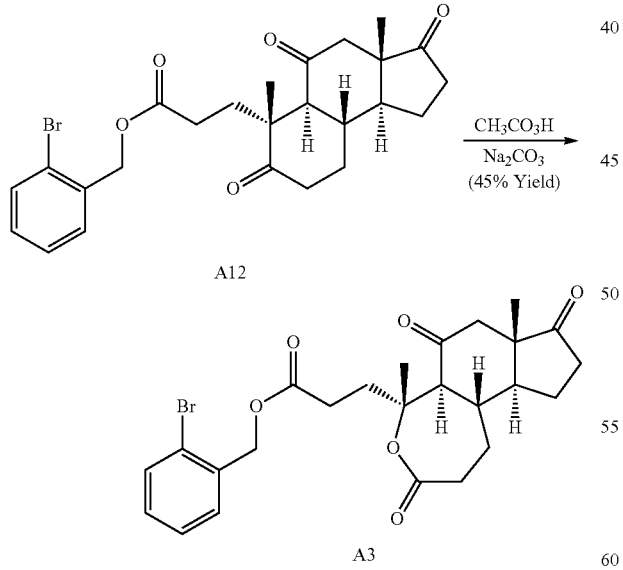

A12

CH$_3$CO$_3$H
Na$_2$CO$_3$
(45% Yield)

A3

Procedure: A12 (100.8 mg, 0.206 mmol) was dissolved in anhydrous dichloromethane (2 mL). Then sodium carbonate (122 mg, 1.15 mmol) was added to the solution and cooled to 0° C. After cooling, a solution of peracetic acid (147 µL of a 32% by weight peracetic acid solution in dilute acetic acid, 0.618 mmol) was added dropwise to the reaction mixture. The reaction slowly warmed to room temperature over several hours and was quenched with a saturated solution sodium bicarbonate of after 19.5 hours. The reaction was then transferred to a separatory funnel and extracted with dichloromethane (3×). The organic layers were collected, dried with magnesium sulfate and concentrated under reduced pressure to give the crude product. The desired lactone was purified via column chromatography using 9:1 to 3:5 hexanes/ethyl acetate to give 46.8 mg (45% yield) A3 as a white foam in addition to 14.8 mg (15% yield) of starting material A12.

$^1$H NMR (CDCl$_3$, 500 MHz): δ 7.55 (dd, J=7.9, 1.1 Hz, 1H), 7.39 (dd, J=7.7, 1.7 Hz, 1H), 7.30 (td, J=7.5, 1.2 Hz, 1H), 7.17 (td, J=7.7, 1.8 Hz, 1H), 5.15 (m, 2H), 2.80 (ddd, J=16.4, 6.9, 1.9 Hz, 1H), 2.68-2.40 (m, 7H), 2.34-2.18 (m, 3H), 2.16-2.06 (m, 2H), 2.05-1.92 (m, 2H), 1.70-1.61 (m, 1H), 1.63 (s, 3H), 1.58-1.44 (m, 1H), 0.84 (s, 3H). $^{13}$C NMR (CDCl$_3$, 125 MHz): δ 215.8, 207.6, 173.9, 173.0, 135.4, 133.0, 130.3, 129.9, 127.7, 123.7, 83.7, 66.1, 62.6, 50.7, 50.4, 50.3, 39.7, 36.7, 35.7, 35.4, 28.6, 27.1, 22.2, 22.0, 14.6. HRMS(ESI): m/z calc. for C$_{15}$H$_{30}$O$_6$Br [M+H]$^+$: 505.1226. found: 505.1223.

Scheme 1.3. Synthesis of A12 and A3 derivatives.

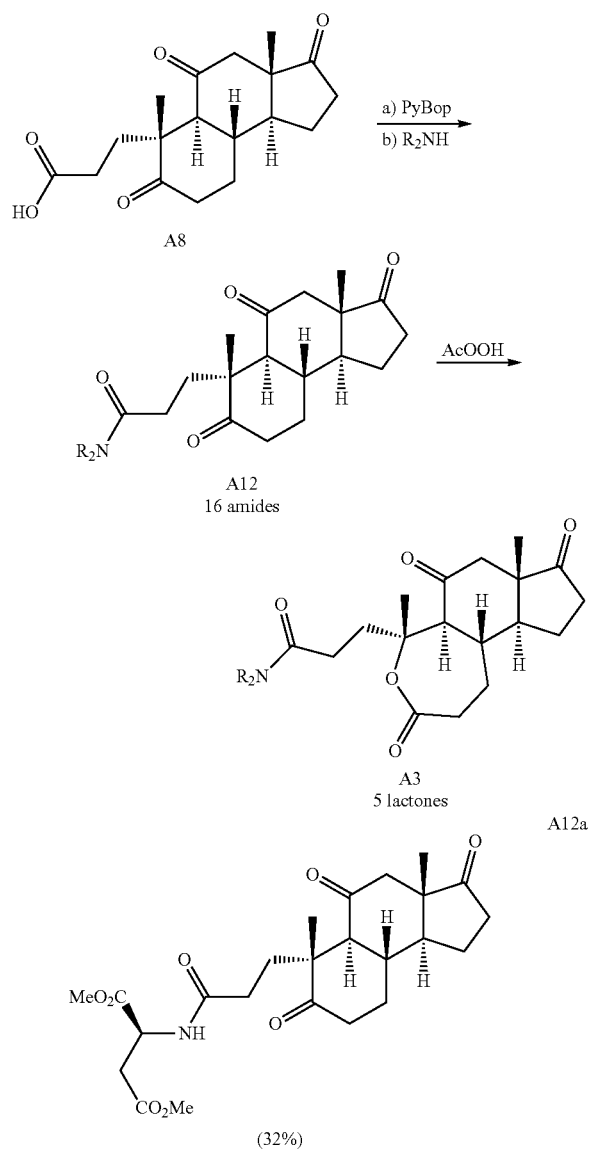

A8 a) PyBop
b) R$_2$NH

A12
16 amides

AcOOH

A3
5 lactones

A12a (32%)

A12b
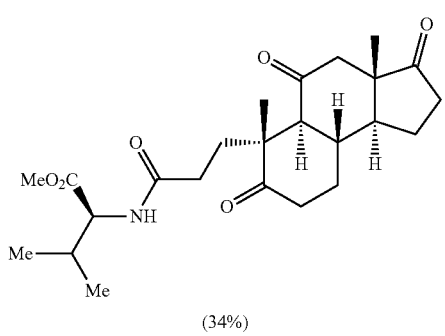
(34%)
A12c
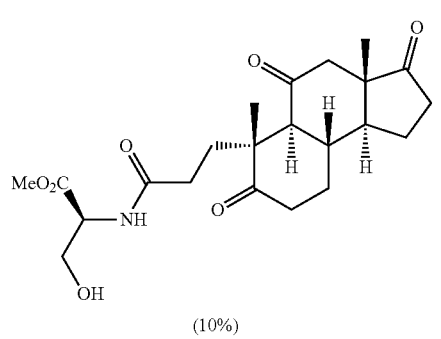
(10%)
A12d
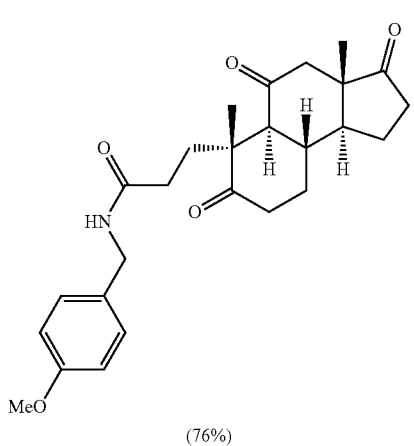
(76%)
A12e
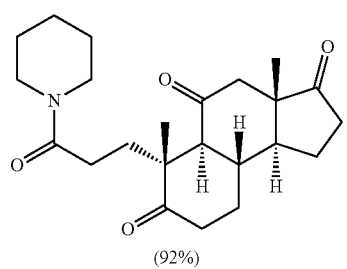
(92%)
A12f
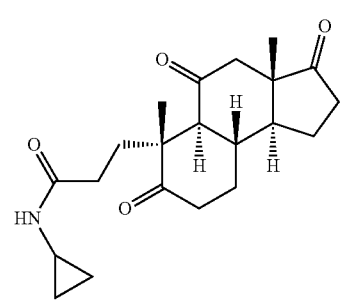
(87%)
A12g
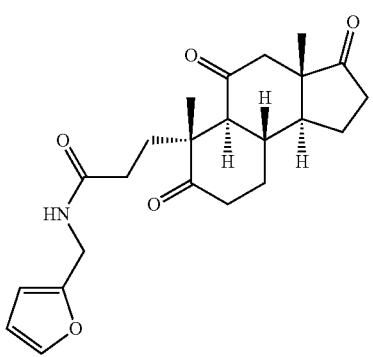
(63%)
A12h
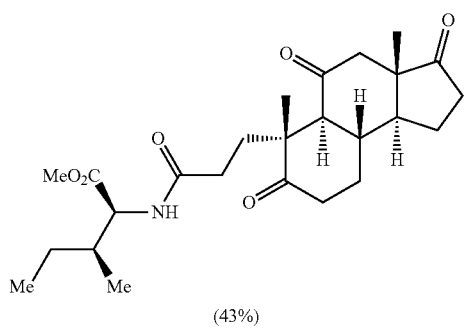
(43%)
A12i
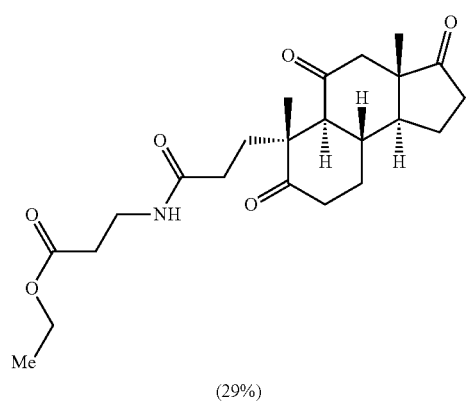
(29%)

A12j
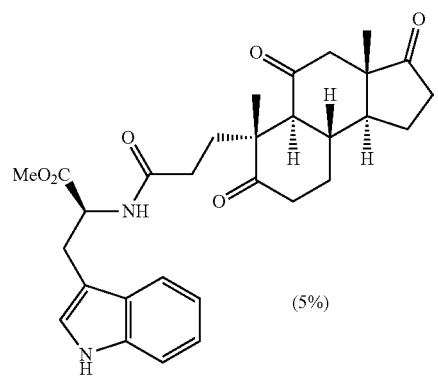
(5%)
A12k
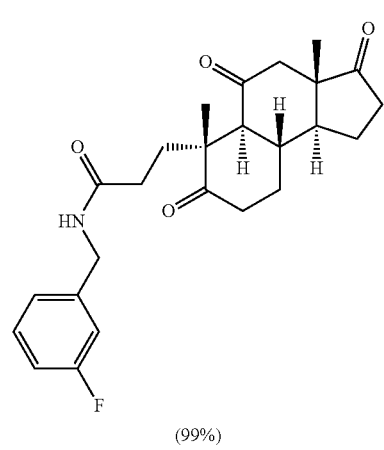
(99%)
A12l
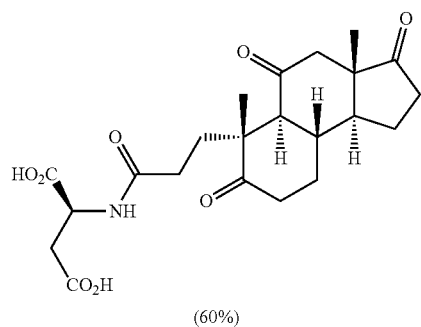
(60%)
A12m
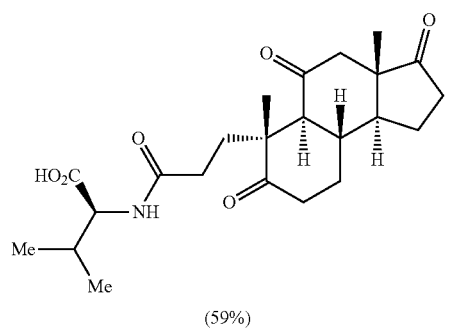
(59%)
A12n
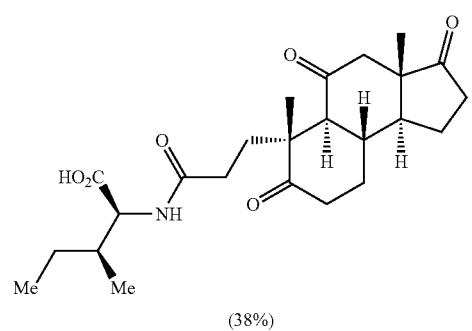
(38%)
A12o
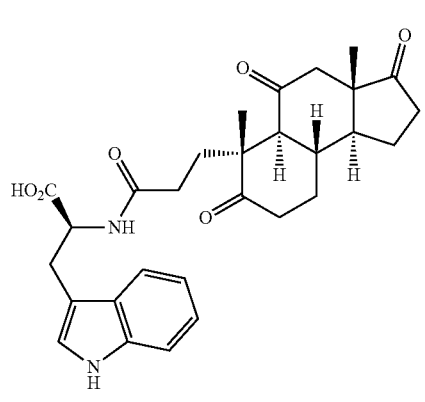
(20%)
A12p
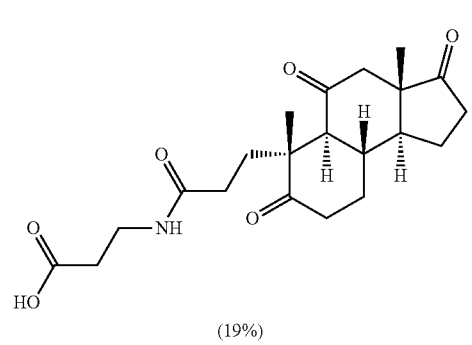
(19%)
A3a
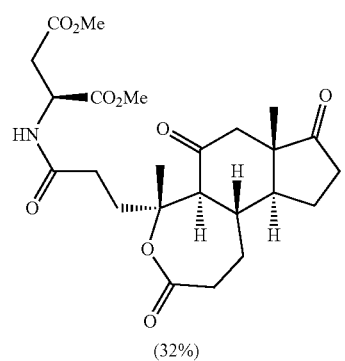
(32%)

-continued

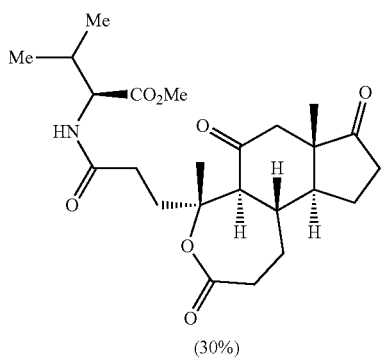

(30%)

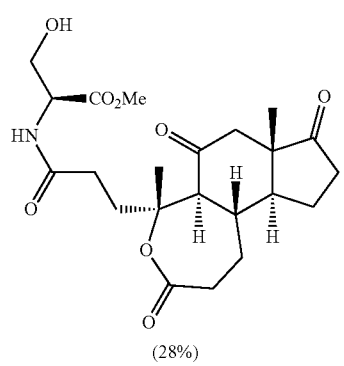

(28%)

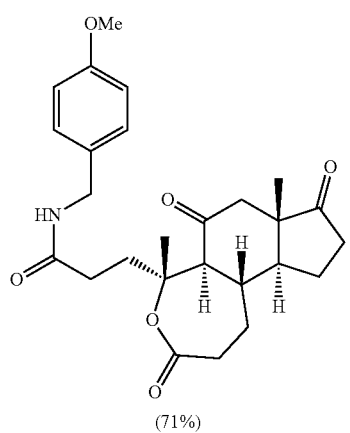

(71%)

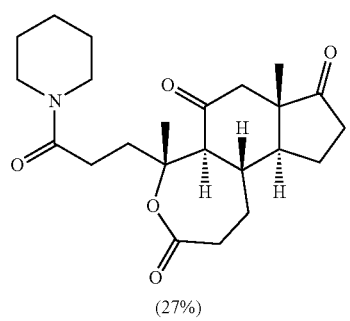

(27%)

-continued

A3b Preparation of A13.

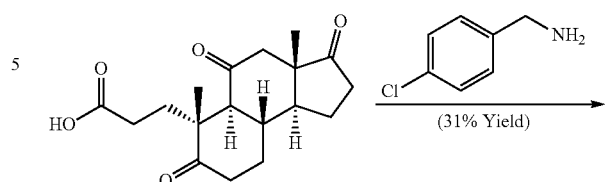

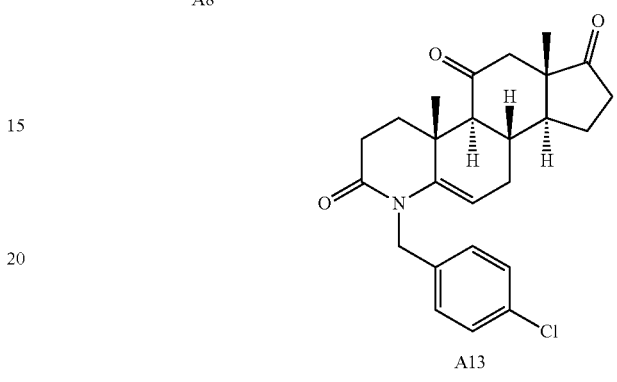

A13

Procedure: Acid A8 (235.5 mg, 0.739 mmol) was dissolved in ethanol (2 mL) in a sealed tube and 4-chlorobenzylamine (447 µL, 3.678 mmol) was added the solution. The tube was sealed and heated to 125° C. for 6.5 hours before being cooled to room temperature (TLC indicated that the starting material was consumed at this time). A 5% solution of aqueous hydrochloric acid solution was added to the reaction vessel and allowed to stir for 5 minutes before being transferred to a separatory funnel where dichloromethane was used to extract the mixture (3×). The organic layers were combined, dried with magnesium sulfate and concentrated under reduced pressure. The product was purified by flash column chromatography using 9:1 to 3:2 hexanes/ethyl acetate to yield 97.9 mg enamide A13 (31% yield) as a white foam.

$^1$H NMR (CDCl$_3$, 500 MHz): δ 7.33-7.20 (m, 2H), 7.08 (d, J=8.2 Hz, 2H), 5.10 (d, J=15.9 Hz, 1H), 4.95 (dd, J=5.8, 2.0 Hz, 1H), 4.66 (d, J=15.8 Hz, 1H), 2.80-2.45 (m, 5H), 2.44-2.15 (m, 3H), 2.10 (ddd, J=13.6, 8.7, 5.5 Hz, 1H), 2.06-1.83 (m, 4H), 1.67 (tt, J=12.3, 9.3 Hz, 1H), 1.54-1.37 (m, 1H), 1.22 (s, 3H), 0.85 (s, 3H). $^{13}$C NMR (CDCl$_3$, 125 MHz): δ 217.3, 207.9, 169.2, 143.7, 136.4, 132.8, 128.9 (2), 128.2 (2), 104.0, 59.8, 50.5, 50.1, 49.9, 47.5, 36.3, 36.0, 32.1, 30.7, 30.4, 29.0, 21.9, 18.1, 15.0. HRMS(ESI): m/z calc. for C$_{25}$H$_{29}$NO$_3$Cl [M+H]$^+$: 426.1836. found: 426.1832.

A3e

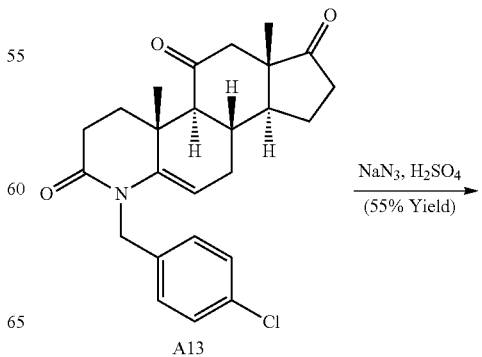

A13

-continued

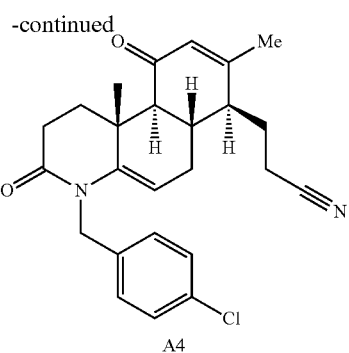

A4

Procedure: A13 (24.2 mg, 0.057 mmol) was dissolved in concentrated sulfuric acid (400 μL) at room temperature and cooled to 0° C. Sodium azide (7.4 mg, 0.114 mmol) was then added to the solution and the reaction was allowed to stir for 1 hour at 0° C. After this time, ice was added to quench the reaction and the solution was allowed to stir for an additional 3 minutes before being transferred to a separatory funnel and partitioned between brine and dichloromethane. Dichloromethane was used to extract the desired product (3×). The organic layers were combined, dried with magnesium sulfate and concentrated under reduced pressure to give a crude white foam. The product was purified via column chromatography using 1:1 to 3:1 ethyl acetate/hexanes to afford 13.3 mg of enamide A4 (55% yield) as a white foam.

$^1$H NMR (CDCl$_3$, 500 MHz): δ 7.27 (d, J=7.6 Hz, 2H), 7.09 (d, J=8.1 Hz, 2H), 5.98 (s, 1H), 5.18 (d, J=15.9 Hz, 1H), 4.92 (dd, J=5.5, 2.0 Hz, 1H), 4.58 (d, J=15.9 Hz, 1H), 3.08 (ddd, J=13.3, 6.6, 1.9 Hz, 1H), 2.80-2.59 (m, 2H), 2.55-2.42 (m, 1H), 2.39-2.27 (m, 2H), 2.26-2.02 (m, 4H), 2.06-1.89 (m, 2H), 1.98 (s, 3H), 1.58 (td, J=13.1, 6.4 Hz, 1H), 1.13 (s, 3H). $^{13}$C NMR (CDCl$_3$, 125 MHz): δ 197.6, 169.4, 157.6, 143.4, 136.4, 132.8, 131.5, 129.0, 128.1, 119.2, 103.1, 54.6, 47.6, 44.9, 36.3, 32.1, 31.7, 30.8, 29.0, 24.4, 21.8, 17.9, 13.0. HRMS(ESI): m/z calc. for C$_{25}$H$_{28}$N$_2$O$_2$Cl [M+H]$^+$: 423.1839. found: 423.1838.

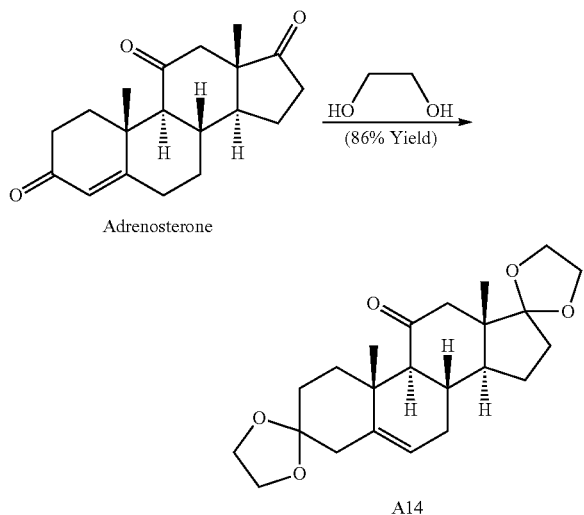

Procedure: Adrenosterone (2.95 g, 9.83 mmol) was dissolved in toluene (250 mL). A catalytic amount of p-toluenesulfonic acid (129 mg, 0.678 mmol) was added to the reaction solution followed by ethylene glycol (25 mL). A Dean-Stark trap was fitted to the reaction flask and the reaction was heated at 145° C. for 6 hours. At this time, the reaction was cooled to room temperature, concentrated under reduced pressure to a third of its original volume and transferred to a separatory funnel. A saturated solution of sodium bicarbonate was added to the separatory funnel and the crude product was extracted with chloroform (3×). The organic layers were then combined, dried with magnesium sulfate and concentrated under reduced pressure to give a crude solid. This product was then purified via recrystallization using petroleum ether and ether to give 3.29 g (86% yield) of the desired ketone A14 as a white crystalline solid. A14 has been previously described in the literature.[1]

$^1$H NMR (CDCl$_3$, 500 MHz): δ 5.34 (dt, J=5.4, 2.0 Hz, 1H), 4.01-3.89 (m, 6H), 3.85-3.76 (m, 2H), 2.68-2.53 (m, 3H), 2.17-1.75 (m, 11H), 1.64 (dq, J=13.8, 3.5 Hz, 1H), 1.43-1.29 (m, 1H), 1.25-1.19 (m, 1H), 1.22 (s, 3H), 0.82 (s, 3H). $^{13}$C NMR (CDCl$_3$, 125 MHz): δ 211.3, 141.4, 120.8, 118.2, 109.3, 65.6, 64.8, 64.6, 64.4, 60.6, 50.4, 49.1, 48.8, 41.8, 37.3, 35.3, 34.6, 34.1, 32.1, 31.0, 22.8, 18.2, 15.1. HRMS(ESI): m/z calc. for C$_{23}$H$_{33}$O$_5$ [M+H]$^+$: 389.2328. found: 389.2327. MP: 180-182° C.

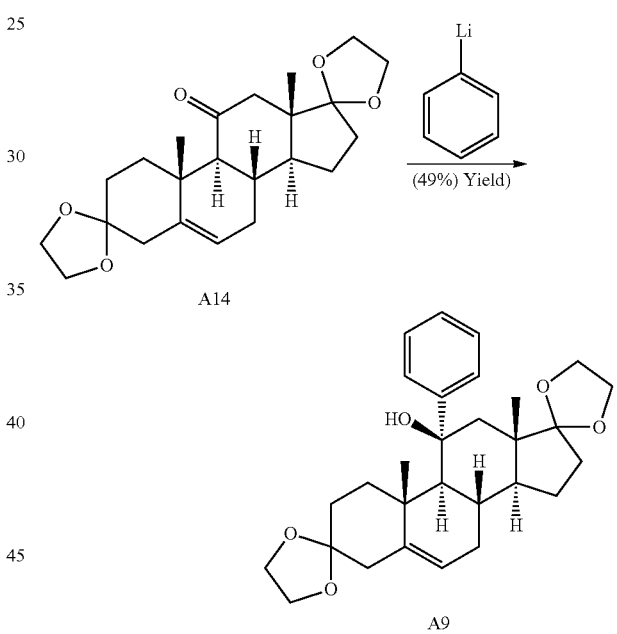

Procedure: Phenyllithium (3.75 mL of a 1.8 M solution in dibutyl ether, 6.76 mmol) was slowly added to a stirring solution of A14 (877 mg, 2.25 mmol) in anhydrous toluene at room temperature. The reaction continued to stir for an additional two hours before being cooled to 0° C. and slowly quenched with a saturated solution of ammonium chloride. The contents of the reaction were then transferred to a separatory funnel and extracted with dichloromethane (3×). The organic layers were then combined, dried with magnesium sulfate and concentrated under reduced pressure to give a crude white foam. This reaction does not go to completion and has been previously described.[2] The desired alcohol A9 and starting ketone A14 are readily separated via column chromatography using 7:1 to 2:1 hexanes/ethyl acetate to give 514 mg of alcohol A9 (49% yield) as a white foam and 229 mg of ketone A14 (26% recovery). Note: Our spectra (room temperature) and melting point obtained for A9 were identical to previously published values. Here we report $^1$H NMR and $^{13}$C NMR spectra for A9 at 50° C. The NMR sample we report was highly concentrated and CDCl$_3$ is buried under the multiplet at 7.30-7.22 ppm.

$^1$H NMR (CDCl$_3$, 500 MHz, 50° C.): δ 7.46 (m, 2H), 7.30-7.22 (m, 2H), 7.15 (td, =7.2, 1.3 Hz, 1H), 5.29 (dt, J=4.6, 2.1 Hz, 1H), 3.86-3.64 (m, 8H), 2.51 (dq, J=14.8, 3.0 Hz, 1H), 2.23 (d, =14.5 Hz, 1H), 2.18 (m, 1H), 2.14-1.96 (m, 4H), 1.93-1.76 (m, 3H), 1.68 (td, J=11.5, 6.1 Hz, 1H), 1.57 (s, 1H), 1.50 (td, J=14.0, 4.5 Hz, 1H), 1.44-1.17 (m, 2H), 1.34 (s, 3H buried in multiplet), 1.26-1.17 (m, 1H) 1.20 (s, 3H buried in multiplet) 0.98 (dt, J=13.6, 3.8 Hz, 1H), 0.67 (td, J=13.9, 4.1 Hz, 1H). $^{13}$C NMR (CDCl$_3$, 125 MHz, 50° C.): δ 153.0, 141.9, 128.0, 126.0, 125.2, 121.2, 119.8, 109.0, 79.8, 65.2, 64.7, 64.5, 64.2, 57.2, 52.9, 51.7, 45.3, 41.7, 40.7, 37.9, 34.5, 32.9, 31.5, 31.2, 23.7, 22.2, 16.3. HRMS(ESI): m/z calc. for C$_{29}$H$_{39}$O$_5$ [M+H]$^+$: 467.2797. found: 467.2790. Melting point: 181-182° C.

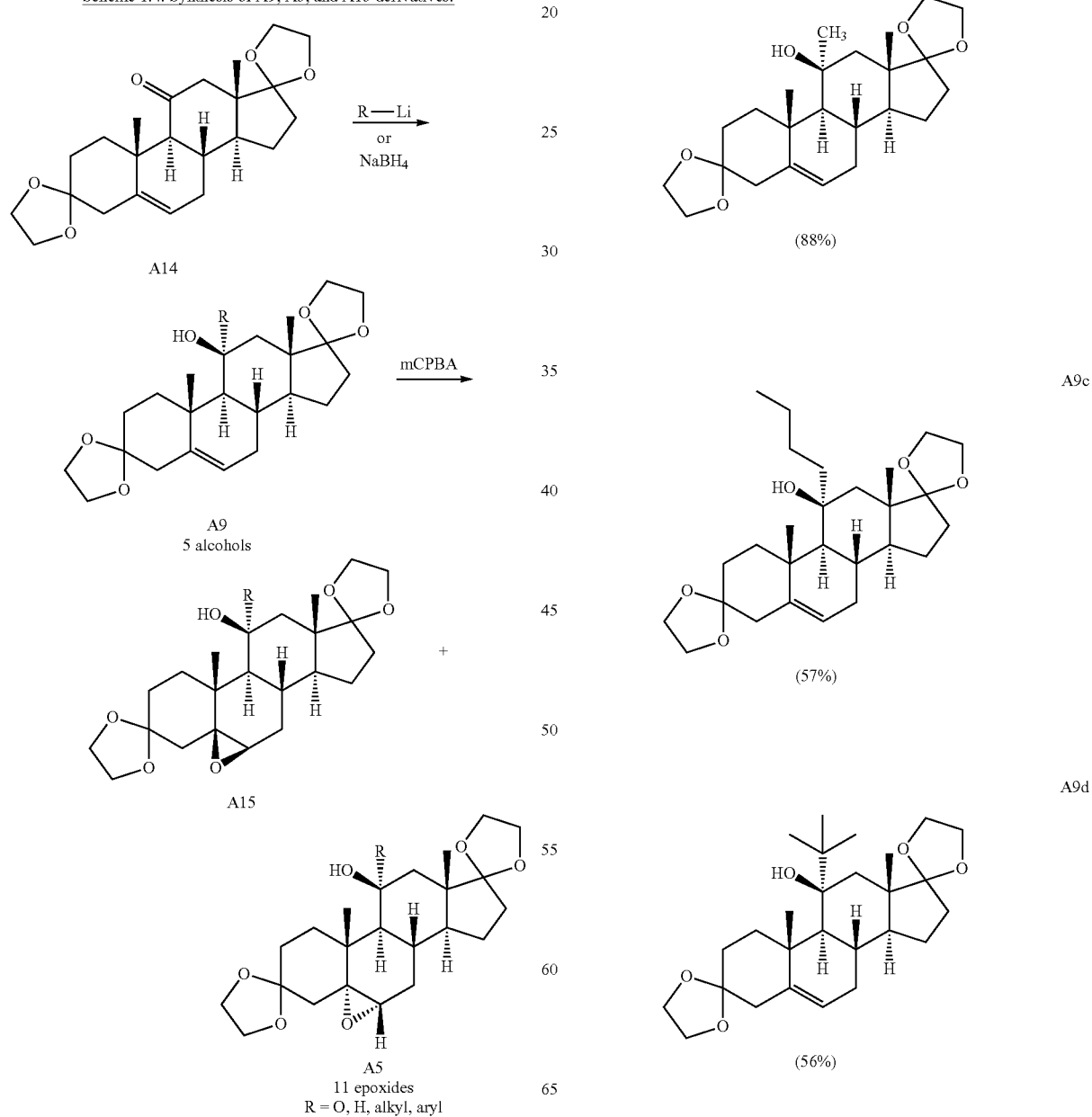

Scheme 1.4. Synthesis of A9, A5, and A15 derivatives.

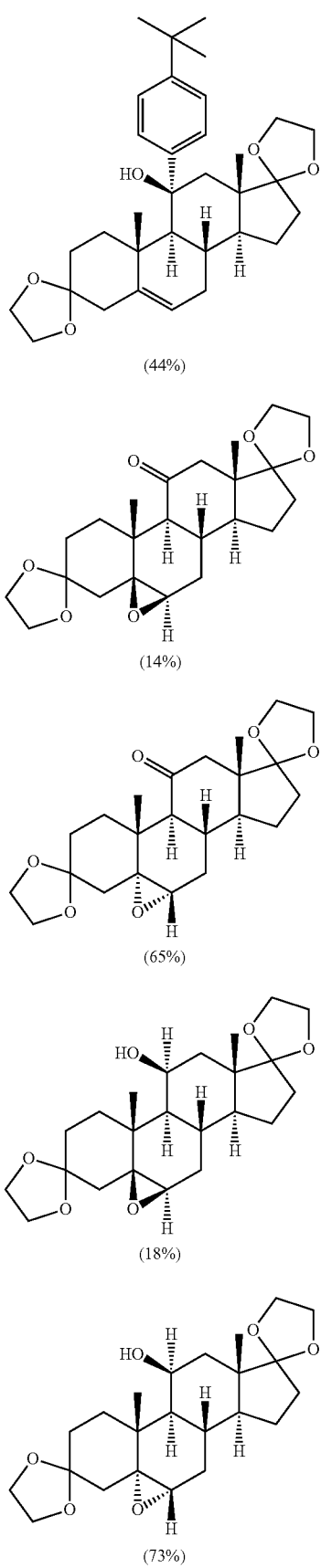
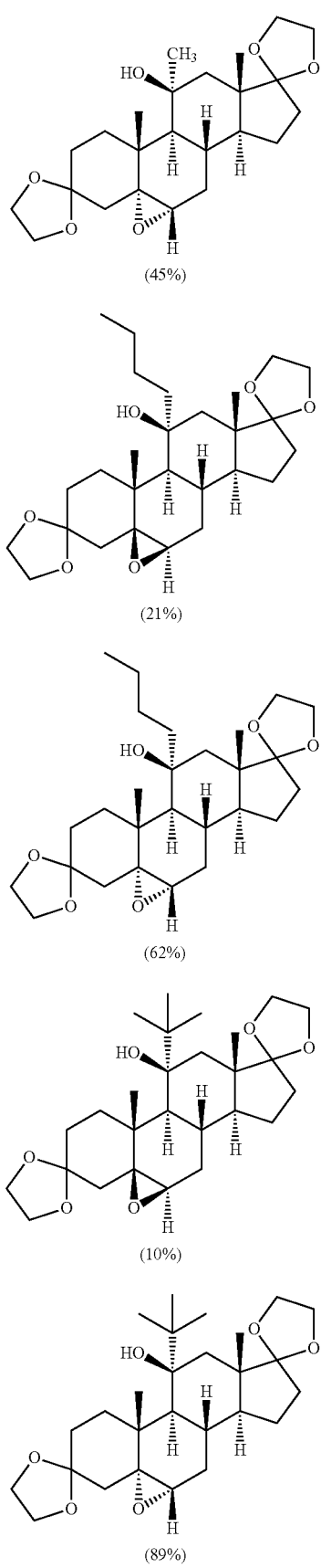

-continued

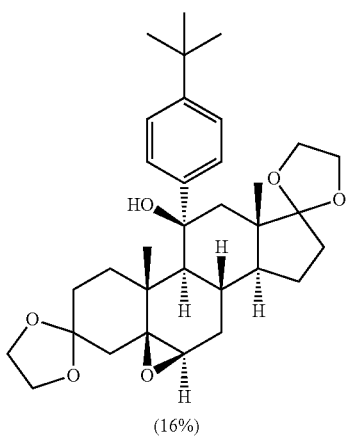

(16%)

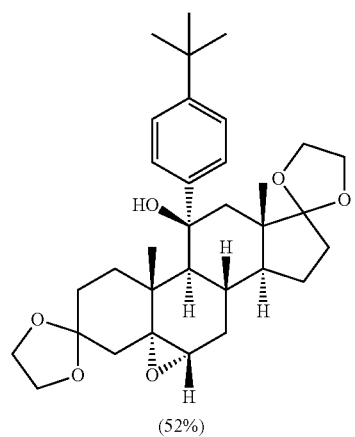

(52%)

Preparation of A5 and A15.

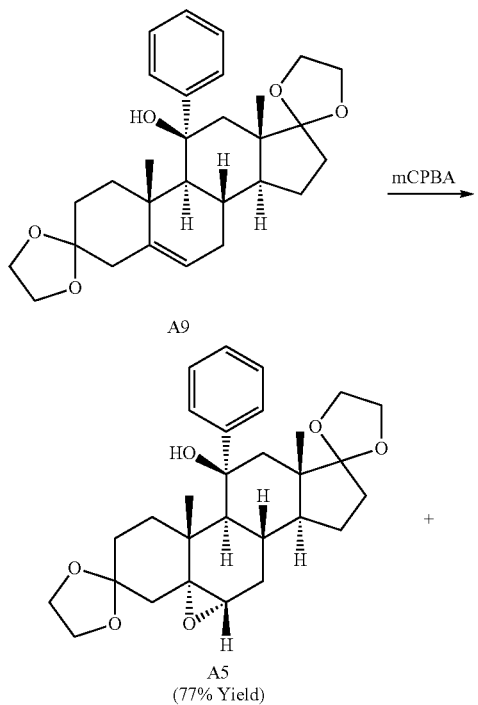

-continued

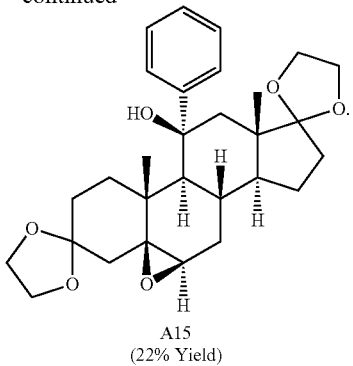

A15
(22% Yield)

Procedure: m-Chloroperoxybenzoic acid (112 mg, 0.449 mmol calculated at 77% purity, dissolved in 1 mL of anhydrous dichloromethane) was added at room temperature to stirring solution of A9 (258.6 mg, 0.203 mmol) in anhydrous dichloromethane (2.6 mL). The reaction continued to stir for 40 minutes before a saturated solution of sodium bicarbonate was added to quench the reaction. The reaction contents were then extracted three times with dichloromethane. The combined organic layers were then washed once more with a saturated solution of sodium bicarbonate. The organic layer was then collected, dried with magnesium sulfate and concentrated to give a crude mixture. The epoxide diastereomers were then separated via column chromatography using 5:1 to 1:1 hexanes/ethyl acetate to afford 206.1 mg of A5 (77% yield) as a white solid and 60.1 mg of A15 (22% yield) as a white solid.

Note: The β/α-stereochemistry of steroidal epoxides (at C5-C6) is well studied and routinely assigned based on the chemical shift of the $^1$H NMR at C6 (δ=3.15-3.00 ppm corresponds to the β-epoxide; δ=2.95-2.75 ppm corresponds to the α-epoxide).[3-4]

A5 $^1$H NMR (CDCl$_3$, 500 MHz): δ 7.52 (m, 1H), 7.32 (m, 1H), 7.28 (m, 2H), 7.15 (t, J=7.3 Hz, 1H), 3.90-3.71 (m, 6H), 3.70-3.60 (m, 2H), 2.76 (d, J=3.7 Hz, 1H), 2.38 (d, J=10.5 Hz, 1H), 2.33 (d, J=14.0 Hz, 1H), 2.14-1.95 (m, 4H), 1.84-1.68 (m, 3H), 1.66-1.56 (m, 2H), 1.47 (s, 1H), 1.41 (s, 3H), 1.36-1.32 (m, 2H), 1.22 (d, J=14.6 Hz, 1H), 1.14-1.08 (m, 1H), 1.12 (s, 3H), 1.04 (dd, J=14.5, 3.0, 1H), 0.79 (td, J=13.9, 4.2 Hz, 1H). $^{13}$C NMR (CDCl$_3$, 125 MHz): δ 153.0, 128.2, 128.0, 126.6, 125.9, 123.1, 119.4, 108.3, 79.7, 66.0, 65.2, 64.6, 64.6, 64.1, 57.0, 53.1, 51.5, 48.2, 45.4, 39.1, 38.2, 34.2, 33.2, 31.1, 29.3, 29.0, 23.3, 18.7, 16.0. HRMS(ESI): m/z calc. for C$_{29}$H$_{39}$O$_6$ [M+H]$^+$: 483.2747. found: 483.2746. Melting point: 272-274° C.

A15 $^1$H NMR (CDCl$_3$, 500 MHz): δ 7.65 (s, 1H), 7.30-7.24 (m, 3H), 7.21-7.10 (m, 1H), 3.90-3.60 (m, 8H), 3.05 (d, J=3.1 Hz, 1H), 2.29-2.19 (m, 1H), 2.25 (d, J=13.5 Hz, 1H), 2.16 (dd, J=11.0, 4.0 Hz, 1H), 2.12 (d, J=14.0 Hz, 1H), 2.10-1.96 (m, 1H), 1.86-1.68 (m, 3H), 1.82 (s, 1H partially buried in multiplet), 1.59 (d, J=11.0 Hz, 1H), 1.57-1.47 (m, 2H), 1.48-1.09 (m, 3H), 1.31 (d, J=14.0 Hz, 1H buried in multiplet), 1.20 (s, 3H buried in multiplet), 1.14 (s, 3H buried in multiplet), 1.04 (dd, J=13.8, 2.7 Hz, 1H), 0.95 (dt, J=13.7, 4.1 Hz, 1H). $^{13}$C NMR (CDCl$_3$, 125 MHz): δ 150.2, 127.6, 126.3, 124.5, 119.7, 108.9, 79.8, 65.1, 64.7, 64.4, 64.3, 63.8, 62.8, 58.7, 51.7, 51.4, 45.6, 41.8, 38.5, 38.0, 34.4, 31.1, 30.7, 28.8, 23.3, 18.2, 16.8. HRMS(ESI): m/z calc. for C$_{29}$H$_{39}$O$_6$ [M+H]$^+$: 483.2747. found: 483.2753. Melting point: 182-183° C.

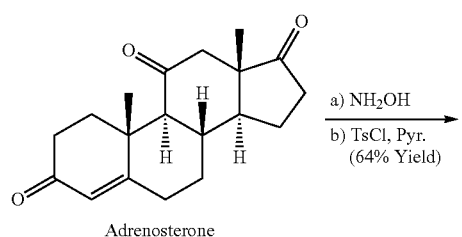

Adrenosterone

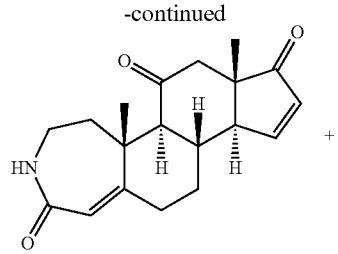

A17
(21% Yield)

+

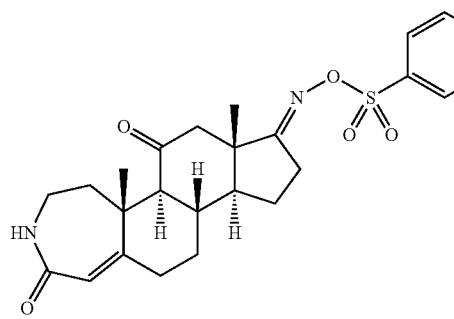

A16

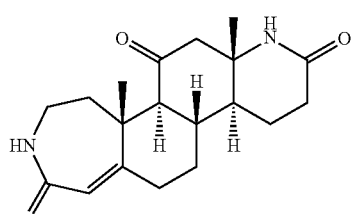

A18
(16% Yield)

Procedure: Adrenosterone (129.6 mg, 0.431 mmol), hydroxylamine hydrochloride (240 mg, 3.451 mmol) and sodium acetate (283 mg, 3.451 mmol) were added to a round bottom flask and dissolved in ethanol (4 mL). The reaction was then refluxed for 2 hours. After this time, the reaction was cooled to room temperature and poured into ice water. Dichloromethane was then used to extract the intermediate oxime (3×). The organic layers were then combined, dried with magnesium sulfate and concentrated. This crude oxime was directly dissolved in pyridine (4 mL) before adding p-toluenesulfonyl chloride (164 mg, 0.862 mmol). The reaction was allowed to stir at room temperature for 4 hours before being diluted with ethyl acetate and washed with a 5% aqueous solution of hydrochloric acid followed by brine (1× each). The organic layers were then combined, dried with magnesium sulfate and concentrated. Lactam A16 was purified by column chromatography using 100:0 to 95:5 dichloromethane/methanol to afford 133.6 mg (64% yield) as a white foam.

$^1$H NMR (CDCl$_3$, 500 MHz): δ 7.86 (d, J=8.5 Hz, 2H), 7.32 (d, J=8.0 Hz, 2H), 5.79 (s, 1H), 2.96 (dt, J=17.6, 3.8 Hz, 1H), 2.70-2.49 (m, 4H), 2.43 (s, 3H), 2.39-2.17 (m, 3H), 2.05-1.85 (m, 3H), 1.83-1.70 (m, 2H), 1.49 (tt, J=12.3, 9.3 Hz, 1H), 1.34-1.10 (m, 3H), 1.26 (s, 3H, buried in multiplet), 0.88 (s, 3H). $^{13}$C NMR (CDCl$_3$, 125 MHz): δ 208.3, 168.2, 163.5, 159.3, 144.9, 133.1, 129.7 (2), 129.0 (2), 116.6, 63.5, 52.8, 52.5, 46.8, 38.0, 36.4, 33.0, 32.2, 31.9, 25.5, 23.1, 21.9, 20.4, 18.3, 17.5. HRMS(ESI): m/z calc. for C$_{26}$H$_{33}$N$_2$O$_5$S [M+H]$^+$: 485.2110. found: 485.2110.

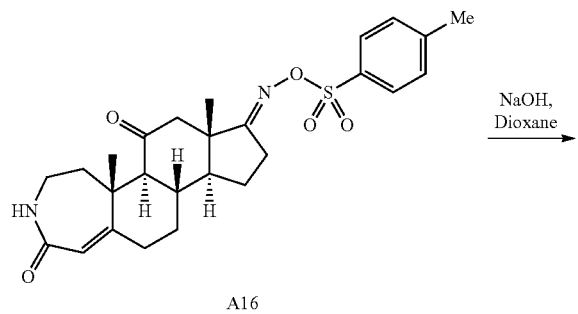

A16

NaOH, Dioxane →

Procedure: Lactam A16 (300 mg, 0.619 mmol) was taken up in a 4:3 water/dioxane solution (18 mL). A 10% NaOH (aq) solution (1.26 mL) was then added and the reaction was heated to 65° C. for 8 hours. The reaction was then cooled to room temperature, quenched with brine and extracted with dichloromethane (3×). The organic layer was collected, dried with magnesium sulfate and concentrated. Enone A17 and bis-lactam A18 were separated via column chromatography using 100:0 to 95:5 dichloromethane/methanol to afford 41 mg A17 (21% yield) as a white solid and 32.4 mg A18 (16% yield) as a white solid.

A17 $^1$H NMR (CDCl$_3$, 500 MHz): δ 7.92 (br s, 1H), 7.68 (d, J=10.3 Hz, 1H), 6.21 (dd, J=10.3, 2.0 Hz, 1H), 6.09 (t, J=1.8 Hz, 1H), 2.68-2.57 (m, 3H), 2.52 (tdd, J=13.6, 4.9, 1.6 Hz, 1H), 2.48-2.37 (m, 2H), 2.20-2.12 (m, 1H), 2.06 (td, J=11.3, 3.6 Hz, 1H), 2.03-1.94 (m, 2H), 1.77 (ddd, J=12.6, 10.7, 6.1 Hz, 1H), 1.54 (tt, J=12.5, 9.3 Hz, 1H), 1.45 (s, 3H), 1.28 (m, 1H), 0.94 (s, 3H). $^{13}$C NMR (CDCl$_3$, 125 MHz): δ 207.9, 186.5, 167.8, 166.1, 155.1, 128.0, 125.1, 61.2, 52.5, 52.4, 47.0, 42.6, 36.1, 33.1, 32.3, 25.5, 23.2, 19.1, 18.5. HRMS(ESI): m/z calc. for C$_{19}$H$_{24}$NO$_3$ [M+H]$^+$: 314.1756. found: 314.1757.

A18 $^1$H NMR (d$_6$-DMSO, 500 MHz): δ 10.51 (s, 1H), 10.30 (s, 1H), 5.73 (s, 1H), 2.79 (dt, J=16.8, 4.0 Hz, 1H), 2.55 (d, J=6.0 Hz, 1H), 2.52-2.38 (m, 4H), 2.36-2.17 (m, 3H), 2.06 (d, J=11.0 Hz, 1H), 1.98 (ddd, J=17.0, 14.2, 5.0 Hz, 1H), 1.93-1.77 (m, 3H), 1.43 (m, 1H), 1.32-1.01 (m, 2H), 1.20 (s, 3H), 0.76 (s, 3H). $^{13}$C NMR (CDCl$_3$, 125 MHz): δ 208.7, 168.5, 156.8, 153.3, 118.7, 63.9, 52.9, 52.7, 46.8, 38.0, 36.5, 33.5, 32.2, 32.0, 25.7, 23.1, 18.8, 18.3, 17.8. HRMS(ESI): m/z calc. for C$_{19}$H$_{27}$N$_2$O$_3$[M+H]$^+$: 331.2022. found: 331.2022.

Example 2. Gibberellic Acid Derived Compounds: Synthesis and Characterization

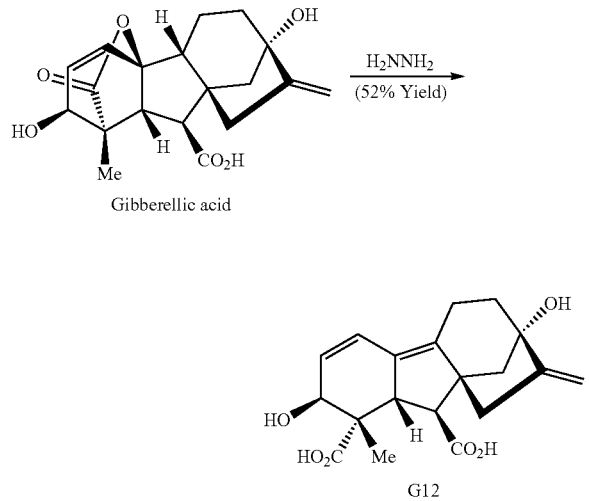

Gibberellic acid

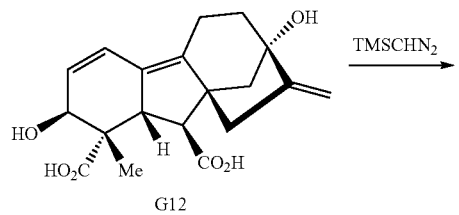

G12

Procedure: Gibberellic acid (3.99 g, 11.5 mmol) was added to a round bottom flask with stir bar, and suspended in hydrazine monohydrate (18 mL). The reaction refluxed at 110° C. for 30 minutes, after which the reaction was cooled for 5 minutes in an ice bath. Following cooling, the reaction was diluted in ice water and acidified to pH 3 with concentrated hydrochloric acid. The aqueous phases were extracted with ethyl acetate (5×), and the combined organic layers were washed with brine, dried over magnesium sulfate, and concentrated. White solid precipitated out during the concentration process to afford known compound G12 as a white solid (2.06 g, 51.6% yield).[5]

$^1$H NMR ($d_6$-acetone, 500 MHz): δ 6.32 (d, J=9.7 Hz, 1H), 5.91 (dd, J=9.7, 5.5 Hz, 1H), 5.14 (t, J=2.4 Hz, 1H), 4.91 (t, J=2.4 Hz, 1H), 4.33 (d, J=5.6 Hz, 1H), 3.98 (s, 1H), 3.72 (d, J=8.5 Hz, 1H), 3.57 (dd, J=8.5, 4.4 Hz, 1H), 2.61 (dd, J=16.1, 6.2 Hz, 1H), 2.51 (dt, J=16.5, 3.0 Hz, 1H), 2.20 (t, J=3.5 Hz, 1H), 2.18 (dd, J=9.0, 2.5 Hz, 1H), 2.11-1.98 (m, 2H), 1.79-1.63 (m, 3H), 1.28 (s, 3H). $^{13}$C NMR ($d_6$-acetone, 125 MHz): δ 176.4, 175.9, 156.2, 139.8, 130.5, 128.2, 124.1, 105.7, 79.2, 69.8, 56.4, 53.1, 50.0, 49.8, 48.5, 40.7, 40.0, 21.2, 20.5. HRMS(ESI): m/z calc. for $C_{19}H_{22}O_6Na$ [M+Na]$^+$: 369.1314. found: 369.1315. Melting point: 189-191° C.

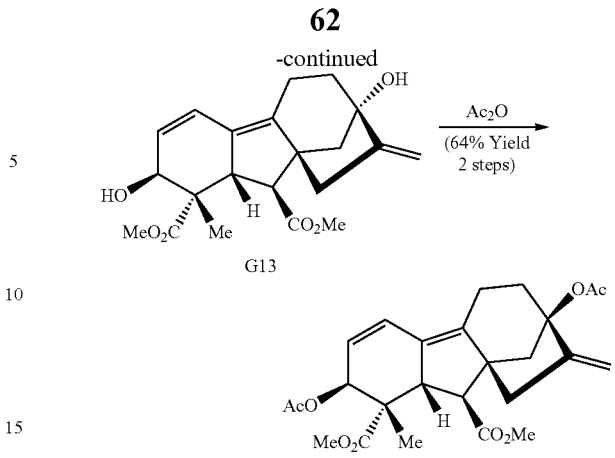

Procedure: In an oven-dried round bottom flask with stir bar under argon, G12 (521 mg, 1.50 mmol) was dissolved in toluene (18 mL) and methanol (3 mL). (Trimethylsilyl)diazomethane (2 M in hexanes, 1.8 mL, 3.60 mmol) was added dropwise at room temperature, and the reaction was stirred for 1 hour at room temperature. The reaction was concentrated, and then dissolved in pyridine (9 mL). Acetic anhydride (1.5 mL, 15.9 mmol) and 4-(dimethylamino)-pyridine (53.1 mg, 0.43 mmol) were added, and the reaction was allowed to stir overnight at room temperature. After 14 hours, the reaction was quenched with chilled hydrochloric acid to pH 3. The aqueous phase was extracted with ethyl acetate (4×), and the combined organic layers were washed with brine, dried over magnesium sulfate, and concentrated. Purification by flash silica chromatography (5:1 hexanes/ethyl acetate) afforded G7 as a white solid (445 mg, 65% yield).

Note: G13 could be isolated and purified following esterification with (trimethylsilyl)diazomethane by flash silica chromatography (3:1 hexanes/ethyl acetate) to afford pure product. G13 NMR (CDCl$_3$, 500 MHz): δ 6.36 (d, J=9.5 Hz, 1H), 5.96 (dd, J=9.7, 5.6 Hz, 1H), 5.16 (t, J=2.5 Hz, 1H), 4.98 (1, J=2.2 Hz, 1H), 4.33 (d, J=5.5 Hz, 1H), 3.73 (s, 3H), 3.63 (d, J=8.4 Hz, 1H), 3.59 (s, 3H), 3.49 (dd, J=8.4, 4.4 Hz, 1H), 2.61 (dd, J=16.3, 6.4 Hz, 1H), 2.30 (dt, J 16.5, 2.8 Hz, 1H), 2.24 (dq, J=16.5, 2.1 Hz, 1H), 2.19 (dd, J=10.4, 2.8 Hz, 1H), 2.13-2.02 (m, 1H), 1.84 (td, J=11.9, 6.4 Hz, 1H), 1.77-1.58 (br s, partially buried, 1H), 1.76 (dd, J=10.4, 2.4 Hz, 1H), 1.74-1.70 (m, 2H), 1.25 (s, 3H). $^{13}$C NMR (CDCl$_3$, 125 MHz): δ 175.1, 174.9, 154.5, 140.3, 128.6, 126.8, 124.8, 106.4, 79.3, 69.9, 56.3, 52.6, 52.0, 51.8, 49.7, 49.3, 48.1, 39.4, 39.2, 20.9, 19.9. HRMS(ESI): m/z calc. for $C_{21}H_{26}O_6Na$ [M+Na]$^+$: 397.1627. found: 397.1629. Melting point: 81-82° C.

G7 $^1$H NMR (CDCl$_3$, 500 MHz): δ 6.43 (d, J=9.6 Hz, 1H), 5.90 (dd, J=9.6, 5.6 Hz, 1H), 5.55 (d, J=5.6 Hz, 1H), 5.08 (dd, J=3.3, 1.8 Hz, 1H), 5.02 (t, J=2.0 Hz, 1H), 3.74 (s, 3H), 3.70 (d, J=8.6 Hz, 1H), 3.64-3.59 (m, 1H), 3.62 (s, 3H), 2.69 (dd, J=10.5, 2.9 Hz, 1H), 2.62 (dd, J=16.2, 6.3 Hz, 1H), 2.39-2.29 (m, 2H), 2.25 (dd, J=16.1, 2.1 Hz, 1H), 2.21-2.11 (m, 2H), 2.08 (s, 3H), 2.05 (s, 3H), 1.70 (ddd, J=10.8, 7.1, 2.6 Hz, 1H), 1.17 (s, 3H). $^{13}$C NMR (CDCl$_3$, 125 MHz): δ 175.0, 173.8, 170.6, 169.9, 150.6, 140.6, 126.8, 126.2, 125.3, 106.7, 85.9, 71.2, 57.2, 52.0, 52.0, 49.0, 48.9, 48.5, 47.9, 38.9, 36.9, 22.3, 21.3, 20.7, 19.9. HRMS(ESI): m/z calc. for $C_{25}H_{30}O_8Na$ [M+Na]$^+$: 481.1838. found: 481.1837.

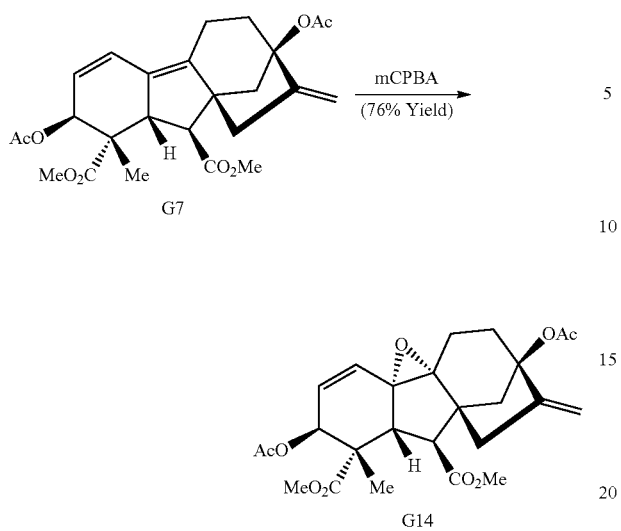

G7

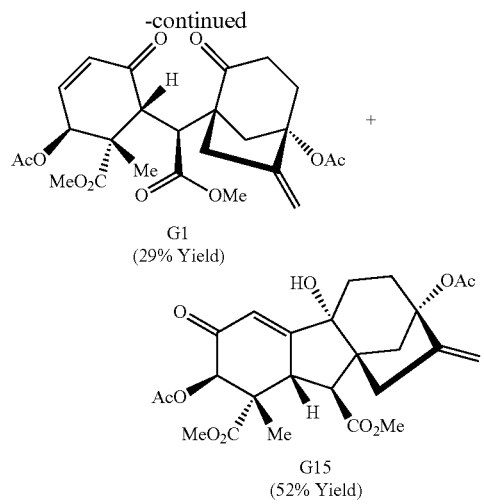

G1
(29% Yield)

G14

G15
(52% Yield)

Procedure: In an oven-dried vial with stir bar, G7 (120 mg, 0.26 mmol) was dissolved in dichloromethane (10.5 mL). Sodium bicarbonate (89 mg, 1.06 mmol) and m-chloroperoxybenzoic acid (69 mg, 0.31 mmol calculated at 77% purity) were added sequentially, and the reaction was allowed to stir at room temperature for 7 hours. The reaction was washed sequentially with saturated aqueous sodium thiosulfate, saturated aqueous sodium bicarbonate, and brine, dried over magnesium sulfate, and concentrated. Flash silica chromatography (3:1 hexanes/ethyl acetate) afforded G14 as a white solid (95 mg, 76% yield). Note: Although the absolute stereochemistry could not be directly determined for this compound, the product of the oxidation and allylic rearrangement of G14 following treatment with PCC afforded G15, whose stereochemistry could be assigned.

$^1$H NMR (CDCl$_3$, 500 MHz): δ 6.32 (dd, J=9.8, 5.1 Hz, 1H), 5.77 (d, J=9.0 Hz, 1H), 5.71 (d, J=5.6 Hz, 1H), 5.09 (t, J=2.6 Hz, 1H), 5.00 (t, J=2.3 Hz, 1H), 3.72 (s, 3H), 3.70 (s, 3H), 3.06 (d, J=10.5 Hz, 1H), 2.94 (d, J=10.5 Hz, 1H), 2.56 (tt, J=12.5, 6.1 Hz, 1H), 2.47 (dd, J=10.8, 1.6 Hz, 1H), 2.44 (dd, J=10.8, 2.3 Hz, 1H), 2.25 (dd, J=17.2, 2.4 Hz, 1H), 2.17 (t, J=2.4 Hz, 1H), 2.14-2.07 (m, 1H buried under methyl), 2.10 (s, 3H), 2.06 (s, 3H), 1.64 (td, J=14.3, 12.3, 5.9 Hz, 2H), 1.15 (s, 3H). $^{13}$C NMR (CDCl$_3$, 125 MHz): δ 173.7, 173.4, 170.3, 169.7, 149.3, 134.7, 125.2, 106.7, 85.8, 72.1, 70.4, 65.7, 52.3, 52.2, 51.4, 47.6, 44.5, 44.3, 41.9, 35.4, 35.0, 22.1, 22.1, 21.2, 19.5. HRMS(ESI): m/z calc. for C$_{25}$H$_{31}$O$_9$ [M+H]$^+$: 475.1968. found: 475.1971. HRMS(ESI): m/z calc. for C$_{25}$H$_{30}$O$_9$Na [M+Na]$^+$: 497.1788. found: 497.1790. Melting point: 62-64° C.

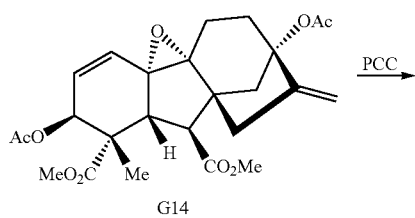

G14

Procedure: In an oven-dried round bottom flask with stir bar, dissolved G14 (97.6 mg, 0.21 mmol) in dichloromethane (7 mL) and added powdered molecular sieves (160 mg) followed by pyridinium chlorochromate (97.5 mg, 0.45 mmol). The reaction was refluxed at 45° C. for 2.5 hours, and was then diluted with ether and filtered over a silica plug to remove the chromium. Purification by flash silica chromatography (4:1 to 3:1 hexanes/ethyl acetate) afforded G1 as a white solid (29.0 mg, 29% yield in 90% purity determined by $^1$H NMR integrations) and G15, which is the product of allylic oxidation and rearrangement, was also recovered as a pure white solid (52.8 mg, 52%).

Note: G1 was not stable to chromatography or storage at room temperature, and would gradually convert to G2 over time. There was a significant contaminant signal in the $^{13}$C NMR spectra for G1 that could not be removed at 56.4 ppm. G15 was used for assigning the absolutely stereochemistry of the precursor epoxide G14. The assignment of the stereochemistry of the tertiary alcohol is based on the NOES observed across the C/D bicycle. A comparison is provided to the opposite diastereomer to identify the interactions that are not observed but would be expected if the alcohol was in the opposite configuration.

$^1$H NMR (CDCl$_3$, 500 MHz): δ 6.49 (dd, J=10.3, 2.1 Hz, 1H), 6.38 (t, J=2.2 Hz, 1H), 5.91 (dd, J=10.3, 2.1 Hz, 1H), 5.17 (t, J=2.6 Hz, 1H), 5.13 (t, J=2.2 Hz, 1H), 3.79 (d, J=11.8 Hz, 1H), 3.66 (s, 3H), 3.59 (s, 3H), 3.12 (dt, J=17.5, 2.5 Hz, 1H), 3.04 (dq, J=17.5, 1.5 Hz, 1H), 2.92 (d, J=11.7 Hz, 1H), 2.55-2.38 (m, 2H), 2.29-2.18 (m, 2H), 2.07 (s, 3H), 2.02 (m, 3H singlet buried in multiplet, 4H), 1.79 (ddd, J=10.3, 7.1, 3.5 Hz, 1H), 1.32 (s, 3H). $^{13}$C NMR (CDCl$_3$, 125 MHz): δ 209.2, 198.7, 172.5, 172.2, 170.0, 169.9, 148.8, 141.7, 130.4, 107.2, 84.5, 69.8, 55.1, 52.7, 51.9, 51.6, 45.3, 43.8, 36.7, 35.6, 33.6, 29.9, 22.1, 21.1, 19.1. HRMS(ESI): m/z calc. for C$_{15}$H$_{30}$O$_{10}$Na [M+Na]$^+$: 513.1737. found: 513.1746.

G15 $^1$H NMR (CDCl$_3$, 500 MHz): δ 6.01 (d, J=2.6, 0.9 Hz, 1H), 5.62 (d, J=0.9 Hz, 1H), 5.03 (t, J=2.5 Hz, 1H), 4.92 (t, J=2.1 Hz, 1H), 3.75 (s, 3H), 3.69 (s, 3H), 3.63 (dd, J=11.1, 2.7 Hz, 1H), 3.60 (d, J=11.1 Hz, 1H), 3.52 (br s, 1H), 2.88 (dd, J=10.8, 2.6 Hz, 1H), 2.71 (ddd, J=12.7, 11.7, 5.2 Hz, 1H), 2.33 (dt, J=17.7, 2.8 Hz, 1H), 2.19-2.14 (m, 1H buried under methyl), 2.18 (s, 3H), 2.07 (s, 3H), 2.07-2.01 (m, 1H buried under methyl), 1.95 (ddd, J=14.0, 5.3, 1.8 Hz, 1H), 1.66 (td, J=13.4, 5.7 Hz, 1H), 1.55-1.42 (m, 1H), 1.21 (s, 3H). $^{13}$C NMR (CDCl$_3$, 125 MHz): δ 192.0, 174.8, 173.2, 171.1, 169.8, 169.6, 148.7, 121.5, 105.7, 86.3, 79.9, 74.2, 55.1, 53.3, 52.5, 47.0, 45.1, 37.5, 35.1, 33.5, 29.9, 27.9, 22.3, 21.0, 19.7. HRMS(ESI): m/z calc. for $C_{25}H_{31}O_{10}$ [M+H]$^+$: 491.1917. found: 491.1916.

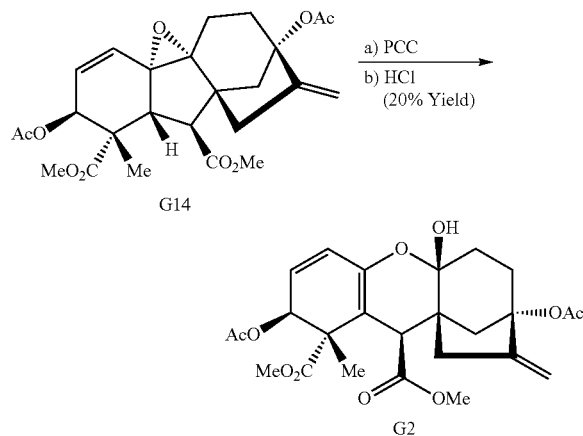

Procedure: In an oven-dried round bottom flask with stir bar, dissolved G14 (100.3 mg, 0.21 mmol) in dichloromethane (7 mL) and added powdered molecular sieves (100 mg) followed by pyridinium chlorochromate (98.0 mg, 0.46 mmol). The reaction was refluxed for 2.5 hours, at which point hydrochloric acid (1 M, 8 mL) was added. The reaction stirred overnight at room temperature, and was then extracted with dichloromethane (3×). Purification by flash silica chromatography (4:1 to 3:1 hexanes/ethyl acetate) afforded G2 as a white solid (20.4 mg, 20% yield).

$^1$H NMR (CDCl$_3$, 500 MHz): δ 6.43 (s, 1H), 5.99 (dd, J=9.9, 4.4 Hz, 1H), 5.92 (d, J=9.9 Hz, 1H), 5.68 (d, J=4.5 Hz, 1H), 5.00 (q, J=2.6 Hz, 2H), 3.76 (s, 3H), 3.66 (s, 3H), 3.23 (s, 1H), 2.63 (dt, J=16.7, 3.0 Hz, 1H), 2.49 (ddd, J=16.7, 3.7, 2.0 Hz, 1H), 2.28-2.20 (m, 3H), 2.12-2.05 (m, 1H), 2.03 (s, 6H), 1.84 (td, J=13.9, 6.6 Hz, 1H), 1.61-1.55 (m, 1H), 1.27 (s, 3H). $^{13}$C NMR (CDCl$_3$, 125 MHz): δ 176.6, 174.0, 170.4, 169.6, 149.4, 145.1, 127.6, 126.8, 106.0, 103.0, 98.7, 85.2, 71.2, 53.1, 52.7, 50.3, 48.5, 45.1, 44.9, 35.7, 35.0, 32.8, 22.2, 21.1, 15.9. HRMS(ESI): m/z calc. for $C_{25}H_{30}O_{10}Na$ [M+Na]$^+$: 513.1737. found: 513.1741.

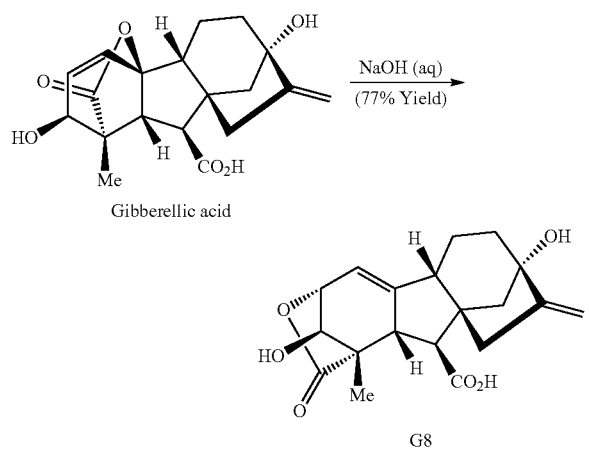

Procedure: Gibberellic acid (1.002 g, 2.89 mmol) and sodium hydroxide (954 mg, 23.9 mmol) were dissolved in water (500 mL) in a round bottom flask. After stirring at room temperature for 1.5 hours, the reaction was acidified to pH 3 and extracted with ethyl acetate (5×). The organic layers were dried over magnesium sulfate and concentrated to afford known compound G8 as a white solid (771 mg, 77% yield).[6]

$^1$H NMR (d$_6$-acetone, 500 MHz): δ 5.80 (dt, J=5.2, 2.6 Hz, 1H), 5.10-5.06 (m, 1H), 4.93-4.90 (m, 1H), 4.70 (t, J=5.3 Hz, 1H), 4.28 (d, J=5.3 Hz, 1H), 3.33 (dd, J=6.1, 2.7 Hz, 1H), 2.81 (br s, 1H), 2.68 (dt, J=16.4, 3.0 Hz, 1H), 2.61-2.55 (m, 1H), 2.44 (d, J=6.1 Hz, 1H), 2.33-2.24 (m, 1H), 1.99-1.89 (m, 1H), 1.77-1.62 (m, 3H), 1.51 (dd, J=11.0, 3.1 Hz, 1H), 1.49-1.42 (m, 1H), 1.34 (ddd, J=10.9, 2.8, 1.1 Hz, 1H), 1.16 (s, 3H). $^{13}$C NMR (d$_6$-acetone, 125 MHz): δ 177.5, 176.0, 155.7, 151.9, 114.6, 106.3, 79.0, 75.8, 74.9, 49.9, 49.8, 49.6, 49.1, 46.7, 46.3, 39.9, 38.6, 19.4, 17.4. HRSM(ESI): m/z calc. for $C_{19}H_{22}O_6Na$ [M+Na]$^+$: 369.1314. found: 369.1317.

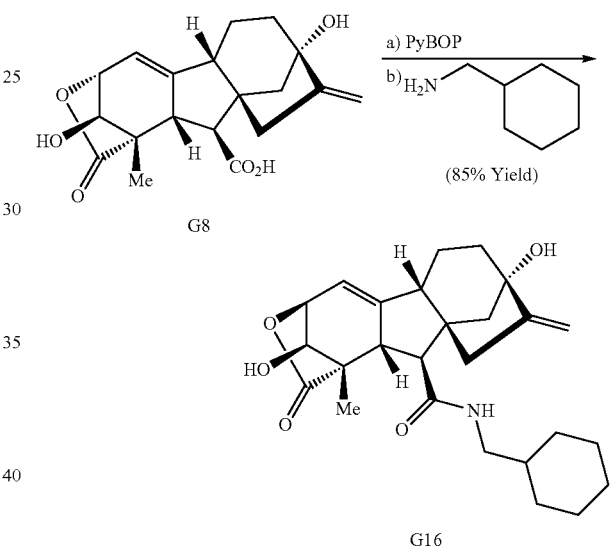

Procedure: In an oven-dried flask, G8 (128.4 mg, 0.37 mmol) and benzotriazol-1-yl-oxytripyrrolidinophosphonium hexafluorophosphate (213.0 mg, 0.41 mmol) were dissolved in dichloromethane (4 mL). Diisopropylethylamine (200 μL, 1.15 mmol) was added, and the reaction was stirred at room temperature for 2 hours. After complete complexation by TLC, cyclohexanemethylamine (50 μL, 0.38 mmol) and additional diisopropylethylamine (50 μL, 0.29 mmol) were added, and the reaction was allowed to stir at room temperature for 16 hours. The reaction was quenched with water, extracted with ethyl acetate (3×), and concentrated. Purification by flash silica chromatography (1:1 to 1:2 hexanes/ethyl acetate) afforded pure G16 as a white solid (138.4 mg, 85% yield).

$^1$H NMR (CDCl$_3$, 500 MHz): δ 6.17 (t, J=5.9 Hz, 1H), 5.77 (dt, J=5.0, 2.4 Hz, 1H), 5.10 (t, J=2.5 Hz, 1H), 4.97 (t, J=2.0 Hz, 1H), 4.77 (t, J=5.3 Hz, 1H), 4.24 (d, J=5.3 Hz, 1H), 3.33 (dd, =5.9, 2.6 Hz, 1H), 3.14 (dt, J=13.3, 6.6 Hz, 1H), 3.06 (dt, J=13.3, 6.0 Hz, 1H), 2.82-2.74 (m, 1H), 2.51 (dt, J=16.5, 2.9 Hz, 1H), 2.38-2.28 (m, 1H), 2.30-2.05 (m, buried, 1H), 2.24 (d, J=5.9 Hz, 1H), 1.97-1.86 (m, 1H), 1.78-1.62 (m, 7H), 1.58-1.52 (m, 1H), 1.51 (dd, J=11.1, 2.7 Hz, 1H), 1.46 (ddp, J=11.0, 7.0, 3.6 Hz, 1H), 1.34 (dd, J=11.0, 2.7 Hz, 1H), 1.29-1.10 (m, 3H singlet buried, 7H), 1.00-0.85 (m, 2H). $^{13}$C NMR (CDCl$_3$, 125 MHz): δ 177.9, 174.0, 153.9, 153.4, 113.1, 107.0, 79.2, 75.8, 74.3, 51.4, 49.5, 49.0, 48.7, 46.3, 45.7, 45.7, 39.1, 38.1, 37.5, 31.1 (2), 26.6, 26.0 (2), 18.9, 17.2. HRMS(ESI): m/z calc. for C$_{26}$H$_{36}$NO$_5$ [M+H]$^+$: 442.2593. found: 442.2585.
Scheme 2.1 Synthesis of G16 derivatives.
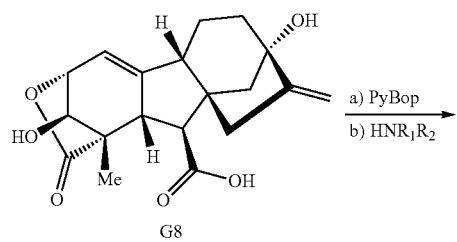
G8
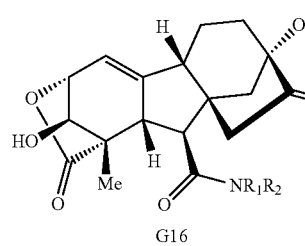
G16
19 amides and esters
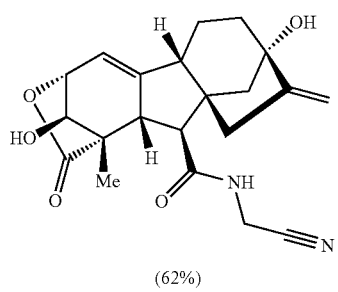
G16c
(62%)
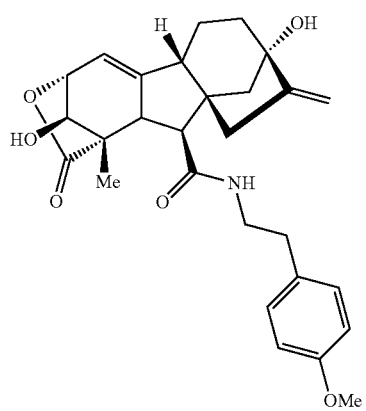
G16d
(92%)
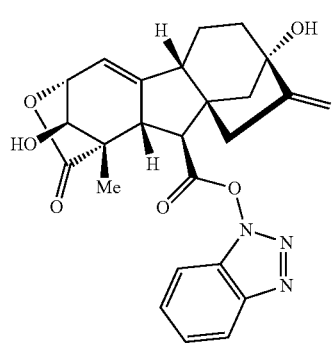
G16a
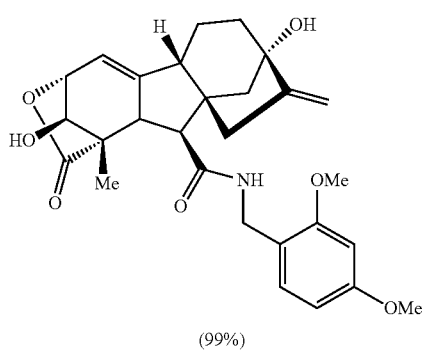
G16e
(99%)
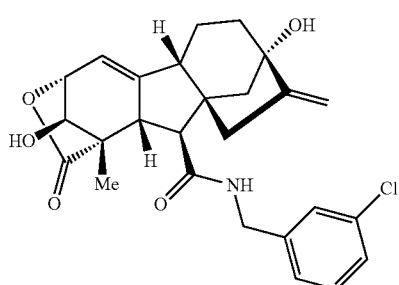
G16b
(91%)
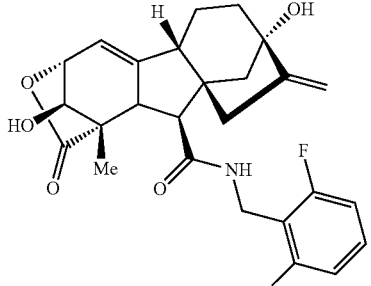
G16f
(57%)

| | |
|---|---|
| 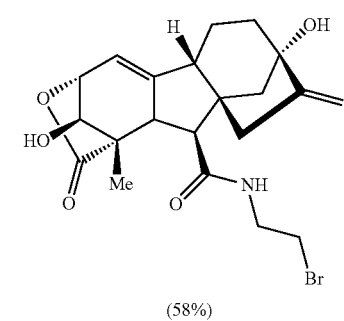 (58%) G16g | 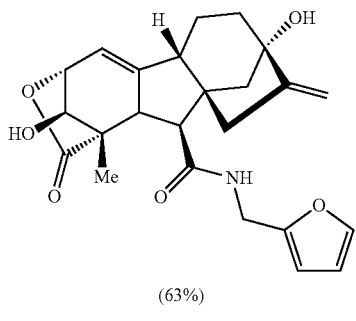 (63%) G16k |
| 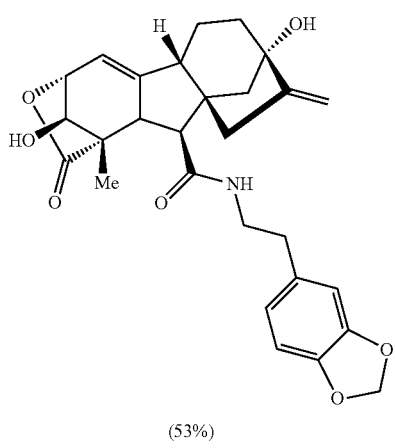 (53%) G16h | 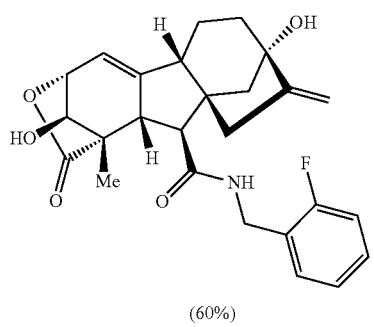 (60%) G16l |
| 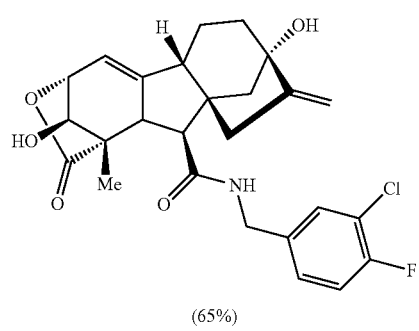 (65%) G16i | 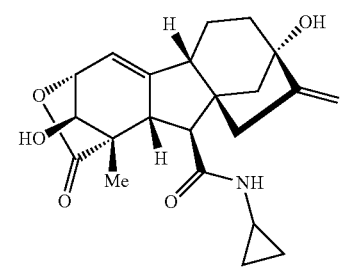 (66%) G16m |
| 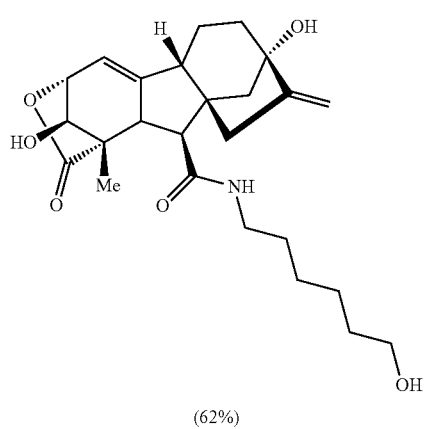 (62%) G16j | 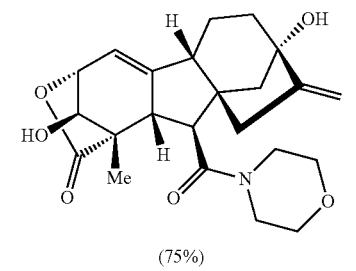 (75%) G16n |
| | 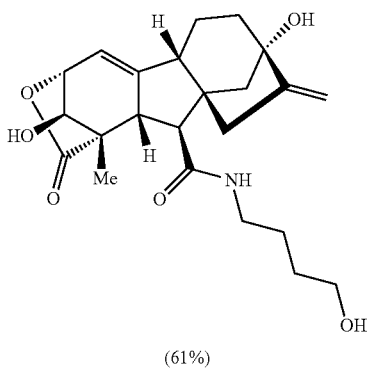 (61%) G16o |

-continued

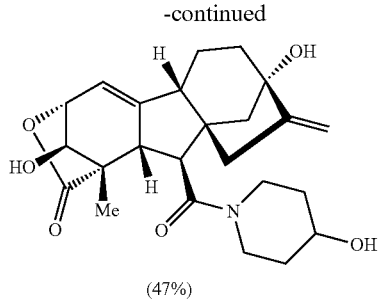

(47%)

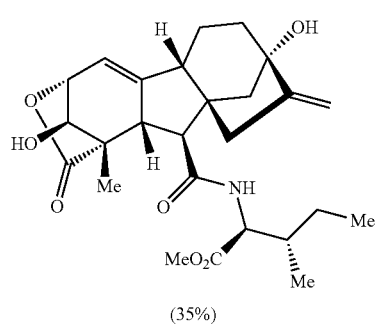

(35%)

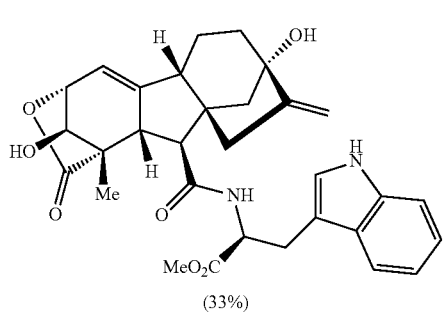

(33%)

Preparation of G3.

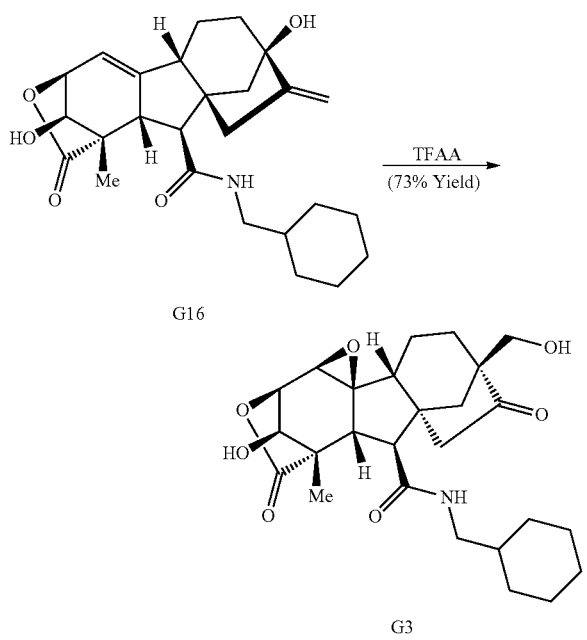

Procedure: In a vial with a stir bar, loaded hydrogen peroxide (30% in water, 15.4 µL, 0.14 mmol), trifluoroacetic anhydride (100 µL, 0.72 mmol), and trifluoroacetic acid (110 µL, 1.44 mmol) were dissolved in dichloromethane. Amide G16 was added in one portion and allowed to react for 15 minutes. The reaction was then washed with water (2×) and saturated aqueous sodium bicarbonate. Purification by flash silica chromatography (1:1 to 1:2 hexanes/ethyl acetate) afforded pure G3 as a white solid (14.8 mg, 73% yield).

$^1$H NMR (CDCl$_3$, 500 MHz): δ 6.33 (t, J=5.8 Hz, 1H), 4.92 (dd, J=5.7, 3.4 Hz, 1H), 4.22 (br s, 1H), 4.01 (br s, 1H), 3.81 (d, J=11.6 Hz, 1H), 3.74 (d, J=3.4 Hz, 1H), 3.42 (d, J=11.6 Hz, 1H), 3.26 (dt, J=13.5, 6.9 Hz, 1H), 3.22 (d, J=3.7 Hz, 1H), 3.03 (dt, J=13.5, 5.7 Hz, 1H), 2.99 (dd, J=12.5, 5.0 Hz, 1H), 2.76 (d, J=3.8 Hz, 1H), 2.26 (dd, J=11, 8 Hz, 1H), 2.26 (d, J=18.8 Hz, 1H), 1.91 (d, J=18.8 Hz, 1H), 1.76-1.56 (m, 7H), 1.52-1.45 (m, 1H), 1.40-1.32 (m, 1H), 1.27-1.12 (m, buried methyl, 8H), 1.02-0.90 (m, 3H). $^{13}$C NMR (CDCl$_3$, 125 MHz): δ 219.1, 177.6, 172.8, 76.9, 71.5, 67.9, 63.8, 56.4, 56.3, 50.5, 48.7, 46.6, 46.4, 46.0, 45.2, 43.6, 40.6, 38.0, 31.1 (2), 30.6, 26.6, 26.0 (2), 19.2, 17.7. HRMS(ESI): m/z calc. for C$_{26}$H$_{36}$NO$_7$ [M+H]$^+$: 474.2492. found: 474.2493.

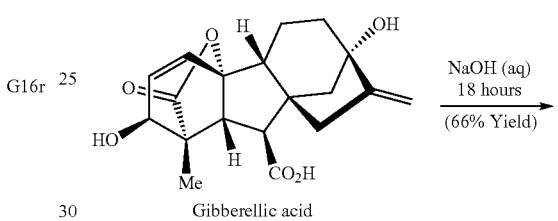

Gibberellic acid

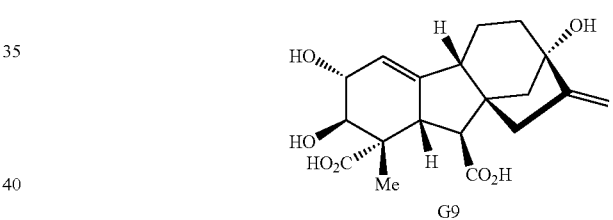

G9

Procedure: Gibberellic acid (2.008 g, 5.80 mmol) and sodium hydroxide (955 mg, 23.9 mmol) were dissolved in water (230 mL, 0.1 M NaOH) and stirred at room temperature for 17.5 hours. The reaction was cooled in an ice bath and quenched with hydrogen chloride (1 M, 40 mL) to a final pH of 2. The reaction was extracted with ethyl acetate (5×) and concentrated. The organic layer was then triturated with hexanes to afford known compound G9 as a white solid (1.403 g, 66% yield).[7]

$^1$H NMR (d$_6$-DMSO, 500 MHz): δ 12.32 (s, 2H), 5.21 (q, J=2.9 Hz, 1H), 5.08 (br m, 1H), 5.00 (m, 1H), 4.87 (m, 1H), 4.76 (s, 1H), 3.88 (q, J=2.8 Hz, 1H), 3.70 (d, J=3.1 Hz, 1H), 2.88-2.83 (m, 1H), 2.75 (d, J=6.0 Hz, 1H), 2.55-2.45 (m, 1H), 2.36-2.31 (m, 1H), 2.13 (dd, J=16.1, 2.6 Hz, 1H), 1.85-1.78 (m, 1H), 1.63 (dd, J=11.1, 2.7 Hz, 1H), 1.61-1.48 (m, 2H), 1.42-1.35 (m, 1H), 1.31 (d, J=10.5 Hz, 1H), 1.15 (s, 3H). $^{13}$C NMR (d$_6$-acetone, 125 MHz): δ 177.1, 176.2, 155.7, 143.2, 115.6, 105.4, 78.7, 75.2, 71.2, 50.0, 49.6, 48.9, 47.3, 46.7, 46.6, 39.5, 38.2, 21.2, 18.8. HRMS(ESI): m/z calc. for C$_{19}$H$_{24}$O$_7$Na [M+Na]$^+$: 387.1420. found: 387.1420. Melting point: 143-145° C.

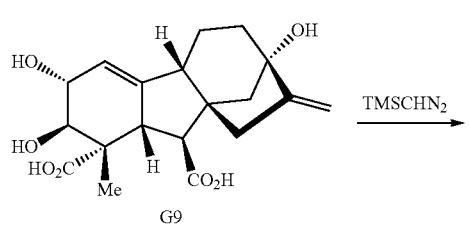

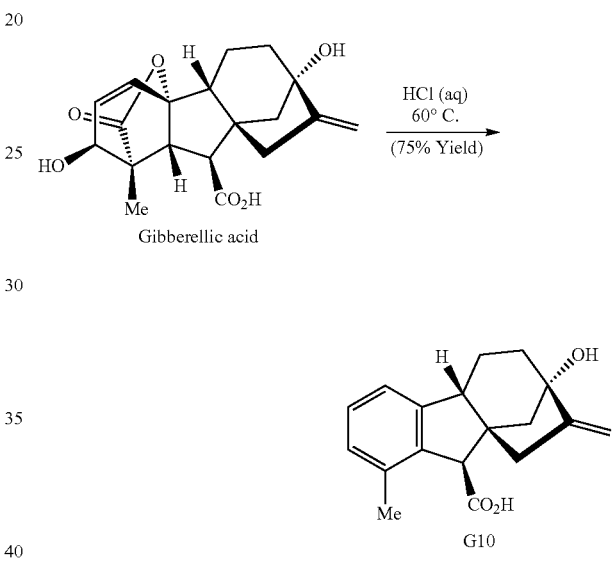

Procedure: In an oven-dried round bottom flask with a stir bar under argon, loaded G9 (55.4 mg, 0.15 mmol) and dissolved in toluene (1.5 mL) and methanol (0.5 mL). Added trimethylsilyldiazomethane (2 M in hexanes, 160 µL, 0.32 mmol) and allowed to stir for 1 hour, at which point the reaction was concentrated. The solid residual was redissolved in dichloromethane (1.5 mL) and water (0.5 mL). Sodium periodate (65.2 mg, 0.31 mmol) was added in a single portion, and the reaction was heated at 40° C. for 6 hours. The reaction was then cooled, extracted with ethyl acetate (3×) and concentrated. Purification by flash silica chromatography (2:1 hexanes/ethyl acetate) afforded pure G4 as a white solid (36.2 mg, 61% yield).

Note: G17 could be isolated and purified following esterification with (trimethylsilyl)diazomethane by flash silica chromatography (2:1 hexanes/ethyl acetate) to afford pure product.

G17 NMR (CDCl$_3$, 500 MHz): δ 5.44 (q, J=2.3 Hz, 1H), 5.12 (t, J=2.5 Hz, 1H), 4.99 (t, J=2.1 Hz, 1H), 4.16 (m, 1H), 3.87 (d, J=4.5 Hz, 1H), 3.72 (s, 3H), 3.66 (s, 3H), 3.10 (d, J=6.6 Hz, 1H), 2.59-2.48 (m, 3H), 2.28-2.15 (m, 2H), 1.97 (dd, J=14.4, 6.1 Hz, 1H), 1.80 (td, J=11.4, 6.1 Hz, 1H), 1.75-1.67 (m, 1H), 1.65 (dd, J=10.7, 2.9 Hz, 1H), 1.61-1.49 (m, 3H), 1.39-1.35 (m, 1H), 1.36 (s, 3H). $^{13}$C NMR (CDCl$_3$, 125 MHz): δ 176.4, 175.4, 154.0, 142.6, 116.2, 106.8, 79.2, 75.2, 70.3, 52.2, 52.0, 50.9, 49.7, 48.9, 48.0, 47.3, 46.1, 39.1, 37.7, 20.3, 18.9. HRMS(ESI): m/z calc. for C$_{21}$H$_{28}$O$_7$Na [M+Na]$^+$: 415.1733. found: 415.1734.

G4 $^1$H NMR (CDCl$_3$, 125 MHz): δ 6.27 (d, J=5.9 Hz, 1H), 6.09 (s, 1H), 5.16 (t, J=1.4 Hz, 1H), 5.02 (d, J=5.9 Hz, 1H), 4.94 (t, J=2.0 Hz, 1H), 3.69 (s, 3H), 3.68 (s, 3H), 3.11 (d, J=6.6 Hz, 1H), 2.42-2.36 (m, 2H), 2.27 (dt, J=15.8, 3.0 Hz, 1H), 2.11-2.02 (m, 1H), 2.00-1.85 (m, 2H), 1.77 (dd, J=7.8, 5.5 Hz, 1H), 1.71-1.63 (m, 2H), 1.63-1.58 (m, 1H), 1.57 (s, 3H), 1.52-1.46 (m, 1H). $^{13}$C NMR (CDCl$_3$, 125 MHz): δ 174.6, 173.4, 155.6, 142.8, 108.1, 106.9, 103.9, 92.7, 78.8, 66.7, 63.4, 54.5, 52.1, 52.0, 51.6, 49.6, 48.1, 42.3, 38.7, 22.3, 18.1. HRMS (ER): m/z calc. for C$_{21}$H$_{26}$O$_7$Na [M+Na]$^+$: 413.1576. found: 413.1578. Melting point: 136-137° C.

Procedure: Gibberellic acid (1.404 g, 4.05 mmol) was dissolved in hydrochloric acid (1.2 M, 20 mL) in a round bottom flask and heated for 2.75 hours at 65° C. The reaction was cooled, and the solid precipitate was filtered and washed with water. G10, a known compound, was isolated as a white solid (863 mg, 75% yield)[8]

$^1$H NMR (d$_6$-acetone, 500 MHz): δ 10.97 (br s, 1H), 7.10 (t, J=7.5 Hz, 1H), 6.98 (d, J=7.6 Hz, 1H), 6.95 (d, J=7.4 Hz, 1H), 4.99 (dt, J=2.7, 1.4 Hz, 1H), 4.70 (t, J=2.0 Hz, 1H), 3.98 (s, 1H), 2.88 (dd, J=12.6, 5.0 Hz, 1H), 2.31-2.21 (m, 3H), 2.20 (s, 3H), 2.08-1.99 (m, 2H), 1.93 (td, J=12.2, 5.1 Hz, 1H), 1.89 (dd, J=10.3, 2.6 Hz, 1H), 1.71-1.62 (m, 1H), 1.54 (qd, J=12.7, 5.1 Hz, 1H). $^{13}$C NMR (d$_6$-acetone, 125 MHz): δ 172.7, 155.9, 145.7, 139.7, 135.8, 129.3, 127.9, 120.3, 103.1, 80.6, 55.2, 53.8, 52.7, 49.1, 40.7, 34.9, 22.8, 20.0. HRMS(ESI): m/z calc. for C$_{18}$H$_{21}$O$_3$ [M+H]$^+$: 285.1491. found: 285.1491. HRMS(ESI): m/z calc. for C$_{18}$H$_{20}$O$_3$Na [M+Na]$^+$: 307.1310. found: 307.1307. MP: 188-190° C.

Scheme 2.2. Synthesis of G10, G19, and G6 derivatives.
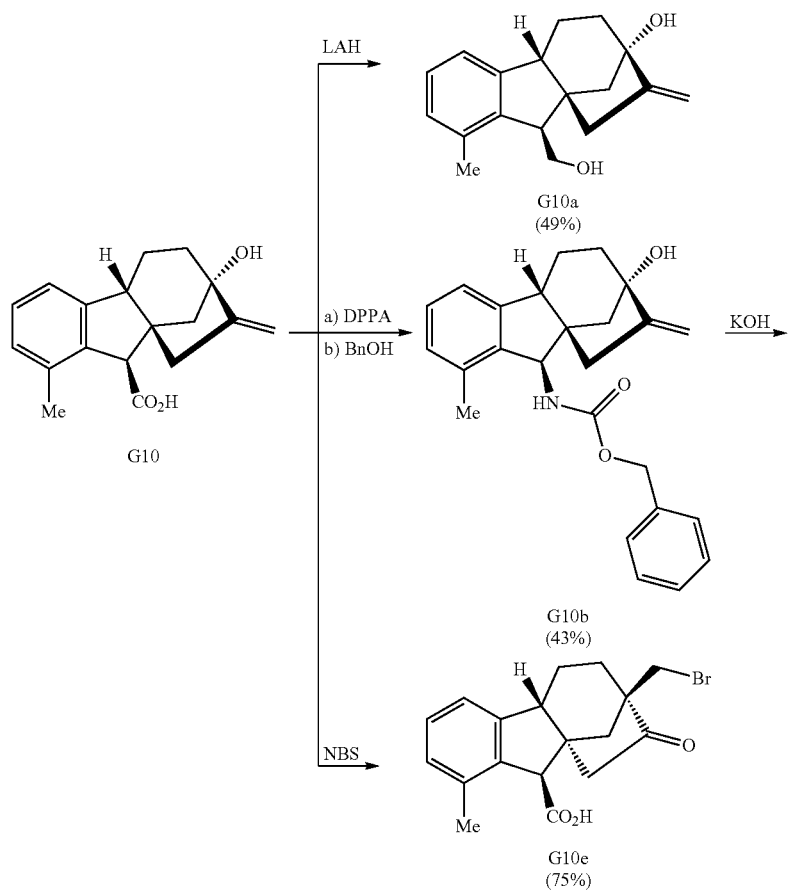
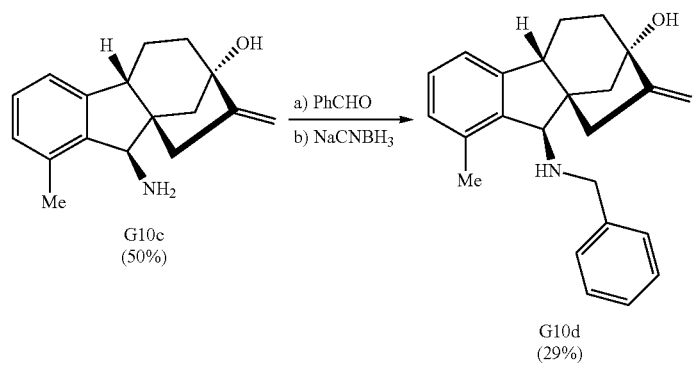

-continued
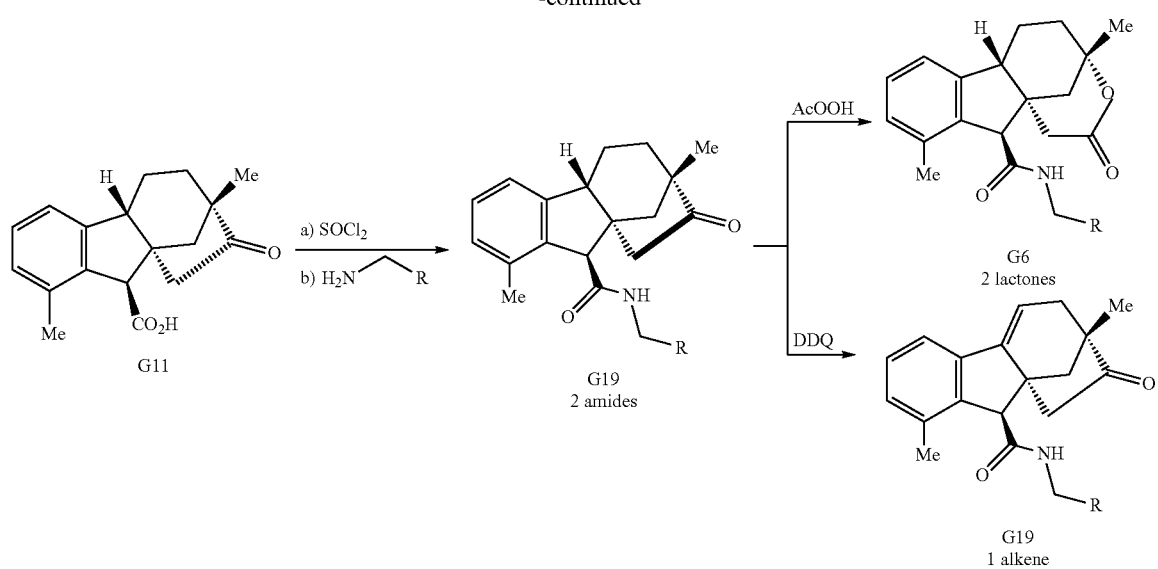
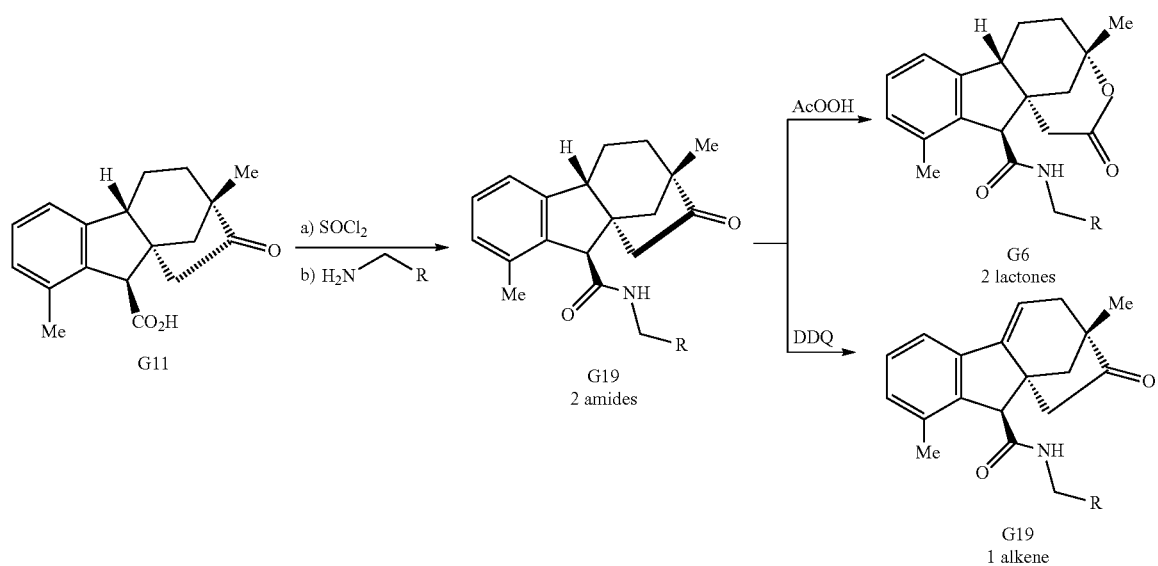
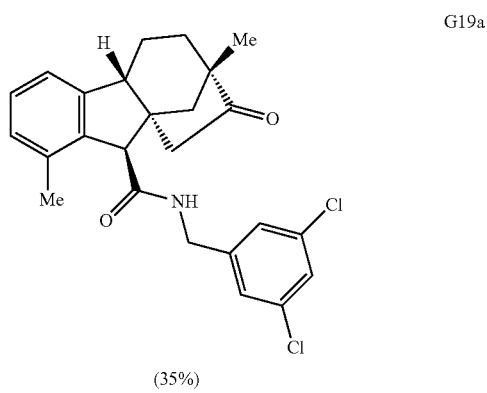

-continued
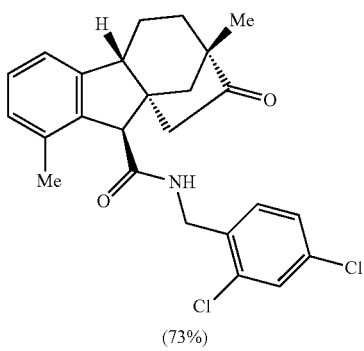
G19b
(73%)
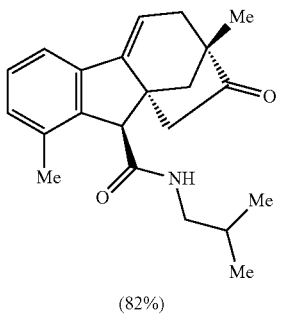
G19c
(82%)
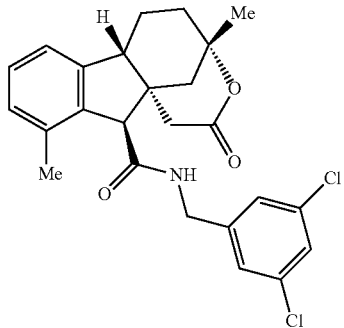
G6a
(38%)
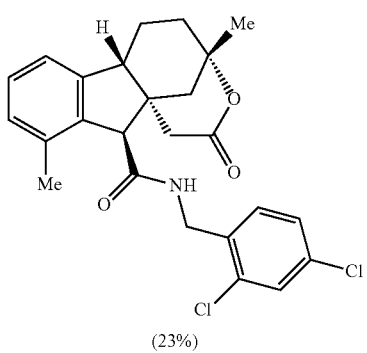
G6b
(23%)

Preparation of G18.

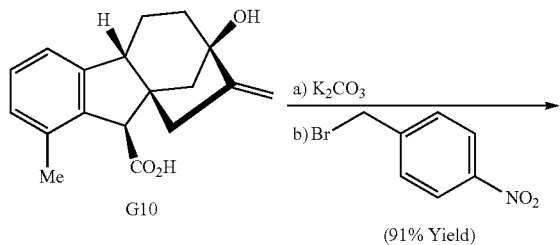

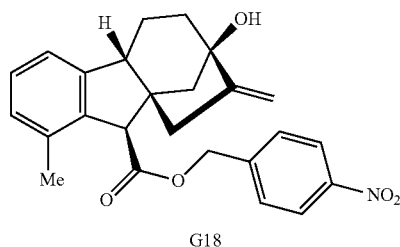

Procedure: In an oven-dried vial with stir bar, G10 (48.7 mg, 0.17 mmol) and 4-nitrobenzyl bromide (92.0 mg, 0.43 mmol) were dissolved in acetone (1 mL). Potassium carbonate (120.9 mg, 0.88 mmol) was then added, and the reaction stirred at room temperature for 15.5 hours. The reaction was diluted with water and extracted with ethyl acetate (2×). Purification by flash silica chromatography (4:1 to 3:1 hexanes/ethyl acetate) afforded pure G18 as a white solid (65.3 mg, 91% yield).

$^1$H NMR (CDCl$_3$, 500 MHz): δ 8.23 (d, J=8.5 Hz, 2H), 7.57 (d, J=8.5 Hz, 2H), 7.14 (t, J=7.5 Hz, 1H), 7.01 (d, J=7.6 Hz, 1H), 6.94 (d, J=7.4 Hz, 1H), 5.36 (d, J=13.2 Hz, 1H), 5.27 (d, J=13.2 Hz, 1H), 4.98 (t, J=2.7 Hz, 1H), 4.72 (t, J=2.2 Hz, 1H), 4.05 (s, 1H), 2.85 (dd, J=12.6, 4.9 Hz, 1H), 2.25 (ddt, J=12.6, 5.2, 2.7 Hz, 1H), 2.16 (dd, J=6.6, 2.5 Hz, 1H), 2.13 (d, J=2.5 Hz, 1H), 2.09 (s, 3H), 2.05 (dt, J=18, 3.0 Hz, 1H), 1.97 (dd, J=12.4, 4.3 Hz, 1H), 1.95-1.92 (m, 1H), 1.73 (ddd, J=9.6, 5.3, 2.3 Hz, 1H), 1.63 (dd, J=12.7, 5.2 Hz, 1H), 1.57 (dd, J=12.6, 5.0 Hz, 1H). $^{13}$C NMR (CDCl$_3$, 125 MHz): δ 171.1, 154.11, 148.0, 144.5, 143.0, 138.0, 135.0, 129.2, 129.0, 127.8, 124.0 (2), 120.0, 103.5, 80.6, 65.3, 65.3, 54.7, 53.7, 52.3, 49.0, 39.6, 34.3, 22.1, 20.0. HRMS(ESI): m/z calc. for C$_{25}$H$_{26}$NO$_5$ [M+H]$^+$: 420.1811. found: 420.1810.

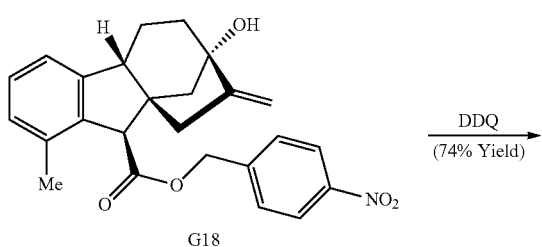

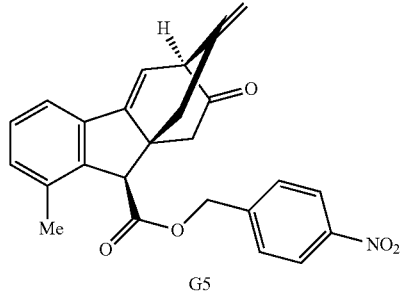

Procedure: In an oven-dried vial with stir bar, G18 (35.0 mg, 0.083 mmol) and 2,3-dichloro-5,6-dicyanobenzoquinone (39.0 mg, 0.172 mmol) were dissolved in toluene (1.5 mL) and heated at 80° C. for 15 hours. The reaction was cooled and diluted with ethyl acetate. The organic layer was washed with saturated aqueous ammonium chloride (2×) and water (4×), and concentrated. Purification by flash silica chromatography (4:1 to 3:1 hexanes/ethyl acetate) afforded pure G5 as a white solid (25.5 mg, 74% yield).

$^1$H NMR (CDCl$_3$, 500 MHz): δ 8.23 (d, J=8.5 Hz, 2H), 7.52 (d, J=8.5 Hz, 2H), 7.33 (d, J=7.6 Hz, 1H), 7.27 (t, J=7.5 Hz, 1H), 7.13 (d, J=7.4 Hz, 1H), 6.35 (d, J=6.4 Hz, 1H), 5.32 (m, 2H), 5.11 (t, J=2.5 Hz, 1H), 4.86 (t, J=2.5 Hz, 1H), 4.13 (s, 1H), 3.78 (d, J=6.5 Hz, 1H), 2.51 (d, J=17.8 Hz, 1H), 2.39 (dt, J=15.7, 2.1 Hz, 1H), 2.34 (dq, J=15.7, 2.5 Hz, 1H), 2.22 (dd, J=17.8, 3.1 Hz, 1H), 2.10 (s, 3H). $^{13}$C NMR (CDCl$_3$, 125 MHz): δ 205.7, 171.1, 153.2, 148.1, 142.6, 142.0, 139.7, 136.5, 136.0, 131.0, 129.3, 129.3 (2), 124.0 (2), 119.3, 112.9, 111.7, 65.5, 60.3, 55.5, 48.9, 45.7, 35.5, 19.0. HRMS (ESI): m/z calc. for C$_{25}$H$_{22}$NO$_5$ [M+H]$^+$: 416.1498. found: 416.1494.

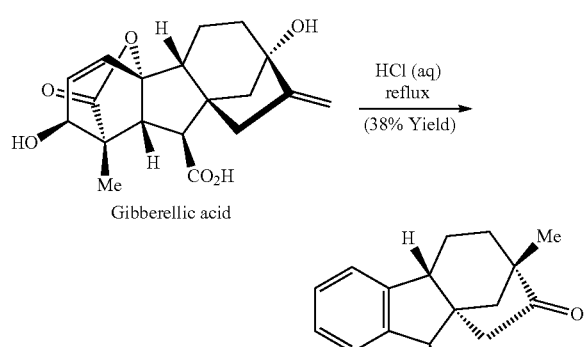

Procedure: Gibberellic acid (959 mg, 2.77 mmol) was suspended in aqueous hydrochloric acid (2.4 M, 150 mL) in a round bottom flask and refluxed for 2 hours. The solid crust that formed during the course of the reaction was periodically broken up with a glass rod. After refluxing, the reaction was filtered hot, and the solid was washed with water to provide known compound G11 as a white solid (298 mg, 38% yield).[8]

$^1$H NMR (CDCl$_3$, 500 MHz): δ 7.22 (t, J=7.5 Hz, 1H), 7.07 (d, J=7.6 Hz, 1H), 7.00 (d, J=7.5 Hz, 1H), 4.21 (s, 1H), 3.04 (t, J=7.8 Hz, 1H), 2.74 (d, J=17.9 Hz, 1H), 2.51 (dd, J=17.8, 3.6 Hz, 1H), 2.25 (s, 3H), 2.15-2.07 (m, 1H), 2.05 (dd, J=12.1, 3.8 Hz, 1H), 1.90 (dq, J=14.3, 8.1 Hz, 1H), 1.83-1.73 (m, 1H), 1.64 (ddd, J=13.5, 7.5, 5.5 Hz, 1H), 1.40 (d, J=12.1 Hz, 1H), 1.07 (s, 3H). $^{13}$C NMR (CDCl$_3$, 125 MHz): δ 221.6, 177.0, 146.2, 137.2, 135.4, 129.2, 128.6, 120.7, 55.8, 51.4, 50.7, 50.0, 48.2, 39.1, 34.6, 23.0, 21.8, 19.7. HRMS(ESI): m/z calc. for C$_{18}$H$_{21}$O$_3$ [M+H]$^+$: 285.1491. found: 285.1492. HRMS(ESI): m/z calc. for C$_{18}$H$_{20}$O$_3$Na [M+Na]$^+$: 307.1310. found: 307.1312.

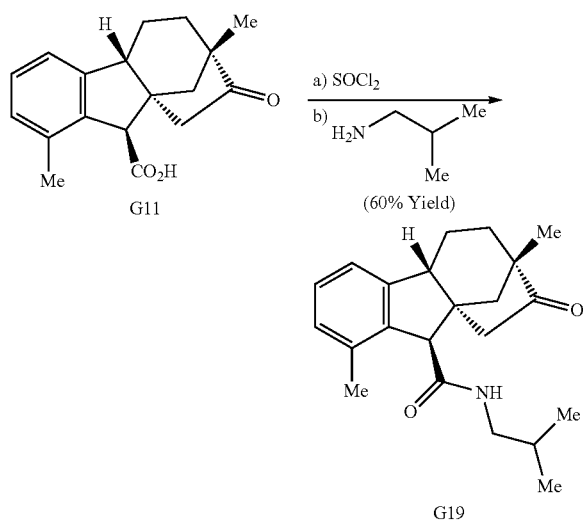

Procedure: In an oven-dried round bottom flask, G11 (799.5 mg, 2.81 mmol) was dissolved in tetrahydrofuran (60 mL). Thionyl chloride (450 µL, 6.20 mmol) was added, and the reaction was refluxed for 50 minutes. The reaction was then cooled in an ice bath, at which point triethylamine (900 µL, 6.46 mmol) and isobutylamine (950 µL, 9.47 mmol) were added and the reaction was allowed to warm to room temperature for 1 hour. The reaction was quenched with water, extracted with ethyl acetate (3×), and purified by flash silica chromatography using 4:1 to 3:1 hexanes/ethyl acetate to afford pure G19 as a white solid (569.6 mg, 60% yield).

$^1$H NMR (CDCl$_3$, 500 MHz): δ 7.22 (t, J=7.5 Hz, 1H), 7.07 (d, J=7.5 Hz, 1H), 7.01 (d, J=7.5 Hz, 1H), 5.55 (br s, 1H), 4.01 (s, 1H), 3.12 (t, J=6.4 Hz, 2H), 2.94 (t, J=8.0 Hz, 1H), 2.71 (d, J=17.7 Hz, 1H), 2.43 (dd, J=17.7, 3.7 Hz, 1H), 2.23 (s, 3H), 2.10 (dq, J=9.0, 7.8 Hz, 1H), 1.96 (dd, J=12.0, 3.7 Hz, 1H), 1.87-1.71 (m, 3H), 1.68-1.59 (m, 1H), 1.47 (d, J=12.0 Hz, 1H), 1.05 (s, 3H), 0.90 (d, J=2.2 Hz, 3H), 0.88 (d, J=2.2 Hz, 3H). $^{13}$C NMR (CDCl$_3$, 125 MHz): δ 222.0, 171.4, 147.2, 137.9, 135.6, 129.4, 128.7, 121.1, 58.5, 52.0, 51.6, 49.4, 48.1, 47.3, 38.6, 34.5, 29.9, 28.6, 23.5, 21.8, 20.5, 19.5. HRMS(ESI): m/z calc. for C$_{22}$H$_{30}$NO$_2$ [M+H]$^+$: 340.2277. found: 340.2267. Melting point: 168-170° C.

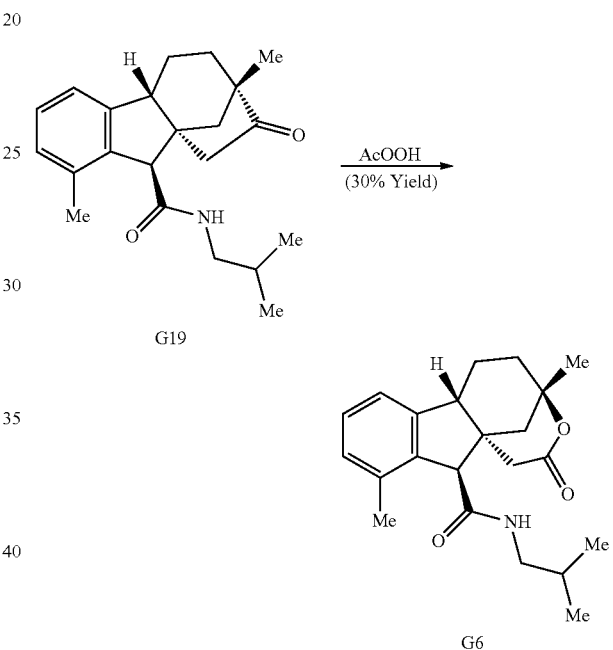

Procedure: An oven-dried vial with stir bar was loaded with G19 (51.4 mg, 0.15 mmol) and dissolved in dichloromethane (4 mL). The reaction was cooled to 0° C. in an ice bath, and sodium carbonate (127.1 mg, 1.20 mmol) and peracetic acid (32% in acetic acid, 170 µL, 0.81 mmol) were added. The reaction stirred for 15 hours, during which time it was allowed to warm to room temperature. Saturated aqueous sodium bicarbonate was added to quench the reaction. The reaction was acidified to pH 3, and the aqueous layer was extracted with ethyl acetate (3×). The combined organic layers were washed with brine, dried over magnesium sulfate, and concentrated. Purification by flash silica chromatography (3:1 to 2:1 hexanes/ethyl acetate) afforded G6 as a white solid (16.0 mg, 30% yield). Unreacted starting material was also recovered as a white solid (7.7 mg).

$^1$H NMR (CDCl$_3$, 500 MHz): δ 7.21 (t, J=7.5 Hz, 1H), 7.07 (d, J=7.6 Hz, 1H), 7.03 (d, J=7.4 Hz, 1H), 5.64 (t, J=6.0 Hz, 1H), 3.47 (s, 1H), 3.24 (dt, J=13.1, 6.4 Hz, 1H), 3.13 (ddd, J=13.2, 7.1, 5.8 Hz, 1H), 2.95 (d, J=17.5 Hz, 1H), 2.90 (d, J=6.5 Hz, 1H), 2.72 (dd, J=17.5, 2.8 Hz, 1H), 2.35-2.19 (m, 1H), 2.22 (s, 3H), 1.94 (ddt, J=15.3, 12.1, 5.8 Hz, 1H), 1.89-1.77 (m, 2H), 1.68 (dd, J=14.0, 2.9 Hz, 1H), 1.49-1.37

(m, 2H), 1.33 (s, 3H), 0.96 (s, 3H), 0.94 (s, 3H). $^{13}$C NMR (CDCl3, 125 MHz): δ 171.5, 169.2, 144.4, 137.9, 136.0, 129.9, 128.1, 119.8, 81.8, 60.2, 48.3, 47.5, 46.9, 40.6, 35.9, 33.1, 29.9, 29.1, 28.6, 20.5, 19.6, 19.0. HRMS(ESI): m/z calc. for $C_{22}H_{30}NO_3$ [M+H]$^+$: 356.2226. found: 356.2219.

Example 3. Quinine Derived Compounds: Synthesis and Characterization

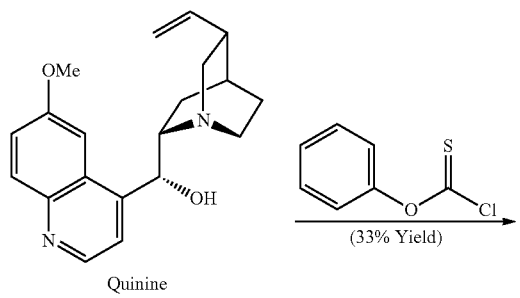

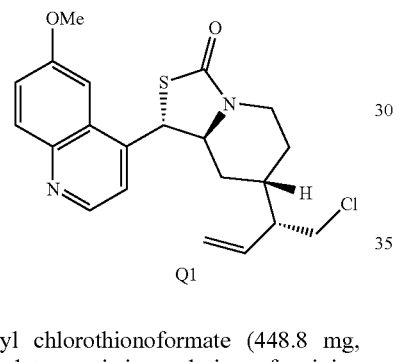

Procedure: O-phenyl chlorothionoformate (448.8 mg, 2.60 mmol) was added to a stirring solution of quinine (324.4 mg, 1.00 mmol) in anhydrous dichloromethane (10 mL) at room temperature. The resulting reaction was allowed to stir for 2.5 hours before the reaction was diluted with dichloromethane and quenched with a saturated solution of sodium bicarbonate. The contents of the quenched reaction were then transferred to a separatory funnel. The biphasic mixture was separated and the organic layer washed with brine, dried with magnesium sulfate, and concentrated under reduced pressure. The crude product was purified by column chromatography 3:2 chloroform/ethyl acetate to provide 133.3 mg (33% yield) of S-thiocarbamate Q1 as a tan foam. Co-crystallization with benzene provided colorless crystals of suitable quality for x-ray diffraction analysis.

Note: Spectral data for Q1 is reported in both CDCl$_3$ and d$_6$-benzene. This was required to attain optimal spectra to fully characterize Q1 in 1-D and 2-D NMR experiments.

$^1$H NMR (CDCl$_3$, 500 MHz): δ 8.81 (d, J=4.6 Hz, 1H), 8.16 (d, J=9.2 Hz, 1H), 7.64 (d, J=4.7 Hz, 1H), 7.47 (dd, J=9.3, 2.6 Hz, 1H), 7.25 (d, J=3.1 Hz, 1H), 5.69 (ddd, J=17.0, 10.1, 9.0 Hz, 1H), 5.21 (dd, J=10.2, 1.4 Hz, 1H), 5.18-5.10 (m, 2H), 4.05-3.96 (m, 2H), 3.98 (s, 3H), 3.53 (dd, J=11.2, 3.4 Hz, 1H), 3.42 (dd, J=11.2, 4.8 Hz, 1H), 2.97 (ddd, J=13.3, 13.3, 3.4 Hz, 1H), 2.61 (ddd, J=14.3, 9.1, 4.1 Hz, 1H), 2.20-2.13 (m, 1H), 2.07-2.00 (m, 1H), 1.88 (ddd, J=13.8, 11.8, 4.7 Hz, 1H), 1.85-1.79 (m, 1H), 1.68 (dddd, J=13.9, 13.9, 4.9, 4.9 Hz, 1H). $^{13}$C NMR (CDCl$_3$, 125 MHz): δ 170.4, 158.7, 147.8, 144.8, 141.8, 137.5, 132.4, 127.8, 122.4, 119.6, 118.6, 100.7, 60.4, 55.9, 47.7, 47.6, 44.0, 39.2, 32.7, 32.0, 26.0.

$^1$H NMR (d$_6$-benzene, 500 MHz): δ 8.71 (d, J=4.5 Hz, 1H), 8.25 (d, J=9.2 Hz, 1H), 7.25 (d, J=4.5 Hz, 1H), 7.21 (dd, J=9.2, 2.7 Hz, 1H), 7.08 (d, J=2.7 Hz, 1H), 5.33 (ddd, J=17.1, 10.2, 9.1 Hz, 1H), 4.89 (dd, J=10.2, 1.7 Hz, 1H), 4.70 (dd, 17.1, 1.0 Hz, 1H), 4.66 (d, J=7.2 Hz, 1H), 3.89 (ddd, J=13.6, 5.1, 2.6 Hz, 1H), 3.45 (s, 3H), 3.37 (dd, J=14.4, 5.1 Hz, 1H), 2.97 (dd, J=11.2, 3.1 Hz, 1H), 2.90 (dd, J=11.2, 4.8 Hz, 1H), 2.44 (td, J=13.2, 3.5 Hz, 1H), 1.83 (ddd, J=9.6, 9.0, 4.6 Hz, 1H), 1.59-1.48 (m, 2H), 1.29-1.08 (m, 3H). $^{13}$C NMR (d$_6$-benzene, 125 MHz): δ 169.6, 158.8, 148.2, 145.8, 141.5, 137.9, 133.3, 128.4, 121.8, 119.4, 117.9, 101.4, 59.6, 55.3, 47.5, 47.4, 43.2, 39.1, 32.1, 31.9, 25.7.

HRMS(ESI): m/z calc. for $C_{21}H_{24}ClN_2O_2S$ [M+H]$^+$: 403.1247. found: 403.1244. MP: 158-160° C. X-ray crystallographic data for Q1 was obtained, confirming the structure and stereochemistry. The crystallographic data have been deposited at the Cambridge Crystallographic Centre, 12 Union Road, Cambridge CB2 1 EZ, UK, and copies can be obtained on request, free of charge, by quoting the publication citation and the deposition number CCDC 872159.

Scheme 3.1. Synthesis of Q1 azides and amines.

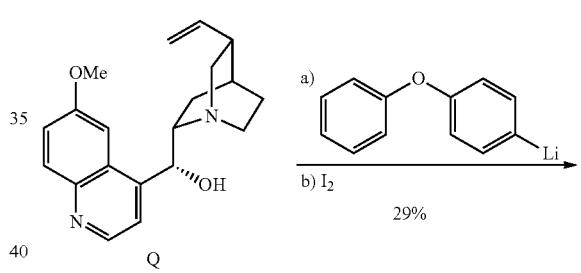

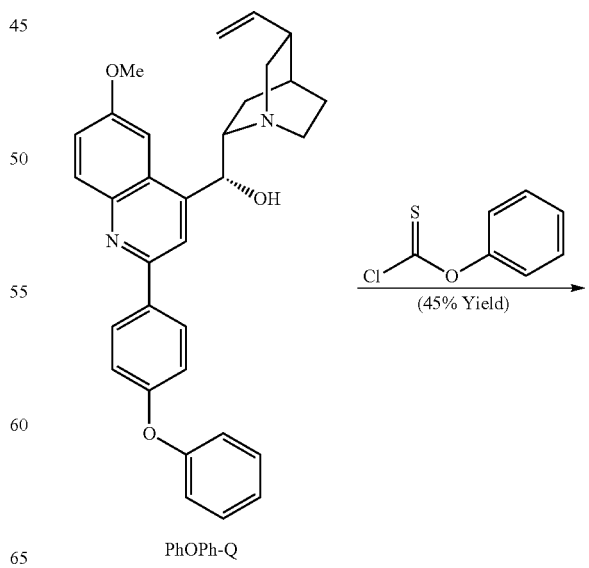

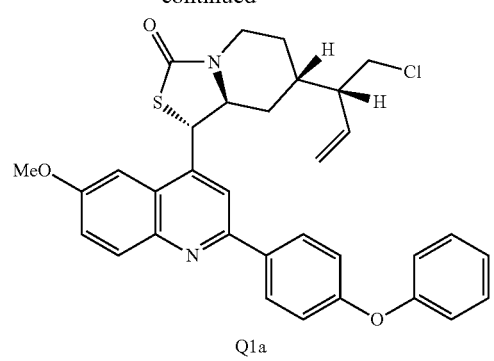
Q1a
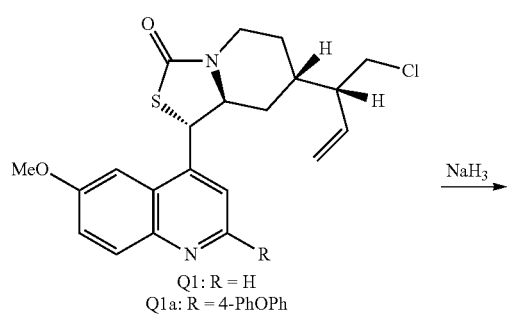
Q1: R = H
Q1a: R = 4-PhOPh
NaH₃ →
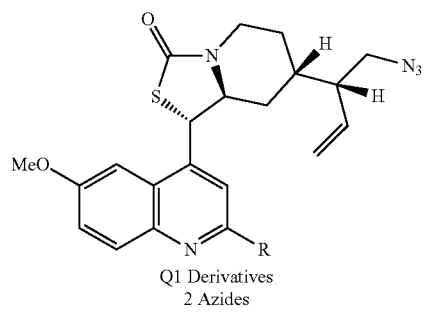
Q1 Derivatives
2 Azides
PPh₃ →
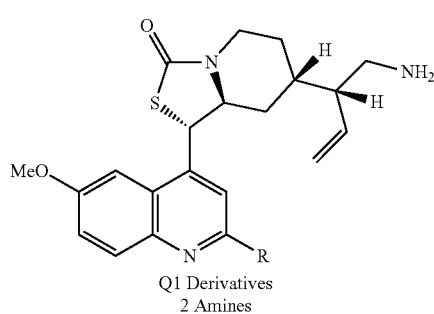
Q1 Derivatives
2 Amines
Q1b
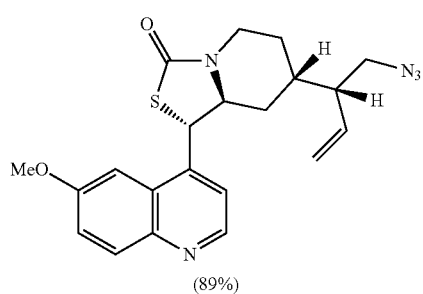
(89%)
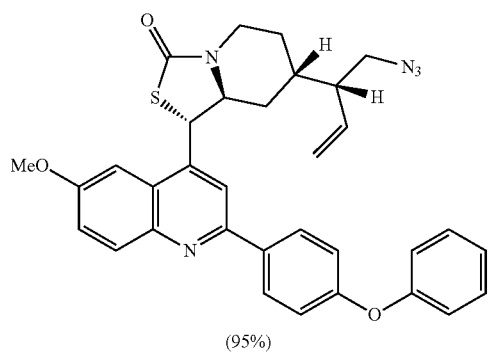
Q1c
(95%)
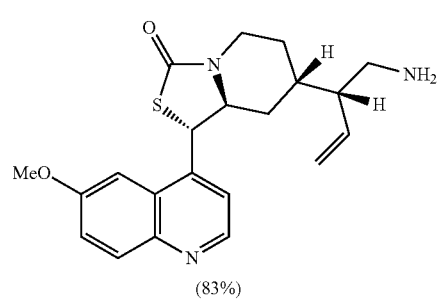
Q1d
(83%)
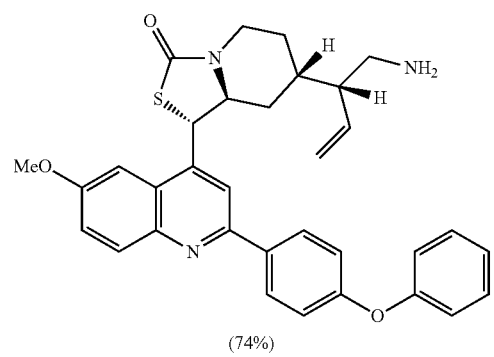
Q1e
(74%)
Scheme 3.2. Synthesis of Q1 triazoles.
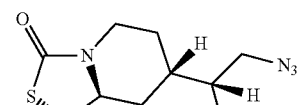
Q1b: R₁ = H
Q1c: R₁ = 4-PhOPh
$\xrightarrow{\equiv\!-\!R_2}{CuSO_4 \cdot 5\,H_2O,\ Sodium\ Ascorbate}$

89
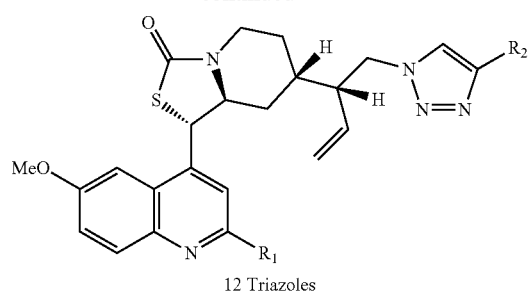
Q1f
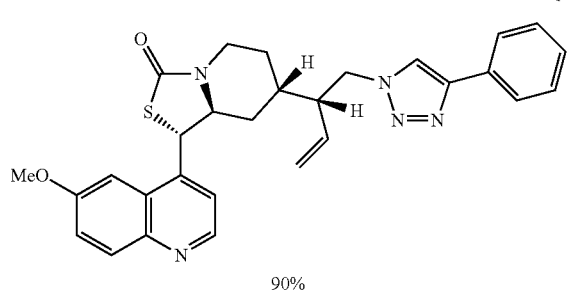
90%
Q1g
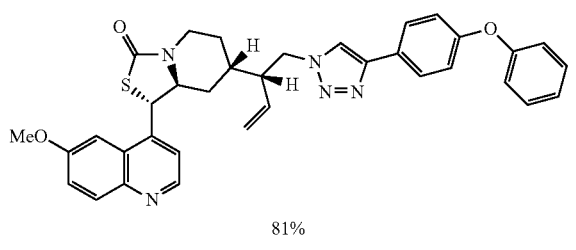
81%
Q1h
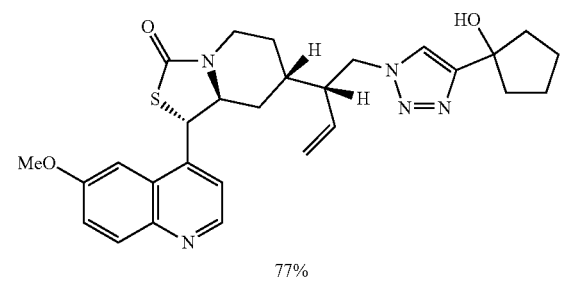
77%
Q1i
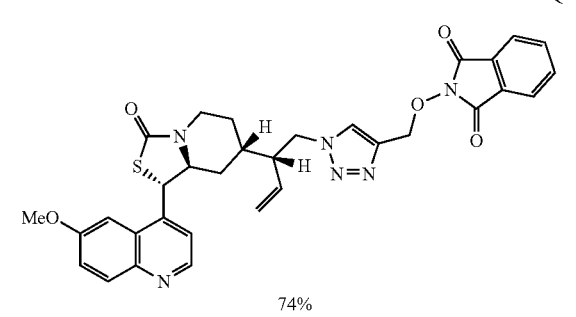
74%
90
Q1j
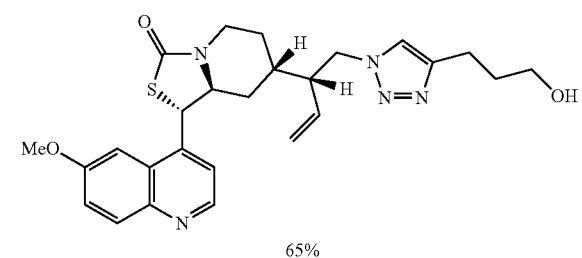
65%
Q1k
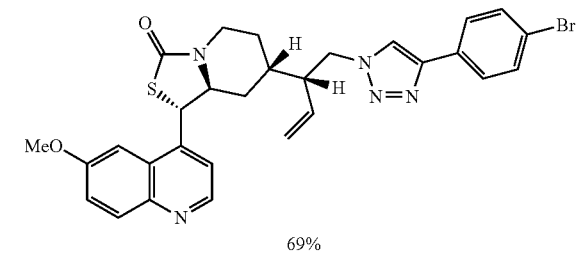
69%
Q1l
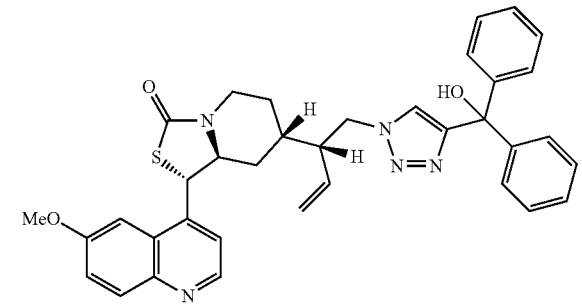
88%
Q1m
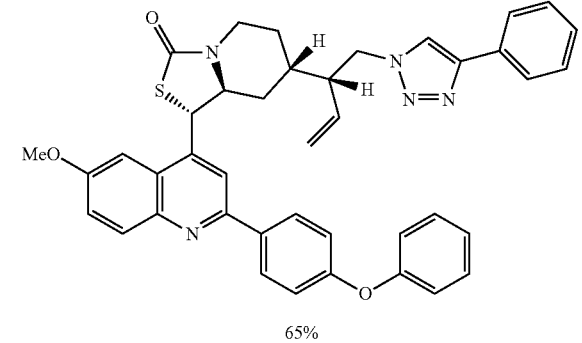
65%
Q1n
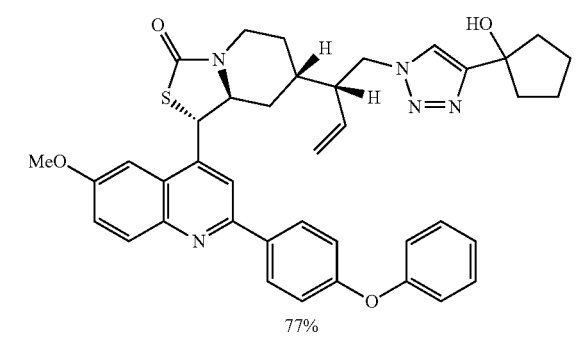
77%

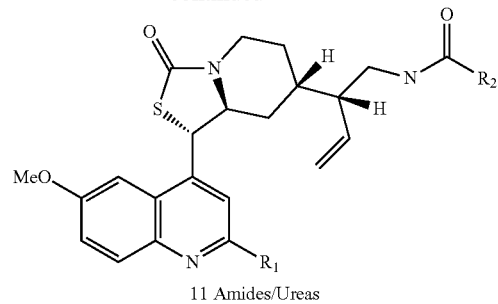
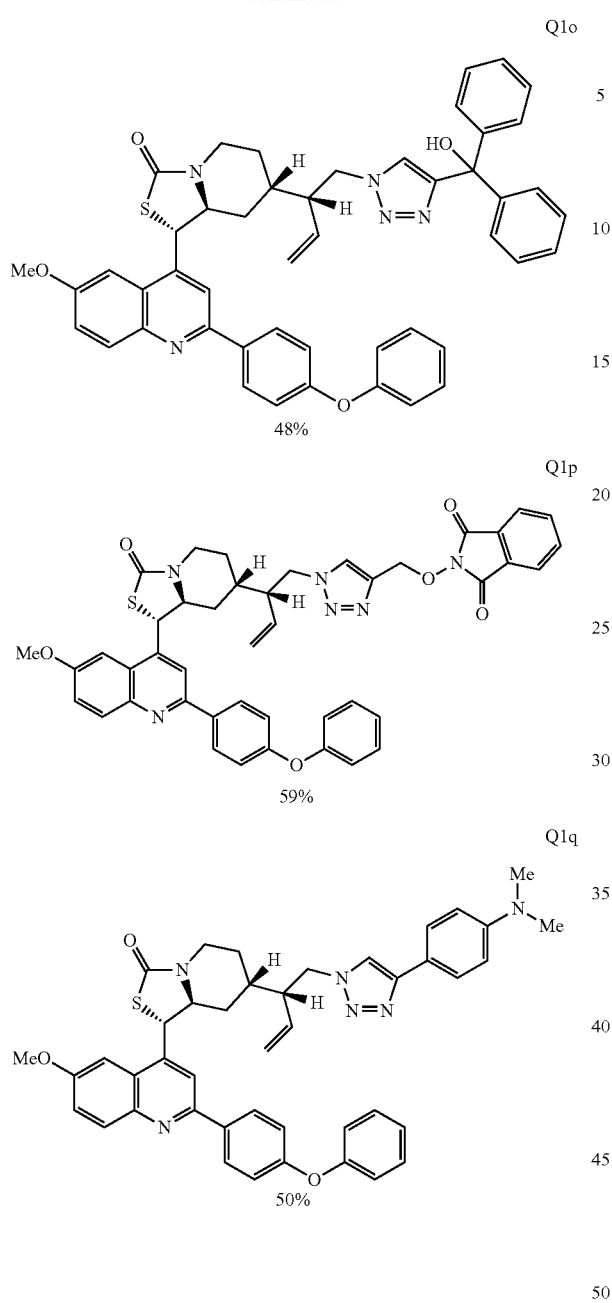
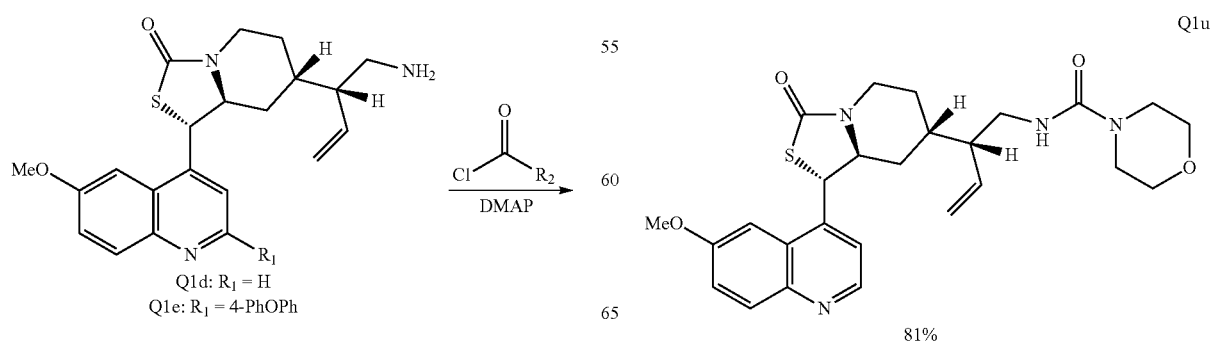
Scheme 3.3. Synthesis of Q1 amides and ureas.

-continued
Q1v
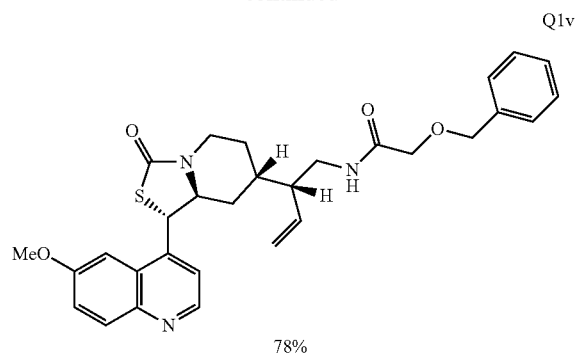
78%
Q1w
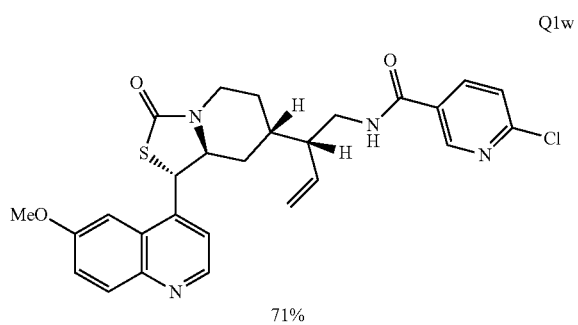
71%
Q1x
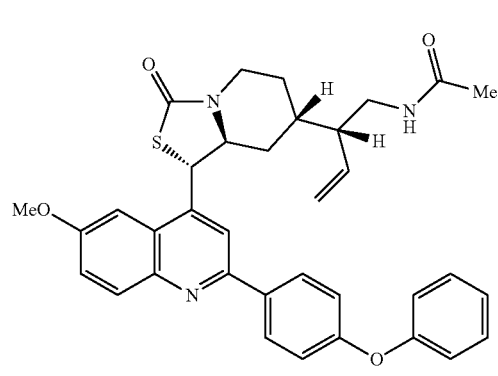
70%
Q1y
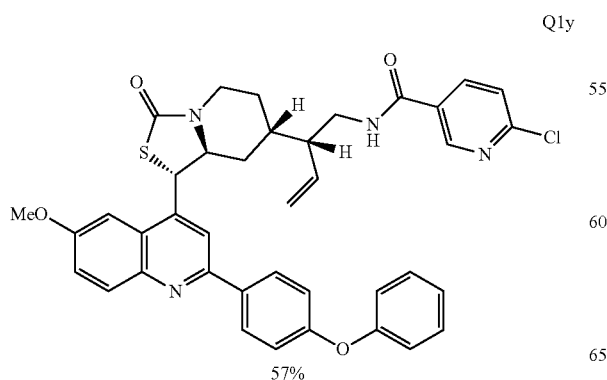
57%
-continued
Q1z
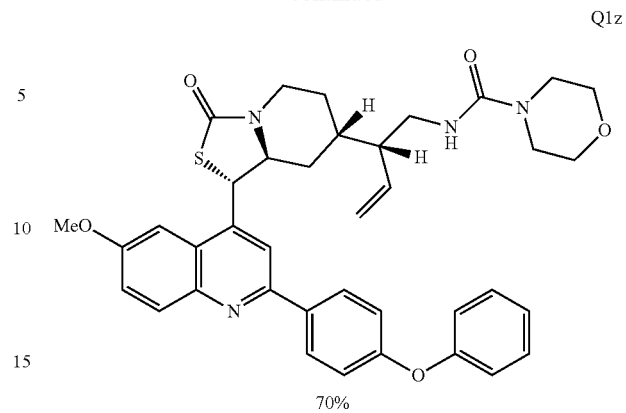
70%
Q1aa
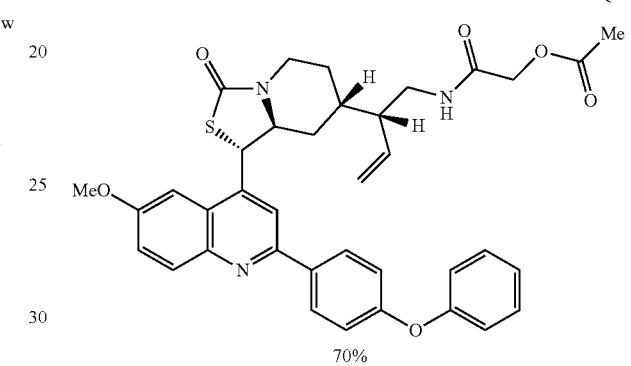
70%
Q1bb
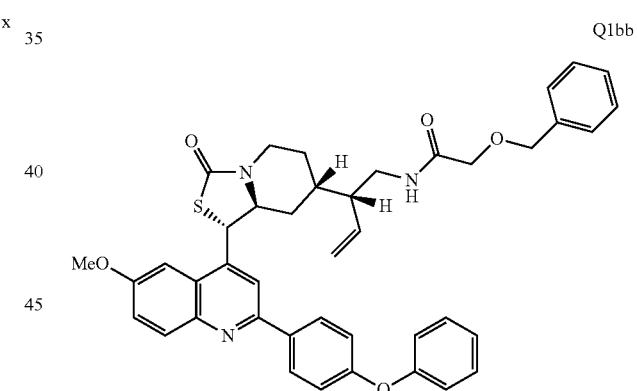
66%
Scheme 3.4. Synthesis of Q1 sulfonamides.
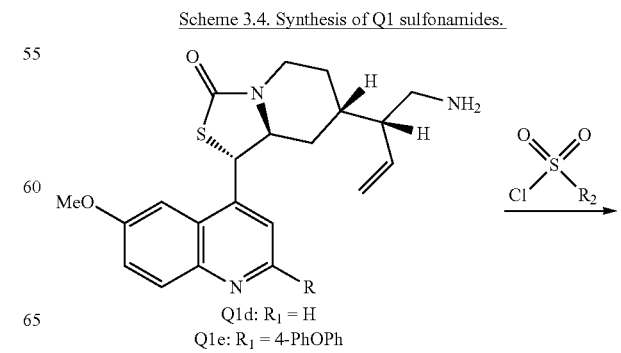
Q1d: R₁ = H
Q1e: R₁ = 4-PhOPh

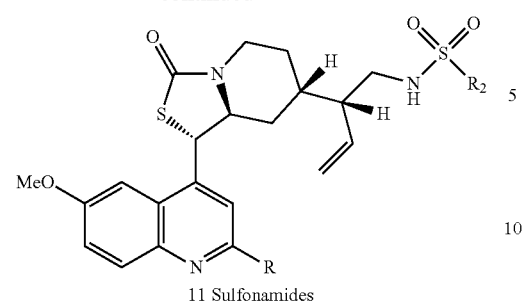
11 Sulfonamides
Q1cc
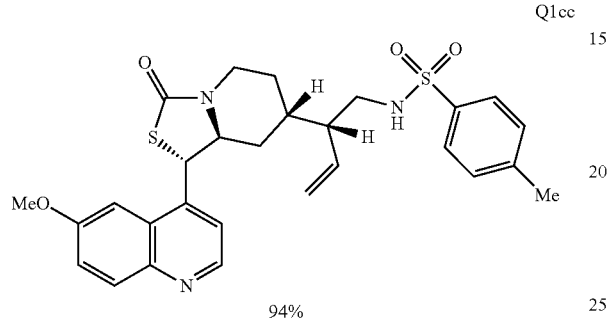
94%
Q1dd
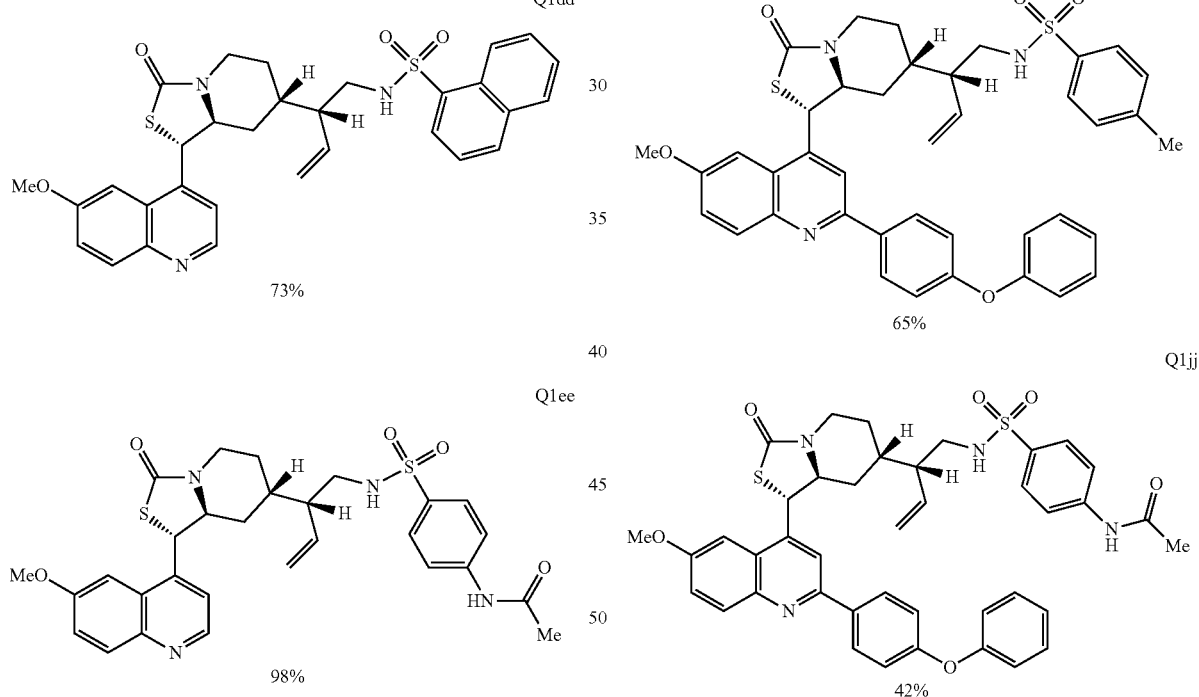
73%
Q1ee
98%
Q1ff
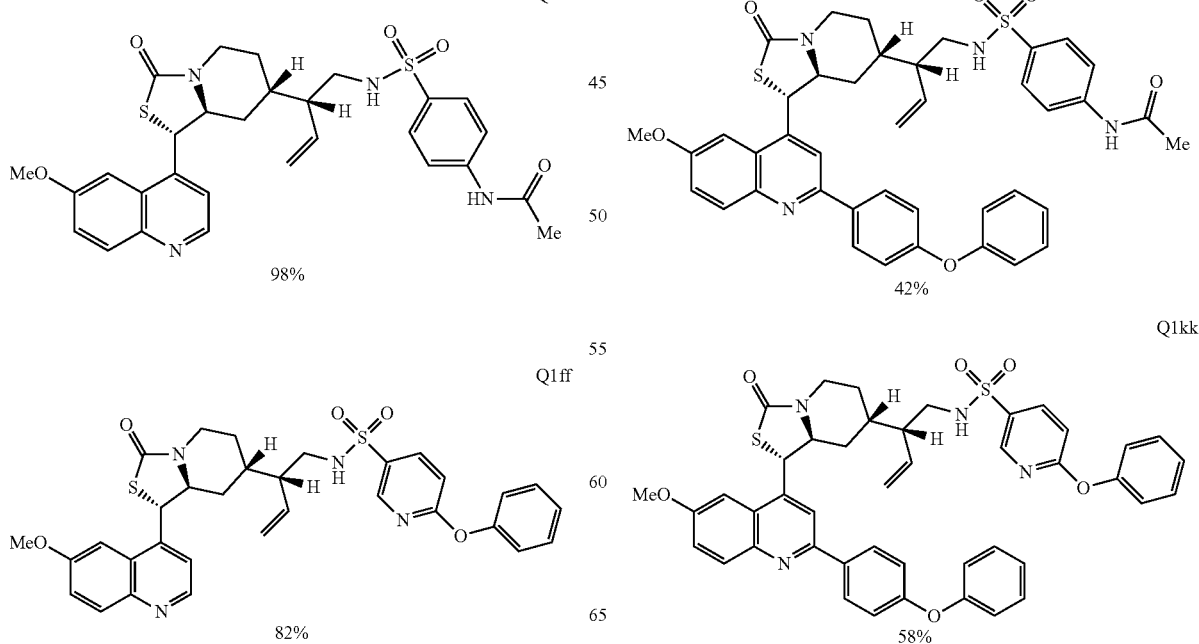
82%
Q1gg
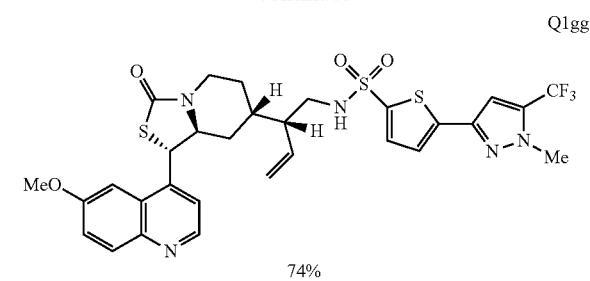
74%
Q1hh
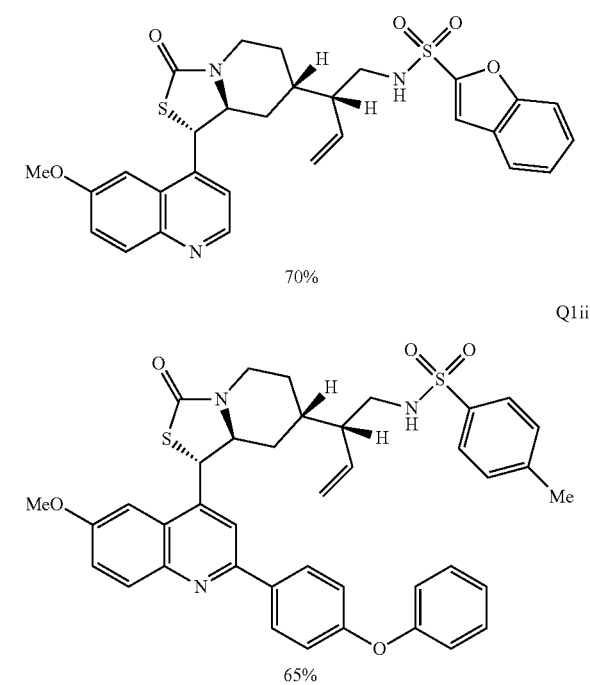
70%
Q1ii
65%
Q1jj
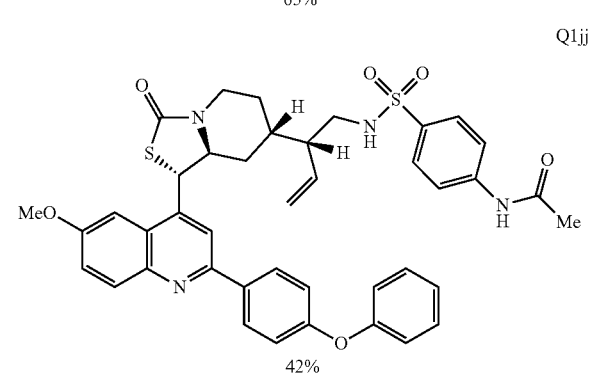
42%
Q1kk
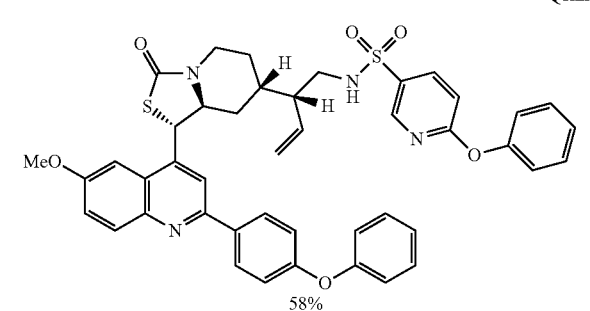
58%

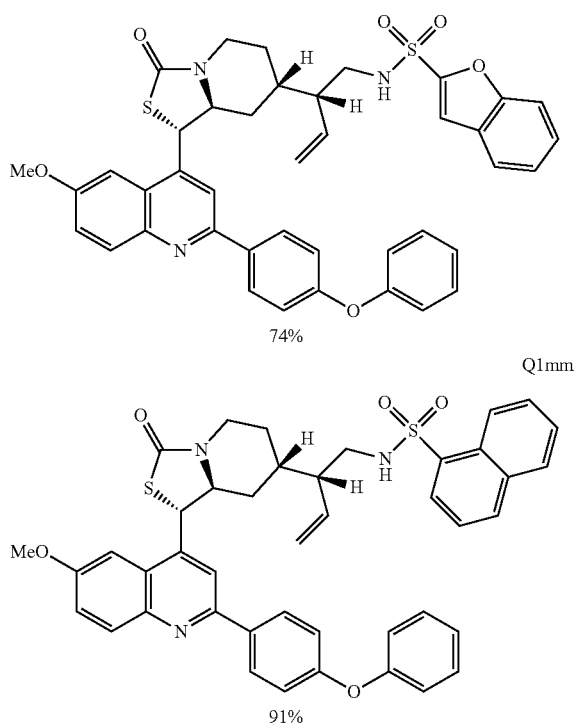

Preparation of Q6.

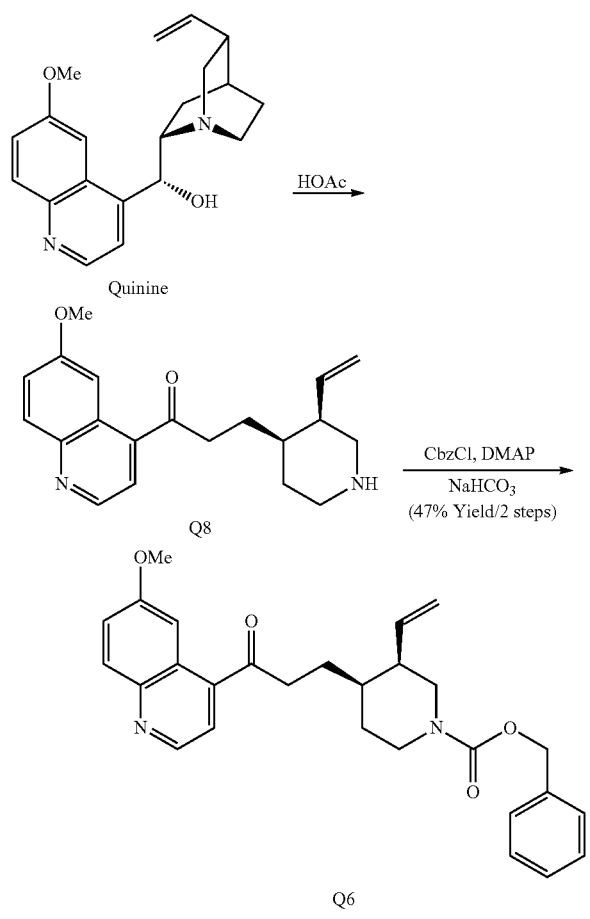

Procedure: Quinine (10 g, 30.8 mmol) was dissolved in a 1.2 M solution of acetic acid (140 mL) and stirred at 102° C. for 72 hours before cooling to room temperature. The reaction mixture was diluted with ethyl acetate followed by addition of 1 M sodium hydroxide until basic. The solution was transferred to a separatory funnel and extracted with ethyl acetate (3×). The combined organic layers were concentrated under reduced pressure to provide crude quinotoxine Q8 which was directly carried on to the next step. Quinotoxine Q8 was dissolved in a 1:1 mixture of ethyl acetate and a saturated solution sodium bicarbonate (460 mL) along with 4-(dimethylamino)-pyridine (40 mg, 0.329 mmol) and cooled to 0° C. with stirring. Benzyl chloroformate (4.43 g, 37.0 mmol) was added to the stirring reaction dropwise and the reaction mixture was warmed to room temperature and allowed to stir overnight. The reaction mixture was then transferred to a separatory funnel and the carbamate product extracted with ethyl acetate (3×). The combined organic layers were washed with brine, dried with magnesium sulfate and concentrated in vacuo to afford a tan residue. Purification by column chromatography using 49:1 ethyl acetate/triethylamine provided 6.70 g (47% yield over two steps) of carbamate Q6 as a tan oil.

Note: Best yields for this reaction sequence were obtained when quinotoxine Q8 was carried on without chromatographic purification; however, flash column chromatography using 3:2:0.1 ethyl acetate/methanol/aqueous ammonium hydroxide afforded Q8 in 66% yield. Spectral data obtained for Q8 were identical to that previously reported and are not reported here.[9] Reaction of pure Q8 with benzyl chloroformate provided Q6 in 60% yield.

$^1$H NMR (d$_6$-DMSO, 500 MHz, 80° C.): δ 8.87 (d, J=4.4 Hz, 1H), 8.01 (d, J=9.2 Hz, 1H), 7.82 (d, J=4.4 Hz, 1H), 7.70 (d, J=2.9 Hz, 1H), 7.47 (dd, J=9.2, 2.9 Hz, 1H), 7.40-7.26 (m, 5H), 5.80 (ddd, J=17.4, 10.5, 8.6 Hz, 1H), 5.16 (ddd, J=17.4, 2.2, 1.1 Hz, 1H), 5.13-5.02 (m, 1H), 5.08 (d, J=6.5 Hz, 2H), 4.01-3.95 (m, 1H), 3.95-3.84 (m, 1H), 3.89 (s, 3H), 3.15-3.06 (m, 3H), 2.92 (ddd, J=12.5, 11.3, 3.30 Hz, 1H), 2.41 (dddd, J=7.6, 3.6, 3.5, 3.5 Hz, 1H), 1.74 (dddd, J=10.8, 7.2, 3.7, 3.7 Hz, 1H), 1.69-1.57 (m, 2H), 1.54 (dddd, J=13.4, 3.4, 3.4, 3.4 Hz, 1H), 1.38 (dddd, J=13.5, 11.2, 11.2, 4.5 Hz, 1H). $^{13}$C NMR (CDCl$_3$, 125 MHz): δ 203.8, 159.6, 155.7, 147.1, 145.9, 140.5, 137.0, 135.4, 131.6, 128.6, 128.1, 128.0, 125.3, 123.0, 120.2, 117.6, 103.2, 67.2, 55.8, 49.2, 44.1, 42.8, 39.3, 38.5, 27.9, 27.6. HRMS(ESI): m/z calc. for C$_{29}$H$_{31}$N$_2$O$_4$ [M+H]$^+$: 459.2284. found: 459.2286.

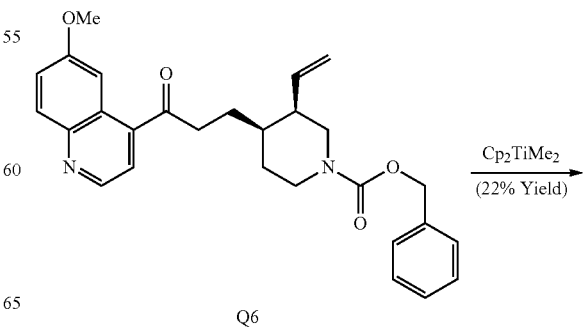

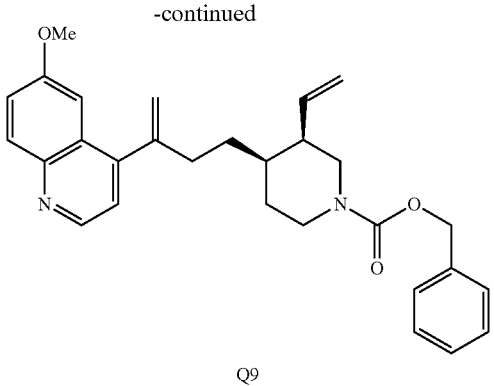

Q9

Procedure: Carbamate Q6 (610 mg, 1.33 mmol) was added to a solution of 12% w/w dimethyl titanocene in toluene (5 mL, 2.5 mmol) containing titanocene dichloride (44 mg, 0.18 mmol).[10] The reaction mixture was heated at 80° C. for 6 hours before cooling to room temperature. Sodium bicarbonate (600 mg), methanol (6 mL), and water (1 mL) were added to the reaction mixture followed by heating at 40° C. for 18 hours to decompose and precipitate the remaining organotitanium residues. The reaction was cooled, filtered, washed with water (3×) and brine, dried with $MgSO_4$, and concentrated under reduced pressure. The crude material was purified by column chromatography using 1:1 hexane/ethyl acetate to yield 135 mg (22% yield) of the desired olefin Q9 as a tan oil.

$^1$H NMR ($d_6$-DMSO, 500 MHz, 80° C.): δ 8.68 (d, J=4.3 Hz, 1H), 7.95 (d, J=9.1 Hz, 1H), 7.42 (dd, J=9.1, 2.9 Hz, 1H), 7.37-7.29 (m, 5H), 7.28 (d, J=2.9 Hz, 1H), 7.22 (d, J=4.3 Hz, 1H), 5.68 (ddd, J=17.3, 11.3, 9.1 Hz, 1H), 5.50 (d, J=1.6 Hz, 1H), 5.14 (m, 1H), 5.11-4.92 (m, 2H), 5.05 (d, J=6.9 Hz, 2H), 3.93 (ddd, J=13.3, 3.8, 3.8 Hz, 1H), 3.90-3.78 (m, 1H), 3.88 (s, 3H), 3.03 (dd, J=13.0, 3.1 Hz, 1H), 2.87 (dd, J=12.4, 12.4 Hz, 1H), 2.58-2.51 (m, 2H), 2.31 (ddd, J=7.5, 3.6, 3.6 Hz, 1H), 1.66 (dddd, J=10.1, 3.4, 3.4, 3.2 Hz, 1H), 1.43 (dd, J=13.3, 3.1 Hz, 1H), 1.39-1.23 (m, 2H). $^{13}$C NMR ($CDCl_3$, 125 MHz): δ 157.8, 155.6, 148.4, 147.5, 146.7, 144.8, 137.0, 135.5, 131.5, 128.5, 128.0, 127.9, 127.5, 121.8, 120.0, 117.2, 116.4, 103.6, 67.1, 55.6, 49.1, 44.2, 42.5, 38.5, 34.9, 31.6, 27.6. HRMS(ESI): m/z calc. for $C_{29}H_{33}N_2O_3$ $[M+H]^+$: 457.2491. found: 457.2482.

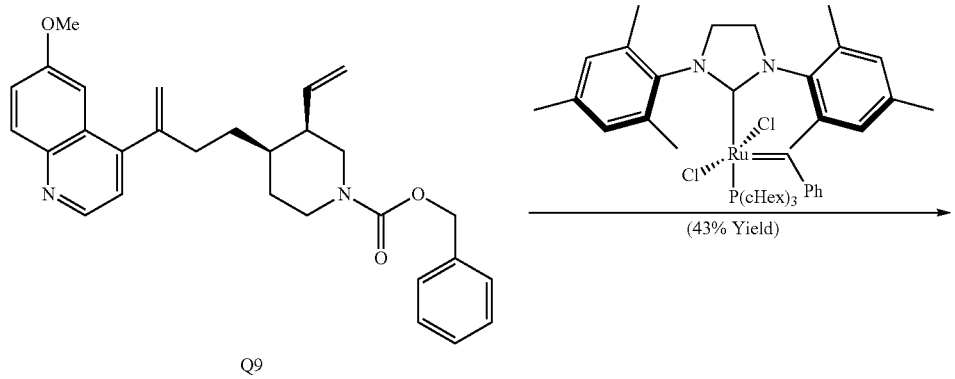

Q9 (43% Yield)

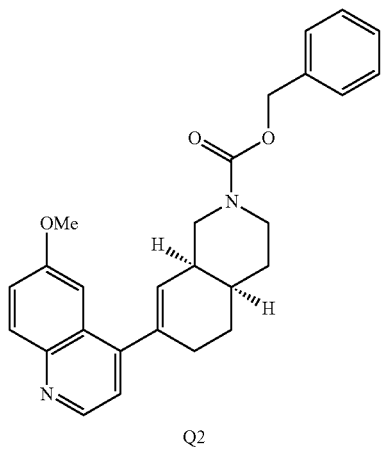

Q2

Procedure: To a solution of Q9 (70 mg, 0.15 mmol) in anhydrous dichloromethane (38 mL) was added Grubbs second-generation catalyst (19.5 mg, 0.023 mmol). The reaction mixture was heated to 40° C. and allowed to stir 24 hours. The reaction was then cooled to room temperature and the solvent was removed in vacuo and the crude mixture purified by column chromatography using 9:1 ethyl acetate/hexane to provide 28.4 mg (43% yield) of the desired [4.4.0]-bicycle Q2 as a tan oil.

$^1$H NMR (d$_6$-DMSO, 500 MHz, 80° C.): δ 8.67 (d, J=4.4 Hz, 1H), 7.95 (d, J=9.1 Hz, 1H), 7.40 (dd, J=9.1, 2.8 Hz, 1H), 7.23 (d, J=2.8 Hz, 1H), 7.23-7.17 (m, 5H), 7.16 (d, J=4.4 Hz, 1H), 5.69-5.61 (m, 1H), 5.06 (d, J=12.7 Hz, 1H), 4.99 (d, J=12.7 Hz, 1H), 3.84 (s, 3H), 3.80-3.65 (m, 2H), 3.46 (dd, J=13.3, 4.2 Hz, 1H), 3.25 (ddd, J=10.6, 9.7, 5.1 Hz, 1H), 2.58 (ddddd, J=7.8, 5.4, 5.4, 3.0, 3.0 Hz, 1H), 2.40-2.34 (m, 2H), 2.11 (dddd, J=11.1, 8.5, 4.6, 4.6 Hz, 1H), 1.94 (dddd, J=12.4, 6.0, 5.9, 5.9 Hz, 1H), 1.83 (dddd, J=13.6, 7.2, 7.1, 3.5 Hz, 1H), 1.77-1.58 (m, 2H). $^{13}$C NMR (d$_6$-DMSO, 125 MHz, 80° C.): δ 156.9, 154.3, 147.9, 147.1, 143.9, 136.6, 136.3, 130.6, 129.1, 127.7, 127.1, 126.8, 126.4, 120.8, 119.3, 103.2, 65.6, 54.9, 46.8, 41.9, 35.0, 30.2, 26.8, 26.4, 24.8. HRMS(ESI): m/z calc. for C$_{27}$H$_{29}$N$_2$O$_3$ [M+H]$^+$: 429.2178. found: 429.2178.

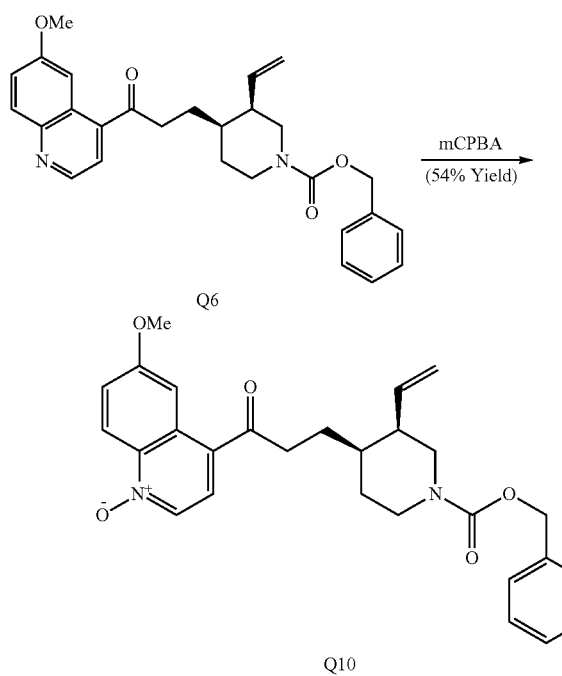

Q6 mCPBA
(54% Yield)

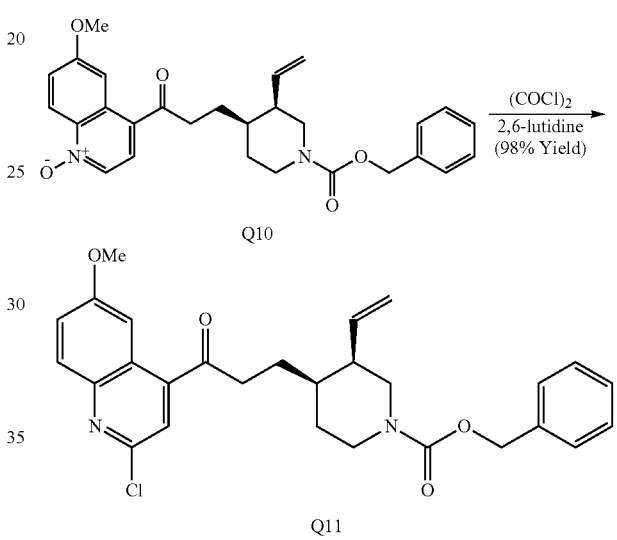

Q10

Procedure: Carbamate Q6 (1.00 g, 2.18 mmol) was dissolved in dichloromethane (50 mL) at room temperature. Sodium bicarbonate (1.48 g, 14.0 mmol) was added and the solution was cooled to 0° C. m-Chloroperoxybenzoic acid (600 mg, 2.68 mmol calculated at 77% purity) was added and the reaction was stirred overnight. Upon warming to room temperature, the reaction was diluted with dichloromethane (50 mL) and quenched with a saturated solution of sodium bicarbonate (50 mL). The reaction mixture was transferred to a separatory funnel and extracted with dichloromethane (3×). The combined organic layers were washed with brine, dried with magnesium sulfate, and concentrated under reduced pressure. The crude material was purified by column chromatography using 9:1 chloroform/acetone to provide 555 mg (54%) of N-oxide Q10 as a yellow oil.

$^1$H NMR (d$_6$-DMSO, 500 MHz, 80° C.): δ 8.52 (d, J=9.5 Hz, 1H), 8.46 (d, J=6.5 Hz, 1H), 8.23 (d, J=2.8 Hz, 1H), 8.03 (d, J=6.5 Hz, 1H), 7.47 (dd, J=9.6, 2.8 Hz, 1H), 7.40-7.27 (m, 5H), 5.81 (ddd, J=17.3, 10.5, 8.5 Hz, 1H), 5.17 (ddd, J=17.3, 2.1, 1.0 Hz, 1H), 5.13-5.03 (m, 3H), 4.01-3.95 (m, 1H), 3.95-3.87 (m, 1H), 3.92 (s, 3H), 3.15-3.07 (m, 3H), 2.94 (ddd, J=13.8, 11.5, 3.5 Hz, 1H), 2.42 (ddd, J=7.9, 4.0, 4.0 Hz, 1H), 1.74 (dddd, J=11.1, 7.4, 3.8, 3.8 Hz, 1H), 1.70-1.51 (m, 3H), 1.39 (dddd, J=13.6, 11.4, 11.3, 4.5 Hz, 1H). $^{13}$C NMR (CDCl$_3$, 125 MHz): δ 200.3, 161.3, 155.6, 138.3, 137.0, 135.5, 132.3, 129.5, 128.5, 128.1, 128.0, 127.9, 123.6, 123.0, 121.3, 117.6, 105.1, 67.1, 55.9, 49.1, 44.1, 42.8, 38.5, 38.2, 27.8, 27.6. HRMS(ESI): m/z calc. for C$_{28}$H$_{31}$N$_2$O$_6$ [M+H]$^+$: 475.2233. found: 475.2234.

Q10

(COCl)$_2$
2,6-lutidine
(98% Yield)

Q11

Procedure: To a solution of N-oxide Q10 (50.0 mg, 0.105 mmol) in dichloromethane (0.525 mL) at 0° C. was added 2,6-lutidine (28.1 mg, 0.263 mmol) followed by dropwise addition of oxalyl chloride (19.9 mg, 0.157 mmol). The reaction warmed to room temperature and stirred 2 hours. Upon completion, the reaction was quenched by cooling to 0° C. followed by careful addition of a cold saturated solution of sodium bicarbonate. The reaction mixture was then transferred to a separatory funnel, washed with additional saturated solution of sodium bicarbonate, and extracted with dichloromethane (3×). The combined organic extracts were washed with brine, dried with magnesium sulfate, and evaporated. The crude product was purified by column chromatography using 9:1 ethyl acetate/hexane to provide 50.8 mg (98% yield) of chloride Q11 as a bright yellow oil.

$^1$H NMR (d$_6$-DMSO, 500 MHz, 80° C.): δ 7.94 (d, J=9.1 Hz, 1H), 7.91 (s, 1H), 7.59 (d, J=2.8 Hz, 1H), 7.53 (dd, J=9.1, 2.8 Hz, 1H), 7.40-7.27 (m, 5H), 5.80 (ddd, J=17.3, 10.5, 8.6 Hz, 1H), 5.17 (ddd, J=17.3, 2.1, 1.0 Hz, 1H), 5.13-5.03 (m, 3H), 4.03-3.94 (m, 1H), 3.94-3.90 (m, 1H), 3.90 (s, 3H), 3.14 (m, 2H), 3.11 (dd, J=13.2, 3.3 Hz, 1H), 2.94 (ddd, J=13.7, 12.6, 3.4 Hz, 1H), 2.43 (dddd, J=7.4, 3.5, 3.5, 3.5 Hz, 1H), 1.74 (dddddd, J=11.0, 7.4, 3.9, 3.7, 3.7 Hz, 1H), 1.69-1.51 (m, 3H), 1.38 (dddd, J=13.4, 11.2, 11.2, 4.5 Hz, 1H). $^{13}$C NMR (CDCl$_3$, 125 MHz): δ 202.5, 159.7, 155.7, 147.4, 145.4, 143.7, 137.0, 135.4, 130.6, 128.6, 128.1, 128.0, 124.3, 123.9, 121.5, 117.8, 103.6, 67.2, 55.9, 49.3, 44.1, 42.8, 39.5, 38.5, 27.6, 27.5. HRMS(ESI): m/z calc. for $C_{21}H_{30}ClN_2O_4$ [M+H]$^+$: 493.1894. found: 493.1901.

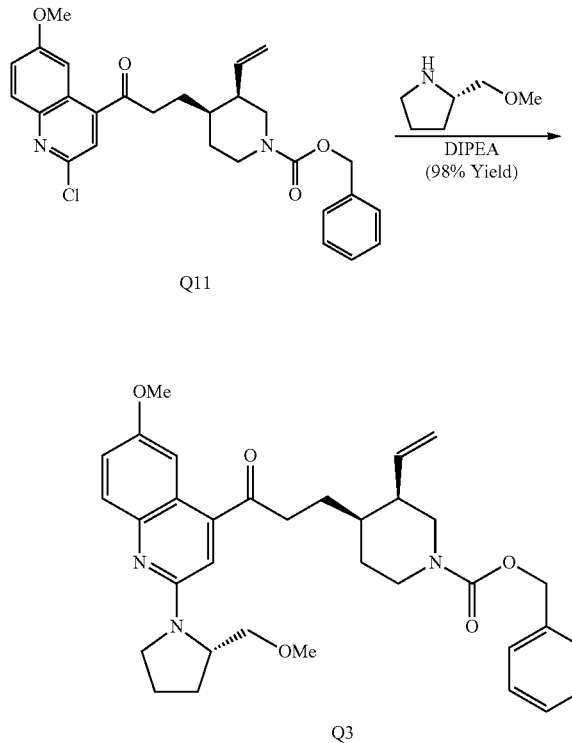

Q11

Q3

Procedure: A solution of chloride Q11 (100 mg, 0.203 mmol), (S)-2-(methoxymethyl)pyrrolidine (47 mg, 0.408 mmol), and N,N-diisopropylethylamine (130 mg, 1.01 mmol) in N-methyl-2-pyrrolidone (0.910 mL) was heated at 140° C. in a sealed tube with stirring for 24 hours. The reaction contents were directly purified by column chromatography using 96:3:1 chloroform/acetone/triethylamine to provide 113 mg (98% yield) of the desired amine Q3 as a yellow oil.

$^1$H NMR (d$_6$-DMSO, 500 MHz, 80° C.): δ 7.56 (d, J=9.1 Hz, 1H), 7.37 (d, J=2.9 Hz, 1H), 7.36-7.29 (m, 5H), 7.24 (dd, J=9.1, 2.9 Hz, 1H), 7.17 (s, 1H), 5.80 (ddd, J=17.3, 10.5, 8.6 Hz, 1H), 5.15 (ddd, J=17.3, 2.1, 1.1 Hz, 1H), 5.13-5.02 (m, 3H), 4.40 (ddddd, J=9.2, 3.2, 3.2, 2.4, 2.4 Hz, 1H), 4.02-3.94 (m, 1H), 3.91 (ddd, J=13.0, 3.6, 1.7 Hz, 1H), 3.80 (s, 3H), 3.68-3.57 (m, 2H), 3.51 (ddd, J=10.2, 8.8, 6.6 Hz, 1H), 3.42 (dd, J=9.6, 6.9 Hz, 1H), 3.32 (s, 3H), 3.14-3.02 (m, 2H), 2.98-2.89 (m, 1H), 2.41 (dddd, J=7.7, 3.7, 3.7, 3.7 Hz, 1H), 2.12-1.93 (m, 5H), 1.73 (dddd, J=11.1, 7.4, 3.8, 3.8 Hz, 1H), 1.67-1.57 (m, 2H), 1.57-1.50 (m, 1H), 1.38 (dddd, J=13.5, 11.3, 11.3, 4.4 Hz, 1H). $^{13}$C NMR (CDCl$_3$, 125 MHz): δ 204.7, 155.7, 155.6, 154.1, 145.3, 143.6, 137.1, 135.5, 128.6, 128.1, 128.0, 121.8, 118.8, 117.9, 117.6, 109.7, 104.0, 74.0, 67.2, 59.4, 57.5, 55.7, 49.3, 48.0, 44.1, 42.8, 39.6, 38.5, 28.9, 28.0, 27.6, 23.9. HRMS(ESI): m/z calc. for $C_{34}H_{42}N_3O_5$ [M+H]$^+$: 572.3124. found: 572.3117.

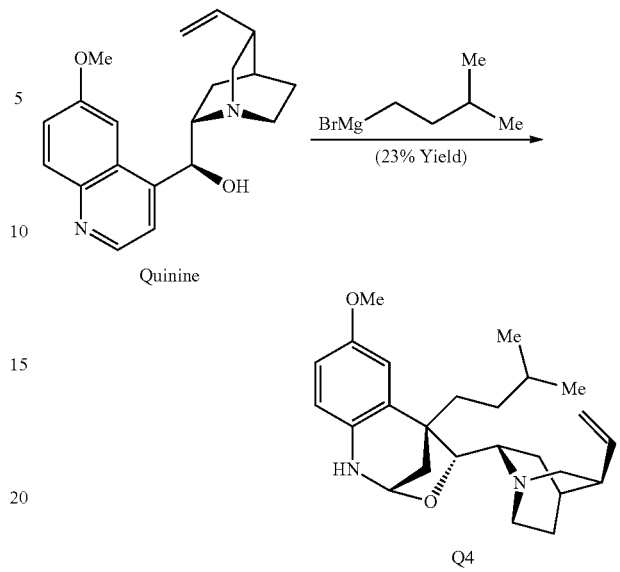

Quinine

Q4

Procedure: A flame dried three necked flask was charged with magnesium (2.43 g, 100 mmol) and heated to 130° C. under vacuum for 30 minutes. The flask was then cooled and flushed with argon. Anhydrous THF (10 mL) and diisobutylaluminum hydride (0.6 mL, 1.0 M in tetrahydrofuran) were then added. Isoamyl bromide (2.40 mL, 20 mmol) was then added dropwise until an exotherm was observed then slow addition maintained a gentle reflux. After complete addition, the reaction mixture was refluxed 2 h and cooled to provide a 0.9 M solution of isoamylmagnesium bromide in tetrahydrofuran (titrated with menthol/2,2'-bipyridine). To a flame dried round bottom flask charged with dry toluene (20 mL) was added isoamylmagnesium bromide (5.0 mL, 0.9 M in tetrahydrofuran, 4.5 mmol) followed by addition of quinine (292 mg, 0.9 mmol) as a single portion with vigorous stirring. The mixture was stirred at 70° C. for 3 hours at which point a second portion of isoamylmagnesium bromide (1.5 mL, 0.9 M in tetrahydrofuran, 1.2 mmol) was added. The reaction was refluxed an additional 12 hours and then cooled to 0° C., diluted with methyl ten-butyl ether, and quenched by careful addition of a saturated solution of ammonium chloride. The biphasic mixture was separated and the organic layer was washed with additional ammonium chloride followed by water. The organic layer was then collected from a separatory funnel, dried with magnesium sulfate and concentrated under reduced pressure. Purification by column chromatography using 49:1 ethyl acetate/triethylamine provided 83.1 mg (23% yield) of aminal Q4 as a tan oil.

$^1$H NMR (500 MHz, CDCl$_3$): δ 6.61 (m, 2H), 6.44 (d, J=9.1 Hz, 1H), 5.67 (ddd, J=17.7, 9.8, 7.9 Hz, 1H), 5.11 (dd, J=5.1, 3.2 Hz, 1H), 4.91-4.82 (m, 2H), 4.49-4.43 (m, 1H), 3.89 (d, J=5.1 Hz, 1H), 3.73 (s, 3H), 2.96 (dd, J=13.7, 10.0 Hz, 1H), 2.92-2.83 (m, 1H), 2.63-2.52 (m, 1H), 2.41 (ddd, J=13.7, 4.6, 2.4 Hz, 1H), 2.38-2.32 (m, 1H), 2.28 (d, J=10.9 Hz, 1H), 2.19 (ddd, J=13.2, 13.1, 3.6 Hz, 1H), 2.15-1.99 (m, 2H), 1.65-1.46 (m, 4H), 1.40-1.30 (m, 2H), 1.23-1.07 (m, 2H), 1.00 (ddd, J=13.7, 8.5, 3.4 Hz, 1H), 0.92 (d, J=6.5 Hz, 3H), 0.90 (d, J=6.6 Hz, 3H). $^{13}$C NMR (CDCl$_3$, 125 MHz): δ 153.2, 142.5, 136.8, 129.1, 116.2, 113.8, 113.1, 112.7, 96.9, 83.8, 57.2, 56.1, 55.9, 47.9, 42.6, 40.5, 37.8, 34.6, 29.8, 28.9, 27.9, 27.6, 23.5, 22.8, 22.8. HRMS(ESI): m/z calc. for $C_{25}H_{37}N_2O_2$ [M+H]$^+$: 397.2855. found: 397.2853.

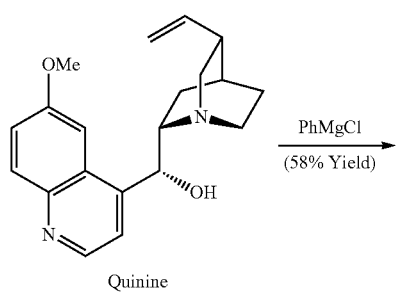

Quinine

PhMgCl
(58% Yield)

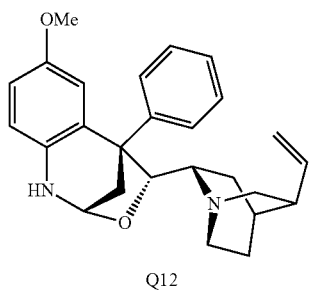

Q12

Procedure: To a flame dried round bottom flask charged with anhydrous toluene (20 mL) was added phenyl magnesium chloride (4.65 mL, 2.0 M in tetrahydrofuran, 9.29 mmol) followed by addition of quinine (600 mg, 1.85 mmol) as a single portion with vigorous stirring. The mixture was stirred at 70° C. for 3 hours and an additional portion of phenyl magnesium chloride (4.65 mL, 2.0 M in tetrahydrofuran, 9.29 mmol) was added. The reaction was refluxed an additional 1.5 hours and then cooled to 0° C., diluted with methyl tert-butyl ether, and quenched by careful addition of a saturated solution of ammonium chloride. The biphasic mixture was separated and the organic layer was washed with ammonium chloride and then water. The organic layer was then dried with magnesium sulfate and concentrated under reduced pressure. Purification by column chromatography using 47:2:1 ethyl acetate/methanol/triethylamine afforded 434 mg (58% yield) of aminal Q12 as a tan crystalline powder that had identical spectra to those that were previously published ($^1$H NMR and $^{13}$C NMR) for this compound.[11]

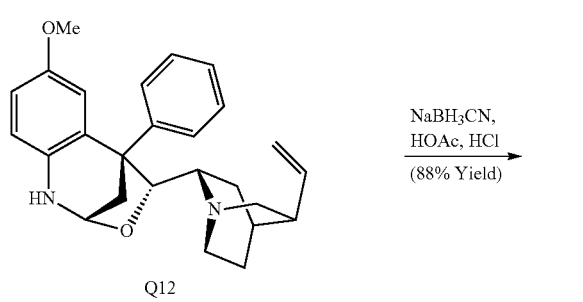

Q12

NaBH$_3$CN,
HOAc, HCl
(88% Yield)

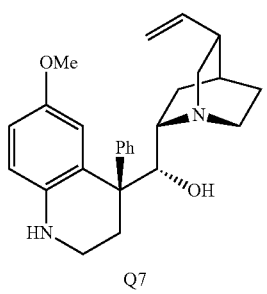

Q7

Procedure: Aminal Q12 (400 mg, 1.00 mmol) was dissolved in a solution of glacial acetic acid (0.25 mL) and methanol (2 mL) at 0° C. Sodium cyanoborohydride (126 mg, 2.00 mmol) was added and the reaction was stirred 2.5 hours before concentrated hydrochloric acid (0.60 mL) was added and stirred for an additional 12 hours. The reaction was quenched by the addition of 2 M sodium hydroxide until pH>9 and transferred to a separatory funnel. The crude mixture was extracted with ethyl acetate (3×), washed with brine, dried with magnesium sulfate, and concentrated under reduced pressure. Purification by column chromatography using 49:1 ethyl acetate/triethylamine yielded 352 mg (88% yield) of tetrahydroquinoline Q7 as a white foam.

$^1$H NMR (CDCl$_3$, 500 MHz): δ 7.33-7.27 (m, 4H), 7.21-7.17 (m, 1H), 6.98 (d, J=2.8 Hz, 1H), 6.69 (dd, J=8.6, 2.8 Hz, 1H), 6.43 (d, J=8.6 Hz, 1H), 5.79 (ddd, J=17.1, 10.4, 7.9 Hz, 1H), 4.97-4.88 (m, 2H), 4.39 (d, J=4.5 Hz, 1H), 3.75 (s, 3H), 3.59-3.48 (m, 1H), 3.30 (dddd, J=11.4, 5.7, 3.0, 3.0 Hz, 1H), 3.22-3.09 (m, 2H), 3.09-3.01 (m, 2H), 2.68-2.55 (m, 2H), 2.49 (ddd, J=13.7, 5.4, 2.4 Hz, 1H), 2.20 (ddd, J=8.0, 8.0, 7.8 Hz, 1H), 1.93-1.82 (m, 2H), 1.80 (d, J=4.6 Hz, 1H), 1.72-1.60 (m, 2H), 1.50 (dddd, J=13.4, 10.4, 3.2, 3.2 Hz, 1H), 1.38 (dddd, J=15.5, 10.7, 5.3, 2.9 Hz, 1H). $^{13}$C NMR (CDCl3, 125 MHz): δ 151.4, 145.0, 142.6, 139.1, 128.6, 128.5, 126.6, 125.6, 115.7, 114.8, 114.4, 114.0, 79.7, 57.0, 56.4, 56.3, 50.5, 42.8, 40.7, 39.0, 28.6, 27.7, 26.8, 22.2. HRMS(ESI): m/z calc. for C$_{26}$H$_{33}$N$_2$O$_2$ [M+H]$^+$: 405.2542. found: 405.2542. Melting point: 143-146° C.

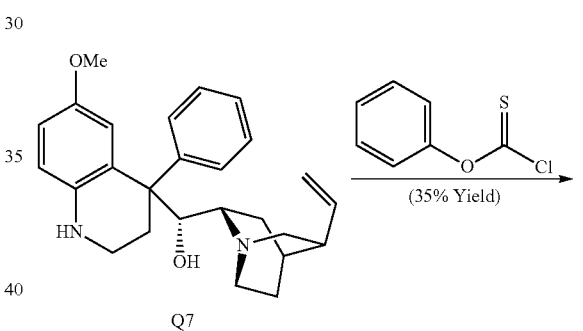

Q7

(35% Yield)

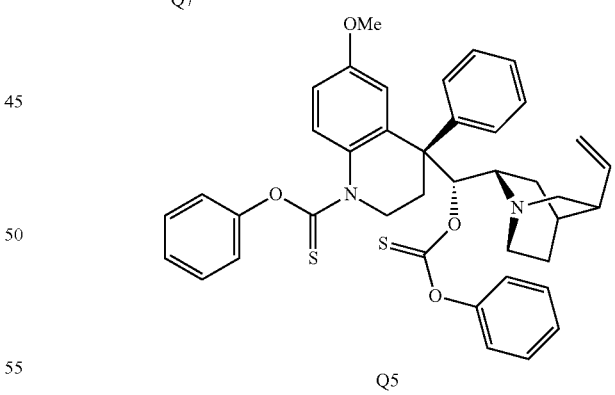

Q5

Procedure: Tetrahydroquinoline Q7 (202 mg, 0.50 mmol) was dissolved in anhydrous dichloromethane (7 mL) and cooled to 0° C. O-phenyl chlorothionoformate (190 mg, 2.20 mmol) was added and the reaction was warmed to room temperature and stirred for 7.5 hours. The reaction mixture was then diluted with dichloromethane, quenched with a saturated solution of sodium bicarbonate and transferred to a separatory funnel. The biphasic mixture was separated and the organic layer washed with brine, dried with magnesium sulfate, and concentrated under reduced pressure. The crude product was purified by column chromatography using 100:0 to 90:10 chloroform/ethyl acetate to provide 119 mg (35% yield) of O-thiocarbonate Q5 as a white solid.

$^1$H NMR (CDCl$_3$, 500 MHz): δ 7.44 (d, J=9.1 Hz, 1H), 7.39-7.32 (m, 3H), 7.31-7.22 (m, 8H), 7.15 (dd, J=8.4, 6.3 Hz, 1H), 6.88 (d, J=8.9 Hz, 1H), 6.88-6.81 (m, 2H), 6.64 (d, J=7.8 Hz, 2H), 6.29 (d, J=2.6 Hz, 1H), 5.85 (ddd, J=17.4, 10.0, 7.4 Hz, 1H), 5.07-4.96 (m, 2H), 4.74-4.66 (m, 1H), 3.90-3.82 (m, 1H), 3.86 (s, 3H), 3.38 (dd, J=8.7, 8.7 Hz, 1H), 3.32-3.22 (m, 1H), 3.12 (dd, J=11.9, 11.9 Hz, 1H), 3.05-2.94 (m, 1H), 2.75-2.64 (m, 1H), 2.63-2.54 (m, 1H), 2.34-2.25 (m, 1H), 2.08 (ddd, J=12.0, 10.9, 6.1 Hz, 1H), 1.93-1.85 (m, 1H) 1.85-1.74 (m, 2H), 1.62-1.47 (m, 2H). $^{13}$C NMR (CDCl$_3$, 125 MHz): δ 187.0, 157.6, 155.9, 154.0, 153.4, 141.9, 139.6, 130.1, 129.8, 129.6, 129.2, 128.2, 127.3, 126.7, 125.9, 122.6, 122.0, 120.7, 115.6, 114.6, 113.2, 112.0, 88.3, 57.6, 56.3, 55.8, 51.4, 47.8, 42.8, 40.0, 29.3, 28.0, 27.7, 23.3. HRMS(ESI): m/z calc. for C$_{40}$H$_{41}$N$_2$O$_4$S$_2$ [M+H]$^+$: 677.2508. found: 677.2514. Melting point: 169-171° C.

Example 4. Adrenosterone Derived Libraries: Synthesis and Characterization

Synthesis of A1 Derivatives

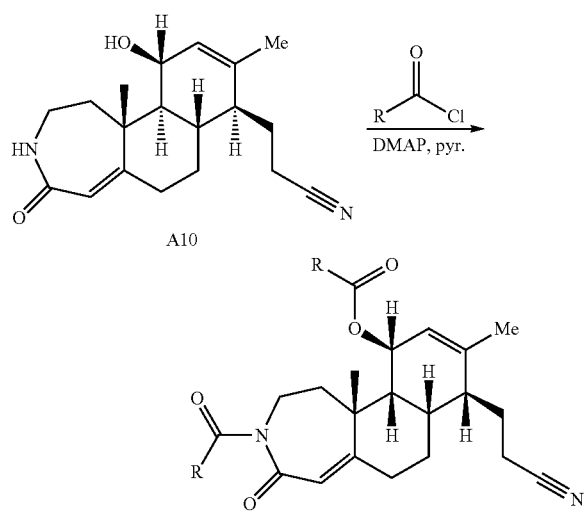

General Procedure for the Preparation of A1 Ester Imides:

Acid chloride (10 equiv.) was added to a solution of pyridine (800 μL) and 4-(dimethylamino)-pyridine (5 equiv.) at room temperature and allowed to stir for one hour. After this time, A10 (25 mg, 0.080 mmol), dissolved in 200 μL pyridine, was added to the reaction mixture and allowed to stir for 12 hours at room temperature before being quenched with a saturated aqueous solution of sodium bicarbonate and extracted with dichloromethane (3×). The organic layer was washed with a 5% aqueous solution of hydrochloric acid followed by brine (1× each). The organic layers were combined, dried with magnesium sulfate and concentrated. Ester imide A1 derivatives were purified by column chromatography using hexanes/ethyl acetate to elute. (Note: The scale of this reaction ranged from 6 to 50 milligrams of A10.)

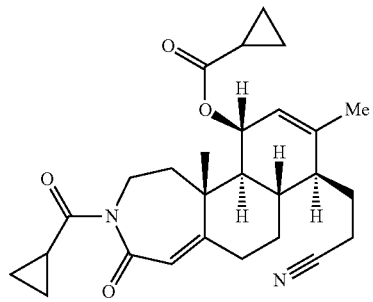

A1a: Prepared from cyclopropanecarbonyl chloride.
Yield: 3.3 mg, 35%.
$^1$H NMR (CDCl$_3$, 500 MHz): δ 5.97 (d, J=1.1 Hz, 1H), 5.36 (m, 1H), 5.35 (m, 1H), 3.90 (dd, J=14.8, 7.9 Hz, 1H), 3.82 (dd, J=14.0, 8.5 Hz, 1H), 2.98 (tt, J=7.9, 4.7 Hz, 1H), 2.54 (m, 1H), 2.31-2.21 (m, 2H), 2.21-2.10 (m, 2H), 2.10-1.95 (m, 4H), 1.88-1.74 (m, 2H), 1.71 (m, 1H), 1.67 (s, 3H), 1.59 (tt, J=7.9, 4.7 Hz, 1H), 1.26 (m, 1H), 1.17 (s, 3H), 1.12-1.08 (m, 2H), 1.03-0.98 (m, 2H), 0.97-0.92 (m, 3H), 0.88 (m, 1H). HRMS(ESI): m/z calc. for C$_{27}$H$_{35}$N$_2$O$_4$ [M+H]$^+$: 451.2597. found: 451.2588.

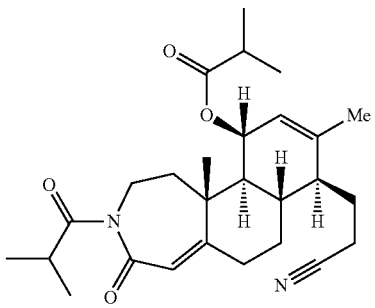

A1b: Prepared from isobutyryl chloride.
Yield: 17.2 mg, 52%.
$^1$H NMR (CDCl$_3$, 500 MHz): δ 5.92 (s, 1H), 5.36 (dd, J=5.0, 1.5 Hz, 1H), 5.28 (d, J=1.0 Hz, 1H), 3.96 (dd, J=14.8, 8.3 Hz, 1H), 3.70 (m, 2H), 2.59-2.43 (m, 2H), 2.31-2.09 (m, 4H), 2.04 (m, 3H), 1.91 (dd, J=15.4, 8.5 Hz, 1H), 1.82-1.62 (m, 3H), 1.66 (s, 3H), 1.25 (m, 1H), 1.20-1.10 (m, 15H). HRMS(ESI): m/z calc. for C$_{27}$H$_{39}$N$_2$O$_4$[M+H]$^+$: 455.2910. found: 455.2903.

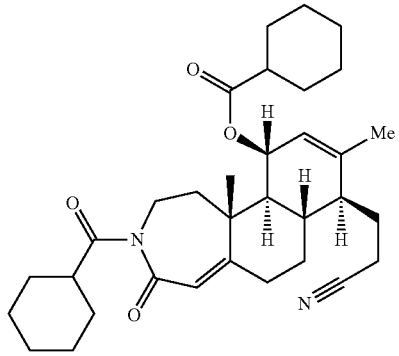

A1c: Prepared from cyclohexanecarbonyl chloride.
Yield: 35.8 mg, 76%.

$^1$H NMR (CDCl$_3$, 500 MHz): δ 5.90 (s, 1H), 5.35 (m, 1H), 5.26 (m, 1H), 3.98 (dd, J=14.7, 8.4 Hz, 1H), 3.59 (dd, J=14.9, 8.4 Hz, 1H), 3.43 (tt, J=11.0, 3.2 Hz, 1H), 2.51 (td, J=12.5, 3.5 Hz, 1H), 2.30-2.07 (m, 4H), 2.03 (m, 3H), 1.96-1.81 (m, 5H), 1.81-1.71 (m, 5H), 1.70-1.59 (m, 4H), 1.65 (s, 3H), 1.49-1.17 (m, 12H), 1.15 (s, 3H). HRMS(ESI): m/z calc. for C$_{33}$H$_{47}$N$_2$O$_4$ [M+H]$^+$: 535.3536. found: 535.3528.

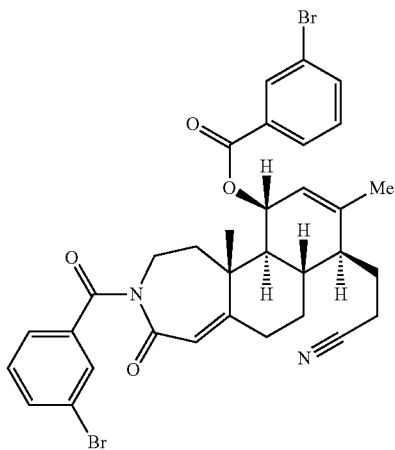

A1d

A1d: Prepared from 3-bromobenzoyl chloride.
Yield: 20.6 mg, 39%.

$^1$H NMR (CDCl$_3$, 500 MHz): δ 8.17 (t, J=1.8 Hz, 1H), 7.96 (dt, J=7.8, 1.3 Hz, 1H), 7.72 (ddt, J=7.9, 2.0, 1.1 Hz, 1H), 7.61 (t, J=1.8 Hz, 1H), 7.57 (ddt, J=7.9, 2.0, 1.0 Hz, 1H), 7.39 (m, 1H), 7.36 (d, J=7.9 Hz, 1H), 7.24 (t, J=7.9 Hz, 1H), 5.90 (s, 1H), 5.68 (dq, J=8.8, 2.1 Hz, 1H), 5.46 (q, J=1.9 Hz, 1H), 3.96 (dd, J=14.9, 8.4 Hz, 1H), 3.71 (dd, J=14.9, 8.7 Hz, 1H), 2.59 (td, J=13.6, 4.5 Hz, 1H), 2.33 (m, 1H), 2.27 (dt, J=14.0, 3.7 Hz, 1H), 2.24-2.18 (m, 2H), 2.18-2.03 (m, 4H), 2.00 (dd, J=11.8, 8.9 Hz, 1H), 1.94 (dd, J=15.5, 8.3 Hz, 1H), 1.82 (qd, J=11.9, 3.9 Hz, 1H), 1.70 (m, 3H), 1.33 (m, 1H), 1.28 (s, 3H).

HRMS(ESI): m/z calc. for C$_{33}$H$_{33}$N$_2$O$_4$Br$_2$[M+H]$^+$: 679.0807. found: 679.0804.

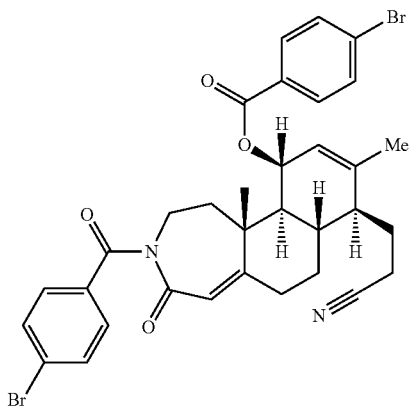

A1e

A1e: Prepared form 4-bromobenzoyl chloride.
Yield: 39.0 mg, 68%.

$^1$H NMR (CDCl$_3$, 500 MHz): δ 7.89 (m, 2H), 7.62 (m, 2H), 7.51 (m, 2H), 7.37 (m, 2H), 5.89 (s, 1H), 5.67 (dq, J=8.7, 2.0 Hz, 1H), 5.46 (q, J=1.9 Hz, 1H), 3.94 (dd, J=14.9, 8.3 Hz, 1H), 3.72 (dd, J=14.8, 8.6 Hz, 1H), 2.59 (m, 1H), 2.34 (m, 1H), 2.27 (m, 1H), 2.24-2.16 (m, 2H), 2.15-2.03 (m, 4H), 1.99-1.92 (m, 2H), 1.82 (ddd, J=12.9, 9.4, 3.9 Hz, 1H), 1.69 (s, 3H), 1.36-1.24 (m, 1H), 1.27 (s, 3H). HRMS (ESI): m/z calc. for C$_{33}$H$_{33}$N$_2$O$_4$Br$_2$[M+H]$^+$: 679.0807. found: 679.0816.

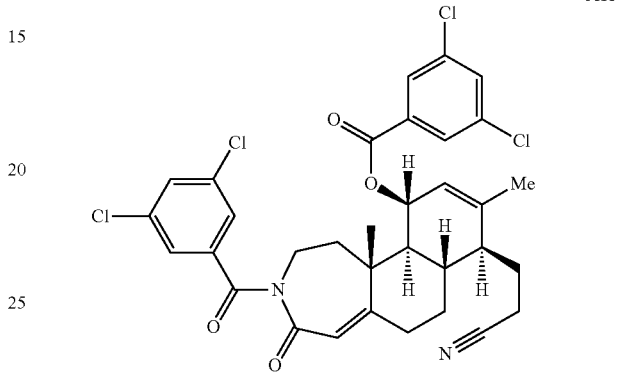

A1f

A1f: Prepared from 3,5-dichlorobenzoyl chloride.
Yield: 7.6 mg, 55%.

$^1$H NMR (CDCl$_3$, 500 MHz): δ 7.89 (d, J=2.0 Hz, 2H), 7.59 (t, J=1.9 Hz, 1H), 7.41 (t, J=1.9 Hz, 1H), 7.31 (d, J=1.9 Hz, 2H), 5.90 (s, 1H), 5.68 (dq, J=8.6, 2.1 Hz, 1H), 5.45 (d, J=1.5 Hz, 1H), 3.99 (dd, J=14.9, 8.3 Hz, 1H), 3.68 (dd, J=14.9, 8.6 Hz, 1H), 2.60 (td, J=13.5, 4.0 Hz, 1H), 2.35 (dq, J=12.4, 3.9 Hz, 1H), 2.29 (m, 1H), 2.25-2.18 (m, 2H), 2.18-1.96 (m, 5H), 1.91 (dd, J=15.6, 8.3 Hz, 1H), 1.88-1.77 (m, 1H), 1.71 (s, 3H), 1.33 (m, 1H), 1.28 (s, 3H). HRMS (ESI): m/z calc. for C$_{33}$H$_{31}$N$_2$O$_4$Cl$_4$[M+H]$^+$: 659.1038. found: 659.1027.

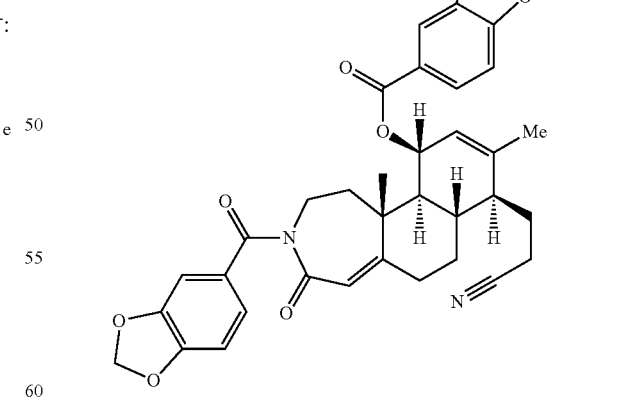

A1g

A1g: Prepared from piperonyloyl chloride.
Yield: 19.7 mg, 39%.

$^1$H NMR (CDCl$_3$, 500 MHz): δ 7.63 (dd, J=8.2, 1.7 Hz, 1H), 7.44 (d, J=1.7 Hz, 1H), 7.16 (dd, J=8.1, 1.7 Hz, 1H), 7.02 (d, J=1.7 Hz, 1H), 6.85 (d, J=8.2 Hz, 1H), 6.78 (d, J=8.1 Hz, 1H), 6.05 (d, J=1.0 Hz, 1H), 6.03 (d, J=1.5 Hz, 1H), 6.02-5.98 (m, 2H), 5.90 (s, 1H), 5.63 (dd, J=8.8, 2.5 Hz, 1H), 5.45 (q, J=1.9 Hz, 1H), 3.86 (dd, J=14.9, 8.3 Hz, 1H), 3.68 (dd, J=14.9, 8.7 Hz, 1H), 2.58 (td, J=13.7, 4.5 Hz, 1H), 2.32 (dq, J=12.3, 3.9 Hz, 1H), 2.26 (dt, J=13.4, 3.5 Hz, 1H), 2.24-2.04 (m, 6H), 2.02-1.88 (m, 2H), 1.86-1.72 (m, 1H), 1.68 (s, 3H), 1.32 (m, 1H), 1.26 (s, 3H). HRMS(ESI): m/z calc. for $C_{35}H_{35}N_2O_8$ [M+H]$^+$: 611.2393. found: 611.2392.

Synthesis of A2 Derivatives.

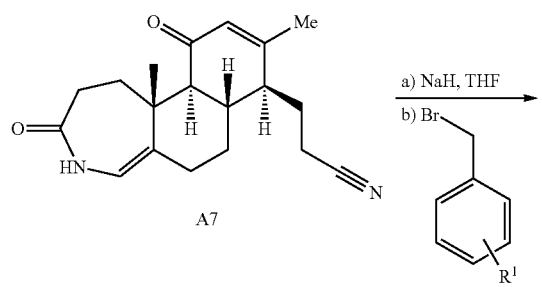

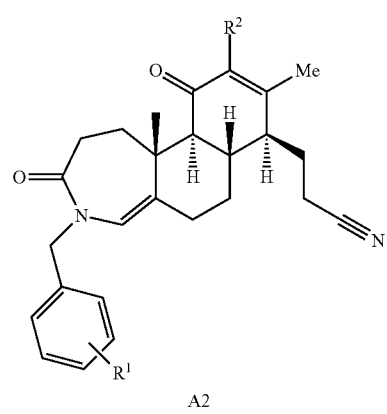

$R^1$ = H or BN

General Procedure for the Preparation of A2 N-Benzylated Enamides:

Enamide A7 (70 mg, 0.224 mmol dissolved in 0.8 mL tetrahydrofuran) was added dropwise to a stirring suspension of sodium hydride (50 mg, 0.986 mmol) in tetrahydrofuran (1.2 mL) at 0° C. The resulting mixture was allowed to stir for 30 minutes before a benzyl bromide derivative (2 equiv.) was added to the reaction. The reaction was allowed to stir at 0° C. for an additional 20 minutes before the ice bath was removed and the reaction stirred at room temperature for 16 hours. Upon completion of the reaction a saturated solution of aqueous ammonia chloride was added to quench the reaction and ethyl acetate was used to extract the product. The ethyl acetate layer was then washed with brine (2×), dried with magnesium sulfate and concentrated under reduced pressure. The crude material was purified by column chromatography using hexanes/ethyl acetate to afford a benzylated enamide.

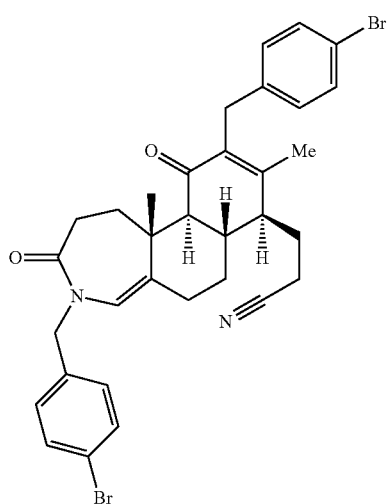

A2a: Prepared from 4-bromobenzyl bromide.

Yield: 15.1 mg, 10%.

NMR (CDCl$_3$, 500 MHz): δ 7.43 (d, J=7.9 Hz, 2H), 7.36 (d, J=7.9 Hz, 2H), 7.10 (d, J=8.0 Hz, 2H), 6.94 (d, J=8.0 Hz, 2H), 5.57 (s, 1H), 4.58 (m, 2H), 3.66 (d, J=15.0 Hz, 1H), 3.50 (d, J=15.0 Hz, 1H), 2.70-2.42 (m, 3H), 2.33 (m, 2H), 2.26-2.03 (m, 5H), 2.03-1.73 (m, 4H), 1.85 (s, 3H), 1.29 (s, 3H), 1.14 (m, 1H).

HRMS(ESI): m/z calc. for $C_{33}H_{35}N_2O_2Br_2$ [M+H]$^+$: 649.1065. found: 649.1057.

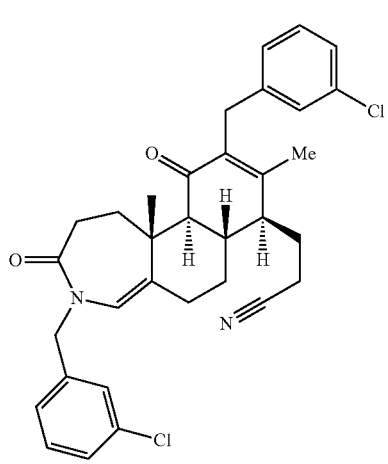

A2b: Prepared from 3-chlorobenzyl bromide.

Yield: 15.9 mg, 12%.

$^1$H NMR (CDCl$_3$, 500 MHz): δ 7.25-7.12 (m, 5H), 7.10 (dt, J=6.9, 1.9 Hz, 1H), 7.02 (m, 1H), 6.93 (dt, J=7.2, 1.6 Hz, 1H), 5.58 (s, 1H), 4.66-4.56 (m, 2H), 3.71 (d, J=15.0 Hz, 1H), 3.53 (d, J=15.0 Hz, 1H), 2.58-2.45 (m, 3H), 2.36 (m, 1H), 2.33 (dd, J=13.5, 3.0 Hz, 1H), 2.24-1.87 (m, 9H), 1.86 (s, 3H), 1.32 (s, 3H), 1.16 (m, 1H).

HRMS(ESI): m/z calc. for $C_{33}H_{35}N_2O_2Cl_2$ [M+H]$^+$: 561.2076. found: 561.2083.

Synthesis of A2 Derivatives.

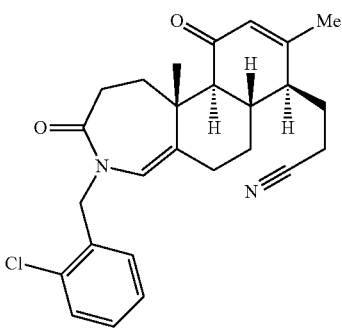

A2c

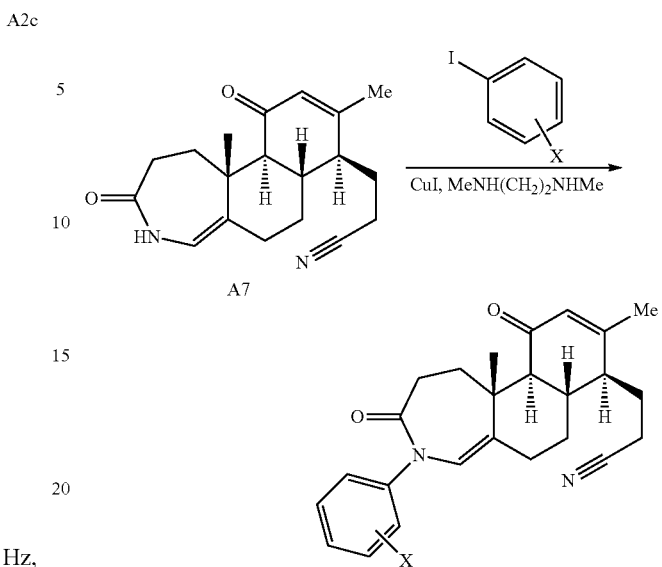

A2c: Prepared from 2-chlorobenzyl bromide.

Yield: 4.4 mg, 5%.

$^1$H NMR (CDCl$_3$, 500 MHz): δ 7.44 (dd, J=7.6, 1.4 Hz, 1H), 7.34 (dd, J=7.9, 1.2 Hz, 1H), 7.28 (m, 1H), 7.19 (td, J=7.6, 1.6 Hz, 1H), 5.69 (s, 1H), 5.65 (d, J=1.7 Hz, 1H), 4.86 (d, J=16.5 Hz, 1H), 4.80 (d, J=16.6 Hz, 1H), 3.54 (dd, J=12.5, 12.0 Hz, 1H), 2.78-2.47 (m, 6H), 2.47-2.42 (m, 1H), 2.09 (dd, J=10.0, 2.0 Hz, 1H), 2.01 (m, 1H), 1.96-1.83 (m, 2H), 1.92 (s, 3H), 1.59-1.45 (m, 2H), 1.29-1.24 (m, 1H), 1.27 (s, 3H).

HRMS(ESI): m/z calc. for C$_{26}$H$_{30}$N$_2$O$_2$Cl[M+H]$^+$: 437.1996. found: 437.1997.

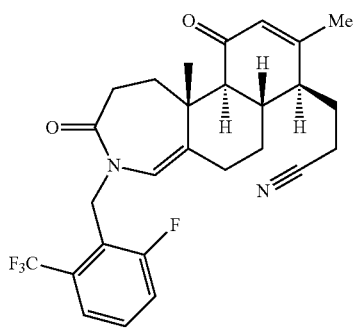

A2d

X = a substituent as defined herein

General Procedure for the Preparation of A2 N-Aryl Enamides:

Enamide A7 (35 mg, 0.112 mmol) and aryl iodide (1.2 equiv.) were dissolved in dry acetonitrile (0.5 mL) and stirred under argon at 70° C. for 20 minutes before potassium carbonate (2 equiv.), N,N'-dimethylethylenediamine (0.8 equiv.) and copper (I) iodide (0.4 equiv.) were added. The reaction vial was sealed and the reaction was refluxed for 15 hours before being cooled to room temperature and quenched with brine and extracted with ethyl acetate. The organic layer was collected, dried with magnesium sulfate and concentrated. The desired aryl enamides were purified using column chromatography using hexanes/ethyl acetate.

A2d: Prepared from 2-fluoro-6-(trifluoromethyl)benzyl bromide.

Yield: 31.4 mg, 36%.

$^1$H NMR (CDCl$_3$, 500 MHz): δ 7.49 (d, J=7.8 Hz, 1H), 7.40 (td, J=8.1, 5.2 Hz, 1H), 7.25 (t, J=8.5 Hz, 1H), 5.86 (dd, J=2.5, 1.4 Hz, 1H), 5.49 (s, 1H), 4.99 (d, J=15.5 Hz, 1H), 4.89 (d, J=15.5 Hz, 1H), 2.62-2.36 (m, 3H), 2.32-2.15 (m, 3H), 2.15-2.00 (m, 6H), 1.96-1.84 (m, 1H), 1.87 (s, 3H), 1.79 (dt, J=13.6, 3.6 Hz, 1H), 1.18 (s, 3H), 0.96 (qd, J=13.0, 4.0 Hz, 1H).

HRMS(ESI): m/z calc. for C$_{23}$H$_{29}$N$_2$O$_2$F$_4$[M+H]$^+$: 489.2165. found: 489.2156.

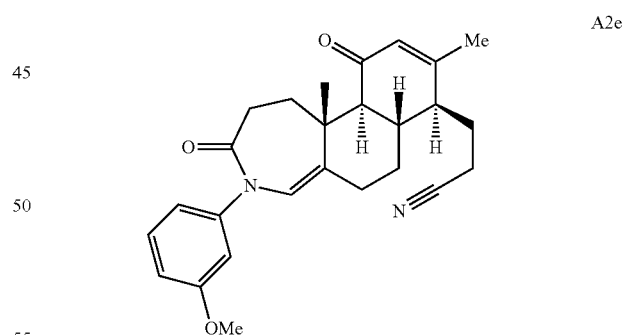

A2e

A2e: Prepared from 3-iodoanisole.

Yield: 8.7 mg, 25%.

$^1$H NMR (CDCl$_3$, 500 MHz): δ 7.30 (t, J=8.1 Hz, 1H), 6.84 (ddd, J=8.3, 2.5, 0.9 Hz, 1H), 6.81 (ddd, J=7.8, 2.0, 0.9 Hz, 1H), 6.76 (t, J=2.2 Hz, 1H), 5.92 (dd, J=2.6, 1.4 Hz, 1H), 5.82 (d, J=1.3 Hz, 1H), 3.80 (s, 3H), 2.75 (dd, J=14.5, 9.5 Hz, 1H), 2.69-2.56 (m, 2H), 2.42-2.11 (m, 9H), 2.06-1.95 (m, 2H), 1.92 (s, 3H), 1.34 (s, 3H), 1.32-1.20 (m, 1H).

HRMS(ESI): m/z calc. for C$_{26}$H$_{31}$N$_2$O$_3$[M+H]$^+$: 419.2335. found: 419.2344.

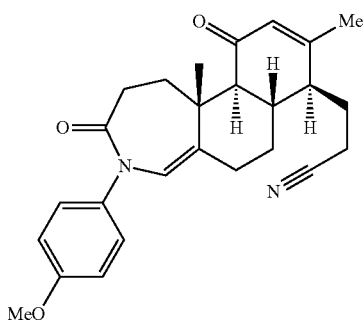

A2f

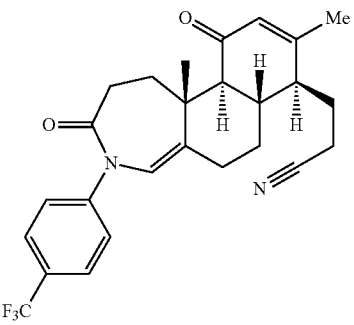

A2h

A2f: Prepared from 4-iodoanisole.

Yield: 9.7 mg, 15%.

$^1$H NMR (CDCl$_3$, 500 MHz): δ 7.12 (m, 2H), 6.91 (m, 2H), 5.91 (dd, J=2.7, 1.4 Hz, 1H), 5.79 (m, 1H), 3.81 (s, 3H), 2.73 (m, 1H), 2.68-2.53 (m, 2H), 2.43-2.31 (m, 2H), 2.31-2.07 (m, 7H), 2.07-1.94 (m, 2H), 1.91 (s, 3H), 1.34 (s, 3H), 1.26 (m, 1H). HRMS(ESI): m/z calc. for C$_{26}$H$_{31}$N$_2$O$_3$ [M+H]$^+$: 419.2335. found: 419.2338.

A2h: Prepared from 4-iodobenzotrifluoride.

Yield: 4.5 mg, 5%.

$^1$H NMR (CDCl$_3$, 500 MHz): δ 7.65 (d, J=8.5 Hz, 2H), 7.37 (d, J=8.2 Hz, 2H), 5.92 (dd, J=2.6, 1.4 Hz, 1H), 5.79 (m, 1H), 2.76 (m, 1H), 2.71-2.57 (m, 2H), 2.46-2.13 (m, 9H), 2.10-1.97 (m, 2H), 1.92 (s, 3H), 1.36 (s, 3H), 1.34-1.23 (m, 1H).

HRMS(ESI): m/z calc. for C$_{26}$H$_{28}$N$_2$O$_2$F$_3$[M+H]$^+$: 457.2103. found: 457.2107.

Synthesis of Compounds Based on A12

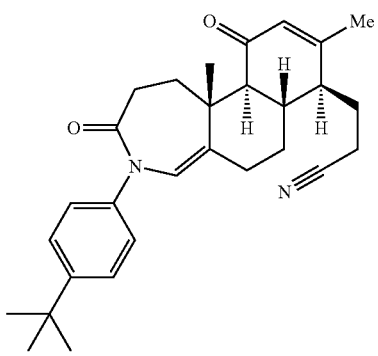

A2g

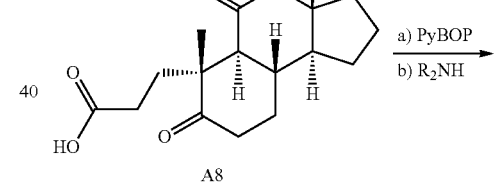

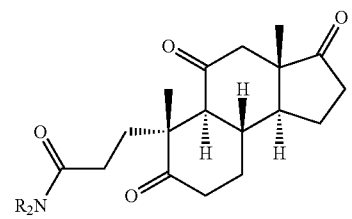

A2g: Prepared from 4-tert-butyliodobenzene.

Yield: 15.9 mg, 26%.

$^1$H NMR (CDCl$_3$, 500 MHz): δ 7.41 (m, 2H), 7.14 (m, 2H), 5.91 (dd, J=2.6, 1.4 Hz, 1H), 5.82 (s, 1H), 2.74 (dd, J=14.0, 9.5 Hz, 1H), 2.69-2.53 (m, 2H), 2.43-2.31 (m, 2H), 2.30-2.07 (m, 7H), 2.06-1.95 (m, 2H), 1.91 (s, 3H), 1.34 (s, 3H), 1.31 (s, 9H), 1.30-1.20 (m, 1H).

HRMS(ESI): m/z calc. for C$_{29}$H$_{37}$N$_2$O$_2$ [M+H]$^+$: 445.2855. found: 455.2846.

General Procedure for the Preparation of A12 Amides:

In an oven-dried vial, A8 (1 equiv.) and benzotriazol-1-yloxytripyrrolidinophosphonium hexafluorophosphate (1.2 equiv.) were dissolved in dichloromethane (0.1 M). Diisopropylethylamine (1 equiv.) was added, and the reaction was stirred at room temperature for 1-2 hours. After complete complexation by TLC, an amine (1-3 equiv.) and additional diisopropylethylamine (1-3 equiv.) were added, and the reaction was allowed to stir at room temperature for 12-16 hours. The reaction was concentrated under reduce pressure and purified by flash chromatography on silica gel (hexanes/ethyl acetate or dichloromethane/methanol) to provide the amide.

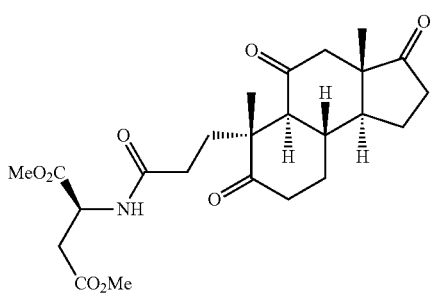

A12a

A12a: Prepared from L-aspartic acid dimethyl ester hydrochloride.

Yield: 75.1 mg, 32%.

$^1$H NMR (CDCl$_3$, 500 MHz): δ 6.62 (d, J=8.1 Hz, 1H), 4.75 (dt, J=8.5, 4.5 Hz, 1H), 3.72 (s, 3H), 3.68 (s, 3H), 2.98 (dd, J=17.2, 4.4 Hz, 1H), 2.83 (dd, J=17.2, 4.6 Hz, 1H), 2.62-2.43 (m, 3H), 2.40-1.92 (m, 12H), 1.70 (tt, J=12.4, 9.2 Hz, 1H), 1.53 (tdd, J=13.4, 11.7, 4.8 Hz, 1H), 1.29 (s, 3H), 0.87 (s, 3H).

HRMS(ESI): m/z calc. for C$_{24}$H$_{34}$NO$_8$ [M+H]$^+$: 464.2284. found: 464.2279.

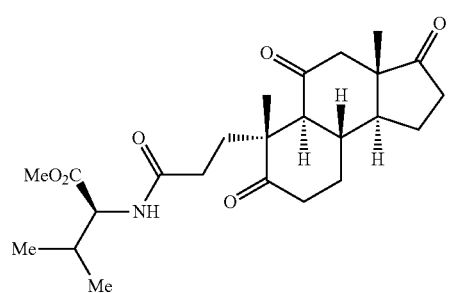

A12b

A12b: Prepared from L-valine methyl ester hydrochloride.

Yield: 113.6 mg, 34%.

$^1$H NMR (CDCl$_3$, 500 MHz): δ 6.24 (d, J=8.7 Hz, 1H), 4.42 (dd, J=8.7, 5.0 Hz, 1H), 3.69 (s, 3H), 2.63-2.50 (m, 2H), 2.44 (d, J=13.1 Hz, 1H), 2.39-1.89 (m, 13H), 1.68 (tt, J=12.4, 9.2 Hz, 1H), 1.50 (qd, J=13.0, 4.5 Hz, 1H), 1.29 (s, 3H), 0.90 (d, J=7.0 Hz, 3H), 0.88 (d, J=7.5 Hz, 3H), 0.86 (s, 3H).

HRMS(ESI): m/z calc. for C$_{24}$H$_{36}$NO$_6$ [M+H]$^+$: 434.2543. found: 434.2534.

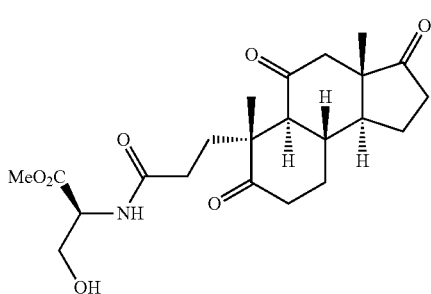

A12c

A12c: Prepared from L-serine methyl ester hydrochloride.

Yield: 43.6 mg, 10%.

$^1$H NMR (CDCl$_3$, 500 MHz): δ 6.62 (d, J=6.6 Hz, 1H), 4.43 (dt, J=6.4, 3.1 Hz, 1H), 3.94 (dd, J=12.0, 3.0 Hz, 1H), 3.85 (dd, J=11.5, 3.0 Hz, 1H), 3.77 (s, 3H), 2.92 (d, J=11.0 Hz, 1H), 2.61-2.50 (m, 2H), 2.48 (d, J=13.5 Hz, 1H), 2.46-2.22 (m, 6H), 2.22-2.09 (m, 4H), 2.08-1.93 (m, 2H), 1.68 (dtt, J=16.5, 11.8, 7.0 Hz, 2H), 1.26 (s, 3H), 0.88 (s, 3H). HRMS(ESI): m/z calc. for C$_{22}$H$_{32}$NO$_7$ [M+H]$^+$: 422.2179. found: 422.2185.

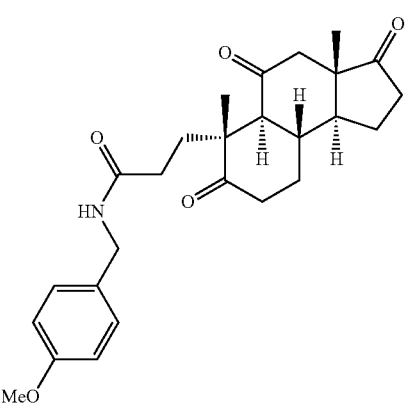

A12d

A12d: Prepared from 4-methoxybenzylamine.

Yield: 25.0 mg, 76%.

$^1$H NMR (CDCl$_3$, 400 MHz): δ 7.20 (d, J=8.6 Hz, 2H), 6.85 (d, J=8.6 Hz, 2H), 5.89 (t, J=5.8 Hz, 1H), 4.32 (dd, J=14.4, 5.6 Hz, 1H), 4.27 (dd, J=14.4, 5.2 Hz, 1H), 3.79 (s, 3H), 2.66-1.86 (m, 15H), 1.70 (tt, J=12.5, 9.2 Hz, 1H), 1.52 (tdd, J=13.6, 11.5, 4.7 Hz, 1H), 1.31 (s, 3H), 0.88 (s, 3H). HRMS(ESI): m/z calc. for C$_{26}$H$_{34}$NO$_5$ [M+H]$^+$: 440.2437. found: 440.2445.

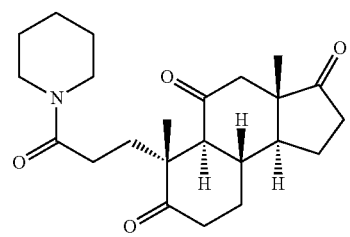

A12e

A12e: Prepared from piperidine.

Yield: 144 mg, 92%.

$^1$H NMR (CDCl$_3$, 500 MHz): δ 3.52-3.30 (m, 4H), 2.65 (d, J=11.1 Hz, 1H), 2.61-2.47 (m, 2H), 2.46-2.31 (m, 3H), 2.31-1.95 (m, 8H), 1.68 (u, J=12.3, 9.2 Hz, 1H), 1.62-1.51 (m, 4H), 1.50-1.42 (m, 2H), 1.40-1.32 (m, 2H), 1.28 (s, 3H), 0.85 (s, 3H).

HRMS(ESI): m/z calc. for C$_{23}$H$_{34}$NO$_4$ [M+H]$^+$: 388.2488. found: 388.2498.

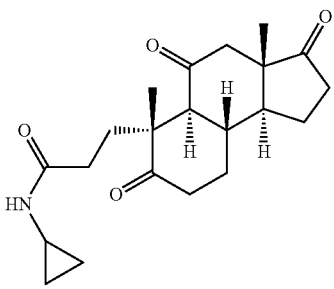

A12f

A12f: Prepared from cyclopropylamine.

Yield: 25.4 mg, 87%.

$^1$H NMR (CDCl$_3$, 500 MHz): δ 5.79 (br s, 1H), 2.65-2.46 (m, 5H), 2.39 (ddd, J=15.2, 4.8, 2.4 Hz, 1H), 2.37-2.13 (m, 7H), 2.02-1.88 (m, 3H), 1.75-1.61 (m, 2H), 1.30 (s, 3H), 0.89 (s, 3H), 0.75-0.69 (m, 2H), 0.50-0.45 (m, 2H). HRMS (ESI): m/z calc. for C$_{21}$H$_{30}$NO$_4$ [M+H]$^+$: 360.2175. found: 360.2180.

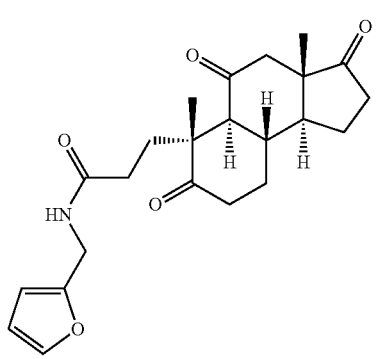

A12g

A12g: Prepared from furfurylamine.

Yield: 18.7 mg, 63%.

$^1$H NMR (CDCl$_3$, 500 MHz): δ 7.34 (dd, J=1.9, 0.8 Hz, 1H), 6.31 (dd, J=3.2, 1.9 Hz, 1H), 6.22 (dd, J=3.1, 0.9 Hz, 1H), 5.95 (t, J=5.5 Hz, 1H), 4.40 (dd, J=15.5, 5.5 Hz, 1H), 4.36 (dd, J=15.5, 5.5 Hz, 1H), 2.66-2.53 (m, 2H), 2.49 (d, J=13.2 Hz, 1H), 2.43 (d, J=11.2 Hz, 1H), 2.39 (ddd, J=15.1, 4.8, 2.4 Hz, 1H), 2.36-1.90 (m, 10H), 1.71 (tt, J=12.5, 9.2 Hz, 1H), 1.58-1.47 (m, 1H), 1.32 (s, 3H), 0.89 (s, 3H). HRMS(ESI): m/z calc. for C$_{23}$H$_{30}$NO$_5$ [M+H]$^+$: 400.2124. found: 400.2121.

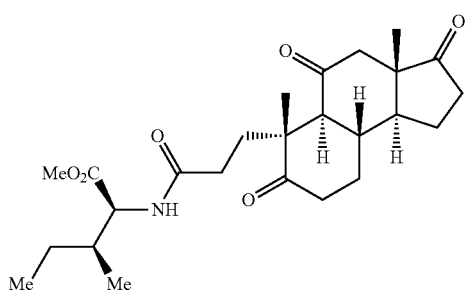

A12h

A12h: Prepared from L-isoleucine methyl ester hydrochloride.

Yield: 60.0 mg, 43%.

$^1$H NMR (CDCl$_3$, 500 MHz): δ 6.37 (d, J=8.5 Hz, 1H), 4.44 (dd, J=8.5, 5.1 Hz, 1H), 3.68 (s, 3H), 2.62-2.48 (m, 2H), 2.41 (d, J=13.1 Hz, 1H), 2.38-1.77 (m, 12H), 1.82 (tdd, J=11.4, 5.8, 2.2 Hz, 1H), 1.68 (tt, J=12.4, 9.2 Hz, 1H), 1.57-1.46 (m, 1H), 1.38 (dtd, J=14.8, 7.4, 4.6 Hz, 1H), 1.27 (s, 3H), 1.13 (ddt, J=14.5, 9.0, 7.3 Hz, 1H), 0.89 (m, 6H) 0.85 (s, 3H). HRMS(ESI): m/z calc. for C$_{25}$H$_{38}$NO$_6$[M+H]$^+$: 448.2699. found: 448.2698.

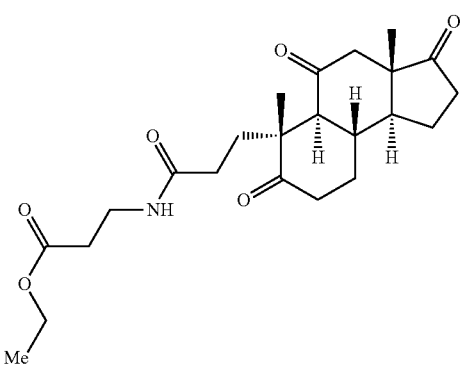

A12i

A12i: Prepared from β-alanine ethyl ester hydrochloride.

Yield: 70.4 mg, 29%.

$^1$H NMR (CDCl$_3$, 500 MHz): δ 6.28-6.14 (t, J=5.5 Hz, 1H), 4.14 (q, J=7.1 Hz, 2H), 3.46-3.40 (m, 2H), 2.62-2.52 (m, 2H), 2.51-2.44 (m, 4H), 2.41-2.11 (m, 8H), 2.05-1.89 (m, 3H), 1.70 (tt, J=12.5, 9.2 Hz, 1H), 1.59-1.47 (m, 1H), 1.29 (s, 3H), 1.25 (t, J=7.1 Hz, 3H), 0.87 (s, 3H). HRMS (ESI): m/z calc. for C$_{23}$H$_{34}$NO$_6$[M+H]$^+$: 420.2386. found: 420.2378.

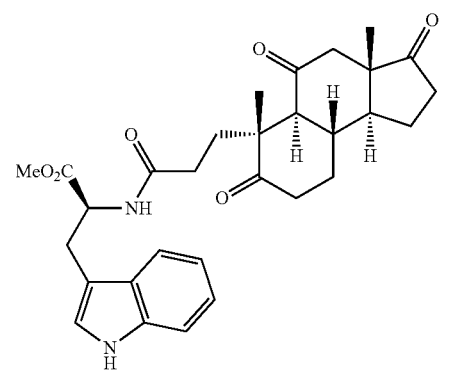

A12j

A12j: Prepared from L-tryptophan methyl ester hydrochloride.

Yield: 30.0 mg, 5%.

$^1$H NMR (CDCl$_3$, 500 MHz): δ 8.56 (d, J=2.4 Hz, 1H), 7.53 (d, J=8.0 Hz, 1H), 7.30 (dd, J=8.1, 1.0 Hz, 1H), 7.16-7.11 (m, 1H), 7.09-7.03 (m, 1H), 7.04 (d, J=2.0 Hz, 1H), 6.26 (d, J=7.8 Hz, 1H), 4.84 (dt, J=7.5, 5.5 Hz, 1H), 3.64 (s, 3H), 3.30 (dd, J=15.0, 5.5 Hz, 1H), 3.25 (dd, J=15.0, 6.0 Hz, 1H), 2.59-2.49 (m, 2H), 2.43 (d, J=13.1 Hz, 1H), 2.36-1.90 (m, 11H), 1.84-1.76 (m, 1H), 1.65 (tt, J=12.3, 9.2 Hz, 1H), 1.43 (qd, J=13.0, 5.0 Hz, 1H), 1.26 (s, 3H), 0.85 (s, 3H).

HRMS(ESI): m/z calc. for C$_{34}$H$_{37}$N$_2$O$_6$[M+H]$^+$: 521.2652. found: 521.2648.

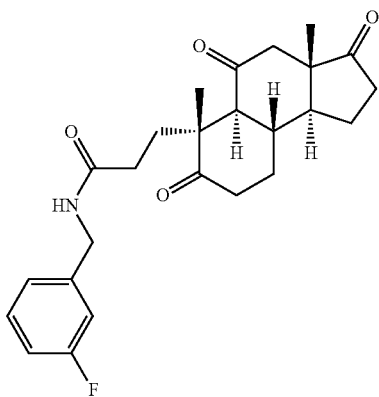

A12k

A12k: Prepared from 3-fluorobenzylamine.
Yield: 40.7 mg, 99%.
$^1$H NMR (CDCl$_3$, 500 MHz): δ 7.30-7.25 (m, 1H), 7.05 (ddd, J=7.6, 1.7, 0.9 Hz, 1H), 6.98 (dt, 10.0, 1.5 Hz, 1H), 6.94 (td, J=8.5, 2.0 Hz, 1H), 6.10 (t, J=5.5 Hz, 1H), 4.39 (dd, J=15.0, 6.0 Hz, 1H), 4.34 (dd, J=15.0, 5.5 Hz, 1H), 2.65-2.53 (m, 2H), 2.48 (d, J=13.2 Hz, 1H), 2.44 (d, J=11.2 Hz, 1H), 2.38 (ddd, J=15.0, 4.7, 2.4 Hz, 1H), 2.35-1.90 (m, 10H), 1.78-1.65 (tt, J=12.5, 9.5 Hz, 1H), 1.59-1.47 (m, 1H), 1.31 (s, 3H), 0.89 (s, 3H).
HRMS(ESI): m/z calc. for C$_{25}$H$_{31}$NO$_4$F [M+H]$^+$: 428.2237. found: 428.2237.

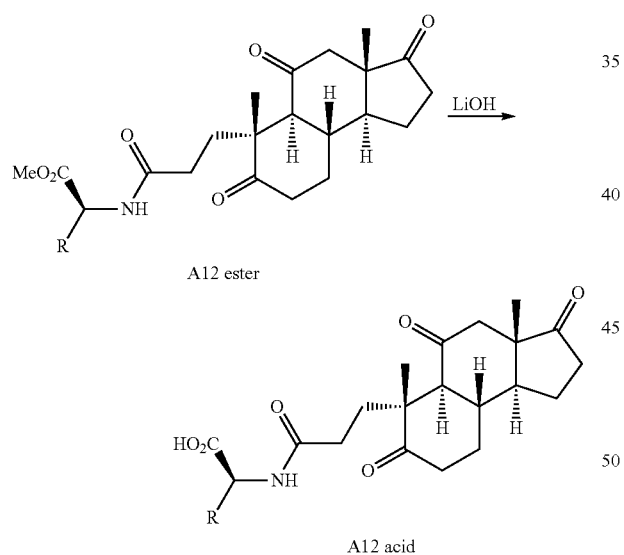

General Procedure for the Preparation of Acids from A12 Amides:

In a vial with stir bar, amide (1 equiv.) and lithium hydroxide (20-30 equiv.) were dissolved in a 1:1 mixture of tetrahydrofuran and water (0.005 M), and stirred at room temperature for 12-16 hours. The reaction mixture was acidified to pH 2 with concentrated hydrochloric acid and extracted with ethyl acetate (3×). The organic layer was washed with brine, dried over magnesium sulfate, filtered, and concentrated under reduced pressure. The residue was purified by flash chromatography on silica gel (dichloromethane/methanol/formic acid) to yield the desired acid.

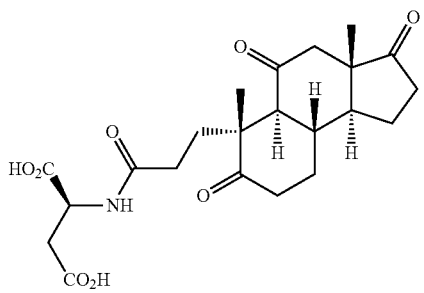

A12l

A12l: Prepared from A12a.
Yield: 17.6 mg, 60%.
$^1$H NMR (CDCl$_3$, 500 MHz): δ 7.45 (br s, 1H), 4.75 (br s, 1H), 2.97 (d, J=16.5 Hz, 1H), 2.85 (d, J=16.5 Hz, 1H), 2.70-2.06 (m, 15H), 1.75-1.50 (m, 2H), 1.28 (s, 3H), 0.86 (s, 3H).
HRMS(ESI): m/z calc. for C$_{22}$H$_{30}$NO$_8$[M+H]$^+$: 436.1971. found: 436.1968.

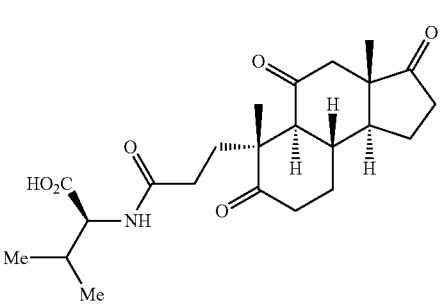

A12m

A12m: Prepared from 12b.
Yield: 23.3 mg, 59%.
$^1$H NMR (CDCl$_3$, 500 MHz): δ 6.46 (d, J=8.5 Hz, 1H), 4.41 (dd, J=8.4, 5.0 Hz, 1H), 2.65-2.52 (m, 2H), 2.47 (d, J=13.2 Hz, 1H), 2.44-1.93 (m, 13H), 1.71 (tt, J=12.4, 9.2 Hz, 1H), 1.53 (qd, J=13.0, 4.5 Hz, 1H), 1.31 (s, 3H), 0.97 (d, J=7.0 Hz, 3H), 0.95 (d, J=7.5 Hz, 3H), 0.89 (s, 3H).
HRMS(ESI): m/z calc. for C$_{13}$H$_{34}$NO$_6$[M+H]$^+$: 420.2386. found: 420.2390.

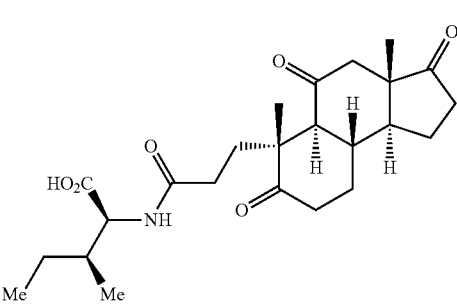

A12n

A12n: Prepared from A12h.
Yield: 21.8 mg, 38%.
$^1$H NMR (CDCl$_3$, 500 MHz): δ 6.45 (d, J=8.3 Hz, 1H), 4.47 (dd, J=8.3, 4.9 Hz, 1H), 2.65-2.52 (m, 2H), 2.47 (d, J=13.2 Hz, 1H), 2.44-1.88 (m, 13H), 1.71 (tt, J=12.4, 9.2 Hz, 1H), 1.58-1.45 (m, 2H), 1.31 (s, 3H), 1.21 (ddd, J=13.5, 9.3, 7.1 Hz, 1H), 0.94 (d, J=6.5 Hz, 3H), 0.92 (t, 7.0 Hz, 3H), 0.88 (s, 3H).

HRMS(ESI): m/z calc. for $C_{24}H_{36}NO_6[M+H]^+$: 434.2543. found: 434.2535.

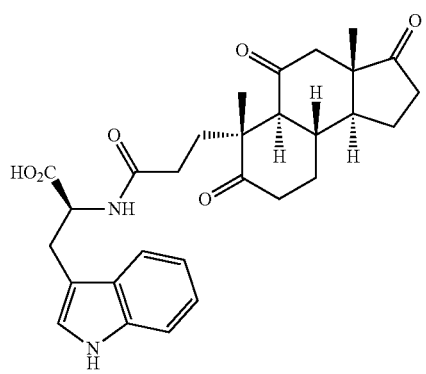

A12o

A12o: Prepared from A12j.
Yield: 5.1 mg, 20%.

$^1$H NMR (CDCl$_3$, 500 MHz): δ 8.66 (br s, 1H), 7.56 (d, J=7.9 Hz, 1H), 7.29-7.25 (m, 1H), 7.10 (t, J=7.5 Hz, 1H), 7.07-6.99 (m, 2H), 6.51 (s, 1H), 4.79 (d, J=7.3 Hz, 1H), 3.36-3.19 (m, 2H), 2.60-1.82 (m, 13H), 1.74-1.52 (m, 2H), 1.48-1.23 (m, 2H), 1.21 (s, 3H), 0.81 (s, 3H).

HRMS(ESI): m/z calc. for $C_{29}H_{35}NO_6$ $[M+H]^+$: 507.2495. found: 507.2499.

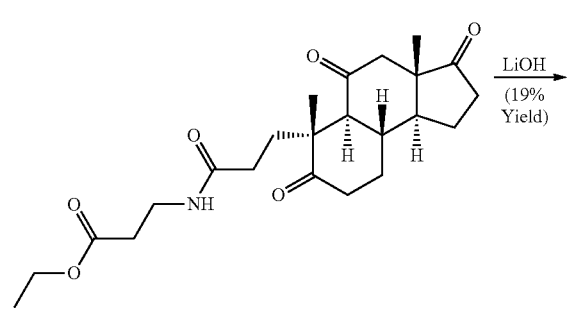

A12i

LiOH
(19% Yield)

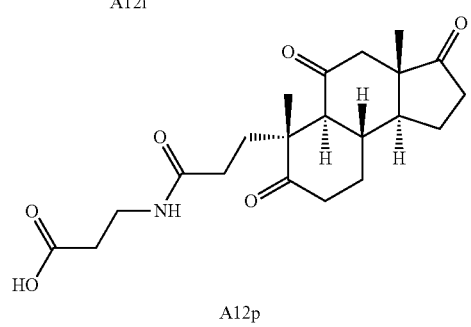

A12p

Procedure: In a vial with stir bar, A12l (106.0 mg, 0.253 mmol) and lithium hydroxide hydrate (306.2 mg, 7.30 mmol) were dissolved in a tetrahydrofuran (10 mL) and methanol (10 mL), and stirred at room temperature for 12 hours. The reaction was diluted with water (10 mL), acidified to pH 2 with concentrated hydrochloric acid, and extracted with ethyl acetate (3×). The organic layer was washed with brine, dried over magnesium sulfate, filtered, and concentrated under reduced pressure. The residue was purified by flash chromatography on silica gel (dichloromethane/methanol 9:1) to yield A12p (19.0 mg, 19.2%).

$^1$H NMR (CDCl$_3$, 500 MHz): δ 6.50 (t, J=6.1 Hz, 1H), 3.51-3.39 (m, 2H), 2.64-2.11 (m, 14H), 2.08-1.95 (m, 3H), 1.70 (tt, J=12.3, 9.2 Hz, 1H), 1.56 (tdd, J=13.2, 11.6, 4.8 Hz, 1H), 1.30 (s, 3H), 0.88 (s, 3H). HRMS(ESI): m/z calc. for $C_{21}H_{30}NO_6[M+H]^+$: 392.2073. found: 392.2079.

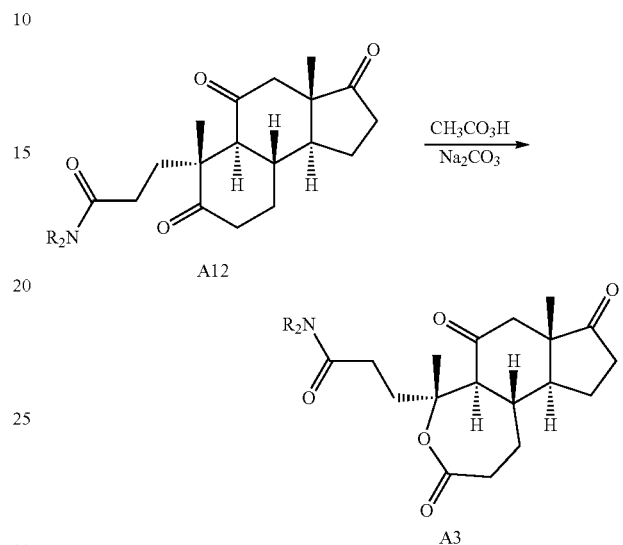

General Procedure for the Preparation of A3 Lactones from A12 Amides:

An A12 amide (1 equiv.) was dissolved in anhydrous dichloromethane (0.1 M). Then sodium carbonate (5 equiv.) was added to the solution and cooled to 0° C. After cooling, a solution of peracetic acid of a 32% by weight peracetic acid solution in dilute acetic acid (3 equiv.) was added dropwise to the reaction mixture. The reaction slowly warmed to room temperature over several hours and was quenched with a saturated solution sodium bicarbonate after 16-20 hours. The reaction was then transferred to a separatory funnel and extracted with dichloromethane (3×). The organic layers were collected, dried with magnesium sulfate and concentrated under reduced pressure to give the crude product. The desired lactone was purified via column chromatography on silica gel (hexanes/ethyl acetate).

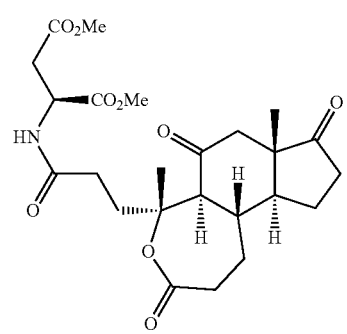

A3a

A3a: Prepared from A12a.
Yield: 13.9 mg, 33.
$^1$H NMR (CDCl$_3$, 500 MHz): δ 6.46 (d, J=8.1 Hz, 1H), 4.83 (dt, J=8.5, 4.4 Hz, 1H), 3.75 (s, 3H), 3.69 (s, 3H), 3.01

(dd, J=17.3, 4.5 Hz, 1H), 2.88-2.79 (m, 2H), 2.74-2.53 (m, 3H), 2.49 (s, 2H), 2.38 (t, J=7.6 Hz, 2H), 2.33-1.97 (m, 8H), 1.67 (tt, J=12.5, 9.5 Hz, 1H), 1.63 (s, 3H), 0.86 (s, 3H).

HRMS(ESI): m/z calc. for $C_{24}H_{33}NO_9[M+H]^+$: 480.2234. found: 480.2230.

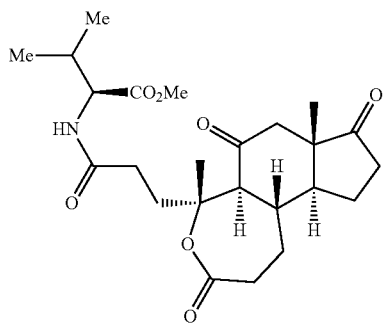

A3b

A3b: Prepared from A12b.
Yield: 15.8 mg, 30%.

$^1$H NMR (CDCl$_3$, 500 MHz): δ 5.96 (d, J=8.0 Hz, 1H), 4.50 (dd, J=8.7, 5.0 Hz, 1H), 3.73 (s, 3H), 2.83 (ddd, J=16.4, 6.9, 1.9 Hz, 1H), 2.69 (d, J=10.9 Hz, 1H), 2.67-2.54 (m, 2H), 2.49 (s, 2H), 2.46-2.23 (m, 4H), 2.19-1.96 (m, 6H), 1.67 (tt, J=12.5, 9.5 Hz, 1H), 1.63 (s, 3H), 1.60-1.50 (m, 1H), 0.91 (d, J=7.0 Hz, 3H), 0.89 (d, J=7.0 Hz, 3H), 0.85 (s, 3H).

HRMS(ESI): m/z calc. for $C_{24}H_{36}NO_7[M+H]^+$: 450.2492. found: 450.2492.

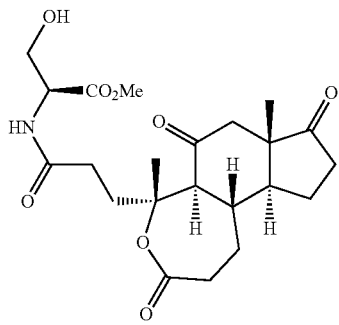

A3c

A3c: Prepared from A12c.
Yield: 12.7 mg, 28%.

$^1$H NMR (CDCl$_3$, 500 MHz): δ 6.49 (d, J=6.9 Hz, 1H), 4.58 (dt, J=6.3, 2.9 Hz, 1H), 4.01 (dd, J=11.6, 3.0 Hz, 1H), 3.89 (dd, J=11.7, 3.0 Hz, 1H), 3.80 (s, 3H), 2.86 (d, J=10.5 Hz, 1H), 2.82 (ddd, J=16.5, 7.0, 2.0 Hz, 1H), 2.68-2.55 (m, 2H), 2.50 (s, 2H), 2.39-2.23 (m, 5H), 2.18-1.97 (m, 4H), 1.67 (tt, J=12.5, 9.0 Hz, 1H), 1.65 (s, 3H), 1.63-1.50 (m, 1H), 0.86 (s, 3H). HRMS(ESI): m/z calc. for $C_{22}H_{32}NO_8$ $[M+H]^+$: 438.2128. found: 438.2134.

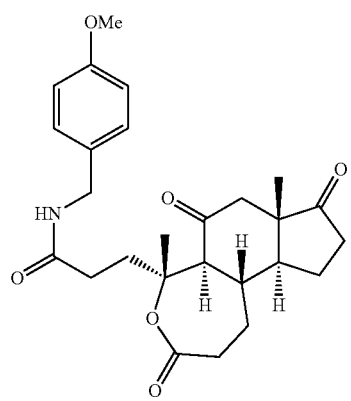

A3d

A3d: Prepared from A12d
Yield: 32.7 mg, 71%.

$^1$H NMR (CDCl$_3$, 500 MHz): δ 7.25-7.19 (m, 2H), 6.90-6.84 (m, 2H), 5.85 (t, J=5.8 Hz, 1H), 4.37 (dd, J=14.0, 5.5 Hz, 1H), 4.30 (dd, J=14.5, 5.5 Hz, 1H), 3.81 (s, 3H), 2.83 (ddd, J=16.6, 6.9, 1.9 Hz, 1H), 2.69-2.62 (m, 2H), 2.59 (dd, J=Hz, 1H) 2.52-2.42 (m, 2H), 2.42-2.17 (m, 5H), 2.17-2.08 (m, 2H), 2.08-1.97 (m, 1H), 1.90 (td, J=11.6, 11.2, 5.7 Hz, 1H), 1.77-1.59 (m, 1H), 1.64 (s, 3H), 1.53 (q, J=12.9 Hz, 1H), 0.86 (s, 3H).

HRMS(ESI): m/z calc. for $C_{26}H_{34}NO_6$ $[M+H]^+$: 456.2386. found: 456.2390.

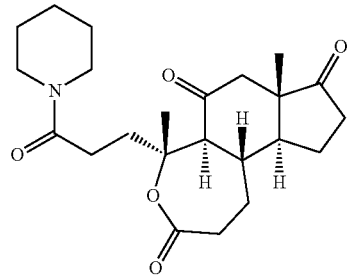

A3e

A3e: Prepared from A12e.
Yield: 34.8 mg, 27%.

$^1$H NMR (CDCl$_3$, 500 MHz): δ 3.52 (dt, J=11.7, 5.3 Hz, 1H), 3.45-3.29 (m, 3H), 2.86-2.75 (m, 2H), 2.69-2.49 (m, 3H), 2.49-2.35 (m, 3H), 2.32-2.19 (m, 2H), 2.19-1.96 (m, 5H), 1.70-1.41 (m, 8H), 1.63 (s, 3H), 0.83 (s, 3H).

HRMS(ESI): m/z calc. for $C_{23}H_{34}NO_5$ $[M+H]^+$: 404.2437. found: 404.2441.

Synthesis of A9 Derivatives.

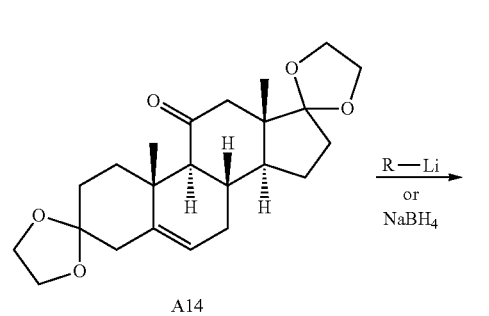

A14

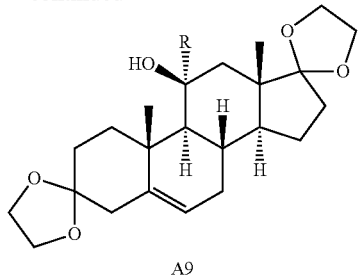

A9

General Procedure for the Preparation of A9 Alcohols Using Organolithium Reagent:

Organolithium (3 equiv.) was slowly added to a stirring solution of A14 (250 mg, 0.644 mmol) in anhydrous tetrahydrofuran at room temperature. The reaction continued to stir for an additional thirty minutes to four hours (depending on organolithium) before being slowly quenched with a saturated solution of ammonium chloride. The contents of the reaction were then transferred to a separatory funnel and extracted with dichloromethane (3×). The organic layers were combined, dried with magnesium sulfate and concentrated under reduced pressure to give a crude product which was purified via column chromatography using hexanes/ethyl acetate to elute. (Notes: The scale for this reaction was typically between 200 and 800 milligrams of A14. The organolithium of 4-tert-butyliodobenzene was generated using 1.0 equiv. of n-butyllithium in ether for 30 minutes at room temperature before cannulation to A14 in toluene. The other organolithium reagents used are commercially available).

Sodium borohydride procedure: A14 (950 mg, 2.45 mmol) was dissolved in 1:1:1 solution of tetrahydrofuran/t-butanol/water (45 mL) and cooled to 0° C. Then sodium borohydride (1.85 g, 48.91 mmol) was added slowly and the reaction was allowed to stir at 0° C. for 2 hours before removal of the ice bath. The reaction continued to stir for an additional 20 hours before being quenched with a saturated solution of aqueous ammonium chloride. Ethyl acetate was used to extract the alcohol product and the organic layer was washed with water and brine (1× each). The organic layer was collected, dried with magnesium sulfate and concentrated. The alcohol was purified by column chromatography using 5:1 to 1:1 hexanes/ethyl acetate to give 847 mg (89% yield) A9a.

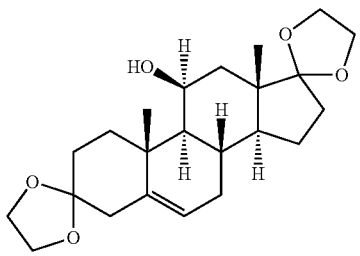

A9a

A9a: Prepared from sodium borohydride.
Yield: 847 mg, 89%.
$^1$H NMR (CDCl3, 500 MHz): δ 5.22 (dt, J=4.6, 2.4 Hz, 1H), 4.43 (q, J=3.3 Hz, 1H), 4.00-3.76 (m, 8H), 2.60 (dq, J=14.7, 3.3 Hz, 1H), 2.20-1.64 (m, 11H), 1.56 (dd, J=13.8, 2.6 Hz, 1H), 1.54-1.30 (m, 4H), 1.28 (s, 3H), 1.18 (dd, J=11.7, 3.8 Hz, 1H), 1.09 (s, 3H). HRMS(ESI): m/z calc. for $C_{23}H_{35}O_5$ [M+H]$^+$: 391.2484. found: 391.2482.

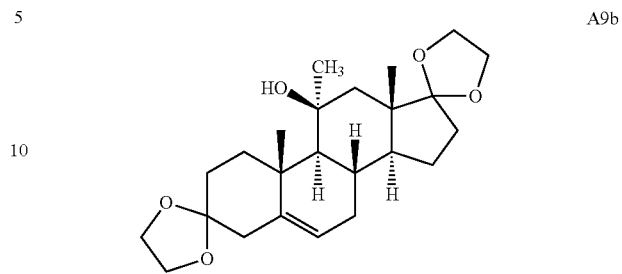

A9b

A9b: Prepared from methyllithium.
Yield: 226 mg, 88%.
$^1$H NMR (CDCl$_3$, 500 MHz): δ 5.29 (m, 1H), 4.01-3.77 (m, 8H), 2.65-2.55 (m, 1H), 2.24 (dt, J=13.0, 2.5 Hz, 1H), 2.14-1.94 (m, 3H), 1.90 (d, J=14.0 Hz, 1H), 1.87-1.65 (m, 6H), 1.61 (td, J=13.6, 4.1 Hz, 1H), 1.44 (s, 3H), 1.40-1.22 (m, 4H), 1.35 (s, 3H), 1.05 (s, 3H).
HRMS(ESI): m/z calc. for $C_{24}H_{37}O_5$ [M+H]$^+$: 405.2641. found: 405.2646.

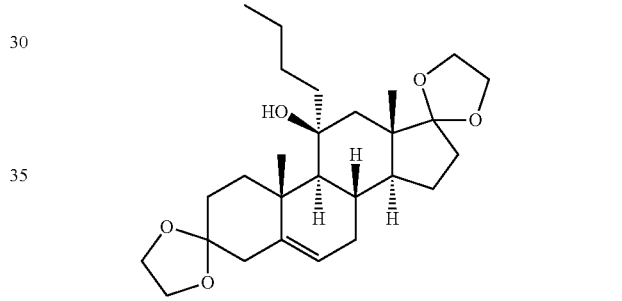

A9c

A9c: Prepared from n-butyllithium.
Yield: 545 mg, 57%.
$^1$H NMR (CDCl$_3$, 500 MHz): δ 5.30 (dt, J=5.6, 2.0 Hz, 1H), 4.02-3.79 (m, 8H), 2.59 (dq, J=14.5, 2.5 Hz, 1H), 2.21 (m, 1H), 2.09 (dd, J=14.5, 3.0 Hz, 1H), 2.07-1.91 (m, 3H), 1.88-1.56 (m, 8H), 1.43-1.18 (m, 9H), 1.37 (s, 3H), 1.04 (s, 3H), 0.88 (td, J=6.9, 1.4 Hz, 31-1). HRMS(ESI): m/z calc. for $C_{29}H_{43}O_5$ [M+H]$^+$: 447.3110. found: 447.3108.

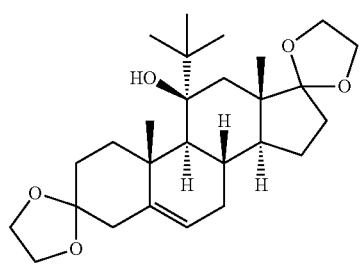

A9d

A9d: Prepared from tert-butyllithium.
Yield: 152 mg, 56%.
$^1$H NMR (CDCl$_3$, 500 MHz): δ 5.40 (m, 1H), 4.01-3.78 (m, 8H), 2.81 (d, J=14.9 Hz, 1H), 2.54 (dq, J=14.5, 2.7 Hz, 1H), 2.30 (dt, J=12.3, 3.2 Hz, 1H), 2.11 (dd, J=14.3, 2.9 Hz, 1H), 1.89 (m, 2H), 1.85-1.52 (m, 10H), 1.45 (s, 3H), 1.23 (m, 1H), 1.03 (s, 3H), 0.96 (s, 9H). HRMS(ESI): m/z calc. for $C_{27}H_{43}O_5$ [M+H]$^+$: 447.3110. found: 447.3110.

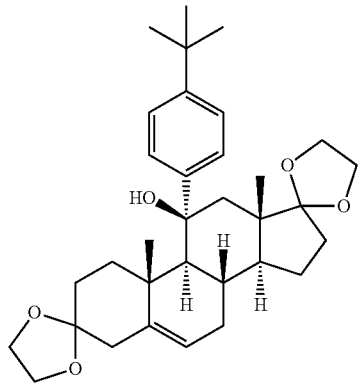

A9e

A9e: Prepared from 4-tert-butylphenyllithium.

Yield: 154 mg, 44%.

$^1$H NMR (CDCl$_3$, 500 MHz): δ 7.49-7.19 (m, 4H), 5.31 (dt, J=4.9, 2.1 Hz, 1H), 3.97-3.63 (m, 8H), 2.52 (dq, J=14.6, 2.9 Hz, 1H), 2.32-2.12 (m, 2H), 2.12-1.97 (m, 3H), 1.92 (d, J=10.9 Hz, 1H), 1.88-1.75 (m, 3H), 1.65 (td, J=11.7, 6.2 Hz, 1H), 1.55-1.45 (m, 2H), 1.39 (m, 1H), 1.32 (s, 3H), 1.30 (s, 9H), 1.25-1.06 (m, 1H), 1.19 (s, 3H), 0.90 (dt, J=13.7, 3.7 Hz, 1H), 0.63 (td, J=14.0, 4.1 Hz, 1H).

HRMS(ESI): m/z calc. for $C_{33}H_{47}O_5$ [M+H]$^+$: 523.3424. found: 523.3422.

Synthesis of A5 and A15 Derivatives

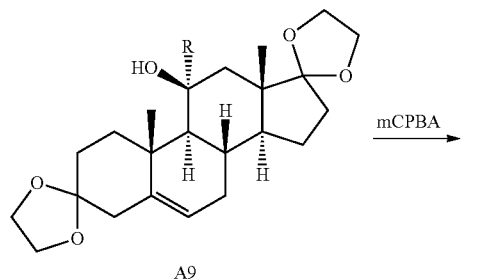

A9 mCPBA →

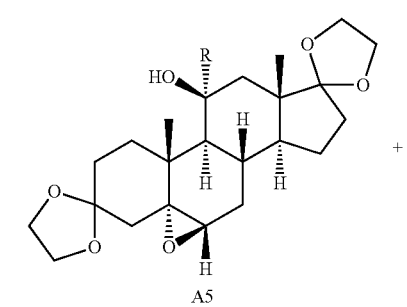

A5

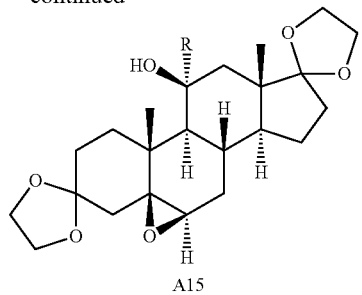

A15

R = O, H, alkyl, aryl

General Procedure for the Preparation of A15 and A5 Epoxides:

m-Chloroperoxybenzoic acid (0.9 equiv. calc. at 77% purity, dissolved in 1 mL of anhydrous dichloromethane) was added at room temperature to stirring solution of A9 alkene (0.15 mmol) in anhydrous dichloromethane (2 mL). The reaction continued to stir for 40 minutes before a saturated solution of sodium bicarbonate was added to quench the reaction. The reaction contents were then extracted with dichloromethane (3×). The combined organic layers were then washed once more with a saturated solution of sodium bicarbonate. The organic layer was then collected, dried with magnesium sulfate and concentrated to give a crude mixture. The epoxide diastereomers were then separated via column chromatography using hexanes/ethyl acetate. The pa-stereochemistry of steroidal epoxides (at C5-C6) is well studied and assigned according to the chemical shift of the $^1$H NMR at C6 (as in A5 and A15).

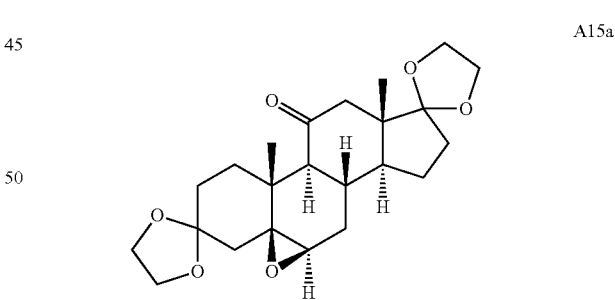

A15a

A15a: Prepared from A14.

Yield: 13.1 mg, 14%.

$^1$H NMR (CDCl$_3$, 500 MHz): δ 3.95-3.85 (m, 6H), 3.84-3.77 (m, 2H), 3.10 (d, J=1.9 Hz, 1H), 2.49 (d, J=14.0 Hz, 1H), 2.41-2.35 (m, 1H), 2.34 (d, J=14.0 Hz, 1H), 2.23 (dt, J=14.5, 2.8 Hz, 1H), 2.10 (d, J=14.1 Hz, 1H), 2.07-1.97 (m, 1H), 1.95-1.80 (m, 3H), 1.76-1.50 (m, 6H), 1.36 (m, 1H), 1.25 (dd, J=15.5, 1.8 Hz, 1H), 1.24 (s, 3H), 0.78 (s, 3H). HRMS(ESI): m/z calc. for $C_{23}H_{33}O_6$ [M+H]$^+$: 405.2277. found: 405.2290.

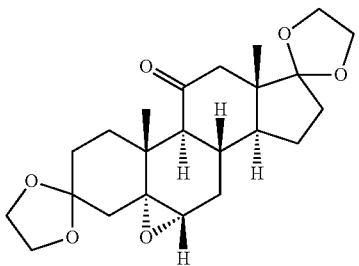

A5a

A5a: Prepared from A14.
Yield: 60.1 mg, 65%.
$^1$H NMR (CDCl$_3$, 500 MHz): δ 4.05-3.72 (m, 8H), 2.83 (d, J=4.3 Hz, 1H), 2.57-2.48 (m, 2H), 2.37 (d, J=14.1 Hz, 1H), 2.31 (m, 1H), 2.12-1.69 (m, 10H), 1.48 (td, J=13.8, 4.1 Hz, 1H), 1.27 (m, 1H), 1.22 (s, 3H), 1.16 (dd, J=14.1, 2.8 Hz, 1H), 0.73 (s, 3H). HRMS(ESI): m/z calc. for C$_{23}$H$_{33}$O$_6$ [M+H]$^+$: 405.2277. found: 405.2290.

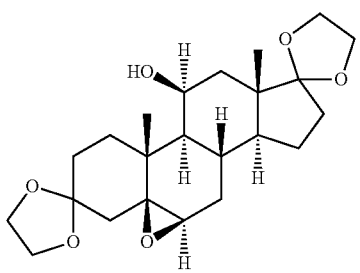

A15b

A15b: Prepared from A9a.
Yield: 12.5 mg, 18%.
$^1$H NMR (CDCl$_3$, 500 MHz): δ 4.26 (q, J=3.0 Hz, Hi), 3.98-3.78 (m, 8H), 3.07 (d, J=3.0 Hz, 1H), 2.36 (d, J=13.8 Hz, 1H), 2.21 (dt, J=14.7, 3.9 Hz, 1H), 2.02 (m, 1H), 1.91 (dq, J=11.0, 4.5 Hz, 1H), 1.84 (dt, J=13.0, 5.0 Hz, 1H), 1.78-1.51 (m, 8H), 1.46-1.06 (m, 3H), 1.41 (dd, J=15.0, 11.5 Hz, 1H), 1.29 (s, 3H), 1.08 (s, 3H), 0.89 (dd, J=11.6, 2.4 Hz, 1H). HRMS(ESI): m/z calc. for C$_{23}$H$_{35}$O$_6$ [M+H]$^+$: 407.2434. found: 407.2425.

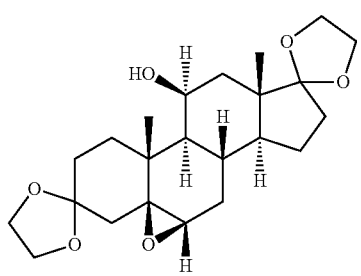

A5b

A5b: Prepared from A9a.
Yield: 52.0 mg, 73%.
$^1$H NMR (CDCl$_3$, 500 MHz): δ 4.28 (q, J=3.3 Hz, 1H), 4.04-3.74 (m, 8H), 2.77 (d, J=3.5, 1H), 2.42 (d, J=14.1 Hz, 1H), 2.05-1.94 (m, 2H), 1.92-1.64 (m, 10H), 1.61 (dd, J=12.0, 3.5 Hz, 1H), 1.49-1.38 (m, 2H), 1.33 (s, 3H), 1.33-1.22 (m, 1H), 1.17 (dd, J=14.1, 2.8 Hz, 1H), 1.03 (s, 3H).
HRMS(ESI): m/z calc. for C$_{23}$H$_{35}$O$_6$ [M+H]$^+$: 407.2434. found: 407.2432.

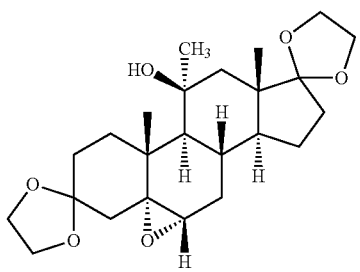

A5c

A5c: Prepared from A9b.
Yield: 34.3 mg, 45%.
$^1$H NMR (CDCl$_3$, 500 MHz): δ 4.05-3.78 (m, 8H), 2.76 (d, J=4.4 Hz, 1H), 2.40 (d, J=14.1 Hz, 1H), 2.19-2.10 (m, 1H), 2.04-1.67 (m, 9H), 1.65 (d, J=11.3 Hz, 1H), 1.54 (dd, J=15.4, 10.1 Hz, 1H), 1.42 (s, 3H), 1.42 (s, 3H), 1.36-1.18 (m, 3H), 1.14 (dd, J=14.1, 2.9 Hz, 1H), 1.00 (s, 3H).
HRMS(ESI): m/z calc. for C$_{24}$H$_{37}$O$_6$ [M+H]$^+$: 421.2590. found: 421.2586.

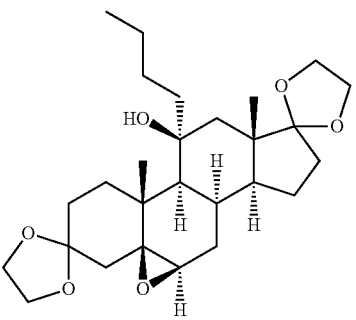

A15c

A15c: Prepared from A9c.
Yield: 16.4 mg, 21%.
$^1$H NMR (CDCl$_3$, 500 MHz): δ 3.98-3.76 (m, 8H), 3.06 (d, J=3.1 Hz, 1H), 2.42 (d, J=13.8 Hz, 1H), 2.16 (dt, J=14.6, 3.7 Hz, 1H), 2.09 (dt, J=12.8, 3.5 Hz, 1H), 2.06-1.92 (m, 2H), 1.76 (m, 3H), 1.71-1.53 (m, 6H), 1.47-1.36 (m, 2H), 1.40 (s, 3H), 1.35-1.16 (m, 6H), 1.12 (dd, J=13.9, 2.6 Hz, 1H), 1.05 (s, 3H), 0.98-0.87 (m, 3H).
HRMS(ESI): m/z calc. for C$_{27}$H$_{13}$O$_6$ [M+H]$^+$: 463.3060. found: 463.3065.

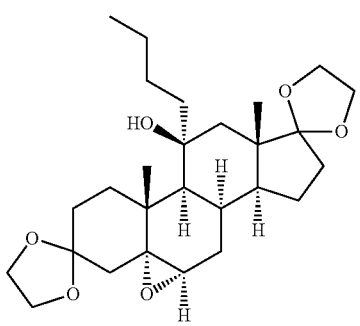

A5d

A5d: Prepared from A9c.

Yield: 49.0 mg, 62%.

¹H NMR (CDCl₃, 500 MHz): δ 4.03-3.93 (m, 2H), 3.93-3.76 (m, 6H), 2.74 (dd, J=4.7, 1.2 Hz, 11), 2.37 (dd, J=14.0, 1.2 Hz, 1H), 2.14 (dd, J=8.4, 2.9 Hz, 1H), 2.01-1.64 (m, 1H), 1.60 (ddd, J=13.6, 12.0, 5.1 Hz, 1H), 1.49 (dd, J=15.4, 10.6 Hz, 1H), 1.42 (s, 3H), 1.36 (m, 1H), 1.31-1.13 (m, 6H), 1.11 (dd, J=14.0, 2.5 Hz, 1H), 0.97 (s, 3H), 0.88 (t, J=7.0 Hz, 3H). HRMS(ESI): m/z calc. for C₂₇H₄₃O₆ [M+H]⁺: 463.3060. found: 463.3068.

A15d

A15d: Prepared from A9d.

Yield: 6.5 mg, 10%.

¹H NMR (CDCl₃, 500 MHz): δ 4.01-3.81 (m, 8H), 3.02 (m, 1H), 2.74 (d, J=14.9 Hz, 1H), 2.36-2.25 (m, 2H), 2.04 (dt, J=14.0, 2.5 Hz, 1H), 1.95-1.60 (m, 7H), 1.57 (d, J=9.0 Hz, 1H), 1.50 (m, 1H), 1.45 (s, 3H), 1.40 (ddd, J=14.0, 11.4, 1.3 Hz, 1H), 1.32 (d, J=14.3 Hz, 1H), 1.29-1.21 (m, 2H), 1.00 (s, 3H), 0.97 (s, 9H).

HRMS(ESI): m/z calc. for C₂₇H₄₃O₆ [M+11]⁺: 463.3060. found: 463.3071.

A5e

A5e: Prepared from A9d.

Yield: 59.5 mg, 89%.

¹H NMR (CDCl₃, 500 MHz): δ 4.03-3.78 (m, 8H), 2.90 (d, J=5.5 Hz, 1H), 2.70 (d, J=14.8 Hz, 1H), 2.41 (d, J=14.0 Hz, 1H), 2.25 (dt, J=12.1, 3.3 Hz, 1H), 2.02 (d, J=10.0 Hz, 1H), 2.01-1.85 (m, 5H), 1.85-1.70 (m, 3H), 1.66 (dt, J=7.8, 3.9 Hz, 1H), 1.52 (s, 3H), 1.44 (dd, J=13.5, 13.5 Hz, 1H), 1.33 (td, J=11.6, 7.5 Hz, 1H), 1.21 (m, 1H), 1.13 (dd, J=14.0, 2.0 Hz, 1H), 0.99 (s, 3H), 0.95 (s, 9H).

HRMS(ESI): m/z calc. for C₂₇H₄₃O₆ [M+H]⁺: 463.3060. found: 463.3066.

A15e

A15e: Prepared from A9e.

Yield: 13.2 mg, 16%.

¹H NMR (CDCl₃, 500 MHz): δ 7.70-6.98 (m, 4H), 3.96-3.60 (m, 8H), 3.05 (d, J=3.2 Hz, 1H), 2.31-2.20 (m, 2H), 2.20-2.10 (m, 2H), 2.10-1.96 (m, 1H), 1.88-1.68 (m, 3H), 1.68-1.47 (m, 3H), 1.39 (m, 1H), 1.35-1.07 (m, 3H), 1.30 (s, 9H), 1.22 (s, 3H), 1.15 (s, 3H) 1.05 (dd, J=14.0, 3.0 Hz, 1H) 0.86 (dt, J=13.5, 3.5 Hz, 1H).

HRMS(ESI): m/z calc. for C₃₃H₄₇O₆ [M+H]⁺: 539.3373. found: 539.3381.

A5f

A5f: Prepared from A9e.

Yield: 42.7 mg, 52%.

¹H NMR (CDCl₃, 500 MHz): δ 7.46-7.14 (m, 4H), 3.92-3.60 (m, 8H), 2.76 (d, J=3.8 Hz, 1H), 2.40-2.28 (m, 2H), 2.15-1.93 (m, 4H), 1.88-1.67 (m, 3H), 1.65-1.52 (m, 2H), 1.40 (s, 3H), 1.38-1.17 (m, 3H), 1.30 (s, 9H), 1.14-1.07 (m, 1H), 1.12 (s, 3H), 1.05 (dd, J=14.5, 3.0 Hz, 1H) 0.79 (td, J=14.0, 4.2 Hz, 1H). HRMS(ESI): m/z calc. for C₃₃H₄₇O₆ [M+H]⁺: 539.3373. found: 539.3375.

Example 5. Gibberellic Acid Derived Libraries: Synthesis and Characterization Synthesis of G16 Derivatives.

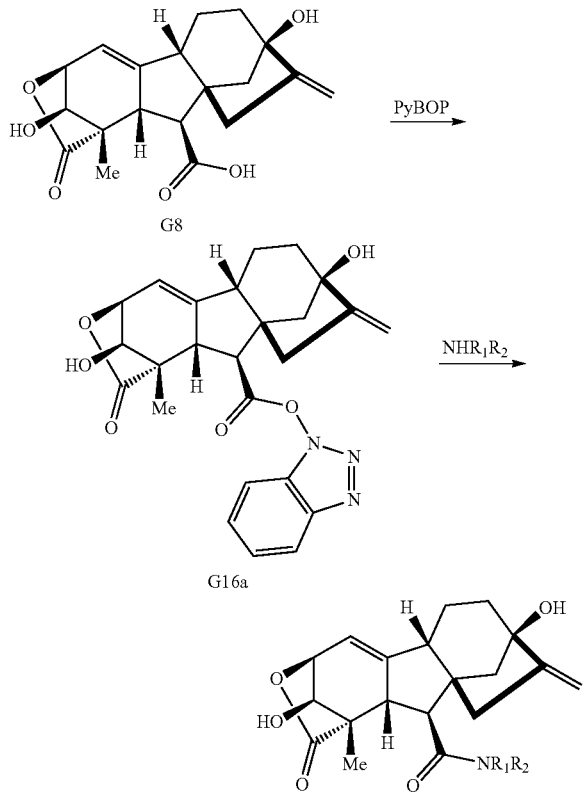

General Procedure for the Preparation of G16 Amides:

In an oven-dried vial, G8 (1 equiv.) and benzotriazol-1-yloxytripyrrolidinophosphonium hexafluorophosphate (1.2 equiv.) were dissolved in dichloromethane (0.1 M). Diisopropylethylamine (1 equiv.) was added, and the reaction was stirred at room temperature for 1-2 hours. After complete complexation by TLC, amine (1-3 equiv.) and additional diisopropylethylamine (1-3 equiv.) were added, and the reaction was allowed to stir at room temperature for 12-16 hours. The reaction was concentrated and purified by flash silica chromatography (hexanes/ethyl acetate) to provide the amide. (Note: G16a can be isolated and purified prior to the addition of amine.)

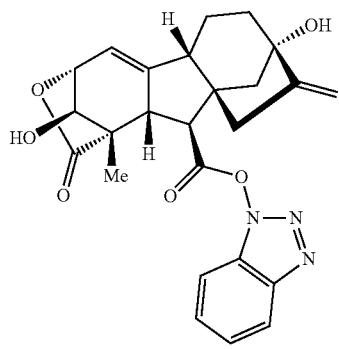

G16a: Prepared from G8.
Yield: N.A./aliquot purified for screening.
$^1$H NMR (d$_6$-acetone, 500 MHz): δ 8.10 (dt, J=8.5, 0.9 Hz, 1H), 7.73-7.66 (m, 2H), 7.54 (ddd, J=8.5, 6.5, 1.5 Hz, 1H), 5.95 (dt, J=5.0, 2.5 Hz, 1H), 5.21 (d, J=5.2 Hz, 1H), 5.17 (ddd, J=3.1, 1.9, 0.9 Hz, 1H), 5.07-5.05 (m, 1H), 4.80 (t, J=5.3 Hz, 1H), 4.41 (t, J=5.2 Hz, 1H), 4.05 (s, 1H), 3.41 (ddt, J=6.3, 2.6, 0.8 Hz, 1H), 3.07-3.00 (m, 2H), 2.67 (d, J=5.9 Hz, 1H), 2.56 (ddt, J=15.5, 2.5, 1.0 Hz, 1H), 2.03-1.98 (m, 1H), 1.81-1.72 (m, 2H), 1.64 (dd, J=10.9, 2.9 Hz, 1H), 1.58 (ddd, J=10.8, 2.7, 1.1 Hz, 1H), 1.54 (tt, J=4.2, 1.6 Hz, 1H), 1.39 (s, 3H).
HRMS(ESI): m/z calc. for C$_{25}$H$_{26}$N$_3$O$_6$ [M+H]$^+$: 464.1822. found: 464.1823.

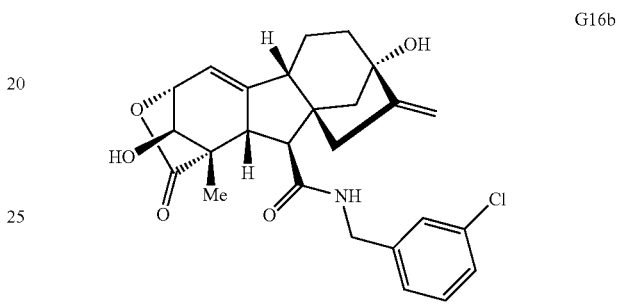

G16b: Prepared from 3-chlorobenzylamine.
Yield: 130.0 mg, 91%.
$^1$H NMR (CD$_3$OD, 500 MHz): δ 7.35 (t, J=1.8 Hz, 1H), 7.33-7.22 (m, 4H), 5.78 (dt, J=5.5, 2.0 Hz, 1H), 5.05 (t, J=2.5 Hz, 1H), 4.91 (t, J=1.9 Hz, 1H), 4.70 (t, J=5.3 Hz, 1H), 4.38 (d, J=15.0 Hz, 1H), 4.34 (d, J=15.0 Hz, 1H), 4.19 (d, J=5.3 Hz, 1H), 3.38-3.33 (m, 1H), 2.68 (d, J=6.0 Hz, 1H), 2.49 (dt, J=16.3, 3.0 Hz, 1H), 2.38 (d, J=6.0 Hz, 1H), 2.16 (ddt, J=16.0, 2.0, 1.0 Hz, 1H), 2.02-1.88 (m, 1H), 1.76-1.62 (m, 2H), 1.51-1.46 (m, 1H) 1.46 (dd, J=11.0, 3.0 Hz, 1H), 1.36 (dd, J=11.0, 2.5 Hz, 1H), 1.15 (s, 3H). HRMS(ESI): m/z calc. for C$_{26}$H$_{29}$NO$_5$Cl[M+H]$^+$: 470.1734. found: 470.1740.

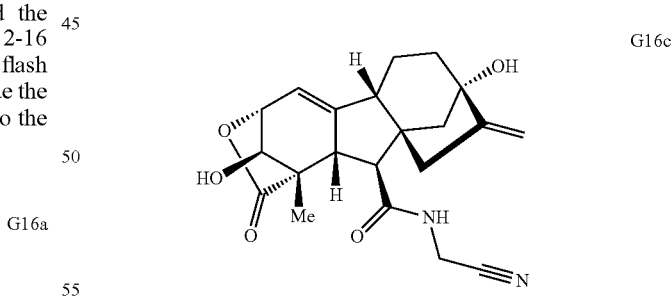

G16c: Prepared from aminoacetonitrile bisulfate.
Yield: 36.0 mg, 63%.
$^1$H NMR (d$_6$-acetone, 500 MHz): δ 8.20 (t, J=5.7 Hz, 1H), 5.76 (dt, J=4.9, 2.1 Hz, 1H), 5.05 (dt, J=3.0, 1.5 Hz, 1H), 4.96 (d, J=5.1 Hz, 1H), 4.89-4.86 (m, 1H), 4.68 (t, J=5.3 Hz, 1H), 4.28 (d, J=4.5 Hz, H), 4.27 (d, J=4.5, 1H), 4.26-4.22 (m, 1H), 3.84 (s, 1H), 3.37 (dd, J=5.9, 2.7 Hz, 1H), 2.64 (d, J=5.5 Hz, 1H), 2.58 (dt, J=16.4, 3.0 Hz, 1H), 2.33 (d, J=5.9 Hz, 1H), 2.21 (ddt, J=16.0, 2.5, 1.5 Hz, 1H), 1.96-1.88 (m, 1H), 1.73-1.60 (m, 2H), 1.48-1.41 (m, 1H), 1.43 (dd, J=10.9, 2.9 Hz, 1H), 1.31 (dd, J=10.0, 2.0 Hz, 1H), 1.09 (s, 3H).

HRMS(ESI): m/z calc. for $C_{21}H_{24}N_2O_5Na$ [M+Na]$^+$: 407.1583. found: 407.1594.

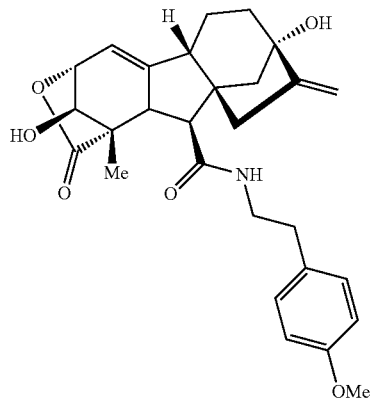
G16d

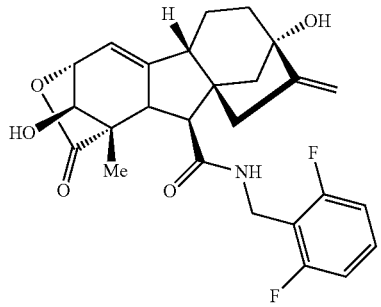
G16f

G16d: Prepared from 4-methoxyphenethylamine.
Yield: 70 mg, 92%.
$^1$H NMR (d$_6$-acetone, 500 MHz): δ 7.56 (t, J=5.7 Hz, 1H), 7.16 (d, J=8.6 Hz, 2H), 6.83 (d, J=8.6 Hz, 2H), 5.71 (dt, J=5.5, 2.0 Hz, 1H), 5.02 (p, J=1.0 Hz, 1H), 4.95 (d, J=5.2 Hz, 1H), 4.85-4.83 (m, 1H), 4.64 (t, J=5.3 Hz, 1H), 4.21 (t, J=5.0 Hz, 1H), 3.78 (s, 1H), 3.74 (s, 3H), 3.75-3.72 (m, 1H), 3.51-3.45 (m, 2H), 3.37 (dd, J=5.8, 2.7 Hz, 1H), 2.78 (t, J=7.2 Hz, 2H), 2.64 (d, J=7.0 Hz, 1H), 2.42 (dt, J=16.5, 2.9 Hz, 1H), 2.18 (d, J=5.8 Hz, 1H), 1.92-1.83 (m, 1H), 1.72-1.52 (m, 2H), 1.44-1.39 (m, 1H), 1.38 (dd, J=10.8, 2.9 Hz, 1H), 1.23 (dd, J=10.5, 2.0 Hz, 1H), 1.05 (s, 3H).
HRMS(ESI): m/z calc. for $C_{28}H_{34}NO_6$ [M+H]$^+$: 480.2386. found: 480.2381.

G16f: Prepared from 2,6-difluorobenzylamine.
Yield: 40.8 mg, 57%.
$^1$H NMR (d$_6$-acetone, 500 MHz): δ 7.87 (t, J=5.2 Hz, 1H), 7.42-7.30 (m, 1H), 7.04-6.94 (m, 2H), 5.71 (dt, J=5.5, 2.0 Hz, 1H), 5.01 (dt, J=m.0, 1.5 Hz, 1H), 4.92 (br s, 1H), 4.82-4.80 (m, 1H), 4.63 (t, J=5.3 Hz, 1H), 4.53 (ddt, J=14.0, 5.5, 1.0 Hz, 1H), 4.48 (ddt, J=12.0, 5.5, 1.5 Hz, 1H) 4.41 (s, 1H), 4.19 (d, J=5.4 Hz, 1H), 3.38 (dd, J=6.0, 2.5 Hz, 1H), 2.62 (d, J=7.5 Hz, 1H), 2.50 (dt, J=16.5, 2.9 Hz, 1H), 2.26 (d, J=5.8 Hz, 1H), 2.00-1.91 (m, 1H), 1.91-1.84 (m, 1H), 1.71-1.56 (m, 2H), 1.45-1.39 (m, 1H), 1.38 (dd, J=10.9, 2.9 Hz, 1H), 1.26 (dd, J=10.9, 2.8 Hz, 1H) 1.04 (s, 3H).
HRMS(ESI): m/z calc. for $C_{26}H_{28}NO_5F_2$ [M+H]$^+$: 472.1936. found: 472.1938.

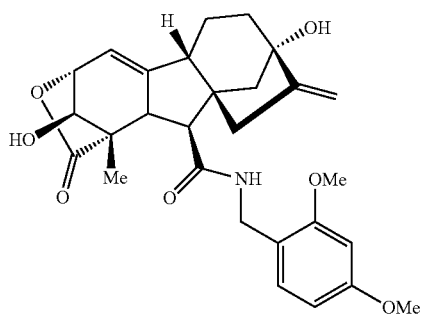
G16e

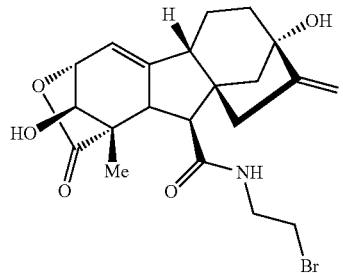
G16g

G16e: Prepared from 2,4-dimethoxybenzylamine.
Yield: 84.4 mg, 99%.
$^1$H NMR (d$_6$-acetone, 500 MHz): δ 7.71 (t, J=5.6 Hz, 1H), 7.18 (d, J=8.3 Hz, 1H), 6.52 (d, J=2.4 Hz, 1H), 6.45 (dd, J=8.3, 2.4 Hz, 1H), 5.71 (dt, J=5.5, 2.0 Hz, 1H), 5.02 (dt, J=2.5, 2.0 Hz, 1H), 4.96 (d, J=5.4 Hz, 1H), 4.87-4.79 (m, 1H), 4.64 (t, J=5.3 Hz, 1H), 4.32 (d, J=5.5 Hz, 2H), 4.20 (t, J=4.9 Hz, 1H), 3.81 (s, 3H), 3.79-3.77 (m, 1H), 3.77 (s, 3H), 3.40 (dd, J=5.8, 2.6 Hz, 1H), 2.64 (d, J=7.0 Hz, 1H), 2.53 (dt, J=16.6, 3.0 Hz, 1H), 2.29 (d, J=5.8 Hz, 1H), 2.14-2.11 (m, 1H), 1.88 (dd, J=13.5, 5.5 Hz, 1H), 1.71-1.55 (m, 2H), 1.45-1.40 (m, 1H), 1.38 (dd, J=10.9, 2.9 Hz, 1H), 1.29 (dd, J=11.1, 2.0 Hz, 1H), 1.08 (s, 3H).
HRMS(ESI): m/z calc. for $C_{28}H_{34}NO_7$ [M+H]$^+$: 496.2335. found: 496.2333.

G16g: Prepared from 2-bromoethylamine hydrobromide.
Yield: 40.2 mg, 58%.
$^1$H NMR (d$_6$-acetone, 500 MHz): δ 7.86 (t, J=5.0 Hz, 1H), 5.74 (dt, J=5.5, 3.0 Hz, 1H), 5.06-5.03 (m, 1H), 4.91 (d, J=5.6 Hz, 1H), 4.89-4.86 (m, 1H), 4.66 (t, J=5.3 Hz, 1H), 4.22 (t, J=5.4 Hz, 1H), 3.77 (s, 1H), 3.67-3.61 (m, 2H), 3.61-3.51 (m, 2H), 3.38 (dd, J=5.9, 2.8 Hz, 1H), 2.69-2.62 (m, 1H), 2.28 (d, J=5.8 Hz, 1H), 2.20 (ddt, J=16.5, 2.5, 2.0 Hz, 1H), 1.93-1.87 (m, 1H), 1.73-1.58 (m, 2H), 1.46-1.38 (m, 2H), 1.32-1.26 (m, 2H), 1.11 (s, 3H).
HRMS(ESI): m/z calc. for $C_{21}H_{27}NO_5Br$[M+H]$^+$: 452.1073. found: 452.1077.

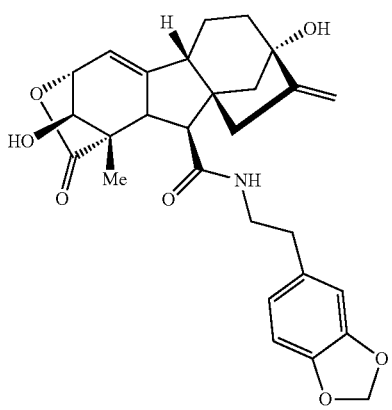

G16h

G16h: Prepared from 3,4-methylenedioxyphenethylamine.

Yield: 52.9 mg, 70%.

¹H NMR (d₆-acetone, 500 MHz): δ 7.53 (t, J=5.7 Hz, 1H), 6.78 (d, J=1.6 Hz, 1H), 6.76-6.68 (m, 2H), 5.92 (dd, J=1.5, 1.0 Hz, 2H), 5.71 (dt, J=5.9, 2.5 Hz, 1H), 5.02 (dt, J=2.5, 1.0 Hz, 1H), 4.95 (d, J=5.5 Hz, 1H), 4.86-4.84 (m, 1H), 4.64 (t, J=5.3 Hz, 1H), 4.20 (t, J=5.4 Hz, 1H), 3.77 (s, 1H), 3.52-3.42 (m, 2H), 3.37 (dd, J=5.8, 2.7 Hz, 1H), 2.78 (d, J=7.1, 1H), 2.76 (d, J=7.1 Hz, 1H), 2.63 (d, J=7.0 Hz, 1H), 2.42 (dt, J=16.6, 3.0 Hz, 1H), 2.17 (d, J=5.7 Hz, 1H), 2.11 (m, 1H), 1.90-1.85 (m, 1H), 1.71-1.53 (m, 2H), 1.45-1.39 (m, 1H), 1.38 (dd, J=10.9, 2.9 Hz, 1H), 1.22 (dd, J=10.9, 2.8 Hz, 1H), 1.05 (s, 3H).

HRMS(ESI): m/z calc. for C₂₈H₃₂NO₇ [M+H]⁺: 494.2179. found: 494.2177.

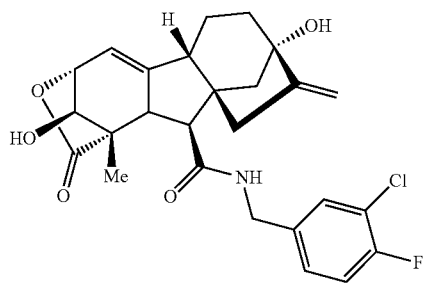

G16i

G16i: Prepared from 3-chloro-4-fluorobenzylamine.

Yield: 47.6 mg, 65%.

¹H NMR (d₆-acetone, 500 MHz): δ 8.09 (t, J=6.1 Hz, 1H), 7.50 (dd, J=7.2, 2.2 Hz, 1H), 7.35 (ddd, J=8.4, 4.6, 2.2 Hz, 1H), 7.26 (dd, J=9.3, 8.5 Hz, 1H), 5.74 (dt, J=5.2, 2.1 Hz, 1H), 5.03 (dt, J=2.5, 2.0 Hz, 1H), 4.93 (d, J=5.5 Hz, 1H), 4.85-4.83 (m, 1H), 4.66 (t, J=5.3 Hz, 1H), 4.46 (dd, J=14.5, 6.0 Hz, 1H), 4.40 (dd, J=15.0, 6.0 Hz, 1H), 4.23 (t, J=5.4 Hz, 1H), 3.39 (dd, J=5.8, 2.7 Hz, 1H), 2.95 (s, 1H), 2.65 (d, J 6.5 Hz, 1H), 2.51 (dt, J=16.4, 3.0 Hz, 1H), 2.29 (d, J=5.8 Hz, 1H), 2.19-2.12 (m, 1H), 1.15 (ddt, J=16.5, 2.5, 1.5 Hz, 1H), 1.72-1.58 (m, 2H), 1.46-1.43 (m, 1H), 1.41 (dd, J=10.8, 3.0 Hz, 1H), 1.28 (dd, J=10.9, 2.8 Hz, 1H), 1.09 (s, 3H).
HRMS(ESI): m/z calc. for C₂₆H₂₈NO₅ClF [M+H]⁺: 488.1640. found: 488.1640.

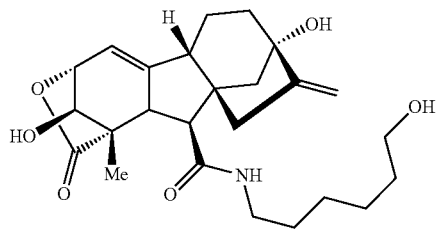

G16j

G16j: Prepared from 6-amino-1-hexanol.

Yield: 42.6 mg, 62%.

¹H NMR (d₆-acetone, 500 MHz): δ 7.55 (t, J=5.7 Hz, 1H), 5.72 (dt, J=5.2, 2.1 Hz, 1H), 5.04 (dt, J=2.0, 1.0 Hz, 1H), 4.96 (d, J=5.5 Hz, 1H), 4.89-4.86 (m, 1H), 4.65 (t, J=5.3 Hz, 1H), 4.22 (t, J=5.4 Hz, 1H), 3.81 (s, 1H), 3.55-3.47 (m, 3H), 3.38 (dd, J=5.8, 2.7 Hz, 1H), 3.24 (td, J=6.9, 5.7 Hz, 2H), 2.97 (s, 1H), 2.66 (d, J=4.0 Hz, 1H), 2.57 (dt, J=16.4, 3.0 Hz, 1H), 2.24-2.18 (m, 2H), 1.91-1.86 (m, 1H), 1.72-1.57 (m, 2H), 1.56-1.47 (m, 4H), 1.46-1.40 (m, 1H), 1.40-1.34 (m, 4H), 1.28 (dd, J=10.9, 2.8 Hz, 1H), 1.09 (s, 3H).

HRMS(ESI): m/z calc. for C₂₅H₃₆NO₆ [M+H]⁺: 446.2543. found: 446.3536.

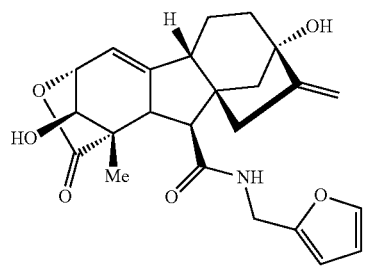

G16k

G16k: Prepared from furfurylamine.

Yield: 52.9 mg, 83%.

¹H NMR (d₆-acetone, 500 MHz): δ 7.94 (t, J=5.7 Hz, 1H), 7.46 (dd, J=1.9, 0.9 Hz, 1H), 6.36 (dd, J=3.2, 1.9 Hz, 1H), 6.27-6.25 (m, 1H), 5.74 (dt, J=5.9, 2.5 Hz, 1H), 5.03 (dt, J=3.0, 1.5 Hz, 1H), 4.94 (d, J=5.5 Hz, 1H), 4.86-4.83 (m, 1H), 4.66 (t, J=5.3 Hz, 1H), 4.45 (dd, J=15.5, 5.5 Hz, 1H), 4.41 (dd, J=15.5, 5.5 Hz, 1H), 4.23 (t, J=5.4 Hz, 1H), 3.79 (s, 1H), 3.41 (dd, J=5.8, 2.7 Hz, 1H), 2.65 (d, J=6.5 Hz, 1H), 2.53 (dt, J=16.5, 3.0 Hz, 1H), 2.31 (d, J=5.8 Hz, 1H), 2.14 (ddt, J=16.5, 2.5, 1.5 Hz, 1H), 1.93-1.87 (m, 1H), 1.73-1.57 (m, 2H), 1.47-1.43 (m, 1H), 1.41 (dd, J=11.0, 2.5 Hz, 1H), 1.30 (dd, J=11.0, 2.5 Hz, 1H), 1.09 (s, 3H).

HRMS(ESI): m/z calc. for C₂₄H₂₈NO₆ [M+H]⁺: 426.1917. found: 426.1913.

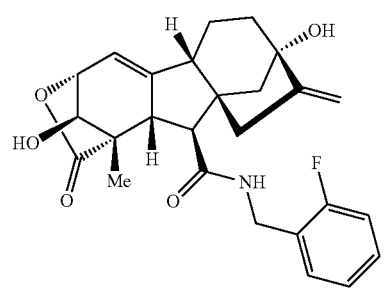

G16l

G16l: Prepared from 2-fluorobenzylamine.

Yield: 21.0 mg, 60%.

$^1$H NMR (d$_6$-acetone, 500 MHz): δ 8.00-7.93 (m, 1H), 7.45 (td, J=7.7, 1.7 Hz, 1H), 7.34-7.27 (m, 1H), 7.15 (t, J=7.5 Hz, 1H), 7.09 (t, J=8.5 Hz, 1H), 5.74-5.71 (m, 1H), 5.02 (dt, J=3.3, 1.6 Hz, 1H), 4.94-4.88 (m, 1H), 4.83-4.80 (m, 1H), 4.65 (t, J=5.3 Hz, 1H), 4.51 (dd, J=15.0, 6.0 Hz, 1H), 4.45 (dd, J=15.0, 5.5 Hz, 1H), 4.21 (t, J=5.0 Hz, 1H), 3.78-3.74 (m, 1H), 3.40 (dd, J=6.0, 2.6 Hz, 1H), 2.90-2.80 (m, 1H), 2.64 (d, J=5.5 Hz, 1H), 2.52 (dt, J=16.5, 3.0 Hz, 1H), 2.31 (d, J=5.8 Hz, 1H), 2.11 (ddt, J=16.5, 3.0, 1.5 Hz, 1H), 1.93-1.86 (m, 1H), 1.72-1.56 (m, 2H), 1.45-1.41 (m, 1H), 1.40 (dd, J=11.0, 2.5 Hz, 1H), 1.28 (dd, J=10.8, 2.6 Hz, 1H), 1.08 (s, 3H). HRMS(ESI): m/z calc. for C$_{26}$H$_{29}$NO$_5$F [M+H]$^+$: 454.2030. found: 454.2034.

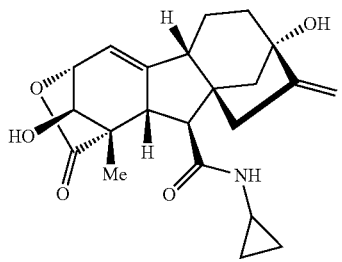

G16m: Prepared from cyclopropylamine.

Yield: 19.3 mg, 66%.

$^1$H NMR (d$_6$-acetone, 500 MHz): δ 7.56 (d, J=2.5 Hz, 1H), 5.72 (dt, J=5.0, 2.0 Hz, 1H), 5.04 (ddd, J=3.3, 2.0, 1.2 Hz, 1H), 4.92 (d, J=5.6 Hz, 1H), 4.89-4.87 (m, 1H), 4.65 (t, J=5.3 Hz, 1H), 4.21 (t, J=5.5 Hz, 1H), 3.76 (s, 1H), 3.38 (dd, J=5.5, 2.5 Hz, 1H), 2.79-2.73 (m, 1H), 2.64 (d, J=6.0 Hz, 1H), 2.53 (dt, J=16.4, 3.0 Hz, 1H), 2.20 (ddt, J=16.5, 2.5, 2.0 Hz, 1H), 2.14 (d, J=5.8 Hz, 1H), 1.92-1.85 (m, 1H), 1.71-1.58 (m, 2H), 1.46-1.40 (m, 1H), 1.39 (dd, J=10.8, 2.9 Hz, 1H), 1.24 (dd, J=10.9, 2.9 Hz, 1H), 1.07 (s, 3H), 0.71-0.64 (m, 2H), 0.53-0.44 (m, 2H). HRMS(ESI): m/z calc. for C$_{22}$H$_{28}$NO$_5$ [M+H]$^+$: 386.1967. found: 386.1961.

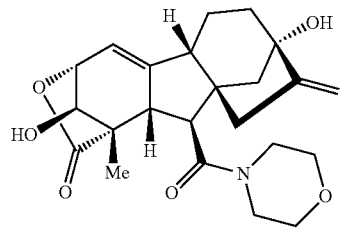

G16n: Prepared from morpholine.

Yield: 23.9 mg, 75%.

$^1$H NMR (CD$_3$OD, 500 MHz): δ 5.80 (dt, J=5.0, 2.5 Hz, 1H), 5.11-5.07 (m, 1H), 5.00-4.96 (m, 1H), 4.72 (t, J=5.3 Hz, 1H), 4.20 (d, J=5.3 Hz, 1H), 3.76-3.55 (m, 8H), 3.45 (dd, J=6.5, 2.6 Hz, 1H), 2.84 (d, J=6.5 Hz, 1H), 2.68 (d, J=3.0 Hz, 1H), 2.42 (dt, J=16.0, 2.5 Hz, 1H), 2.24 (ddt, J=16.0, 2.5, 2.0 Hz, 1H), 1.98-1.92 (m, 1H), 1.78-1.66 (m, 2H), 1.54-1.48 (m, 2H), 1.40 (dd, J=11.0, 1.5 Hz, 1H), 1.38-1.34 (m, 2H), 1.10 (s, 3H).

HRMS(ESI): m/z calc. for C$_{23}$H$_{30}$NO$_6$ [M+H]$^+$: 416.2073. found: 416.2067.

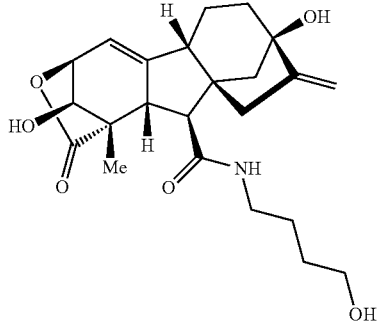

G16o: Prepared from 4-amino-1-butanol.

Yield; 19.4 mg, 61%.

$^1$H NMR (4-acetone, 500 MHz): δ 7.53 (t, J=5.7 Hz, 1H), 5.72 (dt, J=5.5, 3.0 Hz, 1H), 5.04 (ddd, J=3.3, 2.0, 1.2 Hz, 1H), 4.93 (d, J=5.4 Hz, 1H), 4.88-4.86 (m, 1H), 4.65 (t, J=5.3 Hz, 1H), 4.22 (t, J=5.2 Hz, 1H), 3.78 (s, 1H), 3.59-3.50 (m, 2H), 3.39 (dd, J=5.8, 2.7 Hz, 1H), 3.30-3.20 (m, 2H), 2.66 (d, J=6.6 Hz, 1H), 2.57 (dt, J=16.4, 3.0 Hz, 1H), 2.30-2.17 (m, 2H), 1.92-1.86 (m, 1H), 1.72-1.51 (m, 7H), 1.46-1.42 (m, 1H), 1.41 (dd, J=10.9, 2.9 Hz, 1H), 1.28 (dd, J=10.9, 2.8, Hz, 1H), 1.09 (s, 3H).

HRMS(ESI): m/z calc. for C$_{23}$H$_{32}$NO$_6$ [M+H]$^+$: 418.2230. found: 418.2238.

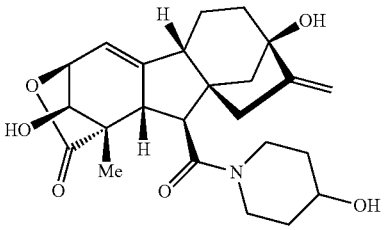

G16p: Prepared from 4-hydroxypiperidine.

Yield: 15.5 mg, 47%.

$^1$H NMR (4-DMSO, 500 MHz): δ 5.87 (t, J=5.0 Hz, 1H), 5.70 (dt, J=5.1, 2.4 Hz, 1H), 5.01-4.97 (m, 1H), 4.87 (d, J=14.5 Hz, 1H), 4.83-4.80 (m, 2H), 4.67 (t, J=5.0 Hz, 1H), 4.10 (q, J=5.0 Hz, 1H), 3.94-3.64 (m, 3H), 3.36-3.24 (m, 2H), 3.18 (ddd, J=13.2, 9.2, 3.1 Hz, 1H), 2.91 (ddd, J=13.4, 10.8, 3.1 Hz, 1H), 2.68 (t, J=7.0 Hz, 1H), 2.27 (ddt, J=24.5, 16.5, 2.5 Hz, 1H), 2.08 (s, 1H), 1.87-1.64 (m, 3H), 1.61-1.44 (m, 2H), 1.39-1.10 (m, 5H), 0.96 (d, J=13.7 Hz, 3H). Note: The doublet at 0.96 ppm gave partial coalescence at 95° C. Higher temperatures were not attempted. HRMS(ESI): m/z calc. for C$_{24}$H$_{32}$NO$_6$ [M+H]$^+$: 430.2230. found: 430.2233.

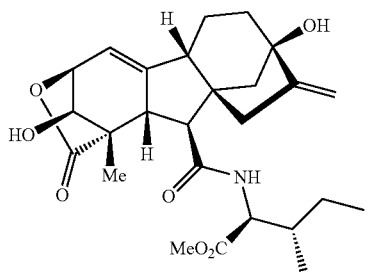

G16q

G16q: Prepared from L-isoleucine methyl ester hydrochloride.

Yield: 36.7 mg, 25%.

$^1$H NMR (CDCl$_3$, 500 MHz): δ 6.75 (d, J=8.7 Hz, 1H), 5.76 (dt, J=5.0, 2.2 Hz, 1H), 5.08 (t, J=2.5 Hz, 1H), 4.94 (t, J=2.0 Hz, 1H), 4.76 (t, J=5.3 Hz, 1H), 4.56 (dd, J=8.7, 5.3 Hz, 1H), 4.23 (d, J=5.4 Hz, 1H), 3.74 (s, 3H), 3.32 (dd, J=5.8, 2.6 Hz, 1H), 2.79 (br s, 1H), 2.73 (d, J=6.7 Hz, 1H), 2.59 (dt, J=16.6, 3.0 Hz, 1H), 2.40 (d, J=5.8 Hz, 1H), 2.23 (ddt, J=17.0, 3.0, 2.0 Hz, 1H), 1.96-1.86 (m, 2H), 1.78-1.63 (m, 2H), 1.57-1.50 (m, 1H), 1.51 (dd, J=10.8, 2.8 Hz, 1H), 1.46-1.35 (m, 2H), 1.27-1.11 (m, 2H), 1.20 (s, 3H), 0.90 (t, J=7.0 Hz, 3H), 0.89 (d, J=6.5, 3H). HRMS(ESI): m/z calc. for C$_{26}$H$_{36}$NO$_7$ [M+H]$^+$: 474.2492. found: 474.2499.

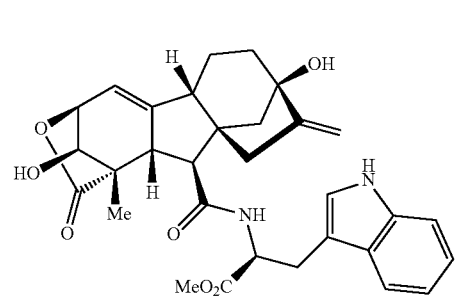

G16r

G16r: Prepared from L-tryptophan methyl ester hydrochloride.

Yield: 60.6 mg, 33%.

$^1$H NMR (CDCl$_3$, 500 MHz): δ 8.64 (br s, 1H), 7.53 (d, J=7.9 Hz, 1H), 7.30 (d, J=8.0 Hz, 1H), 7.16 (t, J=8.0 Hz, 1H), 7.09 (t, J=7.0, 2H), 6.98 (d, J=2.3 Hz, 1H), 5.69 (dt, J=5.2, 2.1 Hz, 1H), 5.04 (t, J=2.4 Hz, 1H), 4.97-4.90 (m, 1H), 4.90 (s, 1H), 4.66 (t, J=5.3 Hz, 1H), 4.02 (d, J=5.4 Hz, 1H), 3.70 (s, 3H), 3.31 (dd, J=15.0, 4.5 Hz, 1H) 3.28-3.19 (m, 2H), 2.68-2.59 (m, 2H), 2.26 (d, J=5.7 Hz, 1H), 2.18 (d, J=17.0 Hz, 1H), 1.85 (d, J=9.1 Hz, 1H), 1.69-1.56 (m, 2H), 1.53-1.50 (m, 1H), 1.42-1.39 (m, 2H), 0.84 (s, 3H).

HRMS(ESI): m/z calc. for C$_{31}$H$_{35}$N$_2$O$_7$ [M+H]$^+$: 547.2444. found: 547.2438.

Synthesis of G10 Derivatives.

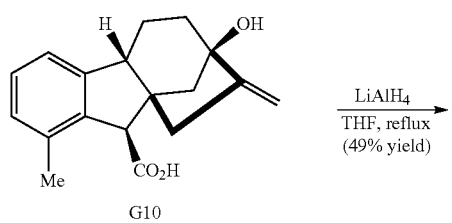

G10

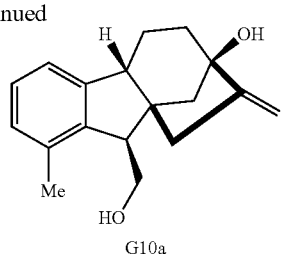

G10a

Procedure: In an oven-dried round bottom flask with a stir bar under nitrogen, loaded G10 (39.7 mg, 0.140 mmol) and dissolved in tetrahydrofuran (2.0 mL). Added lithium aluminum hydride (103.7 mg, 2.73 mmol) and refluxed for 16 hours. The reaction was cooled to 0° C. and quenched with water (0.12 mL), followed by 15% aqueous sodium hydroxide (0.12 mL) and additional water (3.0 mL). The mixture stirred for 15 minutes, at which point anhydrous magnesium sulfate was added. After an additional 15 minutes of stirring, the solids were filtered and washed thoroughly with ethyl acetate. The aqueous layer was extracted with ethyl acetate (3×). The combined organic layers were washed with brine, dried over magnesium sulfate, filtered, and concentrated under reduced pressure. The residue was purified by flash chromatography on silica gel (1:4 hexanes/ethyl acetate) to yield the product as a white solid (18.4 mg, 49%).

$^1$H NMR (CDCl$_3$, 500 MHz): δ 7.09 (t, J=7.5 Hz, 1H), 6.95 (d, J=8.5 Hz, 1H), 6.94 (d, J=8.0 Hz, 1H), 5.02 (t, J=2.6 Hz, 1H), 4.79 (t, J=2.2 Hz, 1H), 4.33 (dd, J=11.1, 4.4 Hz, 1H), 4.06 (dd, J=11.1, 7.3 Hz, 1H), 3.26 (dd, J=7.5, 4.5 Hz, 1H), 2.71 (dd, J=12.6, 5.0 Hz, 1H), 2.47 (dt, J=17.0, 3.0 Hz, 1H), 2.39 (s, 3H), 2.32 (dd, J=10.1, 2.5 Hz, 1H), 2.22 (dtd, J=13.1, 5.1, 1.7 Hz, 1H), 2.16-2.06 (m, 2H), 2.00-1.91 (m, 2H), 1.84 (dd, J=10.1, 2.6 Hz, 1H), 1.73 (ddt, J=11.7, 5.1, 2.0 Hz, 1H), 1.55 (qd, J=12.7, 5.3 Hz, 1H). HRMS(ESI): m/z calc. for C$_{18}$H$_{23}$O$_2$ [M+H]$^+$: 271.1698. found: 271.1704.

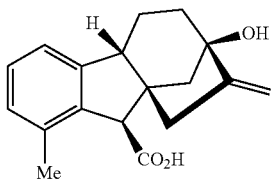

a.) DPPA
b.) BnOH
(34% yield)

G10

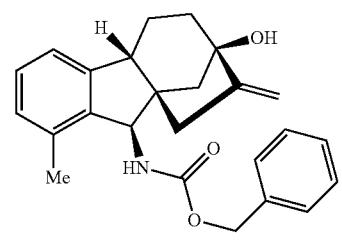

G10b

Procedure: In an oven-dried round bottom flask with a stir bar under nitrogen, loaded G10 (321.0 mg, 1.13 mmol) and dissolved in benzene (11 mL). Added triethylamine (170 μL, 1.22 mmol) and diphenylphosphoryl azide (250 μL, 1.21 mmol) and refluxed. When G10 had fully dissolved, benzyl alcohol (240 μL, 2.32 mmol) was added and the reaction refluxed for 14 hours. The reaction was cooled to room temperature, quenched with water (10 mL), extracted with ethyl acetate (3×), washed with brine, dried over magnesium sulfate, filtered, and concentrated under reduced pressure. The residue was purified by flash chromatography on silica gel (9:1 to 1:9 hexanes/ethyl acetate) to yield the product as a white solid (151.2 mg, 34%).

¹H NMR (CDCl₃, 500 MHz): δ 7.41-7.30 (m, 5H), 7.11 (t, J=7.4 Hz, 1H), 6.97-6.91 (m, 2H), 5.31 (d, J=10.3 Hz, 1H), 5.21 (d, J=12.1 Hz, 1H), 5.13 (d, J=12.2 Hz, 1H), 5.04 (t, J=2.5 Hz, 1H), 4.97 (d, J=10.3 Hz, 1H), 4.79 (t, J=2.1 Hz, 1H), 2.75 (dd, J=12.5, 5.2 Hz, 1H), 2.34-2.19 (m, 2H), 2.27 (s, 3H), 2.06 (dd, J=10.5, 2.5 Hz, 1H), 1.95 (td, J=12.0, 5.0 Hz, Hi), 1.90-1.84 (m, 2H), 1.77-1.68 (m, 2H), 1.55 (qd, J=12.8, 5.2 Hz, 1H). HRMS(ESI): m/z calc. for $C_{25}H_{28}NO_3$ [M+H]⁺: 390.2069. found: 390.2063.

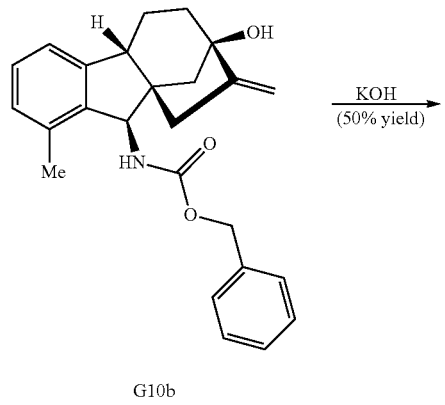

G10b

Procedure: In a round bottom flask with a stir bar, dissolved G10 (41.5 mg, 0.107 mmol) and potassium hydroxide (237.3 mg, 4.23 mmol) in methanol (2 mL) and water (2 mL). The reaction was refluxed for 24 hours, and then the reaction was cooled to room temperature, extracted with dichloromethane (3×), washed with brine, dried over magnesium sulfate, and concentrated under reduced pressure. The residue was purified by flash chromatography on silica gel (98:1:1 to 97:2:1 dichloromethane/methanol/triethylamine) to yield the product as a white solid (13.6 mg, 50%).

¹H NMR (CDCl₃, 500 MHz): δ 7.08 (t, J=7.4 Hz, 1H), 6.95 (d, J=8.0 Hz, 1H), 6.92 (d, J=7.0 Hz, 1H), 5.02 (t, J=2.6 Hz, 1H), 4.79 (t, J=2.2 Hz, 1H), 4.29 (s, 1H), 2.66 (dd, J=12.3, 4.9 Hz, 1H), 2.49 (s, 3H), 2.40 (dt, J=17.0, 2.9 Hz, 1H), 2.25 (dtd, J=13.1, 5.2, 1.7 Hz, 1H), 2.09 (dd, J=10.3, 2.3 Hz, 1H), 1.97 (td, J=12.2, 5.2 Hz, 1H), 1.80 (q, J=2.0 Hz, 1H), 1.77 (q, J=2.4 Hz, 1H), 1.74 (q, J=2.5 Hz, 1H), 1.72 (q, J=2.5 Hz, 1H), 1.56 (qd, J=12.7, 5.3 Hz, 1H). HRMS(ESI): m/z calc. for $C_{17}H_{22}NO$ [M+H]⁺: 256.1701. found: 256.1712.

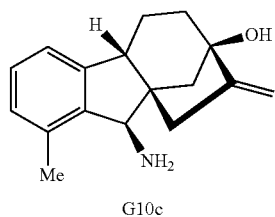

Procedure: In an oven-dried vial with a stir bar under N₂, G10c (10.5 mg, 0.0411 mmol) and benzaldehyde (8.0 μL, 1.76 mmol) were dissolved in methanol (0.5 mL) and stirred at room temperature for 20 minutes. Sodium cyanoborohydride (14.1 mg, 5.45 mmol) was added and the reaction continued to stir for 8 hours. The reaction was quenched with aqueous saturated sodium bicarbonate, extracted with dichloromethane (3×), dried over magnesium sulfate, filtered, and concentrated under reduced pressure. The resulting residue was purified by flash chromatography on silica gel (196:3 to 97:3 dichloromethane/ethyl acetate) to yield a white solid (4.1 mg, 29%).

¹H NMR (CDCl₃, 500 MHz): δ 7.45-7.41 (m, 2H), 7.38-7.32 (m, 2H), 7.29-7.24 (m, 1H), 7.07 (t, J=7.5 Hz, 1H), 6.95 (d, J=7.5 Hz, 1H), 6.90 (d, J=7.3 Hz, 1H), 5.04 (t, J=2.6 Hz, 1H), 4.83 (t, J=1.0 Hz, 1H), 4.24 (s, 1H), 4.12 (d, J=13.1 Hz, 1H), 4.07 (d, J=13.1 Hz, 1H), 2.64 (dd, J=12.5, 5.1 Hz, 1H), 2.57 (t, J=2.9 Hz, 1H), 2.53 (s, 3H), 2.25 (dtd, J=13.0, 5.5, 1.5 Hz, 1H) 2.21 (dd, J=10.0, 2.0 Hz, 1H), 1.95 (td, J=12.2, 5.2 Hz, 1H), 1.89-1.82 (m, 2H), 1.75-1.67 (m, 2H), 1.57 (td, J=12.8, 5.3 Hz, 1H). HRMS(ESI): m/z calc. for $C_{24}H_{28}NO$ [M+H]⁺: 346.2171. found: 346.2169.

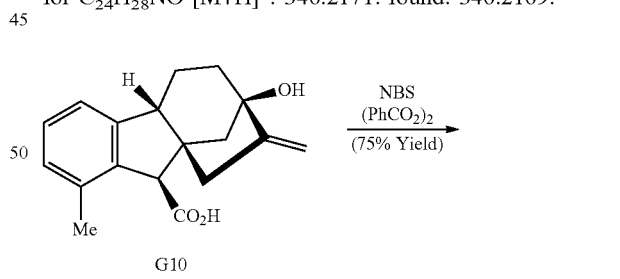

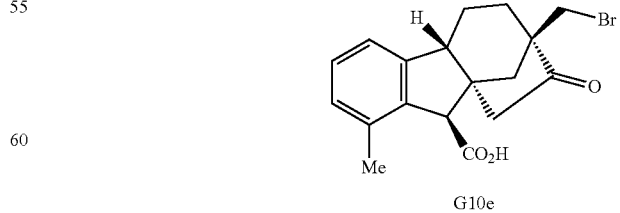

Procedure: In an oven-dried 7 mL vial with stir bar, G10 (20.7 mg, 0.073 mmol), N-bromosuccinamide (15.8 mg, 0.089 mmol), and benzoyl peroxide (0.1 mg, 0.0004 mmol)

were dissolved in carbon tetrachloride (0.5 mL). The reaction was heated at 67° C. for 24 hours, after which the reaction was concentrated and purified directly using flash silica chromatography (3:1 hexanes/ethyl acetate to ethyl acetate) to afford G10e as a white solid (19.8 mg, 75%).

$^1$H NMR (CDCl$_3$, 500 MHz): δ 7.23 (t, J=7.5 Hz, 1H), 7.09 (d, J=7.5 Hz, 1H), 6.99 (d, J=7.5 Hz, 1H), 4.25 (s, 1H), 3.57 (d, J=10.4 Hz, 1H), 3.35 (d, J=10.4 Hz, 1H), 3.06 (t, J=7.8 Hz, 1H), 2.76 (d, J=17.8 Hz, 1H), 2.57 (dd, J=17.8, 3.5 Hz, 1H), 2.27 (s, 3H), 2.18 (td, J=7.0, 3.4 Hz, 1H), 2.14 (dd, J=12.2, 3.5 Hz, 1H), 1.93-1.81 (m, 3H), 1.81-1.72 (m, 1H). HRMS(ESI): m/z calc. for C$_{18}$H$_{20}$O$_3$Br [M+H]$^+$: 363.0596. found: 363.0586.

Synthesis of G19 Derivatives.

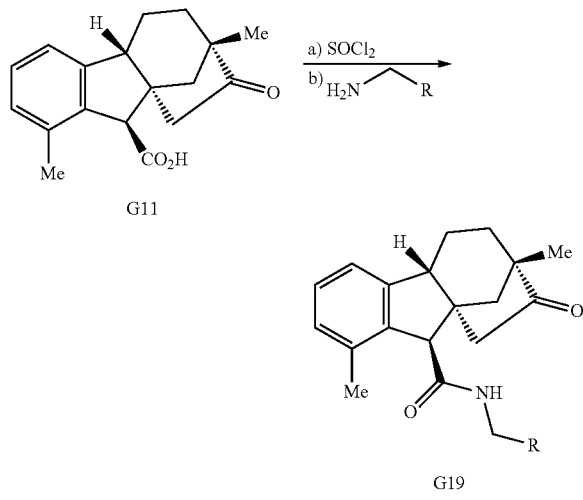

General procedure for the preparation of amides from G11: In an oven-dried round bottom flask with stir bar, G11 (1 equiv.) was dissolved in tetrahydrofuran (0.05 M). Thionyl chloride (1.2 equiv.) was added, and the reaction was refluxed for 30 minutes. The reaction was then cooled in an ice bath, at which point triethylamine (2.2 equiv.) and amine (1.5 equiv.) were added and the reaction was allowed to warm to room temperature for 1 hour. The reaction was quenched with water, extracted with ethyl acetate (3×), and purified by flash silica chromatography (hexanes/ethyl acetate) to provide the amide.

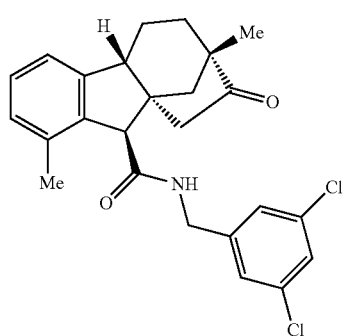

G19a: Prepared from 3,5-dichlorobenzylamine.
Yield: 26.6 mg, 35%.

$^1$H NMR (CDCl$_3$, 500 MHz): δ 7.27 (t, J=1.9 Hz, 1H), 7.22 (t, J=7.6 Hz, 1H), 7.20 (s, 1H), 7.19 (s, 1H), 7.07 (d, J=7.5 Hz, 1H), 7.01 (d, J=7.6 Hz, 1H), 5.90 (br s, 1H), 4.49 (dd, J=14.9, 6.4 Hz, 1H), 4.36 (dd, J=14.9, 6.0 Hz, 1H), 4.07 (s, 1H), 2.95 (t, J=8.5 Hz, 1H), 2.70 (d, J=15.1 Hz, 1H), 2.44 (dd, J=17.6, 3.7 Hz, 1H), 2.17 (s, 3H), 2.10 (tt, J=7.3, 3.5 Hz, 1H), 1.89 (dd, J=11.9, 3.5 Hz, 1H), 1.83-1.72 (m, 2H), 1.63 (dt, J=6.4, 3.3 Hz, 1H), 1.38 (d, J=11.5 Hz, 1H), 1.04 (s, 3H).

HRMS(ESI): m/z calc. for C$_{25}$H$_{26}$NO$_2$Cl$_2$ [M+H]$^+$: 442.1341. found: 442.1342.

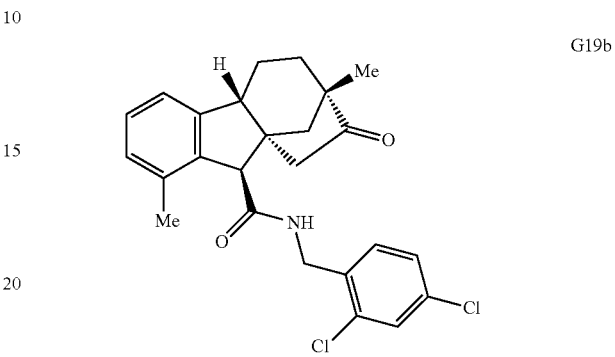

G19b: Prepared from 2,4-dichlorobenzylamine.
Yield: 202.9 mg, 73%.

$^1$H NMR (CDCl$_3$, 500 MHz): δ 7.46 (d, J=8.2 Hz, 1H), 7.37 (d, J=2.1 Hz, 1H), 7.23 (dd, J=8.2, 2.1 Hz, 1H) 7.21 (t, J=7.5 Hz, 1H), 7.05 (d, J=7.6 Hz, 1H), 6.99 (d, J=7.5 Hz, 1H), 5.98 (s, 1H), 4.51 (dd, J=14.8, 6.2 Hz, 1H), 4.48 (dd, J=14.8, 6.2 Hz, 1H), 3.99 (s, 1H), 2.92 (t, J=8.0 Hz, 1H), 2.65 (d, J=17.7 Hz, 1H), 2.42 (dd, J=17.6, 3.7 Hz, 1H), 2.12-2.06 (m, 1H), 2.08 (s, 3H), 1.85-1.69 (m, 3H), 1.64-1.54 (m, 1H), 1.17 (d, J=12.0 Hz, 1H), 0.96 (s, 3H).

HRMS(ESI): m/z calc. for C$_{25}$H$_{26}$NO$_2$Cl$_2$ [M+H]$^+$: 442.1341. found: 442.1350.

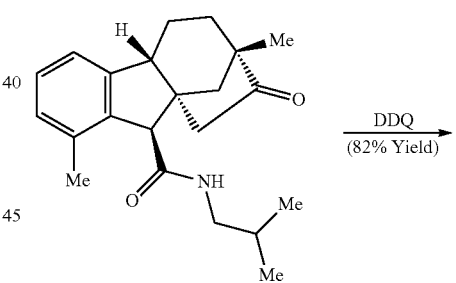

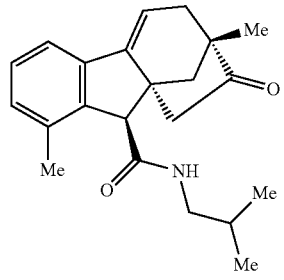

Procedure: In an oven-dried vial with stir bar, G19 (15.3 mg, 0.048 mmol) and 2,3-dichloro-5,6-dicyanobenzoquinone (12.2 mg, 0.054 mmol) were dissolved in toluene (0.5 mL) and refluxed for 20 hours. The reaction was then diluted with ethyl acetate, washed with saturated aqueous ammonium chloride (2×) and water (2×), and concentrated. Purification by flash silica chromatography (4:1 hexanes/ethyl acetate) afforded G19c as a white solid (12.4 mg, 82%).

$^1$H NMR (CDCl$_3$, 500 MHz): δ 7.32 (d, J=7.7 Hz, 1H), 7.26 (t, J=7.5 Hz, 1H), 7.13 (d, J=7.4 Hz, 1H), 5.97 (t, J=3.6 Hz, 1H), 4.96 (t, J=6.1 Hz, 1H), 3.90 (s, 1H), 3.08 (dt, J=13.4, 6.7 Hz, 1H), 2.89 (ddd, J=12.8, 6.8, 5.5 Hz, 1H), 2.49 (d, J=17.4 Hz, 1H), 2.43 (dd, J=17.4, 3.3 Hz, 1H), 2.34-2.23 (m, 3H), 2.27 (s, 3H), 1.86 (dd, J=11.3, 3.3 Hz, 1H), 1.69-1.58 (m, 1H), 1.20 (s, 3H), 0.76 (d, J=6.5 Hz, 3H), 0.75 (d, J=6.5 Hz, 3H). HRMS(ESI): m/z calc. for C$_{22}$H$_{28}$NO$_2$ [M+H]$^+$: 338.2120. found: 338.2112.

Synthesis of G6 Derivatives.

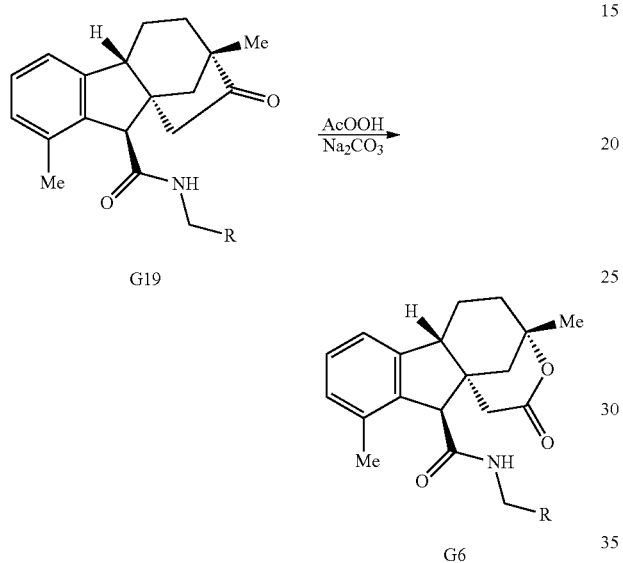

G19

G6

General Procedure for the Preparation of Lactones from G19:

In oven-dried vial with stir bar, G19a or G19b (1 equiv.) was dissolved in dichloromethane (0.05 M). The reaction was cooled to 0° C. in an ice bath, and sodium carbonate (7.5 equiv.) and peracetic acid (32% in acetic acid, 5 equiv.) were added. The reaction stirred for 15 hours, during which time it was allowed to warm to room temperature. Saturated aqueous sodium bicarbonate was added to quench the reaction. The reaction was acidified to pH 3, and the aqueous layer was extracted with ethyl acetate (3×). The combined organic layers were washed with brine, dried over magnesium sulfate, and concentrated. Purification by flash silica chromatography (hexanes/ethyl acetate) afforded the lactone along with unreacted starting material.

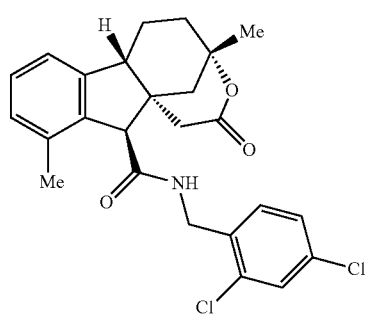

G6a

G6a: Prepared from G19a.

Yield: 10.4 mg, 38%, 79% brsm.

$^1$H NMR (CDCl$_3$, 500 MHz): δ 7.29 (t, J=1.9 Hz, 1H), 7.23 (s, 1H), 7.22 (s, 1H), 7.20 (t, J=7.9 Hz, 1H), 7.05 (d, J=7.5 Hz, 1H), 7.03 (d, J=7.5 Hz, 1H), 6.29 (br s, 1H), 4.60 (dd, J=14.8, 6.8 Hz, 1H), 4.31 (dd, J=14.9, 5.4 Hz, 1H), 3.55 (s, 1H), 2.92 (d, J=17.6 Hz, 1H), 2.89 (s, 1H), 2.70 (dd, J=17.6, 2.8 Hz, 1H), 2.22 (ddt, J=15.1, 5.0, 2.4 Hz, 1H), 2.14 (s, 3H), 1.92 (ddt, J=15.1, 12.0, 5.8 Hz, 1H), 1.84 (dq, J=14.0, 2.6 Hz, 1H), 1.64 (d, J=14.0 Hz, 1H), 1.45-1.39 (m, 1H), 1.39-1.35 (m, 1H), 1.31 (s, 3H).

HRMS(ESI): m/z calc. for C$_{25}$H$_{26}$NO$_3$Cl$_2$ [M+H]$^+$: 458.1290. found: 458.1291.

G6b

G6b: Prepared from G19b.

Yield: 9.1 mg, 23%, 34% brsm.

$^1$H NMR (CDCl$_3$, 500 MHz): δ 7.46 (d, J=8.2 Hz, 1H), 7.40 (d, J=2.1 Hz, 1H), 7.24 (dd, J=8.2, 2.1 Hz, 1H), 7.19 (t, J=7.5 Hz, 1H), 7.03 (d, J=7.5 Hz, 1H), 7.01 (d, J=7.5 Hz, 1H), 6.16 (t, J=5.4 Hz, 1H), 4.61 (dd, J=14.4, 6.4 Hz, 1H), 4.47 (dd, J=14.4, 5.6 Hz, 1H), 3.49 (s, 1H), 2.90 (d, J=17.6 Hz, 1H), 2.89 (s, 1H), 2.69 (dd, J=17.6, 2.8 Hz, 1H), 2.29-2.14 (m, 2H), 2.04 (s, 3H), 1.91 (ddt, J=15.2, 12.1, 5.9 Hz, 1H), 1.85-1.77 (m, 1H), 1.56 (d, J=14.2 Hz, 1H), 1.38 (td, J=13.5, 5.4 Hz, 1H), 1.25 (s, 3H).

HRMS(ESI): m/z calc. for C$_{25}$H$_{26}$NO$_3$Cl$_2$ [M+H]$^+$: 458.1290. found: 458.1290.

Example 6. Quinine Derived Libraries: Synthesis and Characterization

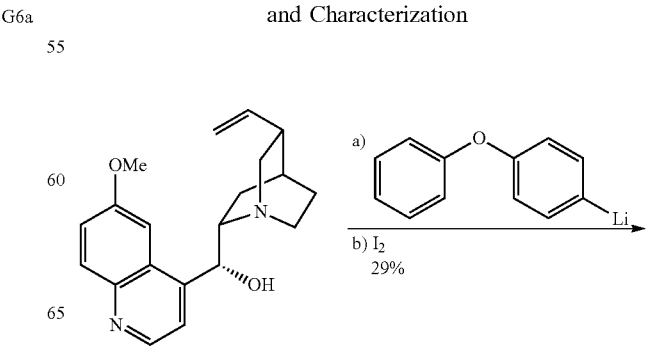

151
-continued

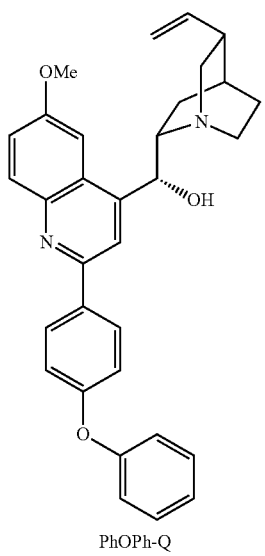

PhOPh-Q

Procedure: To a flame dried round bottom flask under argon containing a suspension of quinine (3.153 g, 9.7 mmol) in methyl t-butyl ether (58 mL) at −10° C. was added (4-phenoxyphenyl)lithium (5.142 g, 29.2 mmol). The reaction mixture was stirred for 20 min at −10° C., warmed to room temperature for 1 h, and quenched by dropwise addition of acetic acid at 0° C. Upon dilution with water and ethyl acetate, solid iodine (~700 mg) was added with vigorous stirring until a dark brown color persisted. A saturated aqueous solution of sodium metabisulfite was then added to quench excess iodine. The reaction mixture was basified with 25% aqueous ammonia and extracted with dichloromethane (3×). The organic layer was washed with brine, dried with magnesium sulfate, and evaporated. Purification by column chromatography using 1:9 methanol/toluene with 2% triethylamine provided 1.406 g (29%) of PhOPh-Q as a white solid. Spectral data for PhOPh-Q ($^1$H NMR, $^{13}$C NMR, and HRMS) matched previously reported spectra.[12]

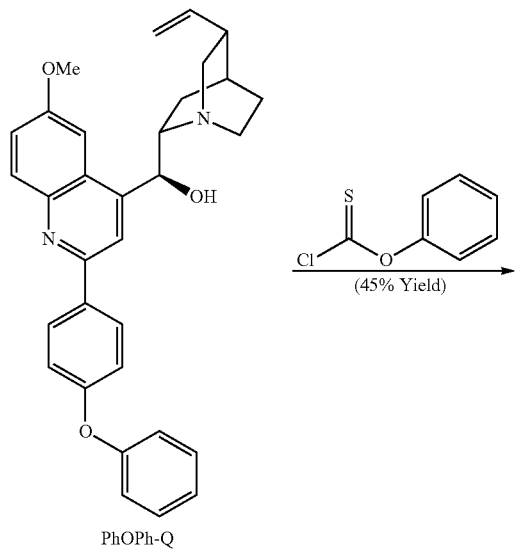

152
-continued

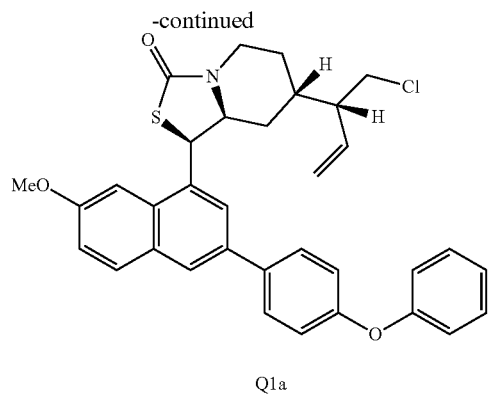

Q1a

Procedure: To a solution of PhOPh-Q (700 mg, 1.42 mmol) in dry dichloromethane (28.4 mL) at 0° C. under argon was added 0-Phenyl chlorothionoformate (295.2 mg, 1.71 mmol). The reaction was warmed to room temperature and stirred overnight. Upon cooling to 0° C., the reaction was quenched by slow addition of aqueous sodium bicarbonate and transferred to a separatory funnel. The crude mixture was washed 3 times with 1 M NaOH to remove phenol then washed with brine, dried with magnesium sulfate, and evaporated. Purification by column chromatography using 1:12 to 0:1 hexanes/chloroform provided Q1a (368 mg, 45%) as a yellow powder.

$^1$H NMR (CDCl$_3$, 500 MHz): δ 8.16-8.10 (m, 3H), 8.07 (s, 1H), 7.44 (dd, J=9.2, 2.6 Hz, 1H), 7.39-7.35 (m, 2H), 7.25 (d, J=2.7 Hz, 1H), 7.18-7.12 (m, 3H), 7.10-7.06 (m, 2H), 5.68 (dt, J=17.1, 9.7 Hz, 1H), 5.21 (dd, J=10.1, 1.5 Hz, 1H), 5.18 (d, J=7.3 Hz, 1H), 5.13 (dd, J=17.0, 1.4 Hz, 1H), 4.06-3.99 (m, 2H), 3.99 (s, 3H), 3.52 (dd, J=11.2, 3.4 Hz, 1H), 3.40 (dd, J=11.1, 5.1 Hz, 1H), 2.97 (td, J=13.3, 3.4 Hz, 1H), 2.61 (dq, J=14.4, 4.5 Hz, 1H), 2.19-2.12 (m, 1H), 2.09 (dd, J=14.1, 2.5 Hz, 1H), 1.95-1.87 (m, 1H), 1.86-1.80 (m, 1H), 1.73-1.64 (m, 1H). HRMS(ESI): m/z calc. for C$_{33}$H$_{32}$N$_2$O$_3$SCl [M+11]$^+$: 571.1822. found: 571.1811.

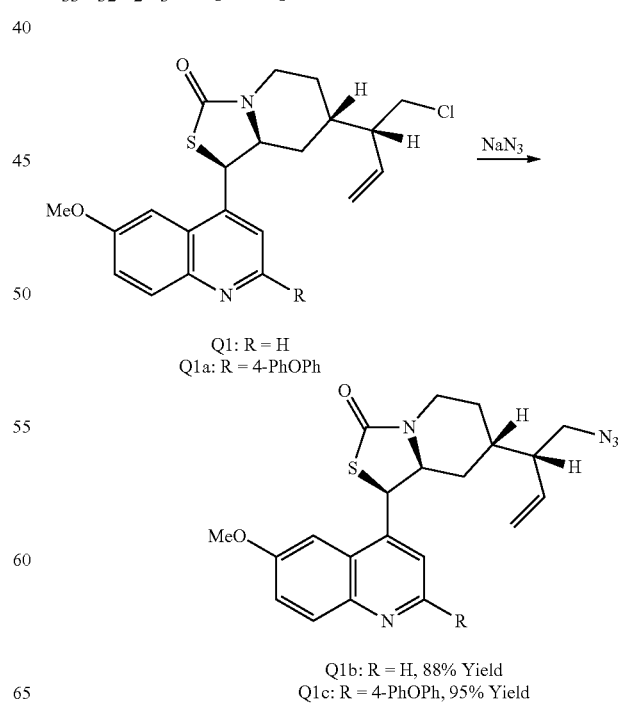

Q1: R = H
Q1a: R = 4-PhOPh

Q1b: R = H, 88% Yield
Q1c: R = 4-PhOPh, 95% Yield

General Procedure for the Preparation of Q1 Azides:

To a solution of chloride Q1 or Q1a (0.26 mmol) in N,N-dimethylformamide (2.6 mL) was added sodium azide (51.4 mg, 0.79 mmol). The reaction mixture was heated to 50° C. and stirred 24 h. Upon cooling, the reaction was poured into brine and extracted with ethyl acetate. Washing the organic layer with brine (4×), drying with magnesium sulfate, and evaporation of solvent provided pure azide. (Note: This procedure was performed at several scales 0.22-1.66 mmol.)

Q1b

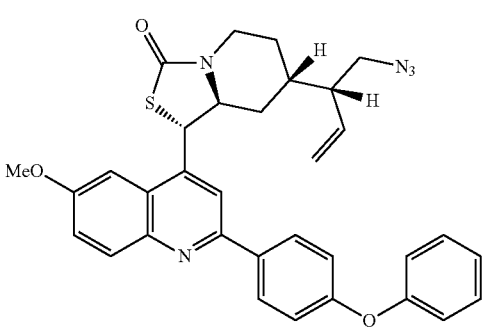

Q1b: Prepared from Q1.

Yield: 451.7 mg, 89% yield.

$^1$H NMR (CDCl$_3$, 500 MHz): δ 8.79 (d, J=4.6 Hz, 1H), 8.08 (d, J=9.2 Hz, 1H), 7.60 (d, J=4.6 Hz, 1H), 7.43 (dd, J=9.2, 2.6 Hz, 1H), 7.25 (d, J=2.7 Hz, 1H), 5.59 (ddd, J=16.9, 10.2, 9.4 Hz, 1H), 5.20 (dd, J=10.2, 1.5 Hz, 1H), 5.16 (dd, J=17.1, 1.5 Hz, 1H), 5.12 (d, J=7.8 Hz, 1H), 4.03-3.96 (m, 2H), 3.96 (s, 3H), 3.26 (dd, J=12.3, 4.7 Hz, 1H), 3.20 (dd, J=12.3, 5.8 Hz, 1H), 2.95 (td, J=13.2, 3.3 Hz, 1H), 2.48 (tt, J=10.5, 5.3 Hz, 1H), 2.02-1.94 (m, 2H), 1.85-1.77 (m, 2H), 1.62 (tt, J=13.7, 4.8 Hz, 1H).

HRMS(ESI): m/z calc. for $C_{21}H_{24}N_5O_2S$ [M+H]$^+$: 410.1651. found: 410.1655.

Q1c

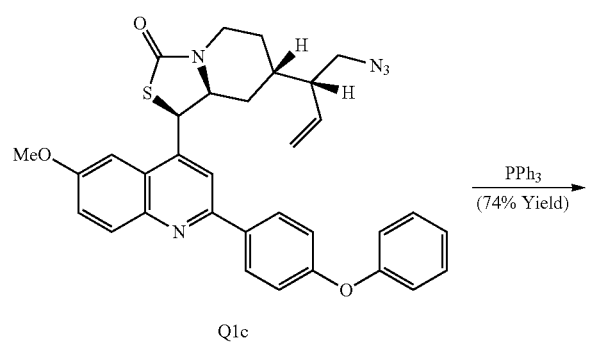

Q1c: Prepared from Q1a.

Yield: 143 mg, 95%.

$^1$H NMR (CDCl$_3$, 500 MHz): δ 8.17-8.10 (m, 3H), 8.09 (s, 1H), 7.45 (dd, J=9.2, 2.6 Hz, 1H), 7.40-7.34 (m, 2H), 7.26 (d, J=2.3 Hz, 1H), 7.18-7.12 (m, 3H), 7.10-7.05 (m, 2H), 5.59 (dt, J=17.1, 9.8 Hz, 1H), 5.23-5.13 (m, 3H), 4.07-4.00 (m, 2H), 3.98 (s, 3H), 3.27 (dd, J=12.3, 4.7 Hz, 1H), 3.19 (dd, J=12.3, 5.9 Hz, 1H), 2.96 (td, J=13.3, 3.3 Hz, 1H), 2.48 (d, J=10.4, 5.3 Hz, 1H), 2.08-2.01 (m, 1H), 2.02-1.95 (m, 1H), 1.90-1.79 (m, 2H), 1.64 (tt, J=13.7, 4.8 Hz, 1H).

HRMS(ESI): m/z calc. for $C_{33}H_{32}N_5O_3S$ [M+H]$^+$: 578.2226. found: 578.2220.

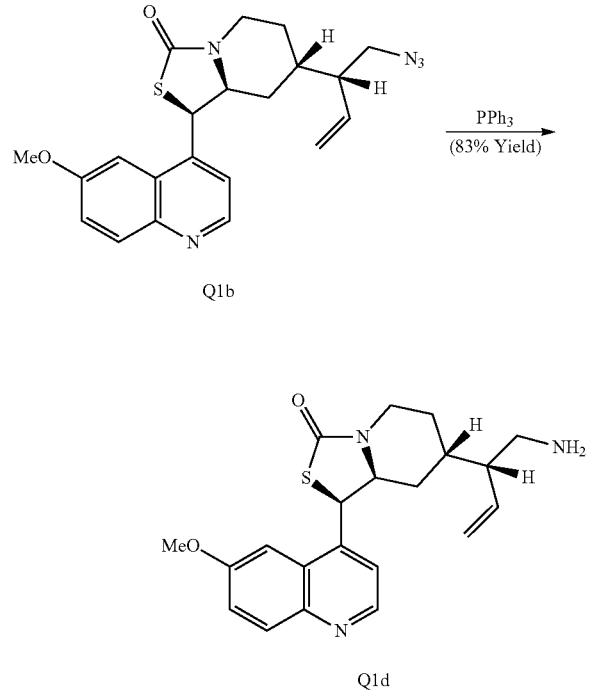 [SMILES: C=C[C@@H](CN=[N+]=[N-])[C@H]1CCN2C(=O)S[C@H](c3ccnc4ccc(OC)cc34)[C@@H]2C1 ; C=C[C@@H](CN)[C@H]1CCN2C(=O)S[C@H](c3ccnc4ccc(OC)cc34)[C@@H]2C1 ; "PPh3"]

Q1b

Procedure: A solution of azide Q1b (481.8 mg, 1.18 mmol) and triphenylphosphine (926 mg, 3.53 mmol) in tetrahydrofuran (30 mL) and water (2 mL) was stirred at 50° C. for 6 hours. The reaction was then cooled to room temperature, washed with brine, dried with magnesium sulfate, and evaporated. Purification by column chromatography using a gradient of 1:49 to 3:22 methanol/ethyl acetate with 2% triethylamine provided amine Q1d (377.3 mg, 83%) as a white solid.

$^1$H NMR (CDCl$_3$, 500 MHz): δ 8.74 (d, J=4.6 Hz, 1H), 8.02 (d, J=9.2 Hz, 1H), 7.55 (d, J=4.6 Hz, 1H), 7.38 (dd, J=9.2, 2.6 Hz, 1H), 7.21 (d, J=2.7 Hz, 1H), 5.39 (dt, J=17.0, 9.7 Hz, 1H), 5.18 (dd, J=10.2, 1.8 Hz, 1H), 5.13-5.06 (m, 2H), 4.01 (ddd, J=11.5, 8.0, 3.0 Hz, 1H), 3.96-3.92 (m, 1H), 3.92 (s, 3H), 2.95 (td, J=13.2, 3.1 Hz, 1H), 2.63 (dd, J=12.1, 3.5 Hz, 1H), 2.33 (dd, J=12.0, 9.2 Hz, 1H), 2.29-2.20 (m, 1H), 1.96-1.90 (m, 1H), 1.85-1.69 (m, 3H), 1.56 (tt, J=13.5, 4.5 Hz, 1H). HRMS(ESI): m/z calc. for $C_{21}H_{26}N_3O_2S$ [M+H]$^+$: 384.1746. found: 384.1750.

Q1c

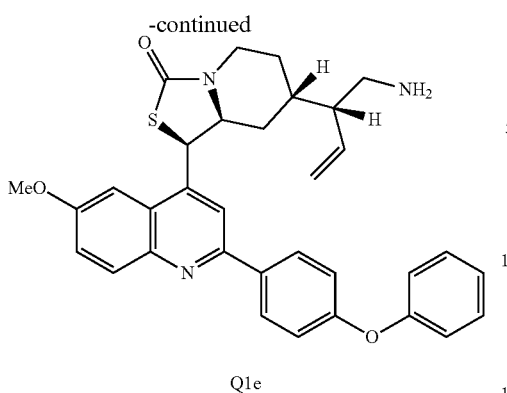

Q1e

Procedure: A solution of azide Q1c (135 mg, 0.234 mmol) and triphenylphosphine (67 mg, 0.257 mmol) in tetrahydrofuran (1.17 mL) and water (5 μL) was stirred at room temperature for 36 hours. The reaction was then evaporated and purified by column chromatography using a gradient of 1:49 to 2:23 methanol/ethyl acetate with 2% triethylamine provided amine Q1e (96 mg, 74%) as a white solid.

$^1$H NMR (CDCl$_3$, 500 MHz): δ 8.15-8.09 (m, 3H), 8.07 (s, 1H), 7.43 (dd, J=9.2, 2.8 Hz, 1H), 7.39-7.34 (m, 2H), 7.25 (d, J=2.9 Hz, 1H), 7.18-7.11 (m, 3H), 7.10-7.04 (m, 2H), 5.44 (dt, J=17.0, 9.8 Hz, 1H), 5.21 (dd, J=10.2, 1.8 Hz, 1H), 5.16 (d, J=7.9 Hz, 1H), 5.13 (dd, J=17.1, 1.8 Hz, 1H), 4.12-4.05 (m, 1H), 4.03-3.98 (m, 1H), 3.97 (s, 3H), 3.00 (td, J=13.1, 3.1 Hz, 1H), 2.67 (dd, J=12.1, 3.5 Hz, 1H), 2.38 (dd, J=12.0, 9.2 Hz, 1H), 2.28 (qd, J=9.5, 3.3 Hz, 1H), 2.07-2.00 (m, 1H), 1.91-1.77 (m, 3H), 1.63 (td, J=8.8, 4.3 Hz, 1H). HRMS(ESI): m/z calc. for C$_{33}$H$_{34}$N$_3$O$_3$S [M+H]$^+$: 552.2321. found: 552.2311.

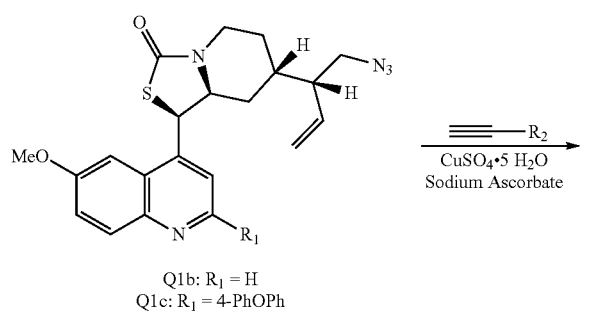

Q1b: R$_1$ = H
Q1c: R$_1$ = 4-PhOPh

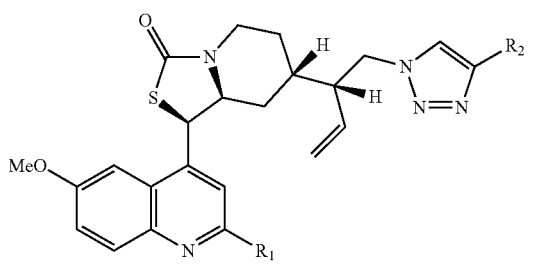

General Procedure for the Preparation of Q1 Triazoles:
To a vial containing azide Q1b or Q1c (0.017 mmol) was added a solution of copper sulfate pentahydrate (2 mg, 0.0080 mmol) and sodium ascorbate (5 mg, 0.025 mmol) in 2:1 water/t-butanol (600 μL) followed by alkyne (0.051 mmol). Dichloromethane (200 μL) was then added to vials containing Q1c to help dissolve the azide. The reaction was stirred at room temperature for 24 hours then diluted with water and extracted with chloroform. The organic layer was washed, dried with magnesium sulfate, evaporated, and purified by preparative TLC (hexanes/ethyl acetate) to provide the triazole. (Note: This procedure was performed at scales from 0.017-0.147 mmol azide)

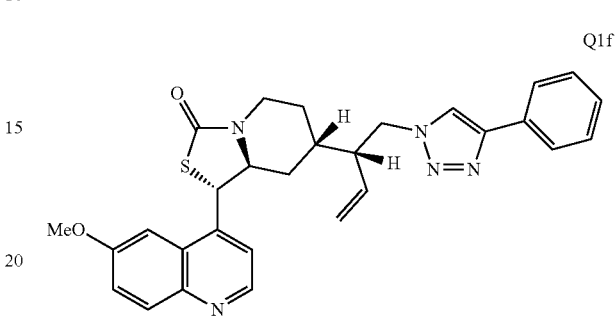

Q1f

Q1f: Prepared from phenylacetylene.
Yield: 32.3 mg, 90%.

$^1$H NMR (CDCl$_3$, 500 MHz): δ 8.86-8.76 (m, 1H), 8.18 (d, J=8.8 Hz, 1H), 7.83-7.71 (m, 3H), 7.68 (s, 1H), 7.49-7.26 (m, 5H), 5.53 (dt, J=16.5, 9.8 Hz, 1H), 5.24-5.10 (m, 2H), 5.01 (d, J=16.5 Hz, 1H), 4.47 (dd, J=13.7, 3.4 Hz, 1H), 4.32-4.24 (m, 1H), 4.20 (dd, J=13.7, 7.8 Hz, 1H), 4.03-3.92 (m, 1H), 3.98 (s, 3H), 3.07-2.97 (m, 1H), 2.99-2.89 (m, 1H), 2.24 (d, J=13.5 Hz, 1H), 2.10-1.88 (m, 2H), 1.89-1.76 (m, 1H), 1.76-1.60 (m, 1H). HRMS(ESI): m/z calc. for C$_{29}$H$_{30}$N$_5$O$_2$S [M+H]$^+$: 512.2120. found: 512.2119.

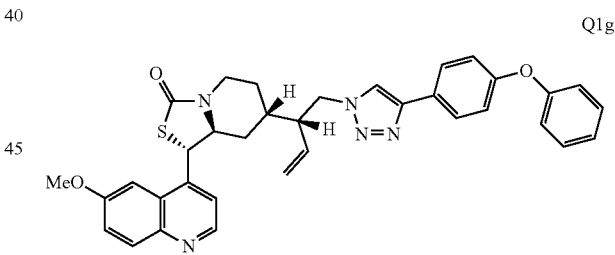

Q1g

Q1g: Prepared from 1-ethynyl-4-phenoxybenzene.
Yield: 71.6 mg, 81%.

$^1$H NMR (CDCl$_3$, 500 MHz): δ 8.80 (d, J=4.6 Hz, 1H), 8.05 (d, J=9.2 Hz, 1H), 7.75-7.69 (m, 2H), 7.64 (d, J=4.6 Hz, 1H), 7.59 (s, 1H), 7.41 (dd, J=9.2, 2.6 Hz, 1H), 7.36-7.30 (m, 2H), 7.25 (d, J=2.7 Hz, 1H), 7.15-7.07 (m, 1H), 7.05-6.99 (m, 4H), 5.50 (dt, J=17.0, 9.9 Hz, 1H), 5.19-5.09 (m, 2H), 4.98 (dd, J=17.0, 1.2 Hz, 1H), 4.41 (dd, J=13.9, 3.8 Hz, 1H), 4.23 (ddd, J=11.3, 7.9, 3.0 Hz, 1H), 4.15 (dd, J=13.8, 8.2 Hz, 1H), 3.97-3.89 (m, 1H), 3.95 (s, 3H), 2.99 (td, J=13.5, 3.3 Hz, 1H), 2.95-2.86 (m, 1H), 2.26-2.17 (m, 1H), 2.00-1.93 (m, 1H), 1.89 (ddd, J=13.9, 11.9, 4.6 Hz, 1H), 1.85-1.77 (m, 1H), 1.65 (tt, J=13.6, 4.8 Hz, 1H).

HRMS(ESI): m/z calc. for C$_{35}$H$_{34}$N$_5$O$_3$S [M+H]$^+$: 604.2382. found: 604.2382.

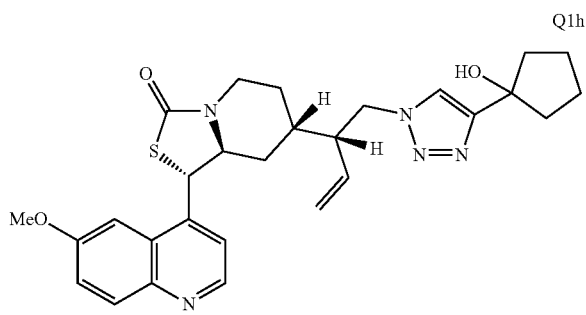 [SMILES: C=C[C@@H](Cn1cc(C2(O)CCCC2)nn1)[C@H]1CCN2C(=O)S[C@@H](c3ccnc4ccc(OC)cc34)[C@@H]2C1]

Q1h

Q1h: Prepared from 1-ethynylcyclopentanol.
Yield: 58.5 mg, 77%.
¹H NMR (d₆-DMSO, 500 MHz, 80° C.): δ 8.79 (d, J=4.6 Hz, 1H), 7.99 (d, J=9.1 Hz, 1H), 7.81 (s, 1H), 7.78 (d, J=4.6 Hz, 1H), 7.49 (d, J=2.7 Hz, 1H), 7.46 (dd, J=9.1, 2.7 Hz, 1H), 5.59 (d, J=6.5 Hz, 1H), 5.49 (dt, J 16.7, 10.1 Hz, 1H), 4.96-4.94 (m, 1H), 4.94-4.90 (m, 1H), 4.61-4.49 (m, 1H), 4.34 (dd, J=13.7, 4.1 Hz, 1H), 4.23 (dd, J=13.7, 9.5 Hz, 1H), 3.94 (s, 3H), 3.79-3.70 (m, 1H), 3.20-3.06 (m, 2H), 2.09-2.02 (m, 1H), 1.97-1.83 (m, 4H), 1.82-1.72 (m, 4H), 1.73-1.66 (m, 1H), 1.66-1.58 (m, 2H), 1.58-1.49 (m, 1H). HRMS (ESI): m/z calc. for C₂₈H₃₄N₅O₃S [M+H]⁺: 520.2382. found 520.2390.

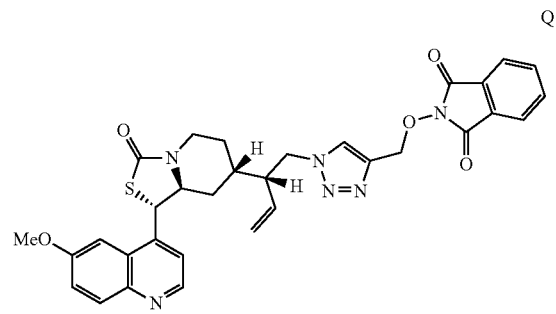

Q1i

Q1i: Prepared from N-(propargyloxy)phthalimide.
Yield: 66.6 mg, 74%.
¹H NMR (CDCl₃, 500 MHz): δ 8.77 (d, J=5.0 Hz, 1H), 8.05 (d, J=9.2 Hz, 1H), 7.77-7.66 (m, 5H), 7.62 (d, =4.6 Hz, 1H), 7.39 (dd, J=9.2, 2.6 Hz, 1H), 7.23 (d, J=2.7 Hz, 1H), 5.50 (dt, J=16.9, 9.8 Hz, 1H), 5.28 (s, 2H), 5.18-5.08 (m, 2H), 4.97 (dd, J=17.1, 1.5 Hz, 1H), 4.39 (dd, J=13.9, 3.7 Hz, 1H), 4.23-4.13 (m, 2H), 3.98-3.92 (m, 1H), 3.93 (s, 3H), 2.98 (td, J=13.3, 3.4 Hz, 1H), 2.88-2.78 (m, 1H), 2.21-2.13 (m, 1H), 1.93-1.84 (m, 2H), 1.83-1.77 (m, 1H), 1.66 (ddq, J=13.4, 9.3, 4.4 Hz, 1H).
HRMS(ESI): m/z calc. for C₃₂H₃₁N₆O₅S [M+H]⁺: 611.2077. found: 611.2071.

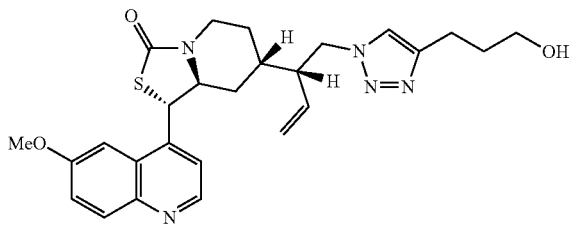

Q1j

Q1j: Prepared from 4-pentyn-1-ol.
Yield: 47.0 mg, 65%.
¹H NMR (CDCl₃, 500 MHz): δ 8.78 (d, J=4.7 Hz, 1H), 8.04 (d, J=9.2 Hz, 1H), 7.64 (d, J=4.6 Hz, 1H), 7.40 (dd, J=9.2, 2.6 Hz, 1H), 7.23 (d, J=2.7 Hz, 1H), 7.16 (s, 1H), 5.44 (dt, J=17.0, 9.9 Hz, 1H), 5.13 (d, J=8.0 Hz, 1H), 5.08 (dd, J=10.1, 1.4 Hz, 1H), 4.92 (dd, J=17.0, 1.4 Hz, 1H), 4.32 (dd, J=13.9, 3.9 Hz, 1H), 4.21 (ddd, J=11.2, 7.9, 3.1 Hz, 1H), 4.06 (dd, J=13.8, 8.2 Hz, 1H), 3.94 (s, 3H), 3.93-3.87 (m, 1H), 3.63 (t, J=6.1 Hz, 2H), 2.96 (td, J=13.3, 3.4 Hz, 1H), 2.84 (tt, J=12.8, 3.8 Hz, 1H), 2.73 (t, J=7.3 Hz, 2H), 2.18-2.09 (m, 1H), 1.91 (dd, J=12.3, 4.2 Hz, 2H), 1.88-1.83 (m, 2H), 1.83-1.75 (m, 1H), 1.63 (tt, J=13.6, 4.9 Hz, 1H).
HRMS(ESI): m/z calc. for C₂₆H₃₂N₅O₃S [M+H]⁺: 494.2226. found: 494.2230.

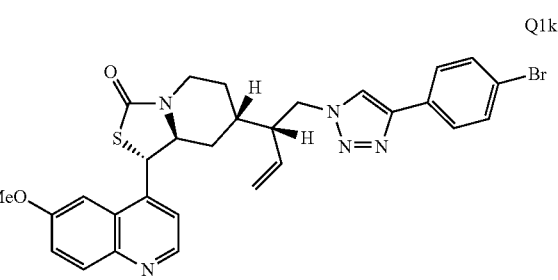

Q1k

Q1k: Prepared from 1-bromo-4-ethynylbenzene.
Yield: 60.0 mg, 69%.
¹H NMR (CDCl₃, 500 MHz): δ 8.87-8.62 (m, 1H), 8.14-7.96 (m, 1H), 7.72-7.57 (m, 1H), 7.39 (d, J=7.7 Hz, 1H), 7.36-7.18 (m, 5H), 7.14-6.94 (m, 1H), 5.40 (dt, J=16.4, 9.7 Hz, 1H), 5.12 (d, J=7.9 Hz, 1H), 5.06 (d, J=10.1 Hz, 1H), 4.88 (d, J=16.9 Hz, 1H), 4.40-4.29 (m, 1H), 4.26-4.16 (m, 1H), 4.04-3.85 (m, 2H), 3.92 (s, 3H), 3.02-2.89 (m, 1H), 2.89-2.76 (m, 1H), 2.19-2.04 (m, 1H), 2.00-1.81 (m, 2H), 1.81-1.74 (m, 1H), 1.64 (tt, J=13.2, 4.8 Hz, 1H).
HRMS(ESI): m/z calc. for C₂₉H₂₉N₅O₂SBr [M+H]⁺: 590.1225. found: 590.1223.

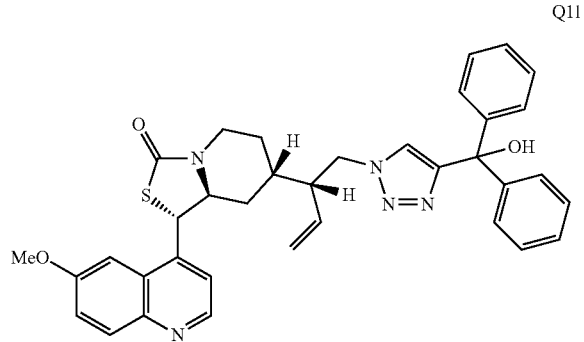 [SMILES: C=C[C@@H](Cn1cc(C(O)(c2ccccc2)c2ccccc2)nn1)[C@H]1CCN2C(=O)S[C@@H](c3ccnc4ccc(OC)cc34)[C@@H]2C1]

Q1l

Q1l: Prepared from 1,1-diphenyl-2-propyn-1-ol.
Yield: 80.2 mg, 88%.
¹H NMR (CDCl₃, 500 MHz): δ ¹H NMR (500 MHz, CDCl₃) δ 8.79 (d, J=4.6 Hz, 1H), 8.05 (d, J=9.2 Hz, 1H), 7.66-7.58 (m, 8H), 7.51-7.46 (m, 4H), 7.41 (dd, J=9.2, 2.6 Hz, 1H), 7.24 (d, J=2.7 Hz, 1H), 5.49 (dt, J=17.0, 9.8 Hz, 1H), 5.16-5.10 (m, 2H), 4.97 (dd, J=17.1, 1.5 Hz, 1H), 4.41 (dd, J=13.9, 3.8 Hz, 1H), 4.21 (ddd, J=11.4, 8.0, 3.0 Hz, 1H), 4.14 (dd, J=13.9, 8.3 Hz, 1H), 3.94 (s, 3H), 3.94-3.90 (m, 1H), 2.98 (td, J=13.3, 3.3 Hz, 1H), 2.94-2.85 (m, 1H), 2.18

(dd, J=13.9, 2.4 Hz, 1H), 1.99-1.93 (m, 1H), 1.89 (ddd, J=13.9, 11.8, 4.6 Hz, 1H), 1.80 (dt, J=14.0, 2.7 Hz, 1H), 1.65 (tt, J=13.9, 4.9 Hz, 1H).

HRMS(ESI): m/z calc. for $C_{36}H_{36}N_5O_3S$ [M+H]$^+$: 618.2539. found: 618.2543.

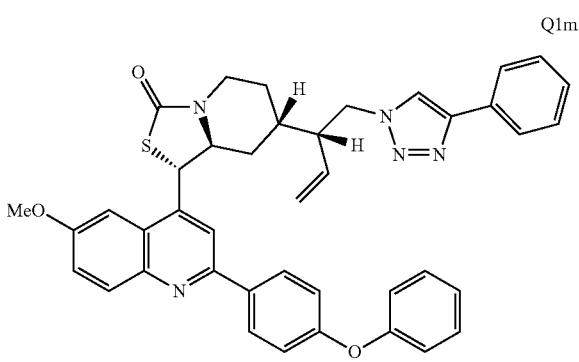 [SMILES: C=C[C@@H](Cn1cc(-c2ccccc2)nn1)[C@H]1CCN2C(=O)S[C@@H](c3cc(-c4ccc(Oc5ccccc5)cc4)nc4ccc(OC)cc34)[C@@H]2C1]

Q1m

Q1m: Prepared from phenylacetylene.
Yield: 7.6 mg, 65%.

$^1$H NMR (CDCl$_3$, 500 MHz): δ 8.20 (d, J=8.7 Hz, 2H), 8.18-8.09 (m, 2H), 7.75-7.70 (m, 2H), 7.57 (s, 1H), 7.44 (dd, J=9.2, 2.6 Hz, 1H), 7.42-7.37 (m, 2H), 7.37-7.31 (m, 3H), 7.28 (d, J=2.6 Hz, 1H), 7.19-7.14 (m, 2H), 7.14-7.10 (m, 1H), 7.06 (dd, J=8.6, 1.1 Hz, 2H), 5.51 (dt, J=17.1, 9.8 Hz, 1H), 5.23 (d, J=7.7 Hz, 1H), 5.13 (dd, J=10.0, 1.2 Hz, 1H), 4.97 (d, J=17.1 Hz, 1H), 4.44 (dd, J=13.7, 3.7 Hz, 1H), 4.30 (td, J=7.9, 4.0 Hz, 1H), 4.16 (dd, J=13.8, 8.3 Hz, 1H), 4.05-3.99 (m, 1H), 3.98 (s, 3H), 3.00 (td, J=13.3, 3.3 Hz, 1H), 2.98-2.87 (m, 1H), 2.36-2.29 (m, 1H), 2.03-1.94 (m, 2H), 1.84 (d, J=14.2 Hz, 1H), 1.76-1.66 (m, 1H).

HRMS(ESI): m/z calc. for $C_{41}H_{38}N_5O_3S$ [M+H]$^+$: 680.2695. found: 680.2709.

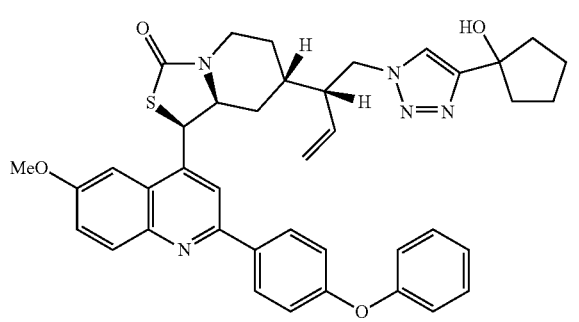

Q1n

Q1n: Prepared from 1-ethynylcyclopentanol.
Yield: 9.0 mg, 77%.

$^1$H NMR (CDCl$_3$, 500 MHz): δ 8.18 (d, J=8.4 Hz, 2H), 8.14-8.11 (m, 2H), 7.47-7.41 (m, 1H), 7.40-7.33 (m, 2H), 7.30-7.22 (m, 2H), 7.17-7.09 (m, 3H), 7.09-7.04 (m, 2H), 5.47 (dt, J=16.9, 9.8 Hz, 1H), 5.21 (d, J=7.9 Hz, 1H), 5.11 (d, J=10.2 Hz, 1H), 4.93 (d, J=16.8 Hz, 1H), 4.36 (dd, J=13.7, 3.7 Hz, 1H), 4.28 (ddd, J=11.1, 7.9, 3.2 Hz, 1H), 4.08 (dd, J=13.8, 8.4 Hz, 1H), 4.03-3.97 (m, 1H), 3.98 (s, 3H), 3.00 (td, J=13.2, 3.5 Hz, 1H), 2.92-2.83 (m, 1H), 2.32-2.23 (m, 1H), 2.14-1.86 (m, 8H), 1.86-1.59 (m, 4H).

HRMS(ESI): m/z calc. for $C_{40}H_{42}N_5O_4S$ [M+H]$^+$: 688.2958. found: 688.2944.

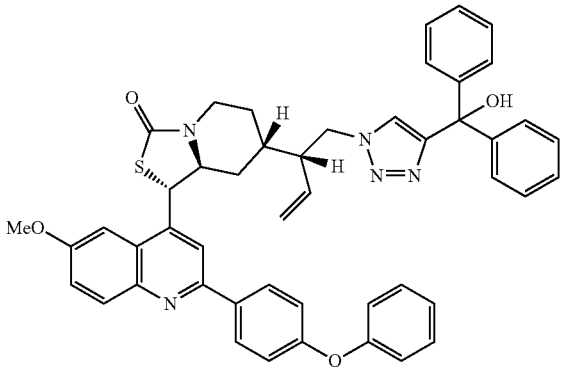

Q1o

Q1o: Prepared from 1,1-diphenyl-2-propyn-1-ol.
Yield: 6.1 mg, 46%.

$^1$H NMR (CDCl$_3$, 500 MHz): δ 8.18 (d, J=8.7 Hz, 2H), 8.14-8.05 (m, 2H), 7.42 (dd, J=9.2, 2.6 Hz, 1H), 7.34 (dd, J=8.6, 7.3 Hz, 2H), 7.26 (q, J=2.5, 1.7 Hz, 11H), 7.17-7.11 (m, 3H), 7.06 (dd, J=8.4, 1.1 Hz, 2H), 6.92 (s, 1H), 5.42 (dt, J=17.0, 9.9 Hz, 1H), 5.21 (d, J=8.1 Hz, 1H), 5.08 (dd, J=10.1, 1.4 Hz, 1H), 4.89 (dd, J=17.2, 1.3 Hz, 1H), 4.40 (dd, J=13.7, 3.8 Hz, 1H), 4.33-4.26 (m, 1H), 4.05-3.95 (m, 2H), 3.96 (s, 3H), 2.99 (td, J=13.1, 3.4 Hz, 1H), 2.95-2.83 (m, 1H), 2.24 (d, J=14.5 Hz, 1H), 2.01 (dd, J=34.3, 8.1 Hz, 2H), 1.84 (d, J=13.9 Hz, 1H), 1.69 (d, J=16.9 Hz, 1H).

HRMS(ESI): m/z calc. for $C_{48}H_{44}N_5O_4S$ [M+H]$^+$: 786.3114. found: 786.3118.

Q1p

Q1p: Prepared from N-(propargyloxy)phthalimide.
Yield: 7.8 mg, 59%.

$^1$H NMR (CDCl$_3$, 500 MHz): δ 8.20-8.02 (m, 4H), 7.73 (dddd, J=18.5, 5.1, 3.3, 2.0 Hz, 4H), 7.68 (d, J=1.7 Hz, 1H), 7.43 (dt, J=9.2, 2.3 Hz, 1H), 7.39-7.32 (m, 2H), 7.27 (d, J=2.3 Hz, 1H), 7.13 (ddd, J=6.6, 4.1, 1.5 Hz, 3H), 7.06 (ddd, J=8.3, 2.0, 1.0 Hz, 2H), 5.51 (dtd, J=17.1, 9.9, 1.9 Hz, 1H), 5.27 (s, 2H), 5.21 (d, J=7.5 Hz, 1H), 5.12 (d, J=10.0 Hz, 1H), 4.97 (d, J=17.1 Hz, 1H), 4.43-4.34 (m, 1H), 4.28-4.13 (m, 2H), 4.05-3.97 (m, 1H), 3.97 (s, 3H), 3.05-2.94 (m, 1H), 2.90-2.78 (m, 1H), 2.27-2.21 (m, 1H), 2.01-1.88 (m, 2H), 1.86-1.78 (m, 1H), 1.71 (d, J=13.9 Hz, 1H).

HRMS(ESI): m/z calc. for $C_{44}H_{39}N_6O_6S$ [M+H]$^+$: 779.2652. found: 779.2640.

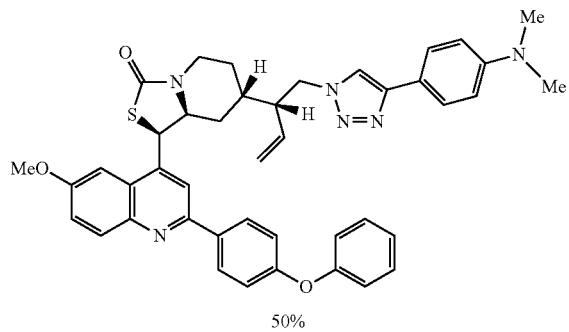

Q1q

50%

Q1q: Prepared from 4-ethynyl-N,N-dimethylaniline.
Yield: 6.1 mg, 50%.
$^1$H NMR (CDCl$_3$, 500 MHz): δ 8.21-8.17 (m, 2H), 8.15 (s, 1H), 8.13 (d, J=9.5 Hz, 1H), 7.62-7.57 (m, 2H), 7.45-7.42 (m, 1H), 7.42 (s, 1H), 7.34 (t, J=7.5 Hz, 2H), 7.28 (d, J=3.3 Hz, 1H), 7.16 (dd, J=8.6, 1.3 Hz, 2H), 7.14-7.10 (m, 1H), 7.06 (d, J=7.9 Hz, 2H), 6.73 (d, J=8.2 Hz, 2H), 5.51 (dt, J=16.8, 9.8 Hz, 1H), 5.21 (d, J=7.6 Hz, 1H), 5.12 (d, J=10.1 Hz, 1H), 4.97 (d, J=17.0 Hz, 1H), 4.38 (dd, J=13.9, 3.7 Hz, 1H), 4.31-4.22 (m, 1H), 4.16 (dd, J=13.8, 7.9 Hz, 1H), 4.02 (t, J=3.8 Hz, 1H), 3.98 (s, 3H), 3.09 (q, J=7.2 Hz, 1H), 2.98 (d, J=1.3 Hz, 6H), 2.88 (d, J=9.3 Hz, 1H), 2.36-2.26 (m, 1H), 1.97 (t, J=11.6 Hz, 2H), 1.83 (d, J=15.7 Hz, 1H), 1.75-1.65 (m, 1H).
HRMS(ESI): m/z calc. for C$_{43}$H$_{43}$N$_6$O$_3$S [M+H]$^+$: 723.3117. found: 723.3124.

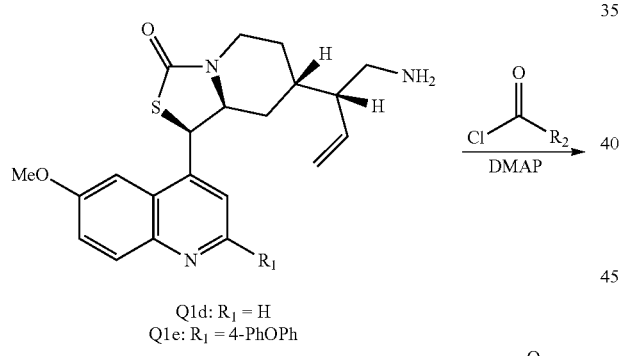

Q1d: R$_1$ = H
Q1e: R$_1$ = 4-PhOPh

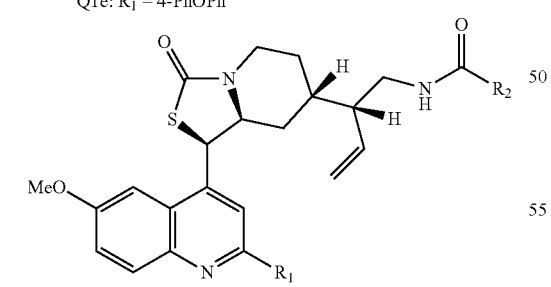

General Procedure for the Preparation of Q1 Amides/ureas:
To a solution of amine Q1d or Q1e, N,N-dimethylaminopyridine (1 mg, 0.008 mmol), and triethylamine (7.5 μL, 0.054 mmol) in dichloromethane (2 mL) was added acyl chloride (0.036 mmol). The reaction was stirred at room temperature 24 hours, quenched with methanol, evaporated, and purified by preparative TLC (hexanes/ethyl acetate) to provide the amide/urea. (Note: This procedure was performed at several scales: 0.018-0.104 mmol amine)

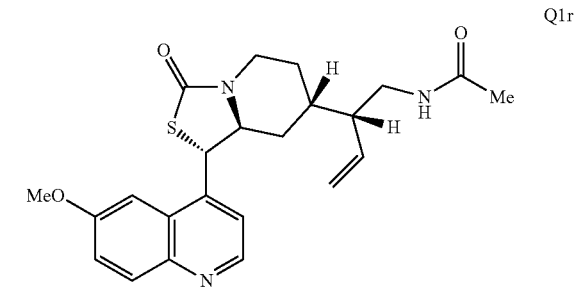 [SMILES: C=C[C@@H](CNC(C)=O)[C@H]1CCN2C(=O)S[C@@H](c3ccnc4ccc(OC)cc34)[C@@H]2C1]

Q1r

Q1r: prepared from acetyl chloride.
Yield: 38.6 mg, 87%.
$^1$H NMR (CDCl$_3$, 500 MHz): δ 8.82 (d, J=4.6 Hz, 1H), 8.03 (d, J=9.2 Hz, 1H), 7.80 (d, J=4.7 Hz, 1H), 7.38 (dd, J=9.2, 2.7 Hz, 1H), 7.21 (d, J=2.7 Hz, 1H), 5.86-5.69 (m, 1H), 5.45 (dt, J=16.9, 9.8 Hz, 1H), 5.21 (dd, J=10.1, 1.7 Hz, 1H), 5.14-5.07 (m, 2H), 4.34 (ddd, J=12.0, 9.0, 3.1 Hz, 1H), 3.95 (s, 3H), 3.96-3.88 (m, 1H), 3.67 (ddd, J=13.0, 7.3, 3.1 Hz, 1H), 2.97 (td, J=13.2, 3.1 Hz, 1H), 2.60 (ddd, J=12.8, 10.1, 4.6 Hz, 1H), 2.56-2.47 (m, 1H), 2.19 (dd, J=13.8, 2.6 Hz, 1H), 1.95 (s, 3H), 1.88-1.77 (m, 2H), 1.74-1.64 (m, 1H), 1.66-1.56 (in, 1H).
HRMS(ESI): m/z calc. for C$_{23}$H$_{28}$N$_3$O$_3$S [M+H]$^+$: 426.1851. found: 426.1854.

Q1s

Q1s: Prepared from benzoyl chloride.
Yield: 33.6 mg, 66%.
$^1$H NMR (CDCl$_3$, 500 MHz): δ 8.86 (d, J=4.6 Hz, 1H), 8.05 (d, J=9.2 Hz, 1H), 7.89 (d, J=4.7 Hz, 1H), 7.76-7.67 (m, 2H), 7.53-7.46 (m, 1H), 7.45-7.37 (m, 3H), 7.24 (d, J=2.7 Hz, 1H), 6.44-6.37 (m, 1H), 5.54 (dt, J=17.0, 9.9 Hz, 1H), 5.25 (dd, J=10.1, 1.7 Hz, 1H), 5.18-5.09 (m, 2H), 4.42 (ddd, J=11.9, 8.8, 3.0 Hz, 1H), 3.96 (s, 3H), 3.99-3.93 (m, 1H), 3.89 (ddd, J=13.2, 7.3, 3.4 Hz, 1H), 2.99 (td, J=13.3, 3.2 Hz, 1H), 2.82 (ddd, J=13.1, 10.1, 4.7 Hz, 1H), 2.73-2.63 (m, 1H), 2.28 (dd, J=13.8, 2.6 Hz, 1H), 1.93-1.82 (m, 2H), 1.75 (ddd, J=13.7, 11.8, 4.3 Hz, 1H), 1.65 (ddt, J=13.3, 8.7, 4.8 Hz, 1H). HRMS(ESI): m/z calc. for C$_{28}$H$_{30}$N$_3$O$_3$S [M+H]$^+$: 488.2008. found: 488.2005.

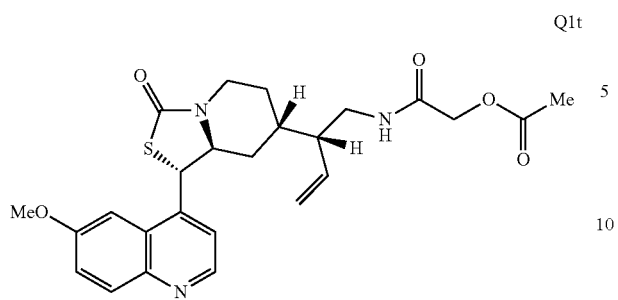

Q1t: Prepared from acetoxyacetyl chloride.

Yield: 29.1 mg, 77%.

$^1$H NMR (CDCl$_3$, 500 MHz): δ 8.83 (dd, J=4.6, 0.9 Hz, 1H), 8.06 (dd, J=9.2, 0.8 Hz, 1H), 7.77 (d, =4.6 Hz, 1H), 7.41 (ddd, J=9.2, 2.7, 0.9 Hz, 1H), 7.22 (d, J=2.6 Hz, 1H), 6.32-6.21 (m, 1H), 5.49 (dt, J=17.3, 9.8 Hz, 1H), 5.28-5.22 (m, 1H), 5.18-5.08 (m, 2H), 4.55 (d, J=3.9 Hz, 2H), 4.31 (ddd, J=11.8, 8.7, 3.0 Hz, 1H), 4.00-3.94 (m, 1H), 3.96 (s, 3H), 3.73 (ddd, J=13.1, 7.4, 3.3 Hz, 1H), 2.98 (td, J=13.3, 3.1 Hz, 1H), 2.68 (ddd, J=13.2, 10.3, 4.5 Hz, 1H), 2.54 (qd, J=10.2, 9.6, 3.1 Hz, 1H), 2.18 (dd, J=13.8, 2.6 Hz, 1H), 2.13 (s, 3H), 1.91-1.79 (m, 2H), 1.74 (ddd, J=13.7, 11.8, 4.2 Hz, 1H), 1.65 (tt, J=13.5, 4.8 Hz, 1H). HRMS(ESI): m/z calc. for C$_{25}$H$_{30}$N$_3$O$_5$S [M+H]$^+$: 484.1906. found: 484.1897.

Q1u: Prepared from 4-morpholinecarbonyl chloride.

Yield: 31.5 mg, 81%.

$^1$H NMR (CDCl$_3$, 500 MHz): δ 8.83 (d, J=4.6 Hz, 1H), 8.06 (d, J=9.2 Hz, 1H), 7.86 (d, J=4.4 Hz, 1H), 7.40 (dd, J=9.3, 2.5 Hz, 1H), 7.22 (d, J=2.6 Hz, 1H), 5.48 (dt, J=17.1, 9.7 Hz, 1H), 5.23 (dt, J=10.1, 1.7 Hz, 1H), 5.18-5.01 (m, 2H), 4.60 (dd, J=8.0, 3.9 Hz, 1H), 4.40 (ddd, J=11.9, 8.9, 3.0 Hz, 1H), 3.97 (s, 3H), 4.00-3.94 (m, 1H), 3.74-3.65 (m, 1H), 3.68 (td, J=4.9, 1.5 Hz, 4H), 3.31 (td, J=4.5, 1.5 Hz, 4H), 2.99 (td, J=13.4, 3.1 Hz, 1H), 2.65-2.49 (m, 2H), 2.24 (dt, J=13.7, 2.5 Hz, 1H), 1.90-1.79 (m, 2H), 1.71 (ddd, J=13.6, 11.9, 4.2 Hz, 1H), 1.67-1.59 (m, 1H).

HRMS(ESI): m/z calc. for C$_{26}$H$_{33}$N$_4$O$_4$S [M+H]$^+$: 497.2223. found: 497.2230.

Q1v: Prepared from benzyloxyacetyl chloride.

Yield: 32.4 mg, 78%.

$^1$H NMR (CDCl$_3$, 500 MHz): δ 8.83 (d, J=4.6 Hz, 1H), 8.06 (d, J=9.2 Hz, 1H), 7.78 (d, J=4.7 Hz, 1H), 7.40 (dd, J=9.2, 2.7 Hz, 1H), 7.38-7.27 (m, 5H), 7.22 (d, J=2.7 Hz, 1H), 6.75 (s, 1H), 5.47 (dt, J=17.0, 9.9 Hz, 1H), 5.22 (dd, J=10.2, 1.7 Hz, 1H), 5.17-5.05 (m, 2H), 4.55 (s, 2H), 4.31 (ddd, J=11.7, 8.6, 3.0 Hz, 1H), 3.97 (d, J=3.2 Hz, 2H), 4.02-3.93 (m, 1H), 3.96 (s, 3H), 3.69 (ddd, J=13.2, 7.4, 3.4 Hz, 1H), 2.98 (td, J=13.4, 3.1 Hz, 1H), 2.71 (ddd, J=13.1, 10.1, 4.8 Hz, 1H), 2.53 (qd, J=10.2, 3.3 Hz, 1H), 2.19 (dd, J=13.8, 2.6 Hz, 1H), 1.90-1.80 (m, 2H), 1.73 (ddd, J=13.8, 11.8, 4.2 Hz, 1H), 1.68-1.58 (m, 1H).

HRMS(ESI): m/z calc. for C$_{30}$H$_{34}$N$_3$O$_4$S [M+H]$^+$: 532.2270. found: 532.2280.

Q1w: Prepared from 6-chloronicotinoyl chloride.

Yield: 28.8 mg, 71%.

$^1$H NMR (CDCl$_3$, 500 MHz): δ 8.83 (s, 1H), 8.69 (d, J=2.5 Hz, 1H), 8.10-8.01 (m, 2H), 7.84 (d, J=4.7 Hz, 1H), 7.48-7.34 (m, 2H), 7.24 (d, J=2.7 Hz, 1H), 6.63 (s, 1H), 5.53 (dt, J=17.1, 9.8 Hz, 1H), 5.24 (dd, J=10.1, 1.7 Hz, 1H), 5.18-5.09 (m, 2H), 4.38 (ddd, J=12.0, 9.0, 3.1 Hz, 1H), 3.96 (s, 3H), 3.97-3.91 (m, 1H), 3.85 (ddd, J=13.2, 7.0, 3.3 Hz, 1H), 2.99 (td, J=13.3, 3.2 Hz, 1H), 2.84 (ddd, J=13.4, 10.3, 4.9 Hz, 1H), 2.67 (ddd, J=20.4, 10.2, 3.1 Hz, 1H), 2.23 (dd, J=13.7, 2.6 Hz, 1H), 1.94-1.81 (m, 2H), 1.80-1.70 (m, 1H), 1.65 (ddt, J=22.7, 9.4, 4.5 Hz, 1H).

HRMS(ESI): m/z calc. for C$_{27}$H$_{25}$N$_4$O$_3$SCl [M+H]$^+$: 523.1571. found: 523.1581.

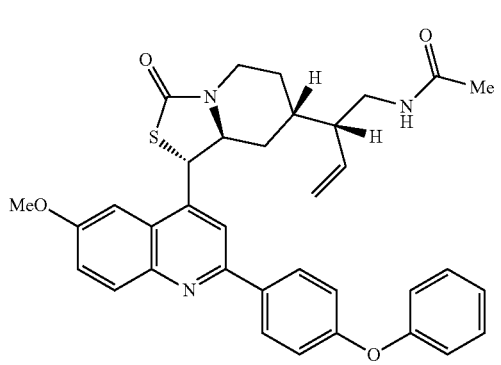

Q1x

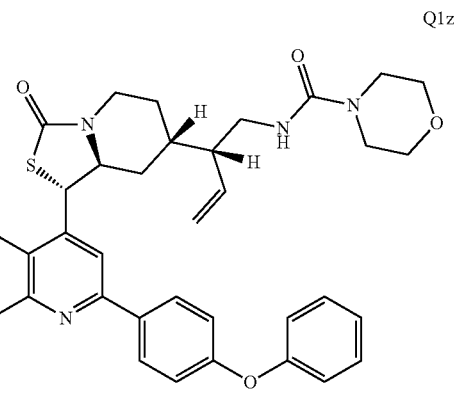

Q1z

Q1x: Prepared from acetyl chloride.

Yield: 7.5 mg, 70%.

¹H NMR (CDCl₃, 500 MHz): δ 8.25-8.14 (m, 3H), 8.11 (dd, =9.3, 0.8 Hz, 1H), 7.42 (dd, J=9.3, 2.7 Hz, 1H), 7.39-7.33 (m, 2H), 7.25 (d, J=2.6 Hz, 1H), 7.17-7.10 (m, 3H), 7.10-7.05 (m, 2H), 5.54-5.41 (m, 2H), 5.21 (dd, J=10.2, 1.7 Hz, 1H), 5.17 (d, J=8.2 Hz, 1H), 5.10 (dd, J=17.0, 1.7 Hz, 1H), 4.39 (ddd, J=11.3, 8.2, 3.1 Hz, 1H), 4.02-3.97 (m, 1H), 3.99 (s, 3H), 3.53 (ddd, J=12.9, 6.4, 3.4 Hz, 1H), 3.01 (td, J=13.3, 3.1 Hz, 1H), 2.69 (ddd, J=13.0, 10.0, 5.0 Hz, 1H), 2.58 (qd, J=10.1, 3.2 Hz, 1H), 2.21 (dd, J=13.5, 2.7 Hz, 1H), 1.88 (s, 3H), 1.87-1.76 (m, 3H), 1.65 (ddt, J=18.4, 9.6, 4.8 Hz, 1H).

HRMS(ESI): m/z calc. for C₃₅H₃₆N₃O₄S [M+H]⁺: 594.2427. found: 594.2434.

Q1z: Prepared from 4-morpholinecarbonyl chloride.

Yield: 8.4 mg, 70%.

¹H NMR (CDCl₃, 500 MHz): δ 8.31-8.15 (m, 3H), 8.10 (d, J=9.1 Hz, 1H), 7.41 (dd, J=9.3, 2.5 Hz, 1H), 7.37 (t, J=7.7 Hz, 2H), 7.27-7.23 (m, 1H), 7.14 (t, J=7.5 Hz, 1H), 7.08 (dd, J=10.5, 8.0 Hz, 4H), 5.45 (dt, J=16.8, 9.6 Hz, 1H), 5.25-5.15 (m, 2H), 5.09 (dd, J=17.3, 1.8 Hz, 1H), 4.53-4.42 (m, 2H), 4.03-3.97 (m, 1H), 3.98 (s, 3H), 3.63-3.52 (m, 5H), 3.25-3.14 (m, 4H), 3.11-2.98 (m, 1H), 2.68-2.51 (m, 2H), 2.29-2.17 (m, 1H), 1.84 (dd, J=9.9, 5.2 Hz, 2H), 1.79-1.68 (m, 1H), 1.70-1.59 (m, 1H).

HRMS(ESI): calc. for C₃₃H₄₁N₄O₅S [M+H]⁺: 665.2798. found: 665.2802.

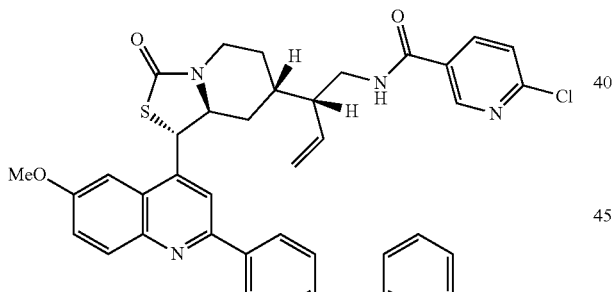

Q1y

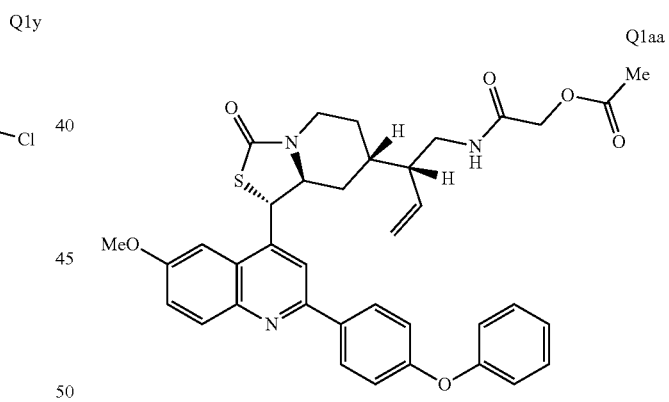

Q1aa

Q1y: Prepared from 6-chloronicotinoyl chloride.

Yield: 7.1 mg, 57%.

¹H NMR (CDCl₃, 500 MHz): δ 8.60-8.56 (m, 1H), 8.26-8.18 (m, 3H), 8.11 (d, J=9.3 Hz, 1H), 7.86 (dd, J=8.3, 2.5 Hz, 1H), 7.42 (dd, J=9.2, 2.7 Hz, 1H), 7.37-7.32 (m, 2H), 7.31 (dd, J=8.3, 0.9 Hz, 1H), 7.27 (d, J=2.8 Hz, 1H), 7.18-7.11 (m, 1H), 7.08-7.00 (m, 4H), 6.29-6.20 (m, 1H), 5.52 (dt, J=16.8, 9.8 Hz, 1H), 5.25-5.20 (m, 2H), 5.11 (dd, J=17.0, 1.7 Hz, 1H), 4.45 (ddd, J=11.8, 8.8, 3.0 Hz, 1H), 4.04-4.00 (m, 1H), 3.99 (s, 3H), 3.75 (ddt, J=9.8, 6.7, 2.9 Hz, 1H), 3.03 (td, J=13.5, 3.2 Hz, 1H), 2.84-2.75 (m, 1H), 2.70 (qd, J=10.3, 3.0 Hz, 1H), 2.29-2.19 (m, 1H), 1.95-1.84 (m, 2H), 1.85-1.74 (m, 1H), 1.74-1.52 (m, 1H).

HRMS(ESI): m/z calc. for C₃₉H₃₆N₄O₄SCl [M+H]⁺: 691.2146. found: 619.2155.

Q1aa: Prepared from acetoxyacetyl chloride.

Yield: 7.8 mg, 66%.

¹H NMR (CDCl₃, 500 MHz): δ 8.21-8.14 (m, 3H), 8.11 (d, J=9.2 Hz, 1H), 7.42 (dd, J=9.1, 2.7 Hz, 1H), 7.39-7.33 (m, 2H), 7.24 (d, J=2.7 Hz, 1H), 7.17-7.10 (m, 3H), 7.10-7.04 (m, 2H), 6.13 (t, J=5.7 Hz, 1H), 5.48 (dt, J=16.8, 10.0 Hz, 1H), 5.23 (dd, J=10.1, 1.7 Hz, 1H), 5.17 (d, J=8.0 Hz, 1H), 5.15-5.08 (m, 1H), 4.52-4.38 (m, 2H), 4.37-4.27 (m, 1H), 4.04-4.00 (m, 1H), 3.99 (s, 3H), 3.56 (ddd, J=13.1, 6.7, 3.5 Hz, 1H), 3.12-2.93 (m, 1H), 2.76 (ddd, J=13.1, 10.1, 5.0 Hz, 1H), 2.56 (ddt, J=13.6, 10.2, 6.2 Hz, 1H), 2.25-2.15 (m, 1H), 2.10 (s, 3H), 1.94-1.74 (m, 3H), 1.75-1.57 (m, 1H).

HRMS(ESI): m/z calc. for C₃₇H₃₈N₃O₆S [M+H]⁺: 652.2481. found: 652.2490.

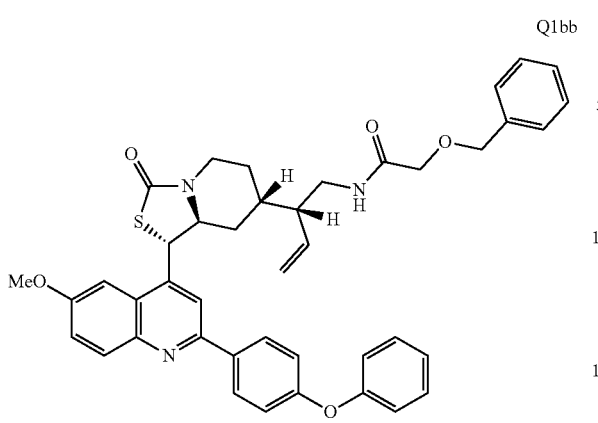

Q1bb

Q1bb: Prepared from benzyloxyacetyl chloride.
Yield: 7.7 mg, 61%.

$^1$H NMR (CDCl$_3$, 500 MHz): δ 8.20-8.14 (m, 3H), 8.11 (d, J=9.3 Hz, 1H), 7.42 (dd, J=9.2, 2.7 Hz, 1H), 7.39-7.29 (m, 5H), 7.28-7.22 (m, 3H), 7.16-7.09 (m, 3H), 7.09-7.03 (m, 2H), 6.67-6.60 (m, 1H), 5.47 (dt, J=17.1, 9.8 Hz, 1H), 5.26-5.13 (m, 2H), 5.09 (d, J=17.1 Hz, 1H), 4.49 (s, 2H), 4.33 (td, J=8.3, 4.1 Hz, 1H), 4.03-3.99 (m, 1H), 3.98 (s, 3H), 3.88 (d, J=2.4 Hz, 2H), 3.52 (ddd, J=13.1, 6.9, 3.7 Hz, 1H), 3.00 (td, J=13.2, 3.3 Hz, 1H), 2.82 (ddd, J=13.5, 10.2, 5.5 Hz, 1H), 2.57 (qd, J=9.8, 3.4 Hz, 1H), 2.25-2.15 (m, 1H), 1.93-1.77 (m, 3H), 1.71-1.61 (m, 1H).

HRMS(ESI): m/z calc. for C$_{42}$H$_{42}$N$_3$O$_5$S [M+H]$^+$: 700.2845. found: 700.2849.

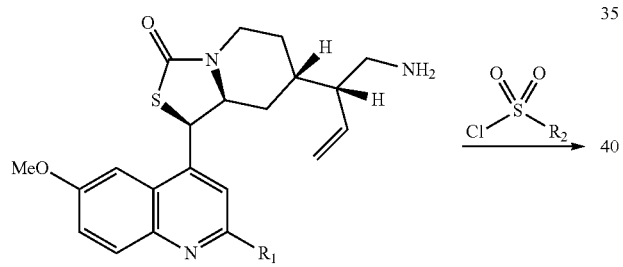

Q1d: R1 = H
Q1e: R1 = 4-PhOPh

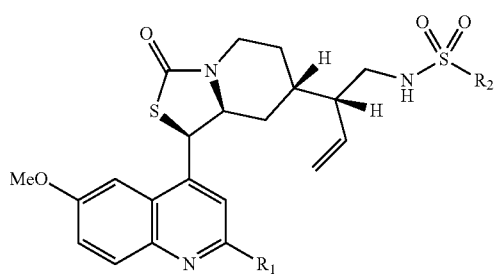

General Procedure for the Preparation of Q1 Sulfonamides:

To a solution of amine Q1d or Q1e and triethylamine (7.5 μL, 0.054 mmol) in dichloromethane (2 mL) was added sulfonyl chloride (0.036 mmol). The reaction was stirred at room temperature 24 hours, quenched with methanol, evaporated, and purified by preparative TLC (hexanes/ethyl acetate) to provide the sulfonamide. (note: This procedure was performed at several scales: 0.018-0.078 mmol amine)

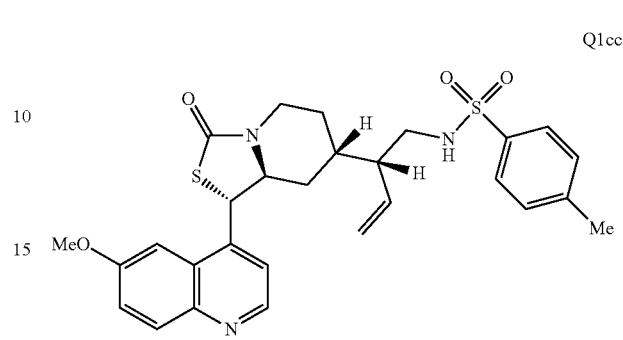

Q1cc

Q1cc: Prepared from p-toluenesulfonyl chloride.
Yield: 39.3 mg, 94%.

$^1$H NMR (CDCl$_3$, 500 MHz): δ 8.85 (d, J=4.8 Hz, 1H), 8.19 (d, J=9.2 Hz, 1H), 7.82 (d, J=4.7 Hz, 1H), 7.52-7.48 (m, 2H), 7.45 (dd, J=9.3, 2.6 Hz, 1H), 7.28 (d, J=2.6 Hz, 1H), 7.16 (d, J=7.9 Hz, 2H), 5.44-5.30 (m, 1H), 5.23 (dd, J=10.2, 1.6 Hz, 1H), 5.20-5.12 (m, 2H), 5.13-5.02 (m, 1H), 4.25 (t, J=9.4 Hz, 1H), 3.99 (s, 3H), 3.98-3.93 (m, 1H), 3.11-3.03 (m, 1H), 2.95 (td, J=13.4, 3.1 Hz, 1H), 2.61-2.47 (m, 2H), 2.36 (s, 3H), 2.13 (d, J=13.4 Hz, 1H), 1.87-1.70 (m, 3H), 1.60 (tt, J=13.5, 4.8 Hz, 1H). HRMS(ESI): m/z calc. for C$_{28}$H$_{32}$N$_3$O$_4$S$_2$ [M+H]$^+$: 538.1834. found: 538.1840.

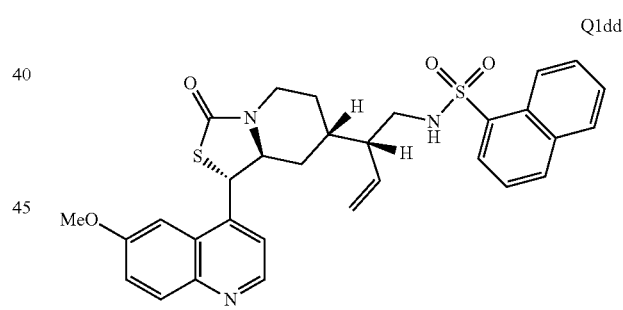

Q1dd

Q1dd: Prepared from 1-naphthalenesulfonyl chloride.
Yield: 32.6 mg, 73%.

$^1$H NMR (CDCl$_3$, 500 MHz): δ 8.82 (d, J=4.6 Hz, 1H), 8.54-8.48 (m, 1H), 8.13 (d, J=9.2 Hz, 1H), 7.95-7.90 (m, 1H), 7.90-7.86 (m, 1H), 7.78 (dd, J=7.3, 1.3 Hz, 1H), 7.67 (d, J=4.7 Hz, 1H), 7.62-7.54 (m, 2H), 7.45 (dd, J=9.2, 2.6 Hz, 1H), 7.25-7.18 (m, 2H), 5.24 (dt, J=16.9, 9.8 Hz, 1H), 5.14 (dd, J=10.2, 1.6 Hz, 1H), 5.07 (d, J=8.6 Hz, 1H), 4.95-4.86 (m, 2H), 4.04 (ddd, J=11.7, 8.6, 3.0 Hz, 1H), 3.97 (s, 3H), 3.92-3.85 (m, 1H), 3.12-3.04 (m, 1H), 2.77 (td, J=13.3, 3.1 Hz, 1H), 2.45 (ddd, J=13.3, 9.7, 3.5 Hz, 1H), 2.36-2.26 (m, 1H), 1.86 (dd, J=13.7, 2.6 Hz, 1H), 1.73-1.66 (m, 2H), 1.61 (ddd, J=13.6, 11.8, 4.2 Hz, 1H), 1.58-1.46 (m, 1H).

HRMS(ESI): m/z calc. for C$_{31}$H$_{32}$N$_3$O$_4$S$_2$ [M+H]$^+$: 574.1834. found: 574.1838.

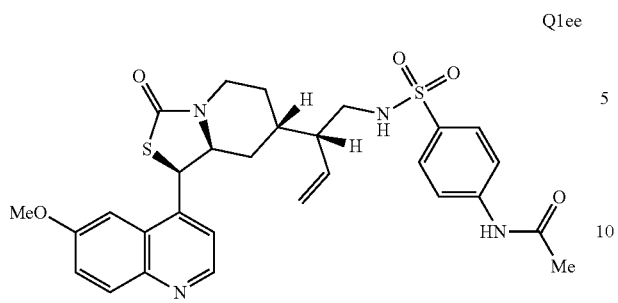

Q1ee

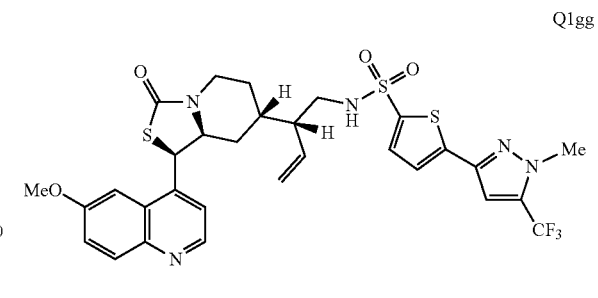

Q1gg

Q1ee: Prepared from N-acetylsulfanilyl chloride.

Yield: 44.6 mg, 98%.

$^1$H NMR (CDCl$_3$, 500 MHz): δ 8.78 (d, J=4.6 Hz, 1H), 8.44 (s, 1H), 8.04 (d, J=9.2 Hz, 1H), 7.68 (d, J=4.6 Hz, 1H), 7.50 (d, J=8.6 Hz, 2H), 7.45-7.42 (m, 2H), 7.41 (dd, J=9.2, 2.6 Hz, 2H), 5.34 (dt, J=16.9, 9.4 Hz, 1H), 5.22 (dd, J=10.1, 1.7 Hz, 1H), 5.18-5.10 (m, 2H), 5.10-5.01 (m, 1H), 4.17-4.08 (m, 1H), 3.96 (s, 3H), 3.96-3.90 (m, 1H), 3.00 (t, J=9.4 Hz, 1H), 2.90 (td, J=13.4, 3.1 Hz, 1H), 2.47 (dtd, J=18.9, 12.1, 11.4, 8.5 Hz, 2H), 2.19 (s, 3H), 2.01-1.92 (m, 1H), 1.83-1.74 (m, 2H), 1.74-1.63 (m, 1H), 1.63-1.53 (m, 1H). HRMS(ESI): m/z calc. for C$_{29}$H$_{33}$N$_4$O$_5$S$_2$ [M+H]$^+$: 581.1892. found: 581.1895.

Q1gg: Prepared from 5-[1-methyl-5-(trifluoromethyl)-1H-pyrazol-3-yl]thiophene-2-sulfonyl chloride.

Yield: 58.5 mg, 74%.

$^1$H NMR (CDCl$_3$, 500 MHz): δ 8.87 (s, 1H), 8.12 (d, J=9.2 Hz, 1H), 7.71 (s, 1H), 7.44 (dd, J=9.1, 2.6 Hz, 1H), 7.26-7.25 (m, 2H), 7.09 (d, J=3.9 Hz, 1H), 6.81 (s, 1H), 5.39 (dt, J=16.8, 9.7 Hz, 1H), 5.29 (dd, J=10.1, 1.7 Hz, 1H), 5.19 (dd, J=16.9, 1.7 Hz, 1H), 5.13 (d, J=8.7 Hz, 1H), 4.78 (d, J=7.4 Hz, 1H), 4.20 (ddd, J=11.9, 8.7, 2.9 Hz, 1H), 4.01 (s, 3H), 3.98 (s, 3H), 3.97-3.93 (m, 1H), 3.24 (ddd, J=12.7, 9.0, 3.4 Hz, 1H), 2.94 (td, J=13.4, 3.1 Hz, 1H), 2.64 (ddd, J=13.0, 9.6, 3.5 Hz, 1H), 2.55 (qd, J=9.5, 3.3 Hz, 1H), 2.09-2.01 (m, 1H), 1.89-1.78 (m, 2H), 1.74 (ddd, J=13.9, 11.9, 4.3 Hz, 1H), 1.64 (ddt, J=13.4, 8.8, 4.8 Hz, 1H). HRMS(ESI): m/z calc. for C$_{30}$H$_{31}$N$_5$O$_4$F$_3$S$_3$ [M+H]$^+$: 678.1490. found: 678.1483.

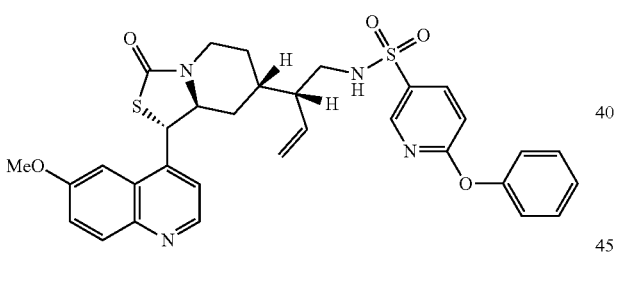

Q1ff

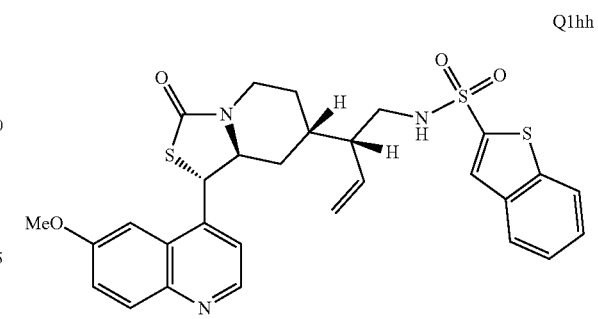

Q1hh

Q1ff: Prepared from 6-phenoxypyridine-3-sulfonyl chloride.

Yield: 39.6 mg, 82%.

$^1$H NMR (CDCl$_3$, 500 MHz): δ 8.78 (d, J=4.5 Hz, 1H), 8.42-8.37 (m, 1H), 8.04 (d, J=9.2 Hz, 1H), 7.77 (dd, J=8.7, 2.4 Hz, 1H), 7.64 (d, J=4.6 Hz, 1H), 7.48-7.41 (m, 2H), 7.39 (dd, J=9.3, 2.6 Hz, 1H), 7.30-7.25 (m, 1H), 7.23 (d, J=2.7 Hz, 1H), 7.15-7.10 (m, 2H), 6.87 (d, J=8.7 Hz, 1H), 5.40-5.31 (m, 1H), 5.24 (dd, J=10.1, 1.7 Hz, 1H), 5.21-5.15 (m, 1H), 5.13 (d, J=8.5 Hz, 1H), 5.00 (dd, J=9.0, 3.1 Hz, 1H), 4.12 (ddd, J=11.7, 8.6, 3.0 Hz, 1H), 3.99-3.93 (m, 1H), 3.95 (s, 3H), 3.07 (t, J=9.2 Hz, 1H), 2.93 (td, J=13.3, 3.1 Hz, 1H), 2.58-2.44 (m, 2H), 1.97 (dd, J=13.7, 2.6 Hz, 1H), 1.87-1.68 (m, 3H), 1.60 (ddq, J=16.9, 9.2, 4.5 Hz, 1H).

HRMS(ESI): m/z calc. for C$_{29}$H$_{33}$N$_4$O$_5$S$_2$ [M+H]$^+$: 617.1892. found: 617.1896.

Q1hh: Prepared from benzofuran-2-sulfonyl chloride.

Yield: 30.8 mg, 70%.

$^1$H NMR (CDCl$_3$, 500 MHz): δ 8.87 (d, J=4.6 Hz, 1H), 8.14 (d, J=9.2 Hz, 1H), 7.73 (d, J=4.7 Hz, 1H), 7.59-7.53 (m, 1H), 7.50-7.41 (m, 2H), 7.36-7.27 (m, 2H), 7.25 (d, J=3.0 Hz, 1H), 7.03 (s, 1H), 5.37 (dt, J=16.9, 9.8 Hz, 1H), 5.27 (dd, J=10.0, 1.8 Hz, 1H), 5.17-5.08 (m, 2H), 5.03-4.96 (m, 1H), 4.15 (ddd, J=11.8, 8.6, 3.0 Hz, 1H), 3.98 (s, 3H), 3.94-3.86 (m, 1H), 3.34 (ddd, J=13.2, 9.1, 3.5 Hz, 1H), 2.77 (td, J=13.4, 3.4 Hz, 1H), 2.69 (ddd, J=13.6, 10.0, 3.6 Hz, 1H), 2.49-2.38 (m, 1H), 2.05 (dt, J=14.3, 2.8 Hz, 1H), 1.85-1.67 (m, 3H), 1.61 (ddd, J=13.4, 8.4, 4.6 Hz, 1H).

HRMS(ESI): calc. for C$_{29}$H$_{30}$N$_3$O$_6$S, [M+H]$^+$: 564.1627. found: 564.1617.

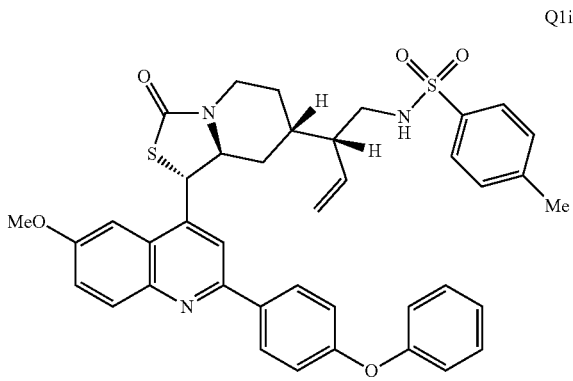 [SMILES: C=C[C@@H](CNS(=O)(=O)c1ccc(C)cc1)[C@H]1CCN2C(=O)S[C@@H](c3cc(-c4ccc(Oc5ccccc5)cc4)nc4ccc(OC)cc34)[C@@H]2C1]

Q1ii

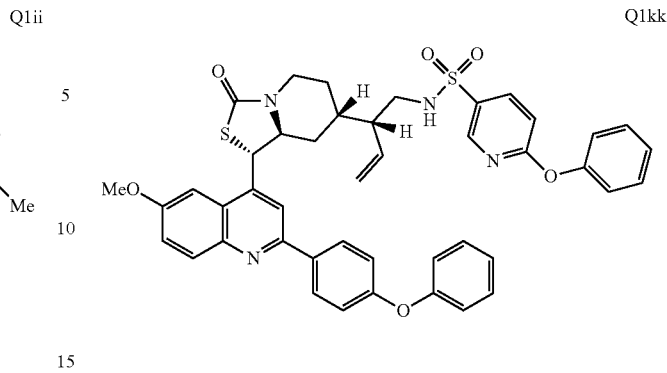

Q1kk

Q1kk: Prepared from 6-phenoxypyridine-3-sulfonyl chloride.

Yield: 8.2 mg, 58%.

$^1$H NMR (CDCl$_3$, 500 MHz): δ 8.26 (d, J=2.6 Hz, 1H), 8.18 (s, 1H), 8.13 (d, J=8.8 Hz, 2H), 8.11 (d, J=9.4 Hz, 1H), 7.48 (dt, J=8.9, 1.8 Hz, 1H), 7.46-7.40 (m, 3H), 7.38-7.32 (m, 2H), 7.30-7.26 (m, 2H), 7.16-7.07 (m, 5H), 7.04 (dd, J=8.6, 1.2 Hz, 2H), 6.75 (d, J=8.7 Hz, 1H), 5.40-5.30 (m, 1H), 5.29-5.14 (m, 3H), 4.50 (dd, J=8.9, 3.0 Hz, 1H), 4.14-4.05 (m, 1H), 4.01 (dd, J=5.1, 2.6 Hz, 1H), 3.97 (s, 3H), 2.94 (td, J=11.6, 10.1, 4.0 Hz, 2H), 2.54-2.40 (m, 2H), 1.96 (d, J=13.6 Hz, 1H), 1.87-1.73 (m, 3H), 1.70-1.58 (m, 1H).

HRMS(ESI): m/z calc. for C$_{44}$H$_{41}$N$_4$O$_6$S$_2$ [M+H]$^+$: 785.2468. found: 785.2478.

Q1ii: Prepared from p-toluenesulfonyl chloride.

Yield: 8.3 mg, 65%.

$^1$H NMR (CDCl$_3$, 500 MHz): δ 8.23-8.09 (m, 4H), 7.47 (dd, J=9.2, 2.0 Hz, 1H), 7.38-7.31 (m, 2H), 7.28 (s, 1H), 7.24 (d, J=8.1 Hz, 2H), 7.16-7.08 (m, 3H), 7.04 (dd, J=7.5, 1.0 Hz, 2H), 7.00 (d, J=7.9 Hz, 2H), 5.33 (dt, J=17.4, 9.8 Hz, 1H), 5.26-5.15 (m, 2H), 5.11 (dd, J=16.9, 2.1 Hz, 1H), 4.38 (dd, J=8.9, 4.2 Hz, 1H), 4.10-4.02 (m, 1H), 4.00 (s, 3H), 3.97-3.92 (m, 1H), 2.99-2.82 (m, 2H), 2.47 (ddd, J=13.1, 9.1, 4.0 Hz, 1H), 2.43-2.33 (m, 1H), 2.30 (s, 3H), 2.02-1.92 (m, 1H), 1.87-1.70 (m, 3H), 1.67-1.58 (m, 1H). HRMS (ESI): m/z calc. for C$_{40}$H$_{40}$N$_3$O$_5$S$_2$ [M+H]$^+$: 706.2409. found: 706.2415.

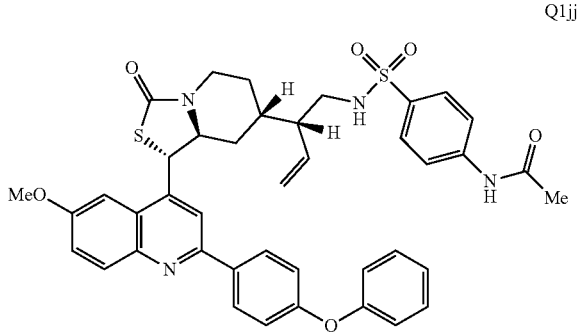 [SMILES: C=C[C@@H](CNS(=O)(=O)c1ccc(NC(C)=O)cc1)[C@H]1CCN2C(=O)S[C@@H](c3cc(-c4ccc(Oc5ccccc5)cc4)nc4ccc(OC)cc34)[C@@H]2C1]

Q1jj

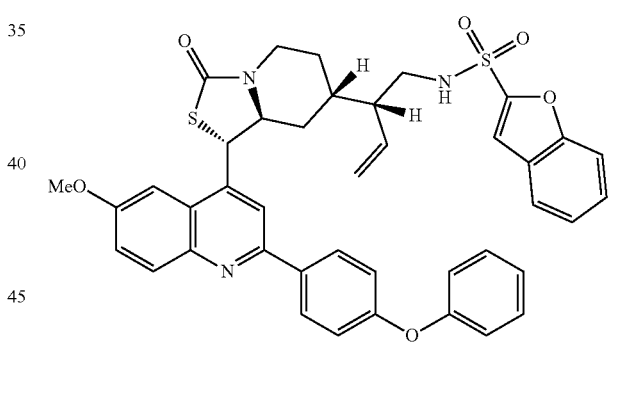

Q1ll

Q1ll: Prepared from benzofuran-2-sulfonyl chloride.

Yield: 9.7 mg, 74%.

$^1$H NMR (CDCl$_3$, 500 MHz): δ 8.24-8.11 (m, 4H), 7.50 (dd, J=9.2, 2.6 Hz, 1H), 7.46-7.40 (m, 2H), 7.39 (dd, J=2.4, 1.2 Hz, 1H), 7.36 (dd, J=8.6, 7.1 Hz, 2H), 7.29 (d, J=3.1 Hz, 1H), 7.27-7.23 (m, 1H), 7.17-7.11 (m, 3H), 7.07-7.02 (m, 2H), 6.64 (s, 1H), 5.38 (dt, J=16.8, 9.7 Hz, 1H), 5.27 (dd, J=10.1, 1.6 Hz, 1H), 5.22 (d, J=7.5 Hz, 1H), 5.17 (dd, J=16.8, 1.7 Hz, 1H), 4.80 (dd, J=8.6, 3.9 Hz, 1H), 4.09-4.03 (m, 1H), 4.02 (s, 3H), 3.99-3.90 (m, 1H), 3.18 (ddd, J=12.9, 8.7, 3.3 Hz, 1H), 2.78 (td, J=13.3, 3.3 Hz, 1H), 2.66 (ddd, J=13.6, 9.7, 4.0 Hz, 1H), 2.43-2.32 (m, 1H), 2.04 (d, J=13.6 Hz, 1H), 1.91-1.80 (m, 2H), 1.77 (d, J=13.4 Hz, 1H), 1.65 (dt, J=18.1, 6.5 Hz, 1H). HRMS(ESI): m/z calc. for C$_{41}$H$_{38}$N$_3$O$_6$S$_2$ [M+H]$^+$: 732.2202. found: 732.2191.

Q1jj: Prepared from N-acetylsulfanilyl chloride.

Yield: 5.7 mg, 42%.

$^1$H NMR (CDCl$_3$, 500 MHz): δ 8.23-8.07 (m, 4H), 7.48 (dd, J=9.3, 2.6 Hz, 1H), 7.39 (s, 1H), 7.38-7.33 (m, 2H), 7.33-7.20 (m, 5H), 7.17-7.08 (m, 3H), 7.07-7.00 (m, 2H), 5.34 (dt, J=16.7, 9.7 Hz, 1H), 5.28-5.16 (m, 2H), 5.11 (dd, J=17.0, 1.8 Hz, 1H), 4.45 (dd, J=8.8, 4.0 Hz, 1H), 4.06-3.99 (m, 1H), 3.99 (s, 3H), 3.98-3.92 (m, 1H), 2.89 (qd, J=12.6, 3.1 Hz, 2H), 2.48 (ddd, J=13.2, 9.3, 3.9 Hz, 1H), 2.35 (qd, J=9.8, 3.5 Hz, 1H), 2.15 (s, 3H), 2.01-1.90 (m, 1H), 1.85-1.67 (m, 3H), 1.62 (ddt, J=15.6, 11.5, 3.6 Hz, 1H). HRMS (ESI): m/z calc. for C$_{41}$H$_{41}$N$_4$O$_6$S$_2$ [M+H]$^+$: 749.2468. found: 749.2476.

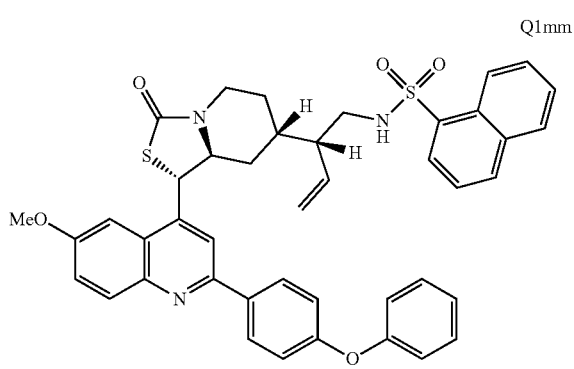 [SMILES: C=C[C@@H](CNS(=O)(=O)c1cccc2ccccc12)[C@H]1CCN2C(=O)S[C@@H](c3cc(-c4ccc(Oc5ccccc5)cc4)nc4ccc(OC)cc34)[C@@H]2C1]

Q1mm

Q1mm: Prepared from 1-naphthalenesulfonyl chloride.
Yield: 12.1 mg, 91%.
$^1$H NMR (CDCl$_3$, 500 MHz): δ 8.45-8.39 (m, 1H), 8.25-8.15 (m, 4H), 7.83-7.74 (m, 2H), 7.59-7.49 (m, 2H), 7.49 (dd, J=9.2, 2.5 Hz, 1H), 7.43 (dd, J=7.3, 1.2 Hz, 1H), 7.32 (dd, J=8.6, 7.3 Hz, 2H), 7.28-7.26 (m, 1H), 7.16-7.09 (m, 3H), 7.05-6.98 (m, 3H), 5.24 (dt, J=16.9, 9.8 Hz, 1H), 5.18-5.08 (m, 2H), 4.90 (dd, J=17.0, 1.7 Hz, 1H), 4.65 (dd, J=9.0, 3.6 Hz, 1H), 3.99 (s, 3H), 3.98-3.95 (m, 1H), 3.92 (ddd, J=13.6, 5.0, 2.4 Hz, 1H), 2.92 (ddd, J=12.8, 8.9, 3.3 Hz, 1H), 2.78 (td, J=13.2, 3.2 Hz, 1H), 2.39 (ddd, J=13.3, 9.5, 3.6 Hz, 1H), 2.24 (qd, J=9.7, 3.0 Hz, 1H), 1.84 (dd, J=12.7, 2.8 Hz, 1H), 1.77-1.62 (m, 3H), 1.57-1.48 (m, 1H). HRMS(ESI): m/z calc. for C$_{43}$H$_{40}$N$_3$O$_5$S$_2$ [M+H]$^+$: 742.2409. found: 742.2419.

Example 7. Computational Analysis

Molecular Property Distribution Histograms.
Library data for the MicroFormat Library was obtained via the ChemBridge website. Molecular properties were calculated in Discovery Studio Client 2.5 (Accelrys, San Diego Calif.) using the Analyze Small Molecules toolset. Fsp3 values were calculated using the electrotopological state (E-State) counts for all possible carbon configurations. Histograms were generated in Excel (Microsoft, Redmond Wash.) using the Analysis ToolPak.
Tanimoto Similarity Analysis.
Compound structure sets were converted to .sdf library format in ChemDraw (Cambridgesoft, Cambridge Mass.). Tanimoto similarity coefficients were calculated using Discovery Studio Client 2.5 (Accelrys, San Diego Calif.). Each structure was saved as an individual .sdf file and used as an input reference ligand for the Library Analysis protocol "Find Similar Molecules by Fingerprints", setting the minimum similarity to 0 and using ECFP_6 molecular fingerprints. This was repeated for all compounds and the resulting Tanimoto coefficients were arranged in a similarity matrix. Heatmaps were generated in Excel (Microsoft, Redmond Wash.) using a three-color scale set to 0.0 (blue), 0.5 (yellow), and 1.0 (red).

CITATIONS FOR EXAMPLES 1-7

1 Bernstein, S., Littell, R. & Williams, J. H. Steroidal cyclic ketals. IV. The conversion of 11-oxo to 11α-hydroxy steroids. The preparation of 11-epihydrocortisone and 4-androsten-11α-ol-3,17-dione. J. Am. Chem. Soc. 75, 1481-1482, (1953).

2 Lecomte, V., Stephan, E., Le Bideau, F. & Jaouen, G. Improved addition of organolithium reagents to hindered and/or enolisable ketones. Tetrahedron 59, 2169-2176, (2003).
3 Yang, D. & Jiao, G. S. Highly beta-selective epoxidation of delta(5)-unsaturated steroids catalyzed by ketones. Chem. Eur. J. 6, 3517-3521, (2000).
4 Cross, A. D. Steroids. CC. Spectra and stereochemistry, Part III. Steroidal 5,6-epoxides. J. Am. Chem. Soc. 84, 3206-3207, (1962).
5 Grove, J. F. & Mulholland, T. P. C. Gibberellic Acid. Part XII. The stereochemistry of allogibberic acid. J. Chem. Soc., 3007-3022, (1960).
6 Henderson, J. H. & Graham, H. D. A possible mechanism for biological and chemical activity of gibberellic acid. Nature 193, 1055-1056, (1962).
7. Cross, B. E., Grove, J. F. & Morrison, A. Gibberellic acid. Part XVII. Some rearrangements of ring A. J. Am. Chem. Soc., 2498-2515, (1961).
8 Cross, B. E. Gibberellic Acid. Part 1. J. Chem. Soc., 4670-4676, (1954).
9 Smith, A. C. & Williams, R. M. Rabe rest in peace: Confirmation of the Rabe-Kindler conversion of d-quinotoxine into quinine: Experimental affirmation of the Woodward-Doering formal total synthesis of quinine. Angew. Chem. Int. Ed. 47, 1736-1740, (2008).
10 Payack, J. F., Hughes, D. L., Cai, D. W., Cottrell, I. F. & Verhoeven, T. R. An improved synthesis of dimethyltitanocene. Org. Prep. Proced. Int. 27, 707-709, (1995).
11 Hintermann et al. Nucleophilic addition of organometallic reagents to cinchona alkaloids: simple access to diverse architectures. Angew. Chem. Int. Ed. 46, 5164-5167, (2007).
12 Seiple, I. B., Su, S., Rodriguez, R. A., Gianatassio, R., Fujiwara, Y., Sobel, A. L. & Baran, P. S. Direct C—H arylation of electron-deficient heterocycles with arylboronic acids. J. Am. Chem. Soc. 132, 13194-13196, (2010).

Example 8. Activity Against Cancer Cells

Compounds prepared according to the methods described herein have been screened for activity against various cancer cell lines. Several compounds were found to have significant anticancer activity, including GA-4 and GA-81.

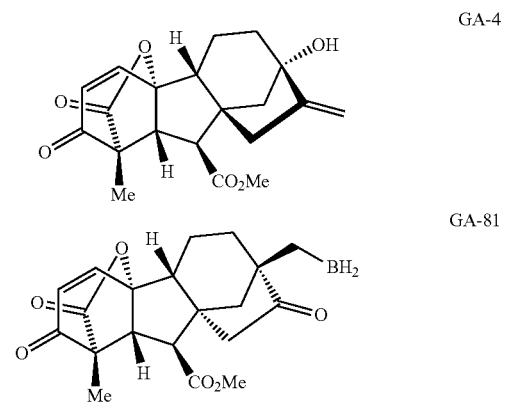

GA-4

GA-81

Inhibitory activity toward several cancer cell lines was determined and GA-4 and GA-81 showed potent 72-hour IC$_{50}$ values, as summarized in Table 8-1 below.

TABLE 8-1

IC$_{50}$ values Toward Various Cancer Cell Lines.

| Compound | Cell Line | IC$_{50}$ |
|---|---|---|
| GA-4 | U-937 (lymphoma) | 0.56 ± 0.18 μM |
| GA-4 | HeLa (cervical) | 1.14 ± 0.03 μM |
| GA-4 | H1299 (NSC lung) | 2.4 ± 0.8 μM |
| GA-4 | MCF7 (breast) | 4.8 ± 1.3 μM |
| GA-4 | B16F10 (melanoma) | 1.0 ± 0.4 μM |
| GA-4 | EL-4 (lymphoma) | 0.850 ± 0.09 μM |
| GA-4 | A549 (lung) | 5.9 ± 0.05 μM |
| GA-81 | U-937 (lymphoma) | 1.78 ± 0.09 μM |
| GA-81 | HeLa (cervical) | 4.9 ± 0.09 μM |
| GA-81 | A549 (lung) | 4.5 ± 0.09 μM |

Figure 11:
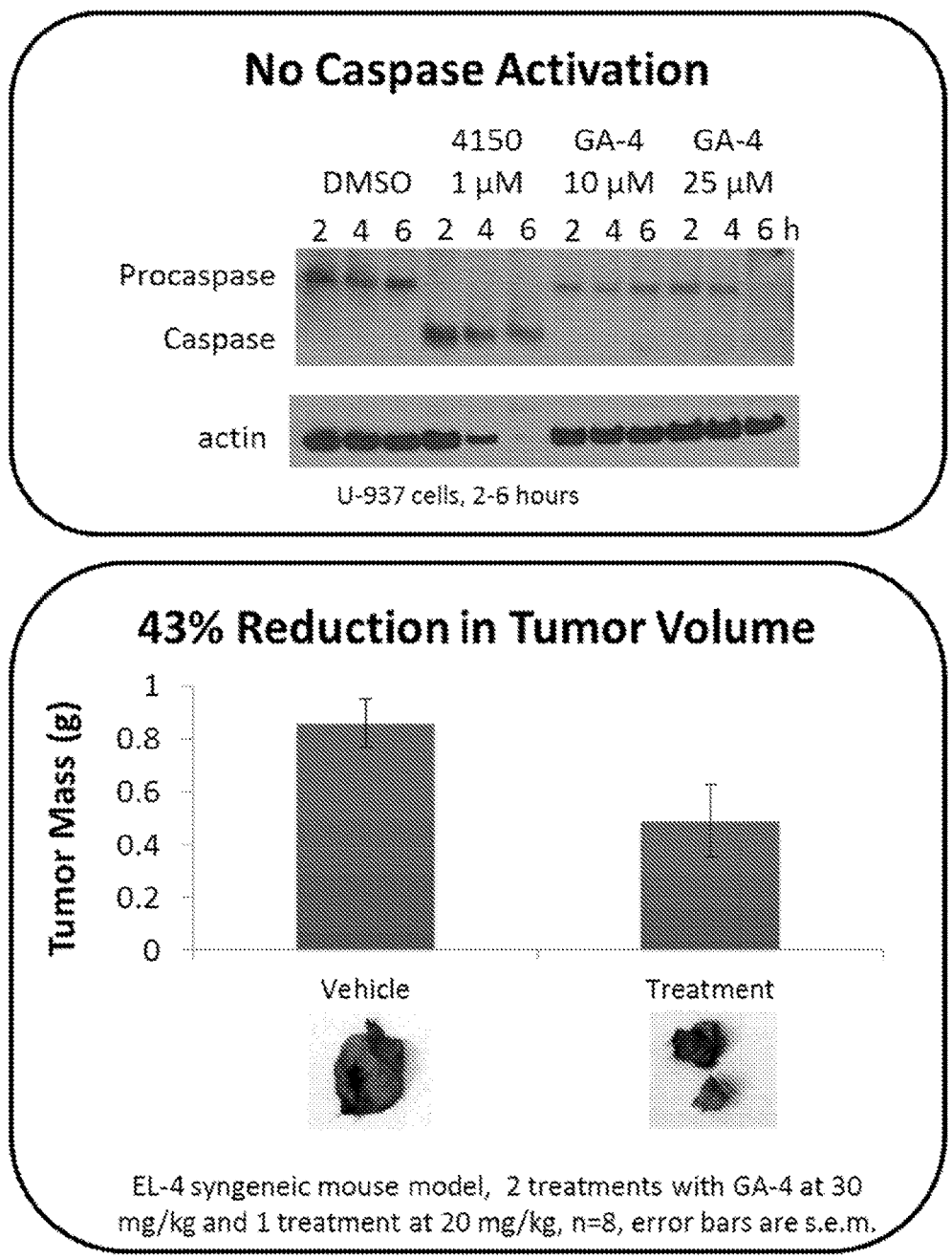
FIG. 11. Western blot showing lack of caspase activation of compound GA-4, and the reduction in tumor volume in EL-4 syngeneic mice after three treatments.
Figure 12:
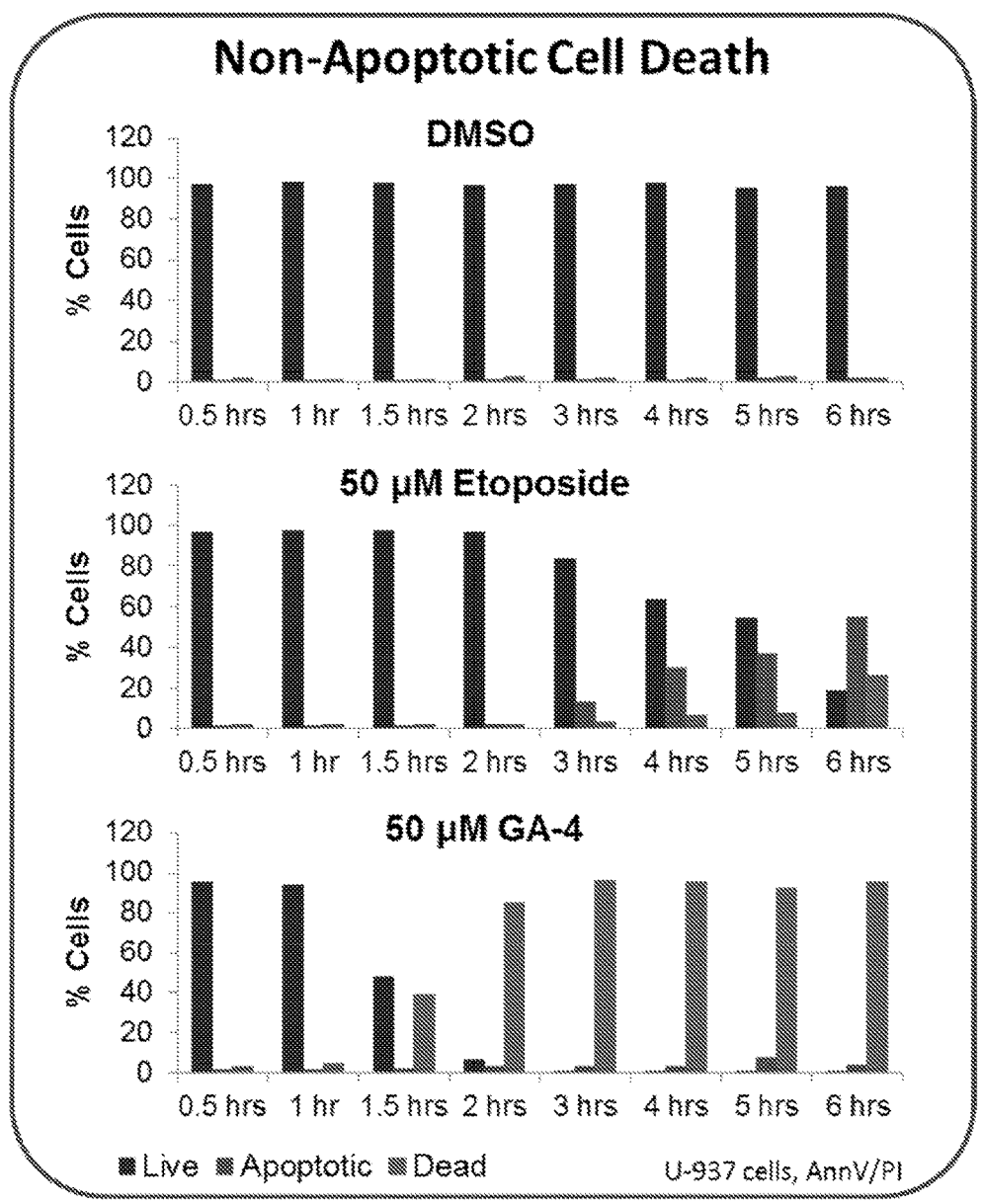
FIG. 12. Non-apoptotic cell death of U-937 cells by compound GA-4.

Compound GA-4 showed a lack of caspase activation and provided a 43% reduction in tumor volume (p=0.023, n=8) in an EL-4 syngeneic mouse model following 2 treatments at 30 mg/kg over one week and a final treatment at 20 mg/kg after the first week (FIG. 11). Compound GA-4 also provided remarkable amounts of non-apoptotic cell death, as shown in FIG. 12.

Example 9. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |

-continued

| (x) Topical Cream 1 | wt. % |
|---|---|
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for preparing a high-throughput screening library comprising:
   a) carrying out a ring expansion reaction, a ring fusion reaction, a ring rearrangement reaction, a ring cleavage reaction, or a combination thereof, on a natural product wherein the natural product is adrenosterone, quinine, gibberellic acid or a derivative of gibberellic acid having Formula X-G:

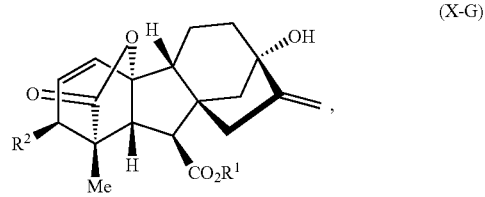

(X-G)

wherein $R^1$ is H or Me; and $R^2$ is OH or OMe;

b) carrying out an oxidation reaction, a reduction reaction, an esterification, an amidation, an addition reaction, a substitution reaction, an elimination reaction, an aromatization reaction, or a protection or deprotection reaction; optionally followed by carrying out an additional ring expansion reaction, a ring fusion reaction, a ring rearrangement reaction, or a ring cleavage reaction; and c) repeating steps a) and b) one to four times on the resulting products using different selections of reactions to provide a series of products for a high-throughput screening library;

wherein the products comprise at least one ring distortion compared to the natural product; the products comprise at least three oxygen atoms, or at least two oxygen atoms and three nitrogen atoms; the products comprise at least two stereogenic centers, and the molecular weights of the products are at least about 300 Daltons and less than about 750 Daltons.

2. The method of claim 1 further comprising a one or more additional ring expansion reactions, ring fusion reactions, ring rearrangement reactions, ring cleavage reactions, oxidation reactions, reduction reactions, esterifications, amidations, addition reactions, substitution reactions, elimination reactions, aromatization reactions, functional group transformations, protection reactions, or deprotection reactions.

3. The method of claim 1 wherein the natural product is gibberellic acid, adrenosterone, or quinine.

4. The method of claim 1 wherein steps a) and b) comprise a ring cleavage reaction and an esterification, and step c) comprises one or more of:
   i) a ring cleavage reaction, an esterification, and ring cleavage reaction or a ring fusion reaction;
   ii) a ring rearrangement reaction, an amidation, and a ring rearrangement reaction;
   iii) a ring cleavage reaction, an esterification, and a ring expansion reaction;
   iv) a ring cleavage reaction with concomitant a decarboxylation and aromatization, an esterification, and a ring rearrangement; and
   v) a ring cleavage reaction with concomitant a decarboxylation and aromatization, a ring rearrangement, and a ring expansion reaction.

5. The method of claim 1 wherein the products of the high-throughput screening library comprise a compound of formula GAX or GAZ:

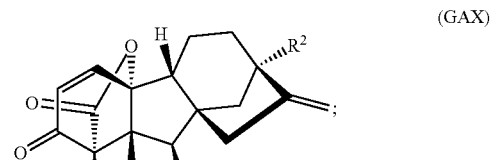

(GAX)

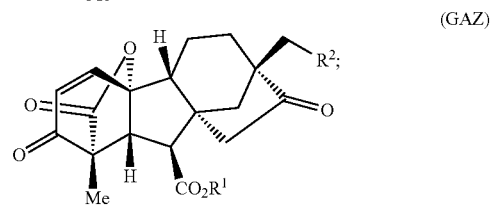

(GAZ)

wherein
R[1] is alkyl, alkylaryl, or aryl; and
R[2] is H, OH, halo, alkoxy, or OP wherein P is an oxygen protecting group.
6. The method of claim 1 wherein the products of the high-throughput screening library comprise the compound GA-4 or GA-81:
(GA-4)
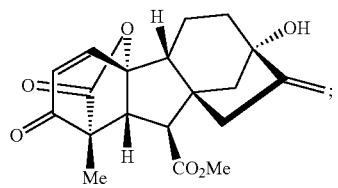
(GA-81)
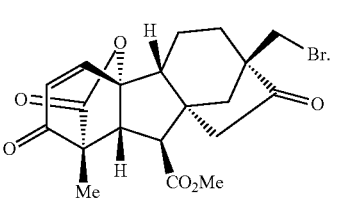
7. The method of claim 1 wherein the products of the high-throughput screening library comprise one or more of:
G1
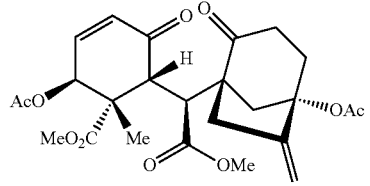
G2
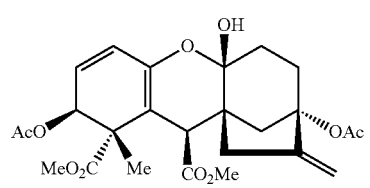
G3
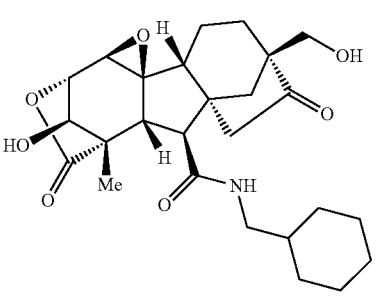
G4
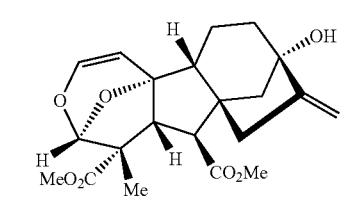
G5
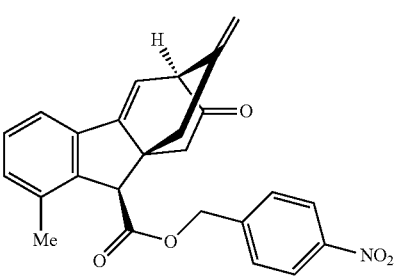
G6
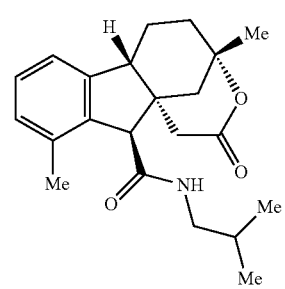
G7
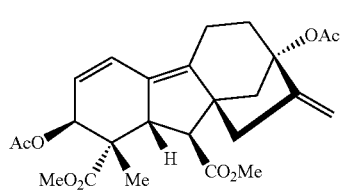
G8
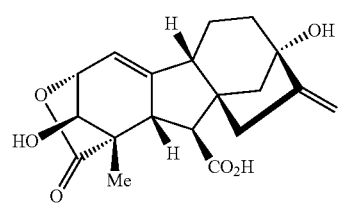
G9
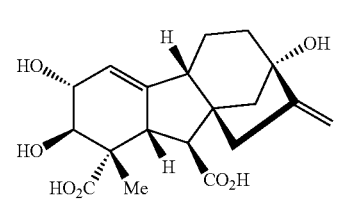
G10
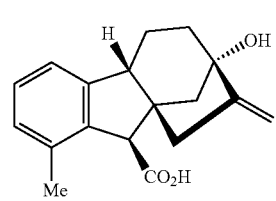
G11
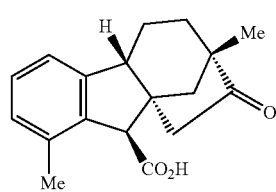

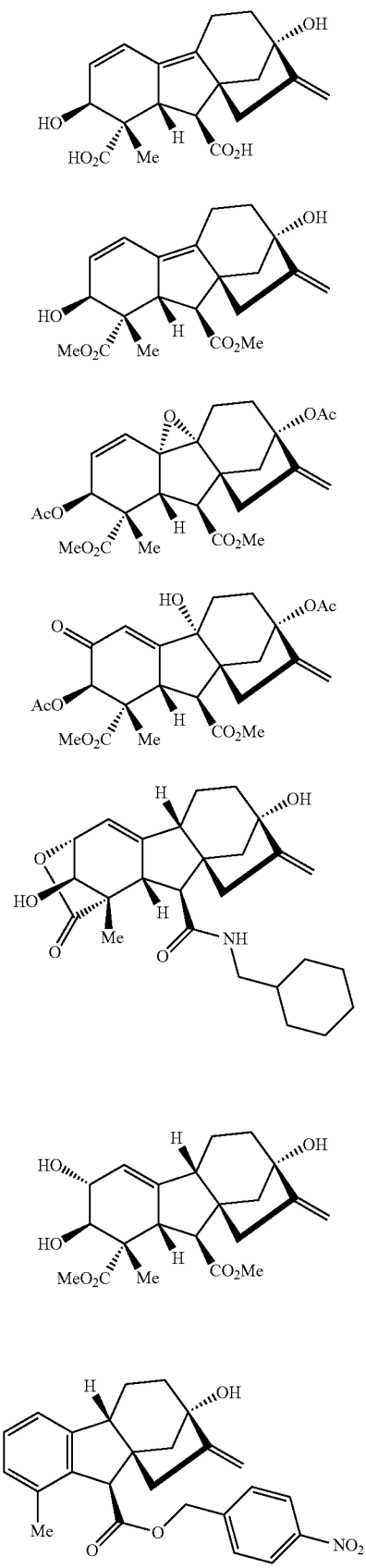
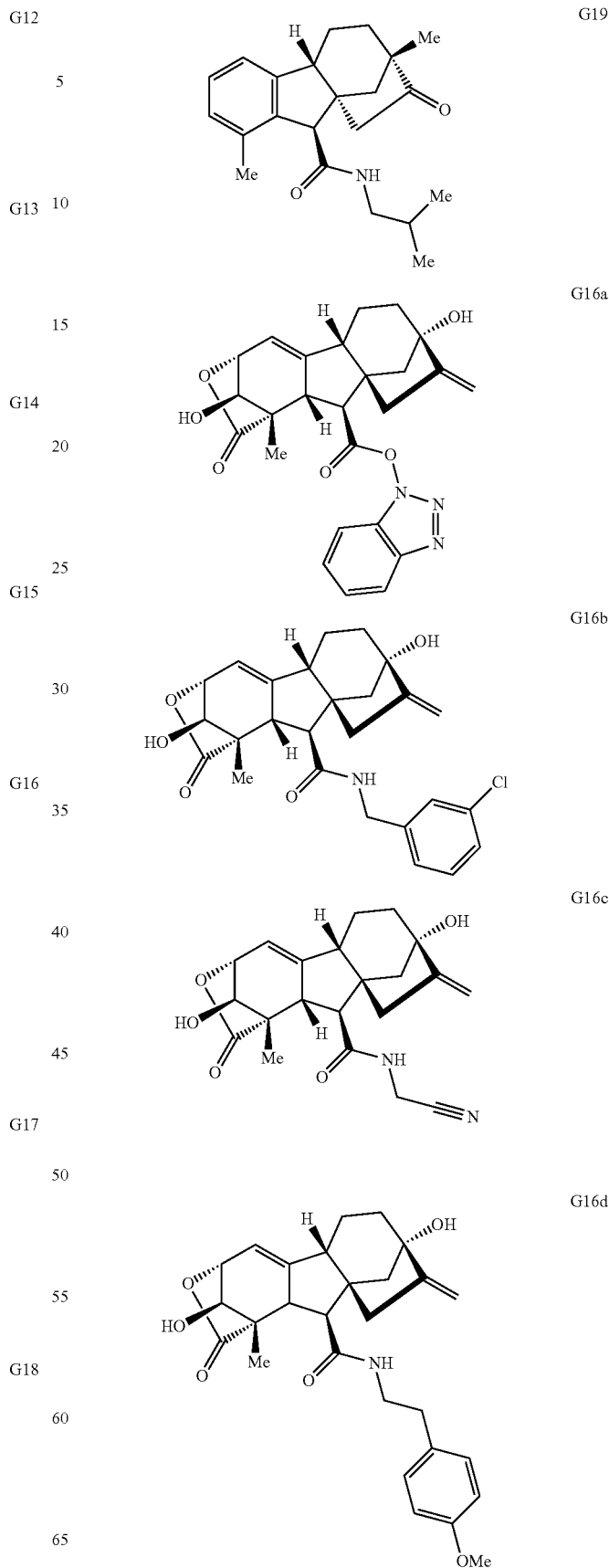

G16e
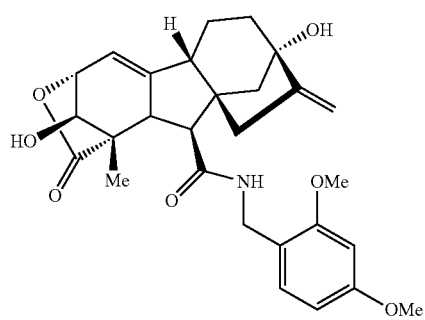
G16f
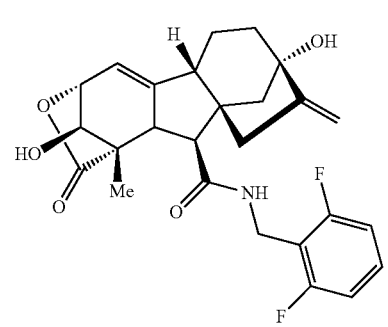
G16g
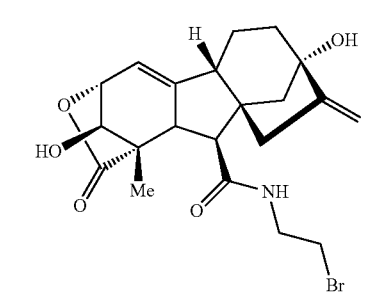
G16h
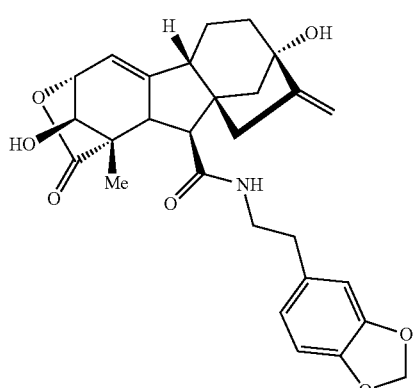
G16i
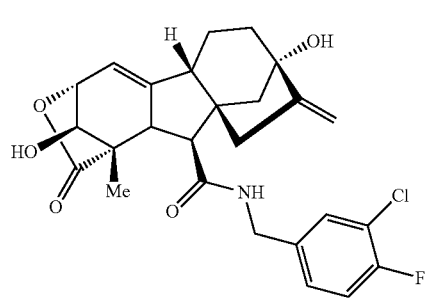
G16j
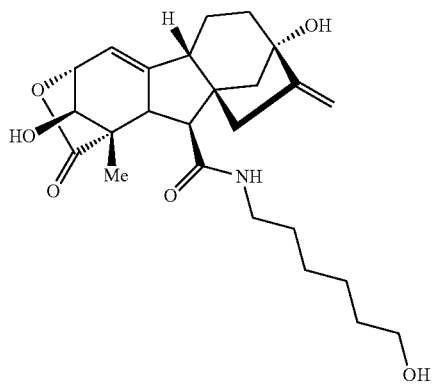
G16k
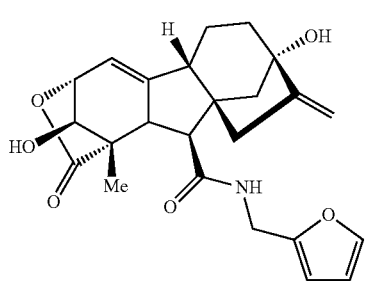
G16l
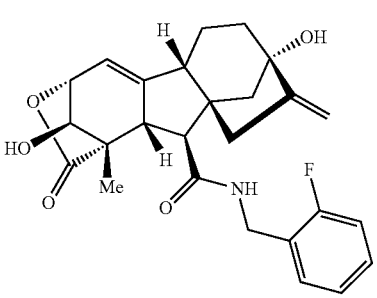
G16m
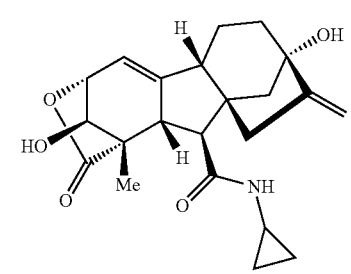
G16n
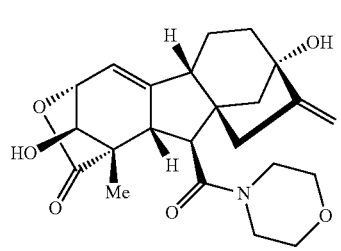

-continued

G16o
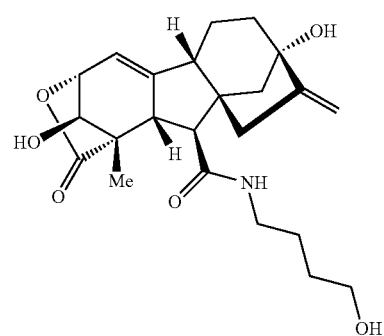

G16p
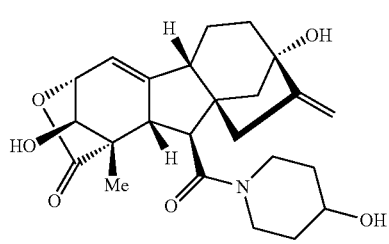

G16q
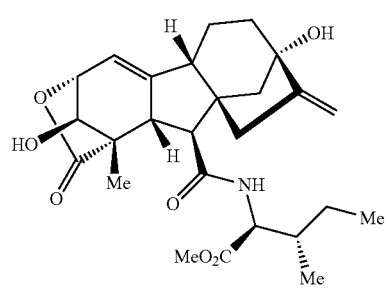

G16r
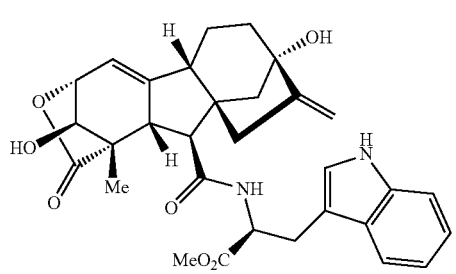

G19a
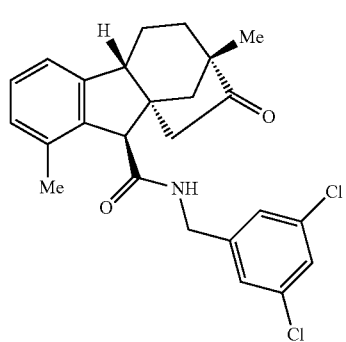

-continued

G19b
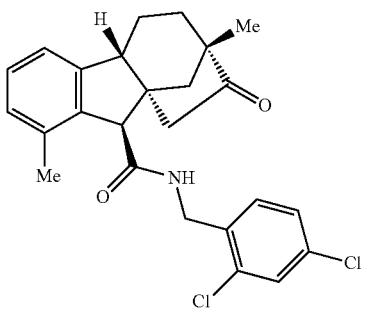

G19c
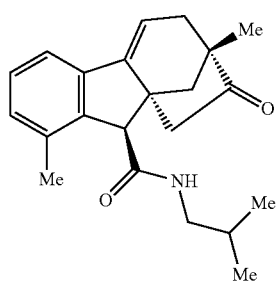

G6a
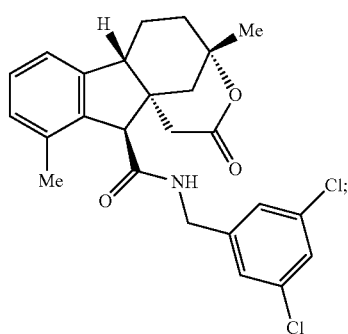

and

G6b
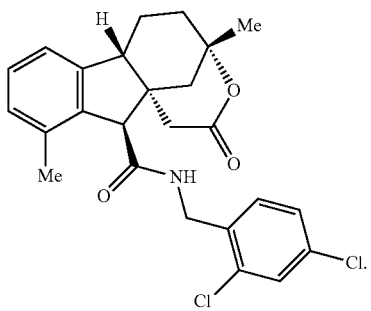

8. A method for preparing a high-throughput screening library comprising:
 a) carrying out a ring expansion reaction, a ring fusion reaction, a ring rearrangement reaction, a ring cleavage reaction, or a combination thereof, on a natural product, wherein the natural product is gibberellic acid or a derivative of gibberellic acid having Formula X-G:

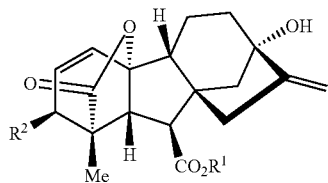
(X-G)

Wherein R¹ is H or Me; and R² is OH or OMe;
  b) carrying out an oxidation reaction, a reduction reaction, an esterification, an amidation, an addition reaction, a substitution reaction, an elimination reaction, an aromatization reaction, or a protection or deprotection reaction; optionally followed by carrying out an additional ring expansion reaction, a ring fusion reaction, a ring rearrangement reaction, or a ring cleavage reaction; and
  c) repeating steps a) and b) one to four times on the resulting products using different selections of reactions to provide a series of products for a high-throughput screening library; wherein the products comprise at least one ring distortion compared to the natural product; the products comprise at least three oxygen atoms, or at least two oxygen atoms and three nitrogen atoms; the products comprise at least two stereogenic centers, the molecular weights of the products are at least about 300 Daltons and less than about 750 Daltons, and the products of the high-throughput screening library comprise a compound of formula GAX or GAZ:

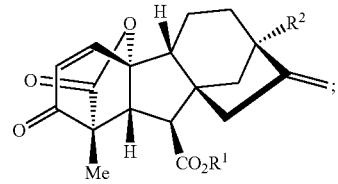
(GAX)

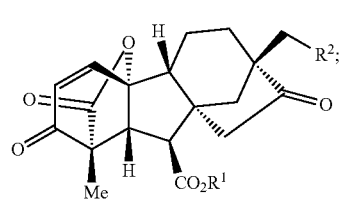
(GAZ)

wherein
  R¹ is alkyl, alkylaryl, or aryl; and
  R² is H, OH, halo, alkoxy, or OP wherein P is an oxygen protecting group.

9. The method of claim 8 wherein the products of the high-throughput screening library comprise the compound GA-4 or GA-81:

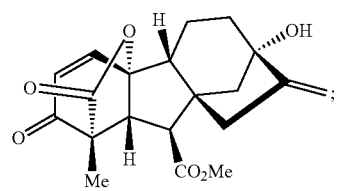
(GA-4)

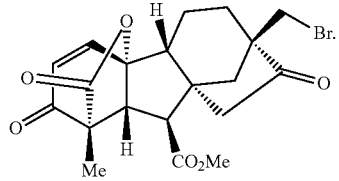
(GA-81)

10. The method of claim 8 wherein the products of the high-throughput screening library comprise one or more of:

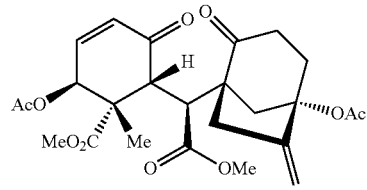
G1

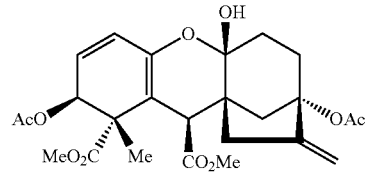
G2

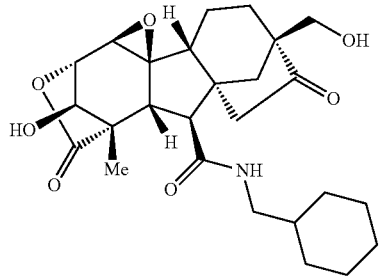
G3

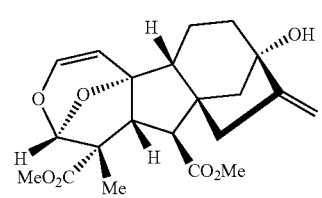
G4

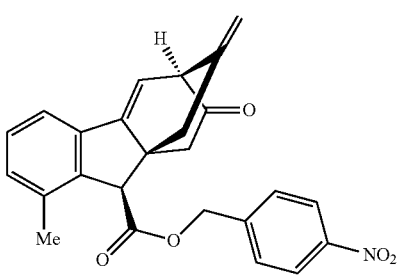
G5

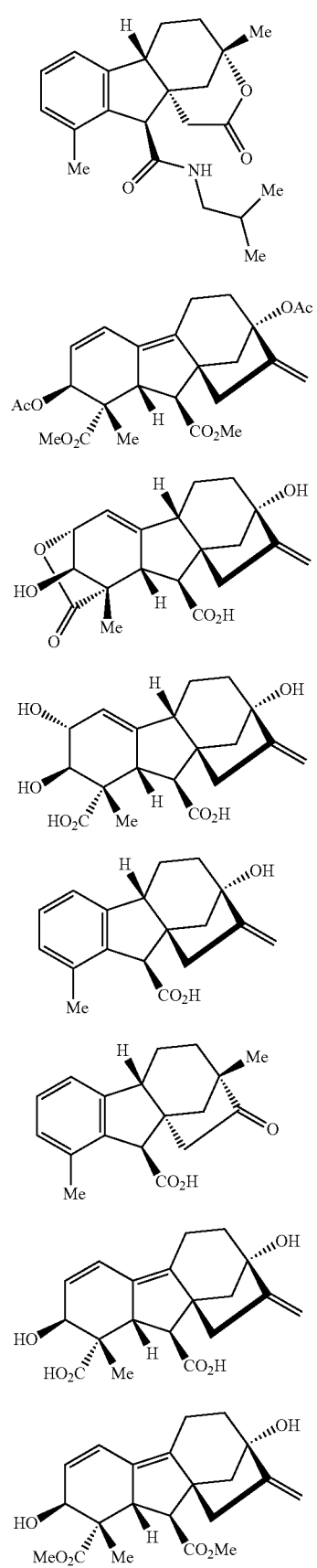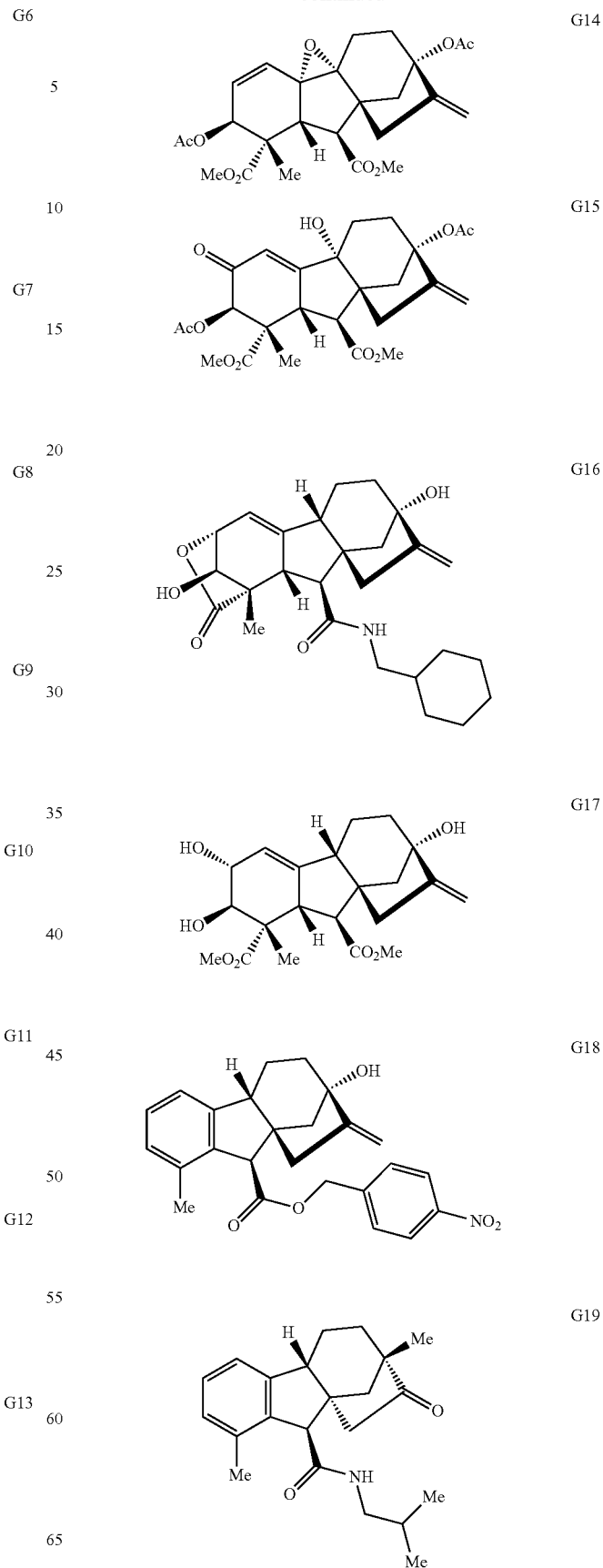

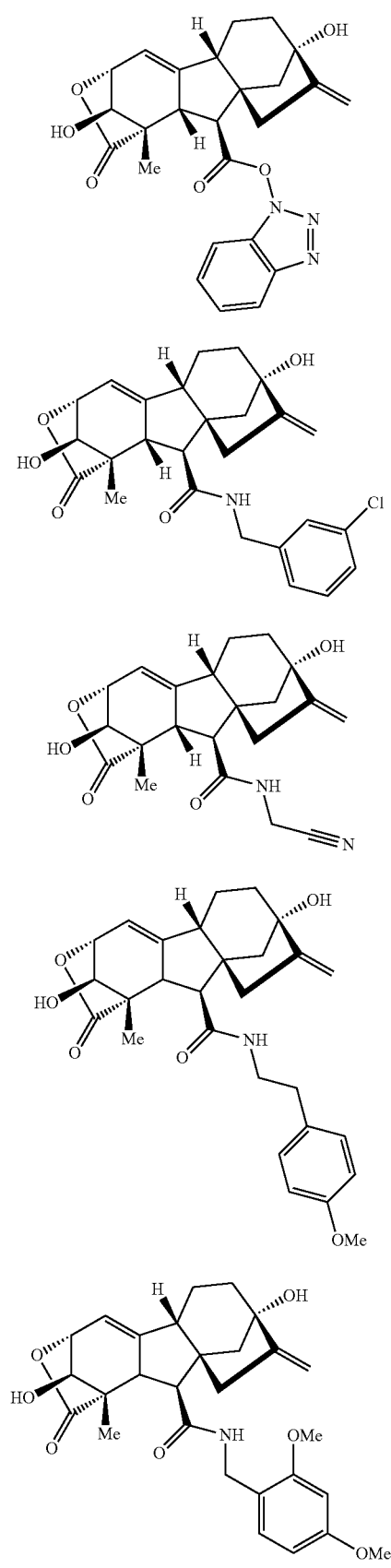
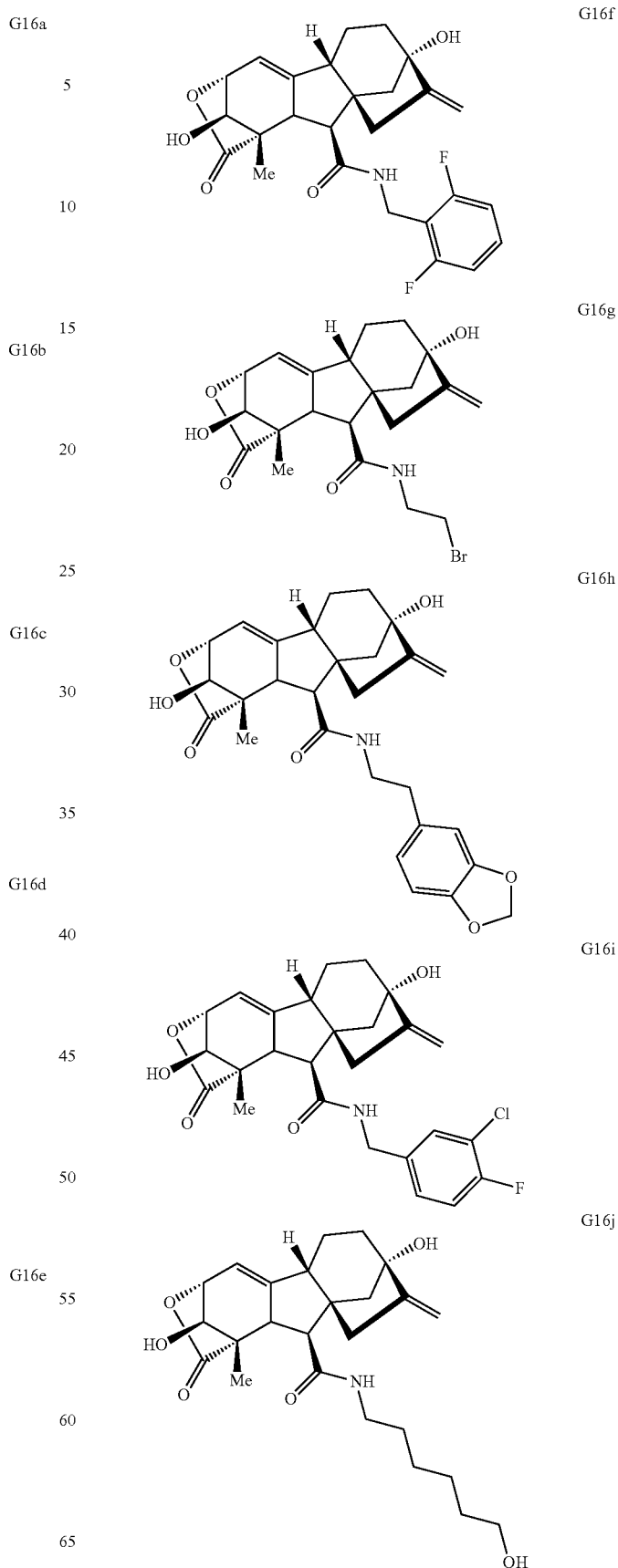

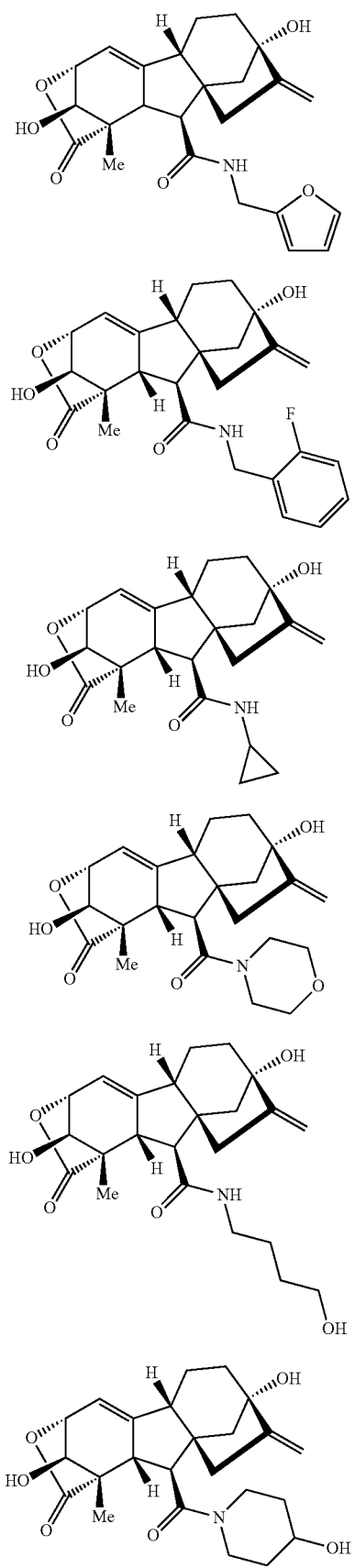
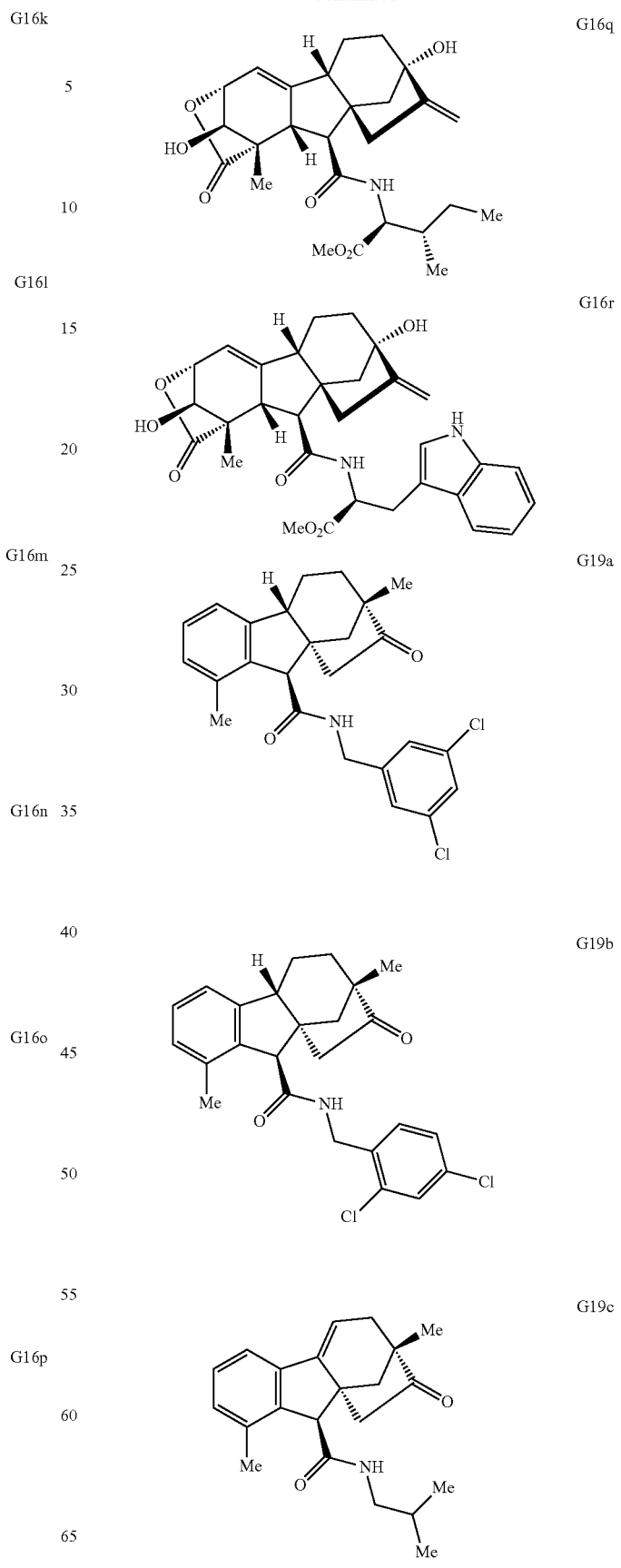

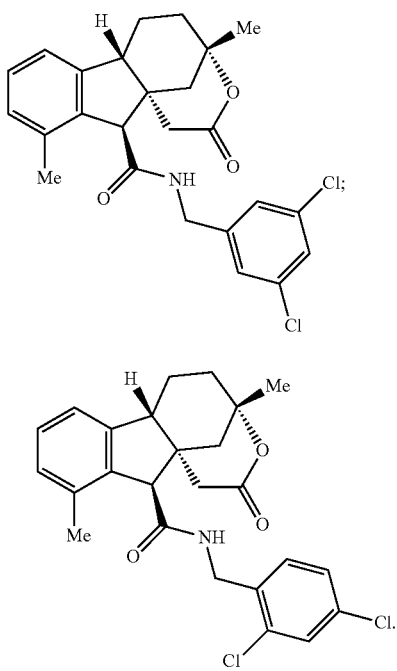
G6a
G6b
11. The method of claim 1 wherein the products of the high-throughput screening library comprise carbon skeletons X1-G to X6-G:
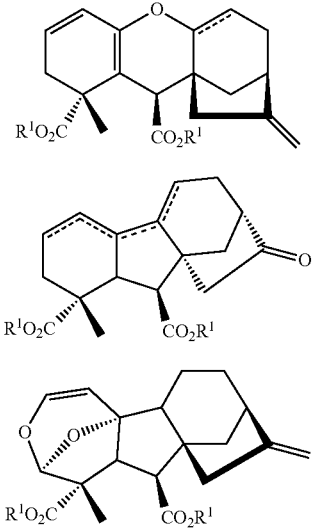
X1-G
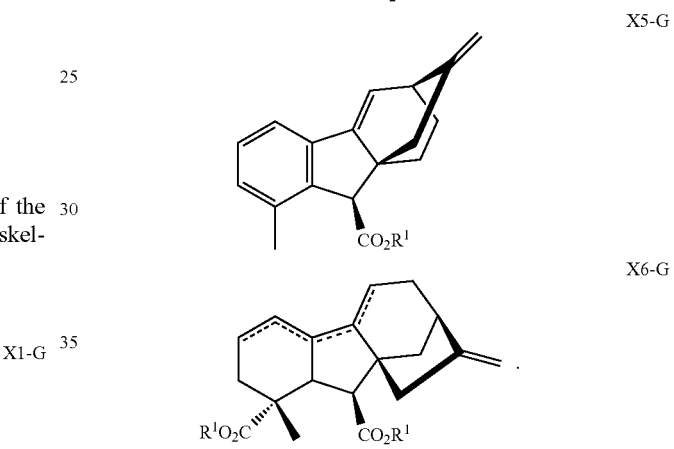
X2-G
X3-G
X4-G
X5-G
X6-G
12. The method of claim 11 wherein the products of the high-throughput screening library comprise carbon skeletons X1-G, X2-G, X4-G and X5-G.
* * * * *